US010717756B2

(12) United States Patent
Calabrese et al.

(10) Patent No.: US 10,717,756 B2
(45) Date of Patent: *Jul. 21, 2020

(54) SPINOSYN DERIVATIVES AS INSECTICIDES

(71) Applicant: AGRIMETIS, LLC, Lutherville, MD (US)

(72) Inventors: Andrew Calabrese, Lutherville, MD (US); Brian Michael Green, Lutherville, MD (US); David R. Spring, Cambridge (GB); Jerome Yves Cassayre, Hesingue (FR); Pasquale N. Confalone, Wilmington, DE (US)

(73) Assignee: AgriMetis, LLC, Lutherville, MD (US)

( * ) Notice: Subject to any disclaimer, the term of this patent is extended or adjusted under 35 U.S.C. 154(b) by 6 days.

This patent is subject to a terminal disclaimer.

(21) Appl. No.: 15/757,317

(22) PCT Filed: Sep. 1, 2016

(86) PCT No.: PCT/US2016/049879
§ 371 (c)(1),
(2) Date: Mar. 2, 2018

(87) PCT Pub. No.: WO2017/040769
PCT Pub. Date: Mar. 9, 2017

(65) Prior Publication Data
US 2019/0071464 A1 Mar. 7, 2019

Related U.S. Application Data

(60) Provisional application No. 62/214,083, filed on Sep. 3, 2015, provisional application No. 62/290,676, filed on Feb. 3, 2016, provisional application No. 62/303,015, filed on Mar. 3, 2016, provisional application No. 62/303,078, filed on Mar. 3, 2016, provisional application No. 62/380,664, filed on Aug. 29, 2016.

(51) Int. Cl.
*C07H 17/08* (2006.01)
*C07H 17/00* (2006.01)
*C07H 1/00* (2006.01)
*A01N 45/02* (2006.01)
*C07D 313/00* (2006.01)

(52) U.S. Cl.
CPC ............ *C07H 17/08* (2013.01); *A01N 45/02* (2013.01); *C07D 313/00* (2013.01); *C07H 1/00* (2013.01); *C07H 17/00* (2013.01)

(58) Field of Classification Search
None
See application file for complete search history.

(56) References Cited

U.S. PATENT DOCUMENTS

| 6,001,981 A | 12/1999 | DeAmicis et al. |
| 6,063,771 A | 5/2000 | Snyder |
| 6,342,482 B1 | 1/2002 | Snyder |
| 6,919,464 B1 | 7/2005 | Crouse et al. |
| 6,927,210 B1 | 8/2005 | Thompson et al. |
| 7,015,001 B2 | 3/2006 | Baltz |
| 7,709,447 B2 | 5/2010 | Hacket et al. |
| 8,470,381 B2 | 6/2013 | Kritikou |
| 8,536,142 B2 | 9/2013 | Hacket et al. |
| 8,697,661 B2 | 4/2014 | Kritikou |
| 9,253,979 B2 | 2/2016 | Sparks et al. |
| 9,873,639 B1 * | 1/2018 | Doccola ............ C05G 3/0047 |
| 9,895,388 B1 * | 2/2018 | Mettert ............ A61K 31/7048 |
| 2012/0172322 A1 | 7/2012 | Sparks et al. |
| 2012/0252746 A1 | 10/2012 | Snyder |
| 2013/0172215 A1 | 7/2013 | Palaniappan et al. |
| 2013/0210755 A1 | 8/2013 | Marr et al. |
| 2015/0111743 A1 | 4/2015 | Gomez et al. |

FOREIGN PATENT DOCUMENTS

| CN | 102977166 A | 3/2013 |
| EP | 1207757 B1 | 2/2005 |
| EP | 2654757 A1 | 10/2013 |
| WO | 97/00265 | 1/1997 |
| WO | 02/077004 A1 | 10/2002 |
| WO | 03070908 | 8/2003 |
| WO | 2017/040763 A1 | 3/2017 |
| WO | 2017/040769 A1 | 3/2017 |
| WO | 2017/040878 A1 | 3/2017 |
| WO | 2017/040882 A1 | 3/2017 |

OTHER PUBLICATIONS

Graupner et al., Spinosyn G: Proof of Structure by Semisythesis, J. Org. Chem. 2005, 70, 2154-2160 (Year: 2005).*
Kirst, "The Spinosyn Family of Insecticides: Realizing the Potential of Natural Products Research", The Journal of Antibiotics, vol. 63, No. 3, Feb. 12, 2010, pp. 101-111.
Mergott et al., "Total synthesis of (−) spinosyn A", Proceedings of The National Academy of Sciences, vol. 101, No. 33, http://www.pnas.org/content/101/33/11955.full.pdf, Aug. 17, 2004, pp. 11955-11959.
Methot et al., "Applications of tricoordinated phosphorus compounds in organocatalysis", Database CAPLUS [Online] Chemical Abstracts Service, Columbus,XP002763249, retrieved from STN Database accession No. 2009:453327 abstract, Science of Synthesis, vol. 42, 2009, pp. 469-501.
PCT/US2016/049870, "International Preliminary Report on Patentability", dated Mar. 15, 2018, 7 pages.
PCT/US2016/049870, "International Search Report and Written Opinion", dated Nov. 3, 2016, 11 pages.

(Continued)

Primary Examiner — Alton N Pryor
(74) Attorney, Agent, or Firm — Kilpatrick Townsend & Stockton LLP

(57) ABSTRACT

Compositions and methods for the production of derivatives of spinosyns are provided. The method produces spinosyn derivatives that exhibit activity towards insects, arachnids, and/or nematodes and are useful in the agricultural and animal health markets.

22 Claims, No Drawings

(56) References Cited

OTHER PUBLICATIONS

PCT/US2016/049879, "International Preliminary Report on Patentability", dated Mar. 15, 2018, 11 pages.
PCT/US2016/049879, "International Search Report and Written Opinion", dated Jan. 2, 2017, 17 pages.
PCT/US2016/050028, "International Preliminary Report on Patentability", dated Mar. 15, 2018, 7 pages.
PCT/US2016/050028, "International Search Report and Written Opinion", dated Oct. 25, 2016, 12 pages.
PCT/US2016/050034, "International Preliminary Report on Patentability", dated Mar. 15, 2018, 7 pages.
PCT/US2016/050034, "International Search Report and Written Opinion", dated Oct. 28, 2016, 10 pages.
"Derivative", Merriam-Webster Online Dictionary, Available online at: https://www.merriam-webster.com/dictionary/derivative, Mar. 29, 2019, pp. 1-9.
U.S. Appl. No. 15/757,204, "Non-Final Office Action", dated Mar. 8, 2019, 9 pages.
EP16766747.6, "Office Action", dated Feb. 28, 2019, 5 pages.
EP16767084.3, "Office Action", dated Feb. 28, 2019, 5 pages.
EP16767424.1, "Office Action", dated Mar. 1, 2019, 5 pages.
PCT/US2016/049879, "Invitation to Pay Additional Fees and Where Applicable Protest Fee", dated Oct. 31, 2016, 6 pages.
U.S. Appl. No. 15/757,307, "Non-Final Office Action", dated Nov. 20, 2019, 22 pages.
AU2016315860, "First Examination Report", dated Oct. 23, 2019, 3 pages.
AU2016317848, "First Examination Report", dated Oct. 25, 2019, 3 pages.

* cited by examiner

SPINOSYN DERIVATIVES AS INSECTICIDES

CROSS-REFERENCE TO RELATED APPLICATIONS

This application is the U.S. national phase of International Application No. PCT/US2016/049879 filed on Sep. 1, 2016, and published on Mar. 9, 2017 as International Publication No. WO 2017/040769 A1, which application claims priority to and the benefit of U.S. Provisional Patent Application No. 62/214,083 filed Sep. 3, 2015; U.S. Provisional Patent Application No. 62/290,676 filed Feb. 3, 2016; U.S. Provisional Patent Application No. 62/303,015 filed Mar. 3, 2016; U.S. Provisional Patent Application No. 62/303,078 filed Mar. 3, 2016; and U.S. Provisional Patent Application No. 62/380,664 filed Aug. 29, 2016, the contents of all of which are incorporated herein by reference in their entireties.

FIELD

Described herein are spinosyn derivatives for use as agrichemicals and in animal health.

BACKGROUND

Spinosyn refers to a large family of compounds produced from the fermentation of soil actinomycetes species of *Saccharopolyspora*. The individual components from the fermentation broth were subsequently given the generic name of spinosyn to connect these compounds with their producing microorganism, *Saccharopolyspora spinosa*. Members of the spinosyn family share a core structure having a polyketide-derived tetracyclic macrolide appended with two saccharides. There are many naturally occurring variants, which exhibit potent insecticidal activities against many commercially significant species that cause extensive damage to crops and other plants. Some of these variants also exhibit activity against important external parasites of livestock, companion animals and humans.

Fermentation of *S. spinosa* produces a natural mixture containing spinosyn A as the major component and spinosyn D as the minor component and named spinosad. The structure of spinosyn A was determined by NMR, MS, and X-ray analyses and comprises a tetracyclic polyketide aglycone to which is attached a neutral saccharide substituent (2,3,4-tri-O-methyl-α-L-rhamnosyl) on the C-9 hydroxyl group and an aminosugar moiety (β-D-forosaminyl) on the C-17 hydroxyl group. This spinosyn tetracyclic ring system composed of a cis-anti-trans-5,6,5-tricyclic moiety fused to a 12-membered lactone is a unique ring system.

The second most abundant fermentation component is spinosyn D, which is 6-methyl-spinosyn A. Spinosyn D is likely formed by incorporation of propionate instead of acetate at the appropriate stage during polyketide assembly.

Numerous structurally related compounds from various spinosyn fermentations have now been isolated and identified. Their structures fall into several general categories of single-type changes in the aglycone or saccharides of spinosyn A.

Spinosyns have a unique mechanism of action (MOA) involving disruption of nicotinic acetylcholine receptors. When compared with many other insecticides, spinosyns generally show greater selectivity toward target insects and lesser activity against many beneficial predators. Structure-activity relationships (SARs) have been extensively studied, leading to development of a semisynthetic second-generation derivative, spinetoram (Kirst (2010) *J. Antibiotics* 63:101-111).

Studies to date have concluded that the mechanism(s) by which spinosyn exerts its insecticidal action is different from those of any other known agents, and thus cross-resistance between spinosyn and other agents was initially absent or low. However, as well known for other insecticides, continued usage is likely to exert selective pressures on insects and to eventually provoke resistance.

The unique and highly complex core structure of the spinosyns has provided challenging opportunities for synthesis. Additionally, with the increase of insect resistance, new spinosyn compounds and methods for their synthesis are needed.

SUMMARY

Spinosyn compounds and methods for making and using spinosyn compounds, including tetracyclic and pentacyclic spinosyn compounds, are provided. The spinosyn compounds described herein exhibit activity towards insects, arachnids, and nematodes and/or are useful in the agricultural and animal health markets.

A spinosyn compound as described herein includes a compound of the following formula:

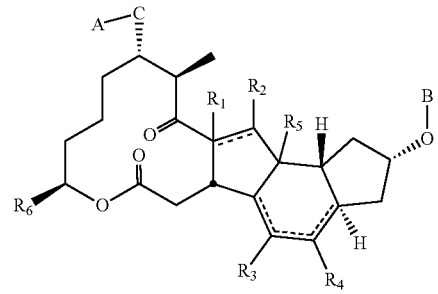

or a salt thereof, wherein ≔ is a single bond or a double bond; A is hydrogen or is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl; B is selected from the group consisting of substituted or unsubstituted cycloalkyl, substituted or unsubstituted heterocycloalkyl, substituted or unsubstituted aryl, and substituted or unsubstituted heteroaryl; C is O or NH; $R^1$ is absent or is selected from hydrogen, hydroxyl, carbonyl, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl; $R^2$, $R^3$, and $R^4$ are each independently selected from hydrogen, hydroxyl, carbonyl, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl; and $R^5$ is hydrogen, halogen, hydroxyl, substituted or unsubstituted amino, substituted or unsubstituted thio, or substituted or unsubstituted alkoxy; and $R^6$ is substituted or unsubstituted alkyl or substituted or unsubstituted aryl.

Optionally, $R^1$ and $R^2$ or $R^3$ and $R^4$ combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, or substituted or unsubstituted heteroaryl.

Optionally, A comprises hydrogen, forosamine, or a forosamine derivative. In certain embodiments where A is a forosamine derivative, one or both of the methyl groups on the forosamine nitrogen group is substituted with substituted or unsubstituted alkyl, substituted or unsubstituted cycloalkyl, substituted or unsubstituted heterocycloalkyl, substituted or unsubstituted alkenyl, substituted or unsubstituted aryl, substituted or unsubstituted heteroaryl, substituted or unsubstituted aldehyde, substituted or unsubstituted benzyl, or substituted or unsubstituted benzoyl. In certain embodiments, the substitution is a group selected from hydrogen, tosyl, benzyl, propyl, 5-methylfuran-2-yl, chlorofluorobenzyl, ethyl, cyclopropyl, octonoyl, (2-methyl)propanoyl, benzoyl, propenoyl, or a —$S(CH_3)O_2$ group. In some examples where A is a forosamine derivative, the forosamine ring is substituted with amino, methylamino, dimethyl amino, benzyl (methyl)amino, methyl(prop-2-en-1-yl) amino, N-methylpropanamide, N-2-dimethylpropanamide, N-methyl-2-propylpentanamide, 2-butyl-N-methyloctanamide, N-methyloctanamide, N-methyldodecanamide, N-methylbenzamide,N-methylbiotinamide, N-methyl-3-oxo-3H-spiro[2-benzofuran-1,9'-xanthene]-5-carboxamide, prop-2-ene-1-yl or methyl(propyl)amino. In some examples, the forosamine derivative is a [(2R,5S,6R)-6-methyl-5-(methylamino)oxan-2-yl]oxy group.

Optionally, B is a substituted or unsubstituted saccharide. Optionally, B comprises rhamnose or a rhamnose derivative, such as a [(2R,5S)-3,4,5-trimethoxy-6-methyloxan-2-yl]oxy group (3,4,5-trimethoxyrhamnose) or a [(2R,5S)-4-ethoxy-3,5-dimethoxy-6-methyloxan-2-yl]oxy group (4-ethoxy-3,5-dimethoxyrhamnose).

Optionally, C comprises oxygen.

Optionally, $R^1$ is absent or is hydrogen or $R^1$ forms a ring with $R^2$.

Optionally, $R^2$ is hydrogen, substituted or unsubstituted alkyl, substituted or unsubstituted alkenyl, substituted or unsubstituted cycloalkyl, or substituted or unsubstituted aryl. Optionally, $R^2$ is phenyl, methoxyphenyl, fluorophenyl, chlorophenyl, ethyl, or ethenyl. Optionally, $R^2$ forms a ring with $R^1$.

Optionally, $R^3$ is hydroxyl, halogen, carbonyl, substituted or unsubstituted alkoxy, substituted or unsubstituted alkyl, substituted or unsubstituted alkenyl, or substituted or unsubstituted aryl, substituted or unsubstituted heteroaryl, substituted or unsubstituted amino, azido. Optionally, $R^3$ is fluoro, chloro, methoxy, ethoxy, methyl, ethyl, ethenyl, phenyl, methoxyphenyl, fluorophenyl, chlorophenyl. Optionally, $R^3$ forms a ring with $R^4$, Optionally, $R^4$ is hydroxyl, halogen, carbonyl, substituted or unsubstituted alkoxy, substituted or unsubstituted alkyl, substituted or unsubstituted alkenyl, or unsubstituted aryl, substituted or unsubstituted heteroaryl, substituted or unsubstituted amino, azido. Optionally, $R^4$ is fluoro, chloro, methoxy, ethoxy, methyl, ethyl, ethenyl, phenyl, methoxyphenyl, fluorophenyl, chlorophenyl. Optionally, $R^4$ forms a ring with $R^3$.

Optionally, $R^5$ is hydrogen, $C_1$-$C_6$ alkyl, $C_1$-$C_6$ alkenyl, or $C_1$-$C_6$ aryl.

Optionally, $R^6$ is $C_1$-$C_6$ alkyl, $C_1$-$C_6$ alkenyl, or $C_1$-$C_6$ aryl. Optionally $R^6$ is ethyl.

In some examples, A is forosamine, B is 3,4,5-trimethoxyrhamnose, C is O, $R^1$ is absent, $R^2$ and $R^5$ are hydrogen, $R^3$ is hydrogen, $R^4$ is an unsubstituted or substituted phenyl group, and $R^6$ is ethyl. Optionally, the spinosyn compound is (2R,3aR,5bS,9S,13S,14R,16aR,16bR)-13-{[(2R,5S,6R)-5-(dimethylamino)-6-methyloxan-2-yl]oxy-9-ethyl-14-methyl-4-phenyl-2-[(2R,3R,4R,5S,6S)-3,4,5-trimethoxy-6-methyloxan-2-yl]oxy}-1H,2H,3H,3 aH,4H,5bH,6H,7H,9H,10H,11H,12H,13H,14H,15H,16aH,16bH-as-indaceno[3,2-d]oxacyclododecane-7,15-dione; (2R,3aR,5bS,9S,13S,14R,16aR,16bR)-4-(4-chlorophenyl)-13-{[(2R,5S,6R)-5-(dimethylamino)-6-methyloxan-2-yl]oxy}-9-ethyl-14-methyl-2-{[(2R,3S,6S)-3,4,5-trimethoxy-6-methyloxan-2-yl]oxy}-1H,2H,3H,3aH,4H,5bH,6H,7H,9H,10H,11H,12H,13H,14H,15H,16aH,16bH-as-indaceno[3,2-d]oxacyclododecane-7,15-dione; (2S,3aR,5bS,9S,13S,14R,16aR,16bR)-4-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5bH,6H,7H,9H,10H,11H,12H,13H,14H,15H,16aH,16bH-as-indaceno[3,2-d]oxacyclododecane-7,15-dione; (2R,3aR,5bS,9S,13S,14R,16aR,16bR)-13-{[(2R,5S,6R)-5-(dimethylamino)-6-methyloxan-2-yl]oxy}-9-ethyl-4-(3-fluorophenyl)-14-methyl-2-{[(2R,3R,4R,5S,6S)-3,4,5-trimethoxy-6-methyloxan-2-yl]oxy}-1H,2H,3H,3aH,4H,5bH,6H,7H,9H,10H,11H,12H,13H,14H,15H,16aH,16bH-as-indaceno[3,2-d]oxacyclododecane-7,15-dione; (2R,3aR,5bS,9S,13S,14R,16aR,16bR)-13-{[(2R,5S,6R)-5-(dimethylamino)-6-methyloxan-2-yl]oxy}-9-ethyl-4-(4-methoxyphenyl)-14-methyl-2-{[(2R,3R,4R,5S,6S)-3,4,5-trimethoxy-6-methyloxan-2-yl]oxy}-1H,2H,3H,3aH,4H,5bH,6H,7H,9H,10H,11H,12H,13H,14H,15H,16aH,16bH-as-indaceno[3,2-d]oxacyclododecane-7,15-dione; or (2R,3aR,5bS,9S,13S,14R,16aR,16bR)-13-{[(2R,5S,6R)-5-(dimethylamino)-6-methyloxan-2-yl]oxy}-9-ethyl-4-(4-fluorophenyl)-14-methyl-2-{[(2R,3R,4R,5S,6S)-3,4,5-trimethoxy-6-methyloxan-2-yl]oxy}-1H,2H,3H,3aH,4H,5bH,6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^6$ is ethyl, $R^1$ is absent, $R^2$ and $R^5$ are hydrogen, $R^4$ is hydrogen, and $R^3$ is an unsubstituted or substituted phenyl group. Optionally, the spinosyn compound is (2S,5aR,5bS,9S,13S,14R,16aS,16bS)-13-{[(2R,5S,6R)-5-(dimethylamino)-6-methyloxan-2-yl]oxy}-9-ethyl-14-methyl-5-phenyl-2-{[(2R,3R,4R,5S,6S)-3,4,5-trimethoxy-6-methyloxan-2-yl]oxy}-1H,2H,3H,5H,5aH,5bH,6H,7H,9H,10H,11H,12H,13H,14H,15H,16aH,16bH-as-indaceno[3,2-d]oxacyclododecane-7,15-dione; (2S,5bS,9S,13S,14R,16aS,16bS)-5-(4-chorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,5H,5aH,5bH,6H,7H,9H,10H,11H,12H,13H,14H,15H,16aH,16bH-as-indaceno[3,2-d]oxacyclododecane-7,15-dione; (2S,5aR,5bS,9S,13S,14R,16aS,16bS)-13-{[(2R,5S,6R)-5-(dimethylamino)-6-methyloxan-2-yl]oxy}-9-ethyl-5-(4-methoxyphenyl)-14-methyl-2-{[(2R,3R,4R,5S,6S)-3,4,5-trimethoxy-6-methyloxan-2-yl]oxy}-1H,2H,3H,5H,5aH,5bH,6H,7H,9H,10H,11H,12H,13H,14H,15H,16aH,16bH-as-indaceno[3,2-d]oxacyclododecane-7,15-dione; (2S,5aR,5bS,9S,13S,14R,16aS,16bS)-13-{[(2R,5S,6R)-5-(dimethylamino)-6- methyloxan-2-yl]oxy}-9-ethyl-5-(4-fluorophenyl)-14-methyl-2-{[(2R,3R,4R,5S,6S)-3,4,5-trimethoxy-6-methyloxan-2-yl]oxy}-d]oxacyclododecane-7,15-dione; (2S,5aR,5bS,9S,13S,14R,16aS,16bS)-13-{[(2R,5S,6R)-5-(dimethylamino)-6-methyloxan-2-yl]oxy}-9-ethyl-5-(3-fluorophenyl)-14-methyl-2-{[(2R,3R,4R,5S,6S)-3,4,5-trimethoxy-6-methyloxan-2-yl]oxy}-1H,2H,3H,5H,5aH,5bH,6H,7H,9H,10H,11H,12H,13H,14H,15H,16aH,16bH-as-indaceno[3,2-d]oxacyclododecane-7,15-dione; or (2R,3aR,5bS,9S,13S,14R,16aS,16bR)-5-(4-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^6$ is ethyl, $R^1$ is absent, $R^2$ and $R^5$ are hydrogen, and $R^3$ and $R^4$ form a substituted cyclopentenone. Optionally, the spinosyn compound is 1S,2R,8R,10S,12R,13S,17R,18S,22S)-18-{[(2R,5S,6R)-5-(dimethylamino)-6-methyloxan-2-yl]oxy}-22-ethyl-5-(4-fluorophenyl)-17-methyl-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione; (1S,2R,8R,10S,12R,13S,17R,18S,22S)-18-{[(2R,5S,6R)-5-(dimethylamino)-6-methyloxan-2-yl]oxy}-22-ethyl-17-methyl-5-(pyrimidin-5-yl)-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione; 4-[(1S,2R,8R,10S,12R,13S,17R,18S,22S)-18-{[(2R,5S,6R)-5-(dimethylamino)-6-methyloxan-2-yl]oxy}-22-ethyl-17-methyl-4,16,24-trioxo-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-dien-5-yl]benzonitrile; (1S,2R,8R,10S,12R,13S,17R,18S,22S)-18-{[(2R,5S,6R)-5-(dimethylamino)-6-methyloxan-2-yl]oxy}-22-ethyl-17-methyl-5-phenyl-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione; or (1S,2R,8R,10S,12R,13S,17R,18S,22S)-18-{[(2R,5S,6R)-5-(dimethylamino)-6-methyloxan-2-yl]oxy}-22-ethyl-17-methyl-5-phenyl-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosane-4,16,24-trione.

In some examples, A is forosamine, B is 3,4,5-trimethoxyrhamnose, C is O, $R^6$ is ethyl, $R^1$ is absent, $R^2$ and $R^5$ are hydrogen, and $R^3$ and $R^4$ form an unsubstituted or substituted, saturated or unsaturated δ-valerolactone ring. Optionally, the spinosyn compound is (1R,2S,6S,10S,11R,15R,16R,18S,20R)-10-{[(2R,5S,6R)-5-(dimethylamino)-6-methyloxan-2-yl]oxy}-6-ethyl-23-(4-fluorophenyl)-11-methyl-18-{[(2R,3R,4R,5S,6S)-3,4,5-trimethoxy-6-methyloxan-2-yl]oxy}-5,25-dioxapentacyclo[13.11.0.0$^{2,13}$.0$^{16,20}$.0$^{21,26}$]hexacosa-13,22-diene-4,12,24-trione; 4-[(1R,2S,6S,10S,11R,15R,16R,18S,20R)-10-{[(2R,5S,6R)-5-(dimethylamino)-6-methyloxan-2-yl]oxy}-6-ethyl-11-methyl-4,12,24-trioxo-18-{[(2R,3R,4R,5S,6S)-3,4,5-trimethoxy-6-methyloxan-2-yl]oxy}-5,25-dioxapentacyclo[13.11.0.0$^{2,13}$.0$^{16,20}$.0$^{21,26}$]hexacosa-13,22-dien-23-yl]benzonitrile; (1R,2S,6S,10S,11R,15R,16R,18S,20R)-10-{[(2R,5S,6R)-5-(dimethylamino)-6-methyloxan-2-yl]oxy}-6-ethyl-11-methyl-23-(pyrimidin-5-yl)-18-{[(2R,3R,4R,5S,6S)-3,4,5-trimethoxy-6-methyloxan-2-yl]oxy}-5,25-dioxapentacyclo[13.11.0.0$^{2,13}$.0$^{16,20}$.0$^{21,26}$]hexacosa-13,22-diene-4,12,24-trione; (1R,2S,6S,10S,11R,15R,16R,18S,20R)-10-{[(2R,5S,6R)-5-(dimethylamino)-6-methyloxan-2-yl]oxy}-6-ethyl-11-methyl-23-(thiophen-2-yl)-18-{[(2R,3R,4R,5S,6S)-3,4,5-trimethoxy-6-methyloxan-2-yl]oxy}-5,25-dioxapentacyclo[13.11.0.0$^{2,13}$.0$^{16,20}$.0$^{21,26}$]hexacosa-13,22-diene-4,12,24-trione; (1R,2S,6S,10S,11R,15R,16R,18S,20R)-23-(3-chlorophenyl)-10-{[(2R,5S,6R)-5-(dimethylamino)-6-methyloxan-2-yl]oxy}-6-ethyl-11-methyl-18-{[(2R,3R,4R,5S,6S)-3,4,5-trimethoxy-6-methyloxan-2-yl]oxy}-5,25-dioxapentacyclo[13.11.0.0$^{2,13}$.0$^{16,20}$.0$^{21,26}$]hexacosa-13,22-diene-4,12,24-trione; or (1R,2S,6S,10S,11R,15R,16R,18S,20R)-10-{[(2R,5S,6R)-5-(dimethylamino)-6-methyloxan-2-yl]oxy}-6-ethyl-11-methyl-23-(3-methylphenyl)-18-{[(2R,3R,4R,5S,6S)-3,4,5-trimethoxy-6-methyloxan-2-yl]oxy}-5,25-dioxapentacyclo[13.11.0.0$^{2,13}$.0$^{16,20}$.0$^{21,26}$]hexacosa-13,22-diene-4,12,24-trione.

In some examples, A comprises forosamine or a forosamine derivative, B comprises rhamnose or a rhamnose derivative, C comprises oxygen, $R^1$ is absent $R^2$ and $R^5$ comprise hydrogen, at least one of $R^3$ and $R^4$ is a substituted triazole and the other is selected from hydrogen, halogen, or hydroxyl. Optionally, the spinosyn compound is (2S,3aR,5aR,5bS,9S,13S,14R,16aR,16bS)-4-[4-(2-chlorophenyl)-1H-1,2,3-triazol-1-yl]-13-{[(2R,5S,6R)-5-(dimethylamino)-6-methyloxan-2-yl]oxy}-9-ethyl-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,4R,5aR,5bS,9S,13S,14R,16aR,16bS)-13-{[(2R,5S,6R)-5-(dimethylamino)-6-methyloxan-2-yl]oxy}-9-ethyl-4-[4-(4-fluorophenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,4R,5aR,5bS,9S,13S,14R,16aR,16bS)-4-(4-tert-butyl-1H-1,2,3-triazol-1-yl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,4R,5aR,5bS,9S,13S,14R,16aR,16bS)-13-{[(2R,5S,6R)-5-(dimethylamino)-6-methyloxan-2-yl]oxy}-9-ethyl-14-methyl-4-[4-(thiophen-2-yl)-1H-1,2,3-triazol-1-yl]-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,4R,5aR,5bS,9S,13S,14R,16aR,16bS)-4-[4-(2-chlorophenyl)-1H-1,2,3-triazol-1-yl]-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,5aR,5bS,9S,13S,14R,16aR,16bS)-13-{[(2R,5S,6R)-5-(dimethylamino)-6-methyloxan-2-yl]oxy}-9-ethyl-5-fluoro-4-[4-(4-fluorophenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,4R,5aR,5bS,9S,13S,14R,16aR,16bS)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-4-[4-(trimethylsilyl)-1H-1,2,3-triazol-1-yl]-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione;

(2S,3aR,4R,5aR,5bS,9S,13S,14R,16aR,16bS)-13-{[(2R,5S,6R)-5-(dimethylamino)-6-methyloxan-2-yl]oxy}-9-ethyl-14-methyl-4-(1H-1,2,3-triazol-1-yl)-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; {1-[(2S,3aR,4R,5aR,5bS,9S,13S,14R,16aR,16bS)-13-{[(2R,5S,6R)-5-(dimethylamino)-6-methyloxan-2-yl]oxy}-9-ethyl-14-methyl-7,15-dioxo-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecan-4-yl]-1H-1,2,3-triazol-4-yl}methyl acetate; (2S,3aR,5aR,5bS,9S,13S,14R,16aR,16bS)-4-[4-(4-aminophenyl)-1H-1,2,3-triazol-1-yl]-13-{[(2R,5S,6R)-5-(dimethylamino)-6-methyloxan-2-yl]oxy}-9-ethyl-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,5aR,5bS,9S,13S,14R,16aR,16bS)-13-{[(2R,5S,6R)-5-(dimethylamino)-6-methyloxan-2-yl]oxy}-9-ethyl-5-hydroxy-14-methyl-4-[4-(3-methylphenyl)-1H-1,2,3-triazol-1-yl]-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,5aR,5bS,9S,13S,14R,16aR,16bS)-13-{[(2R,5S,6R)-5-(dimethylamino)-6-methyloxan-2-yl]oxy}-9-ethyl-5-fluoro-14-methyl-4-[4-(3-methylphenyl)-1H-1,2,3-triazol-1-yl]-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,5aR,5bS,9S,13S,14R,16aR,16bS)-13-{[(2R,5S,6R)-5-(dimethylamino)-6-methyloxan-2-yl]oxy}-9-ethyl-5-hydroxy-14-methyl-4-(4-phenyl-1H-1,2,3-triazol-1-yl)-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,5aR,5bS,9S,13S,14R,16aR,16bS)-13-{[(2R,5S,6R)-5-(dimethylamino)-6-methyloxan-2-yl]oxy}-9-ethyl-5-fluoro-14-methyl-4-(4-phenyl-1H-1,2,3-triazol-1-yl)-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,5aR,5bS,9S,13S,14R,16aR,16bS)-4-[4-(3-chlorophenyl)-1H-1,2,3-triazol-1-yl]-13-{[(2R,5S,6R)-5-(dimethylamino)-6-methyloxan-2-yl]oxy}-9-ethyl-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,4S,5S,5aR,5bS,9S,13S,14R,16aR,16bS)-4-[4-(3-chlorophenyl)-1H-1,2,3-triazol-1-yl]-13-{[(2R,5S,6R)-5-(dimethylamino)-6-methyloxan-2-yl]oxy}-9-ethyl-5-fluoro-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2S,3aR,4S,5S,5aR,5bS,9S,13S,14R,16aR,16bS)-9-ethyl-5-fluoro-4-[4-(4-methoxyphenyl)-1H-1,2,3-triazol-1-yl]-14-methyl-13-{[(2R,5S,6R)-6-methyl-5-(methylamino)oxan-2-yl]oxy}-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2R,3aR,5R,5aR,5bS,9S,13S,14R,16aR,16bR)-5-(4-tert-butyl-1H-1,2,3-triazol-1-yl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; (2R,3aR,5R,5aR,5bS,9S,13S,14R,16aR,16bR)-13-{[(2R,5S,6R)-5-(dimethylamino)-6-methyloxan-2-yl]oxy}-9-ethyl-5-[4-(4-fluorophenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione; or (2R,3aR,5R,5aR,5bS,9S,13S,14R,16aR,16bR)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-5-[4-(trimethylsilyl)-1H-1,2,3-triazol-1-yl]-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione.

In some examples, A is forosamine, B is 3,4,5-trimethoxyrhamnose, C is O, $R^6$ is ethyl, $R^1$, $R^3$, $R^4$, and $R^5$ are hydrogen, and $R^2$ is akyl, alkenyl, or unsubstituted or substituted phenyl. Optionally, the spinosyn compound is (2R,3aS,5aS,5bS,9S,13S,14R,16aS,16bR)-13-{[(2R,5S,6R)-5-(dimethylamino)-6-methyloxan-2-yl]oxy}-9-ethyl-14-methyl-16-phenyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,15aH,16H,16aH,16bH-as-indaceno[3,2-d]oxacyclododecane-7,15-dione; (2R,5bS,9S,13S,14R,16aS,16bR)-13-{[(2R,5S,6R)-5-(dimethylamino)-6-methyloxan-2-yl]oxy}-9-ethyl-14-methyl-16-phenyl-2-{[(2R,3R,4R,5S,6S)-3,4,5-trimethoxy-6-methyloxan-2-yl]oxy}-icosahydro-1H-as-indaceno[3,2-d]oxacyclododecane-7,15-dione; (2R,3aS,5aS,5bS,9S,13S,14R,16aS,16bR)-13-{[(2R,5S,6R)-5-(dimethylamino)-6-methyloxan-2-yl]oxy}-9-ethyl-16-(3-methoxy phenyl)-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,15aH,16H,16aH,16bH-as-indaceno[3,2-d]oxacyclododecane-7,15-dione; (2R,5bS,9S,13S,14R,16aS,16bR)-13-{[(2R,5S,6R)-5-(dimethylamino)-6-methyloxan-2-yl]oxy}-9-ethyl-16-(3-methoxyphenyl)-14-methyl-2-{[(2R,3R,4R,5S,6S)-3,4,5-trimethoxy-6-methyloxan-2-yl]oxy}-icosahydro-1H-as-indaceno[3,2-d]oxacyclododecane-7,15-dione; (2R,3aS,5aS,5bS,9S,13S,14R,16aS,16bR)-13-{[(2R,5S,6R)-5-(dimethylamino)-6-methyloxan-2-yl]oxy}-9-ethyl-16-(4-fluorophenyl)-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,15aH,16H,16aH,16bH-as-indaceno[3,2-d]oxacyclododecane-7,15-dione; (2R,5bS,9S,13S,14R,16aS,16bR)-13-{[(2R,5S,6R)-5-(dimethylamino)-6-methyloxan-2-yl]oxy}-9-ethyl-16-(4-fluorophenyl)-14-methyl-2-{[(2R,3R,4R,5S,6S)-3,4,5-trimethoxy-6-methyloxan-2-yl]oxy}-icosahydro-1H-as-indaceno[3,2-d]oxacyclododecane-7,15-dione; (2R,3aS,5aS,5bS,9S,13S,14R,16aS,16bR)-16-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,15aH,16H,16aH,16bH-as-indaceno[3,2-d]oxacyclododecane-7,15-dione; (2R,5bS,9S,13S,14R,16aS,16bR)-16-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-icosahydro-1H-as-indaceno[3,2-d]oxacyclododecane-7,15-dione; (2R,3aS,5aS,5bS,9S,13S, 14R,16aS,16bR)-13-{[(2R,5S,6R)-5-(dimethylamino)-6-methyloxan-2-yl]oxy}-16-ethenyl-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,15aH,16H,16aH,16bH-as-indaceno[3,2-d]oxacyclododecane-7,15-dione; or (2R,3aR,5aS,5bS,9S,13S,14R,16aS,16bR)-13-{[(2R,5S,6R)-5-(dimethylamino)-6-methyloxan-2-yl]oxy}-9,16-diethyl-14-methyl-2-{[(2R,3R,4R,5S,6S)-3,4,5-trimethoxy-6-methyloxan-2-yl]oxy}-icosahydro-1H-as-indaceno[3,2-d]oxacyclododecane-7,15-dione.

In some examples, A is a forosamine derivative, B is 3,4,5-trimethoxyrhamnose, C is O, $R^6$ is ethyl, $R^1$ is absent, $R^2$, and $R^5$ are hydrogen, and $R^3$, and $R^4$ are hydrogen or methyl. Optionally, the spinosyn compound is (2R,3aS,5aR,5bS,9S,13S,14R,16aS,16bR)-9-ethyl-14-methyl-13-{[(2R,5S,6R)-6-methyl-5[methyl(propyl)amino]oxan-2-yl]oxy}-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione; (2R,3aS,5aR,5bS,9S,13S,14R,16aS,16bR)-13-{[(2R,5S,6R)-5-[benzyl(methy)amino]-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione; (2R,3aS,5aR,5bS,9S,13S,14R,16aS,16bR)-9-ethyl-14-methyl-13-{[(2R,5S,6R)-6-methyl-5-[methyl(prop-2-en-1-yl)amino]oxan-2-yl]oxy}-2-{[(2R,3R,4R,5S,6S)-3,4,5-trimethoxy-6-methyloxan-2-yl]oxy}-2-1H,2H,3H,3aH,5aH,5bH,6H,7H,9H,10H,11H,12H,13H,14H,15H,16aH,16bH-as-indaceno[3,2-d]oxacyclododecane-7,15-dione; N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N,2-dimethylpropanamide; N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methyl-2-propylpentanamide; N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-2-butyl-N-methyloctanamide; N-[2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH as-indaceno[3,2-d]oxacyclododecan-13-yl]oxy}-2-methyloxan-3-yl]-N-methyloctanamide; N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methyldodecanamide; N-[(2R,3 S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methylbenzamide; 5-[(3aS,4S,6aR)-2-oxo-hexahydro-1H-thieno[3,4-d]imidazol-4-yl]-N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methylpentanamide; 5-[(3aS,4S,6aR)-2-oxo-hexahydro-1H-thieno[3,4-d]imidazol-4-yl]-N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methylpentanamide; N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-3',6'-dihydroxy-N-methyl-3-oxo-3H-spiro[2-benzofuran-1,9'-xanthene]-5-carboxamide; prop-2-en-1-yl N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methylcarbamate; (2S,3aR,5aS,5bS,9S,13S,14R,16aS,16bS)-9-ethyl-4,14-dimethyl-13-{[(2R,5S,6R)-6-methyl-5-[methyl(propyl)amino]oxan-2-yl]oxy}-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione; (2S,3aR,5 aS,5bS,9S,13S,14R,16aS,16bS)-13-{[(2R,5S,6R)-5-[benzyl(methyl)amino]-6-methyloxan-2-yl]oxy}-9-ethyl-4,14-dimethyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione; (2S,3aR,5aS,5bS,9S,13S,14R,16aS,16bS)-9-ethyl-4,14-dimethyl-13-{[(2R,5S,6R)-6-methyl-5-[methyl(prop-2-en-1-yl)amino]oxan-2-yl]oxy}-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione; N-[(2R,3S,6R)-6-{[(2S,3aR,5aS,5bS,9S,13S,14R,16aS,16bS)-9-ethyl-4,14-dimethyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methylpropanamide; N-[2R,3S,6R)-6-{[(2S,3aR,5aS,5bS,9S,13S,14R,16aS,16bS)-9-ethyl-4,14-dimethyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N,2-dimethylpropanamide; N-[(2R,3S,6R)-6-{[(2S,3aR,5aS,5bS,9S,13S,14R,16aS,16bS)-9-ethyl-4,14-dimethyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methyl-2-propylpentanamide; N-[(2R,3S,6R)-6-{[(2S,3aR,5aS,5bS,9S,13S,14R,16aS,16bS)-9-ethyl-4,14-dimethyl-7,15-dioxo-2-{[(2R,3R,4R,5S,6S)-3,4,5-trimethoxy-6- methyloxan-2-yl]oxy}-1H,2H,3H,3aH,5aH,5bH,6H,7H,9H,
10H,11H,12H,13H,14H,15H,16aH,16bH-as-indaceno[3,2-
d]oxacyclododecan-13-yl]oxy}-2-methyloxan-3-yl]-2-bu-
tyl-N-methyloctanamide; N-[(2R,3 S,6R)-6-{[(2S,3aR,5aS,
5bS,9S,13S,14R,16aS,16bS)-9-ethyl-4,14-dimethyl-7,15-
dioxo-2-{[(2R,3R,4R,5S,6S)-3,4,5-trimethoxy-6-
methyloxan-2-yl]oxy}-1H,2H,3H,3aH,5aH,5bH,6H,7H,9H,
10H,11H,12H,13H,14H,15H,16aH,16bH-as-indaceno[3,2-
d]oxacyclododecan-13-yl]oxy}-2-methyloxan-3-yl]-N-
methyloctanamide; or N-[(2R,3 S,6R)-6-{[(2S,3aR,5 aS,5b
S,9S,13S,14R,16aS,16bS)-9-ethyl-4,14-dimethyl-7,15-di
oxo-2-{[(2R,3R,4R,5S,6S)-3,4,5-trimethoxy-6-methyl-
oxan-2-yl]oxy}-1H,2H,3H,3aH,5aH,5bH,6H,7H,9H,10H,
11H,12H,13H,14H,15H,16aH,16bH-as-indaceno[3,2-d]ox-
acyclododecan-13-yl]oxy}-2-methyloxan-3-yl]-N-
methylbenzamide.

Also described herein are formulations. A formulation as described herein comprises at least one spinosyn compound as described herein and an acceptable carrier. Optionally, the formulation can further comprise at least one additional active ingredient and/or at least one plant or plant product treatment compound. The at least one additional active ingredient can comprise, for example, an insecticide or a miticide (e.g., a contact-acting insecticide or contact-acting miticide).

Further described herein is a method for controlling pests. A method for controlling pests as described herein comprises contacting a pest with an effective amount of a spinosyn compound or a formulation as described herein. Optionally, the pest is an insect, an arachnid, or a nematode.

Also described herein are methods for making tetracyclic and pentacyclic spinosyn compounds. A method for making a spinosyn compound comprises using a substitution modification on a natural spinosyn or spinosyn analogue. Optionally, the substitution modification is selected from the group consisting of a Meerwein arylation, a Schwartz hydrozirconation, a Woehl-Ziegler bromination, a Prius reaction, and a Wacker oxidation.

The details of one or more embodiments are set forth in the drawings and the description below. Other features, objects, and advantages will be apparent from the description and drawings, and from the claims.

DETAILED DESCRIPTION

Provided herein are tetracyclic and pentacyclic spinosyn compounds. The compositions are useful in the agricultural and animal health markets having activity towards pests such as insects, arachnids, nematodes and the like. Methods for making the compounds are also provided.

I. Compounds

A class of spinosyn compounds described herein is represented by Formula I:

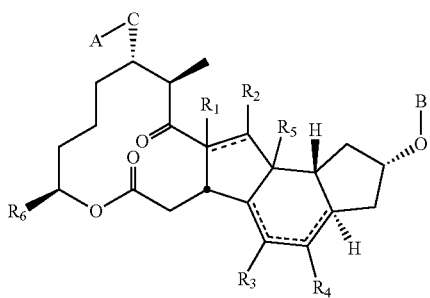

and salts thereof.

In Formula I, === is a single bond or a double bond.

Also, in Formula I, A is hydrogen or is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl. Optionally, A can be a substituted or unsubstituted saccharide. For example, A can be forosamine or a forosamine derivative, where one or both of the methyl groups on the forosamine nitrogen group is substituted with a substituted or unsubstituted alkyl, substituted or unsubstituted cycloalkyl, substituted or unsubstituted heterocycloalkyl, substituted or unsubstituted alkenyl, substituted or unsubstituted aryl, substituted or unsubstituted heteroaryl, substituted or unsubstituted aldehyde, substituted or unsubstituted benzyl, or substituted or unsubstituted benzoyl. In certain embodiments, the substitution is a group selected from hydrogen, tosyl, benzyl, propyl, 5-methylfuran-2-yl, chlorofluorobenzyl, ethyl, cyclopropyl, octonoyl, (2-methyl)propanoyl, benzoyl, propenoyl, or a —S(CH$_3$)O$_2$ group. In some examples, the forosamine derivative is a [(2R,5S,6R)-6-methyl-5-(methylamino)oxan-2-yl]oxy group.

Additionally, in Formula I, B is selected from the group consisting of substituted or unsubstituted cycloalkyl, substituted or unsubstituted heterocycloalkyl, substituted or unsubstituted aryl, and substituted or unsubstituted heteroaryl. Optionally, B can be a substituted or unsubstituted saccharide. For example, B can be rhamnose or a rhamnose derivative, such as 3,4,5-trimethoxyrhamnose or 4-ethoxy-3,5-dimethoxyrhamnose.

Further, in Formula I, C is O or NH.

Also, in Formula I, R$^1$ is absent, is hydrogen, or forms a ring with R$^2$.

Also, in Formula I, R$^2$, R$^3$, and R$^4$ are each independently selected from hydrogen, hydroxyl, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, azido, or carbonyl. Optionally, R$^2$, R$^3$, and R$^4$ are each independently selected from substituted or unsubstituted C$_{1-6}$ alkyl and aryl. Optionally, one or more of R$^2$, R$^3$, and R$^4$ are hydrogen. Optionally, R$^3$ or R$^4$ is hydroxyl, halogen, carbonyl, substituted or unsubstituted alkoxy, substituted or unsubstituted alkyl, substituted or unsubstituted alkenyl, or substituted or unsubstituted aryl, substituted or unsubstituted heteroaryl, substituted or unsubstituted amino, azido. Optionally, R$^3$ or R$^4$ is fluoro, chloro, methoxy, ethoxy, methyl, ethyl, ethenyl, phenyl, methoxyphenyl, fluorophenyl, chlorophenyl.

Optionally, adjacent R groups in Formula I, e.g., R$^1$ and R$^2$ or R$^3$ and R$^4$, can be combined to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl. For example, R$^1$ and R$^2$ or R$^3$ and R$^4$ can combine to form a substituted or unsubstituted cyclopropyl group. Optionally, R$^3$ and R$^4$ can combine to form a substituted or unsubstituted cyclopentanone group or a substituted or unsubstituted cyclopenteone group. Optionally, R$^3$ and R$^4$ can combine to form a substituted or unsubstituted cyclic ester group, wherein the cyclic ester may be saturated or unsaturated Additionally, in Formula I, $R^5$ is hydrogen, halogen, hydroxyl, substituted or unsubstituted amino, substituted or unsubstituted thio, or substituted or unsubstituted alkoxy.

Additionally, in Formula 1, $R^6$ is substituted or unsubstituted alkyl or substituted or unsubstituted aryl. Optionally $R^6$ can be ethyl.

Optionally, $R^5$ is hydrogen and $R^6$ is ethyl. In these examples, Formula I can represented by Structure I-A:

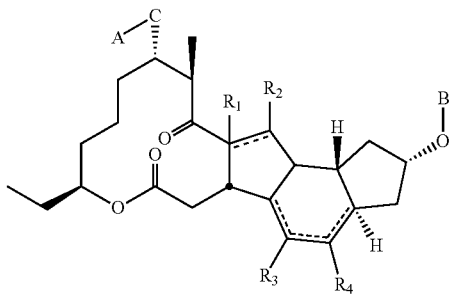

In Structure I-A, A, B, C, $R^1$, $R^2$, $R^3$, and $R^4$ are as defined above for Formula I. Optionally, A is forosamine; B is 3,4,5-trimethoxyrhamnose; C is O; $R^1$ is absent; $R^2$, $R^3$, and $R^5$ are hydrogen; and $R^6$ is ethyl. In these examples, Formula I can be represented by Structure I-B:

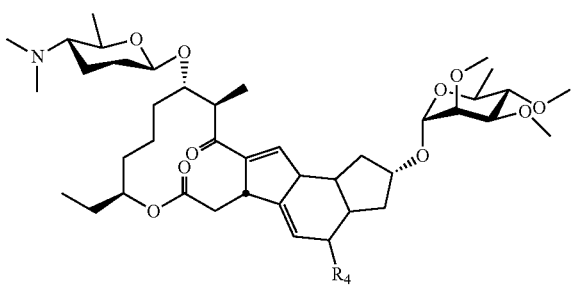

In Structure I-B, $R^4$ is as defined above for Formula I.

Optionally, A is forosamine; B is 3,4,5-trimethoxyrhamnose; C is O; $R^1$ is absent; $R^2$, $R^4$, and $R^5$ are hydrogen; and $R^6$ is ethyl. In these examples, Formula I can be represented by Structure I-C:

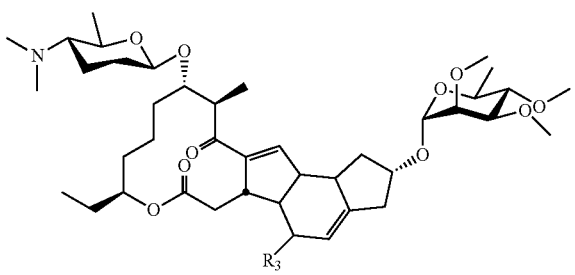

In Structure I-C, $R^3$ is as defined above for Formula I.

Optionally, A is forosamine; B is 3,4,5-trimethoxyrhamnose; C is O; $R^1$ is absent, $R^2$ and $R^5$ are hydrogen, and $R^6$ is ethyl, and $R^3$ and $R^4$ join to form a cyclopentanone ring or a cyclopentenone ring optionally substituted with $R^7$. In these examples, Formula I can be represented by Structure I-D:

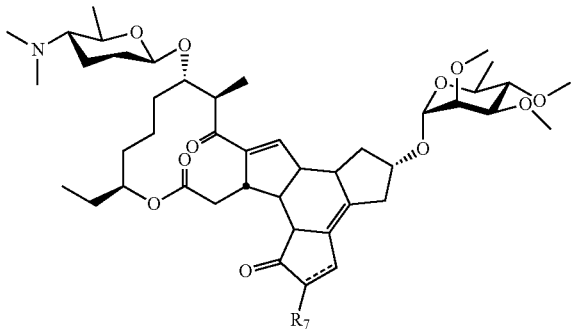

In Structure I-D, $R^7$ is hydrogen, alkyl, pyridiminyl, and/or substituted or unsubstituted phenyl. The phenyl group may be substituted with halogen, methyl, methoxy, cynano, or thiophene. (Examples 15-19, 43-46, 54-59)

Optionally, B is 3,4,5-trimethoxyrhamnose; C is O; $R^1$ is absent; $R^2$, $R^3$, and $R^5$ are hydrogen; and $R^4$ is hydrogen (I-E) or methyl (I-E'); $R^6$ is ethyl. In these examples, Formula I can be represented by Structure I-E:

Structure I-E

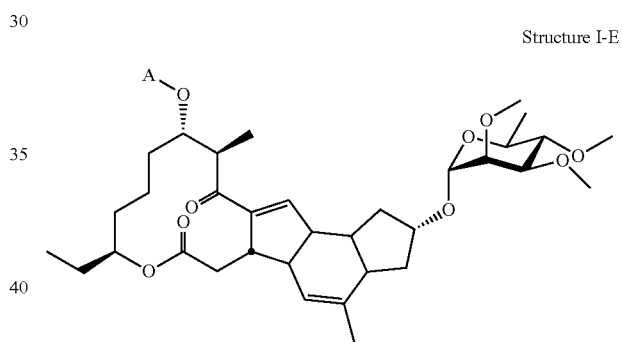

Structure I-E'

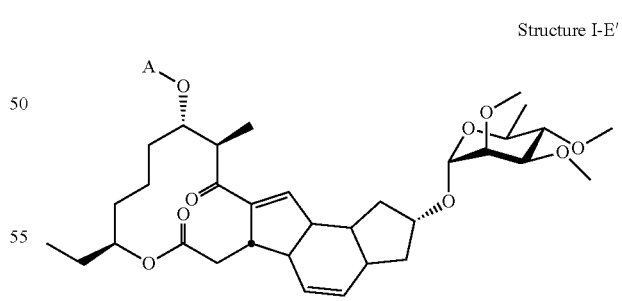

In Structure I-E, A is a forosamine derivative as defined above for Formula I. (Examples 21-4)

Optionally, A is forosamine; B is 3,4,5-trimethoxyrhamnose; C is O; $R^1$ is absent, $R^2$ and $R^5$ are hydrogen, $R^6$ is ethyl, and $R^3$ and $R^4$ join to form an optionally substituted 6-valerolactone ring, which may optionally contain a double bond. In these examples, Formula I can be represented by Structure I-F:

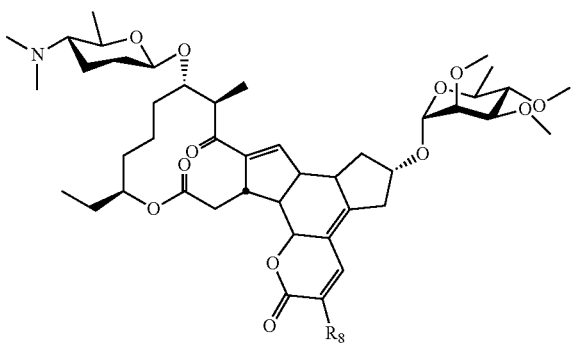

Structure I-F

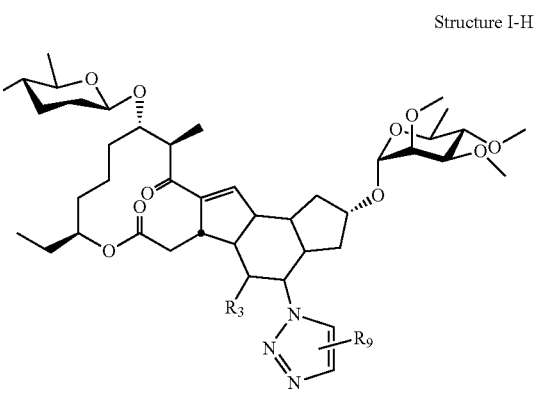

Structure I-H

In Structure I-F, $R^8$ is alkyl, substituted or unsubstituted phenyl, pyrimidinyl, or a thiophene group. The phenyl group may be substituted with halogen, methyl, methoxy, or cynano. (Examples 60-65)

Optionally, A is forosamine; B is 3,4,5-trimethoxyrhamnose; C is O; $R^1$ is absent, $R^2$ and $R^5$ are hydrogen, one of $R^3$ and $R^4$ is carbonyl, and $R^6$ is ethyl. In these examples, Formula I can be represented by Structures I-G and I-G'.

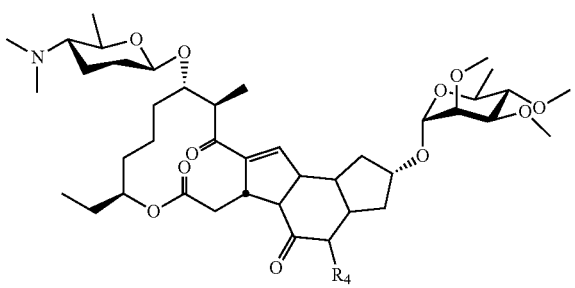

Structure I-G

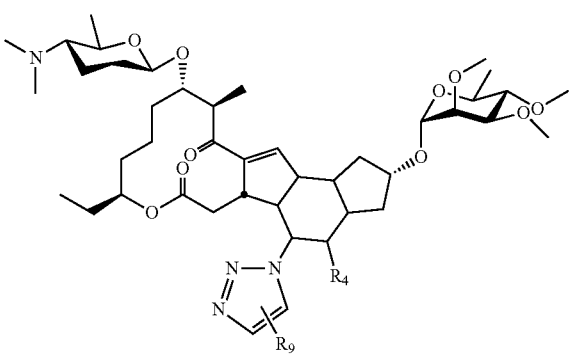

Structure I-H'

In Structures I-H and I-H', the one of $R^3$ and $R^4$ that is not a substituted triazole is selected from hydrogen, hydroxyl, and halogen; and $R^9$ is selected from alkyl, thiophene, trimethylsiloxy, $C_1$-$C_4$ methyl ester, substituted or unsubstituted phenyl, wherein the substituted phenyl may have one or more $R^9$ substitutions including but not limited to halogen, alkyl, halo alkyl, alkoxy, haloalkoxy, or ester, and wherein the substituted phenyl triazole may have one or more substitutions including but not limited to halogen, alkyl, alkoxy, phenyl, and amino. (Examples 71-90, 101-108, 110-114)

Optionally, A is forosamine; B is 3,4,5-trimethoxyrhamnose; C is O; $R^1$, $R^3$, and $R^5$ are hydrogen, $R^4$ is hydrogen or methyl, and $R^6$ is ethyl. In these examples, Formula I can be represented by Structure I-I and I-I'.

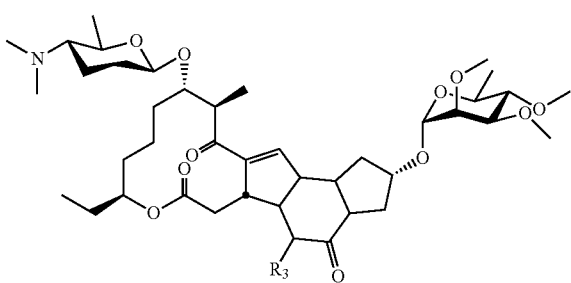

Structure I-G'

In Structure I-G and I-G', the one of $R^3$ and $R^4$ that is not carbonyl is alkoxy or hydroxyl. (Examples 50-53)

Optionally, A is forosamine; B is 3,4,5-trimethoxyrhamnose; C is O; $R^1$ is absent, $R^2$ and $R^5$ are hydrogen, one of $R^3$ and $R^4$ is a substituted triazole, and $R^6$ is ethyl. In these examples, Formula I can be represented by Structures I-H and I-H'.

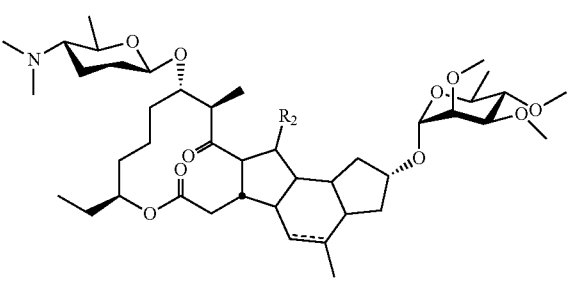

Structure I-I

Structure I-I'
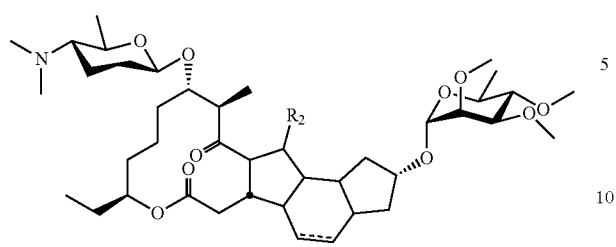
In Structure I-I, $R^2$ is alkyl, alkenyl, or substituted or unsubstituted phenyl, wherein the substituted phenyl may have one or more substitutions including but not limited to halogen, alkyl, halo alkyl, alkoxy, haloalkoxy, or ester. (Examples 118-129)
Examples of Formula I include the following compounds:
1
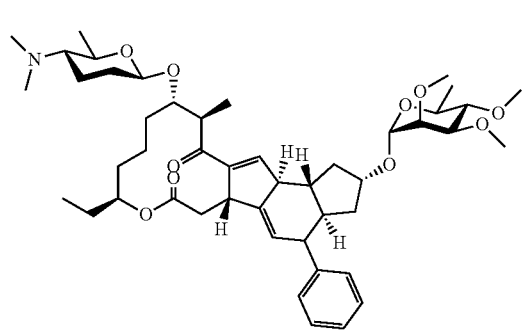
2
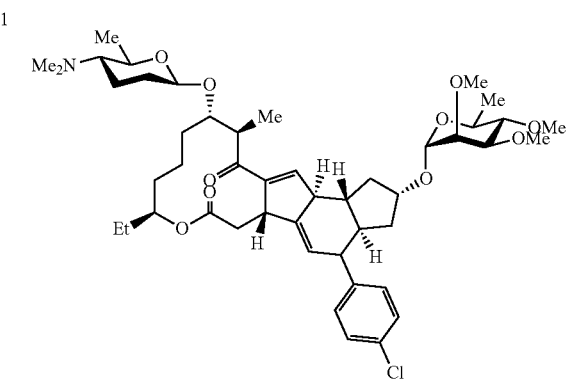
3
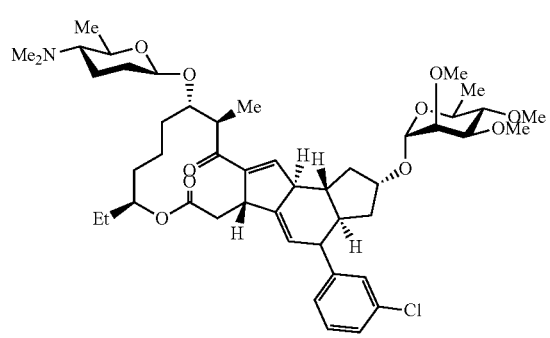
4
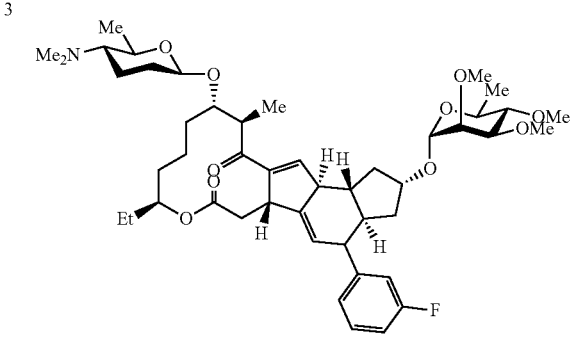
5
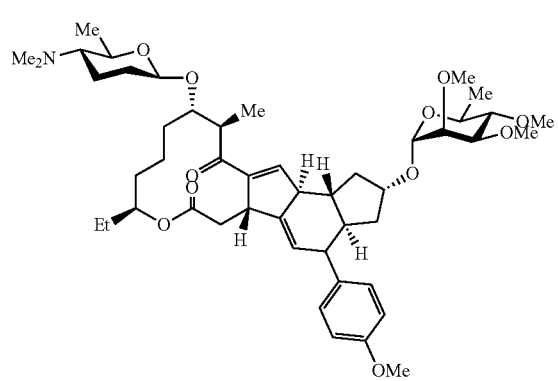
6
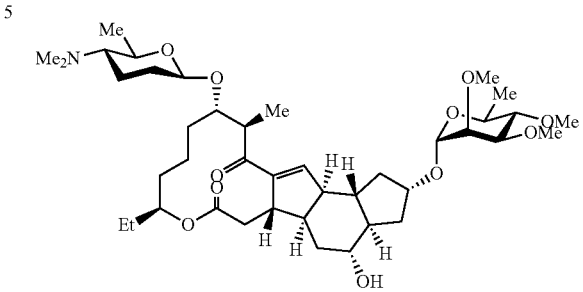

-continued
7
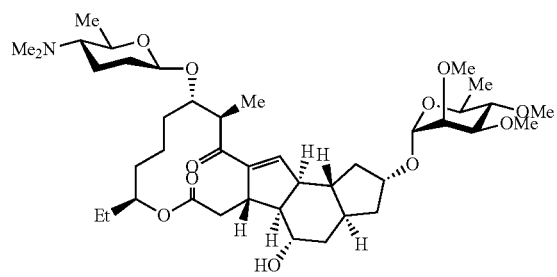
8
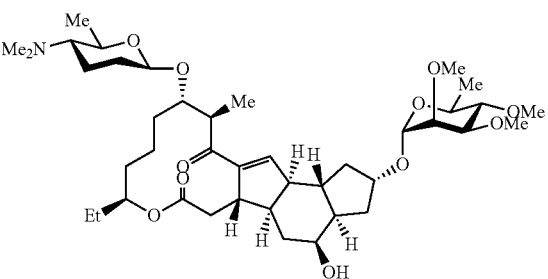
9
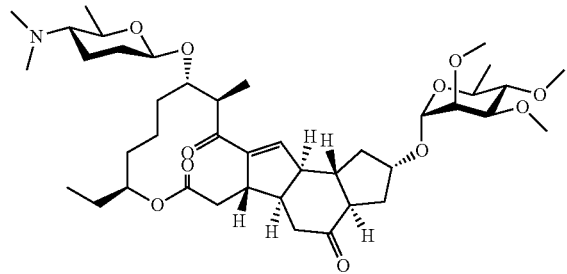
10
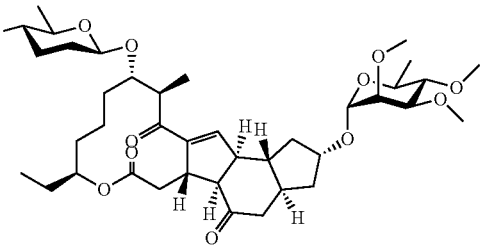
11
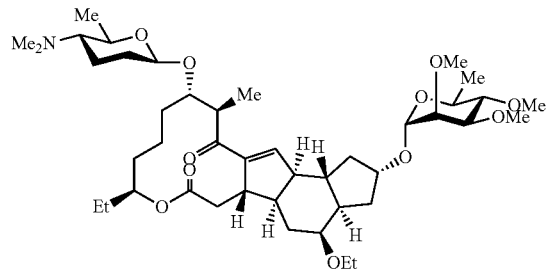
12
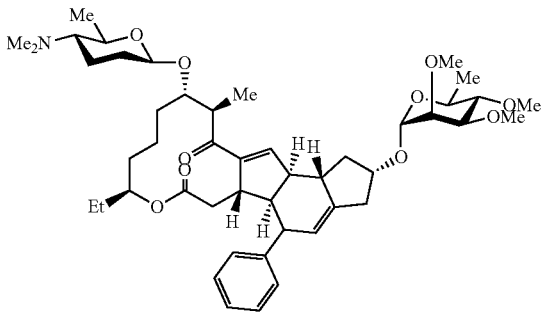
13
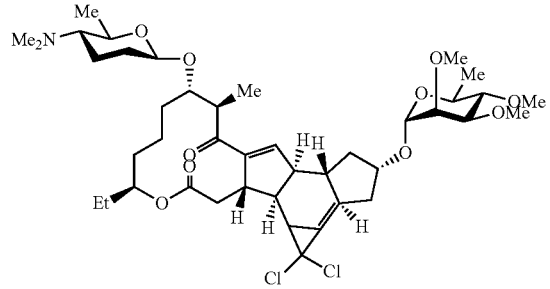
14
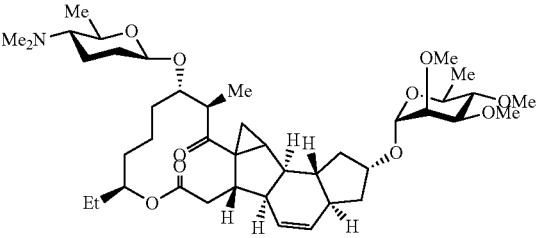
15
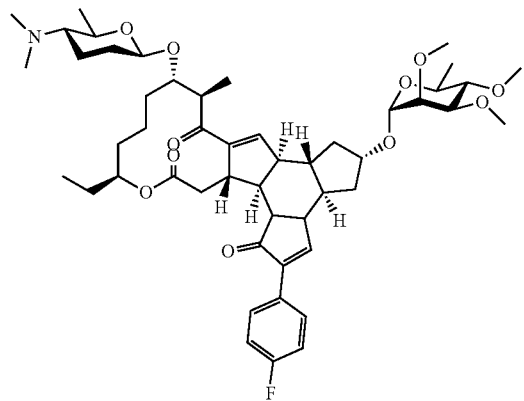
16
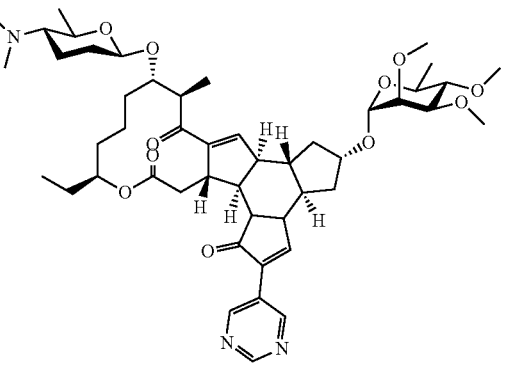

-continued
17
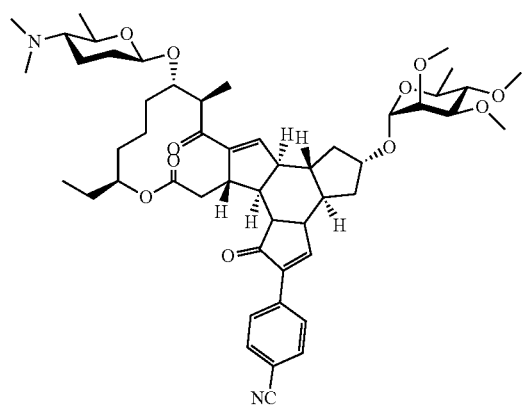
18
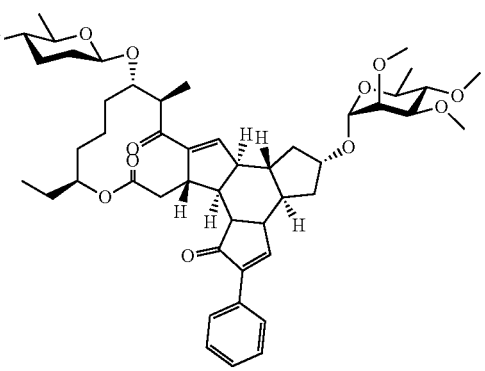
19
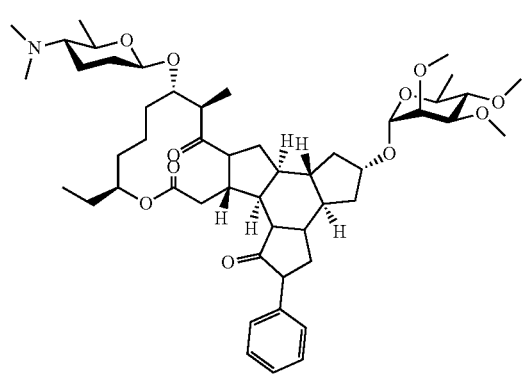
20
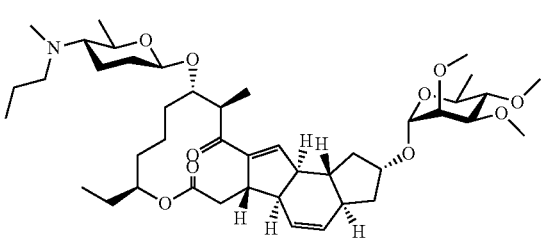
21
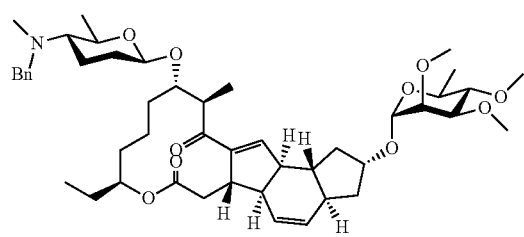
22
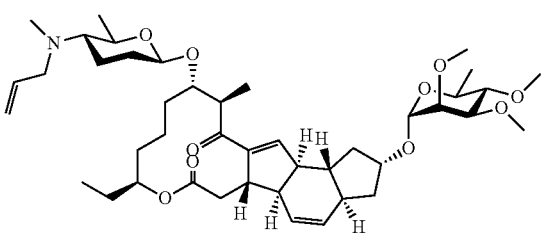
23
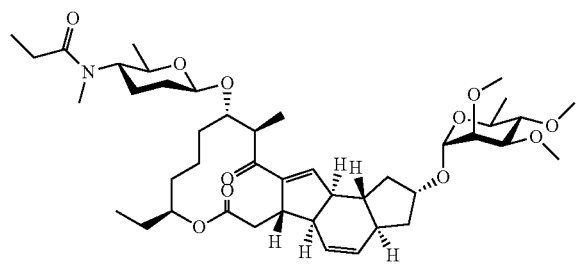
24
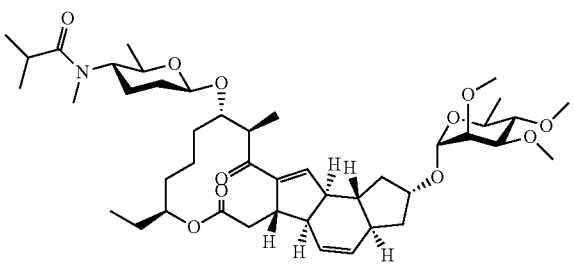
25
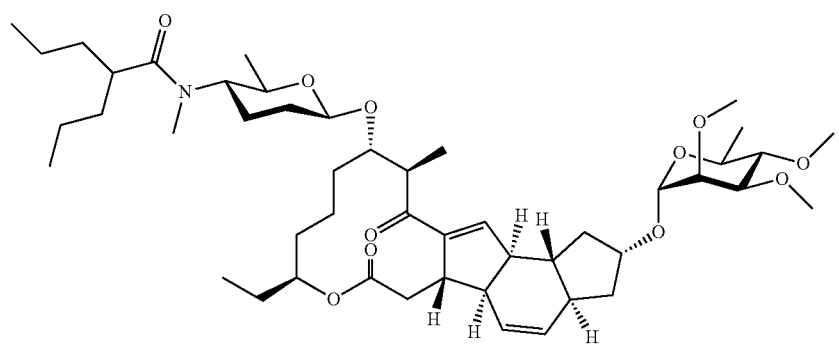

-continued
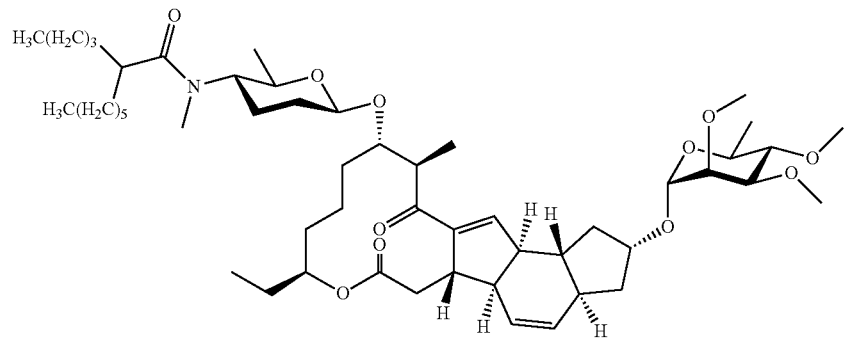
26
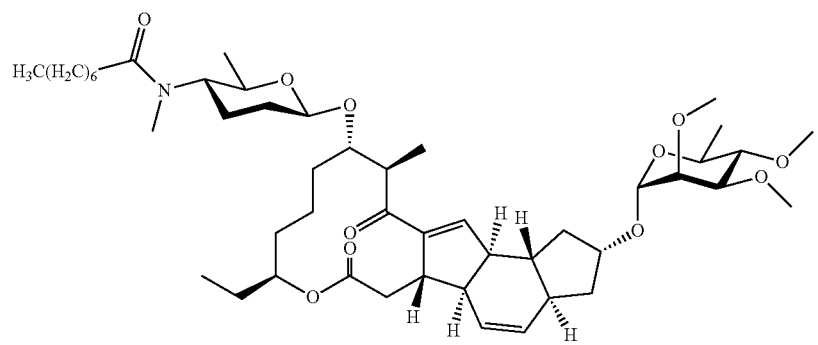
27
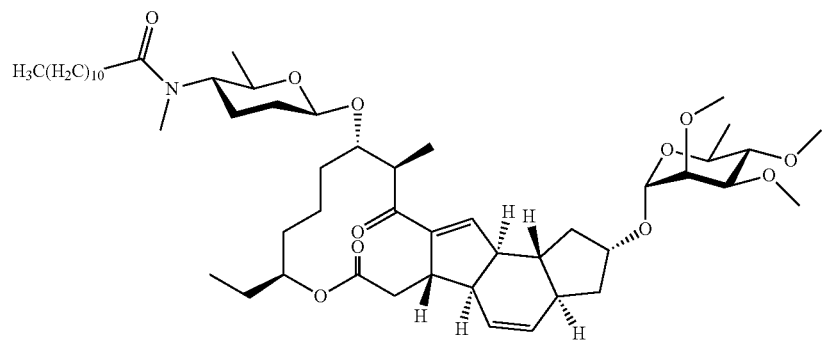
28
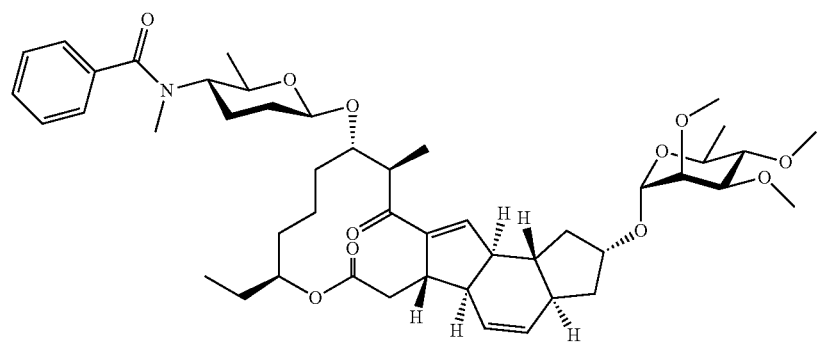
29

-continued
30
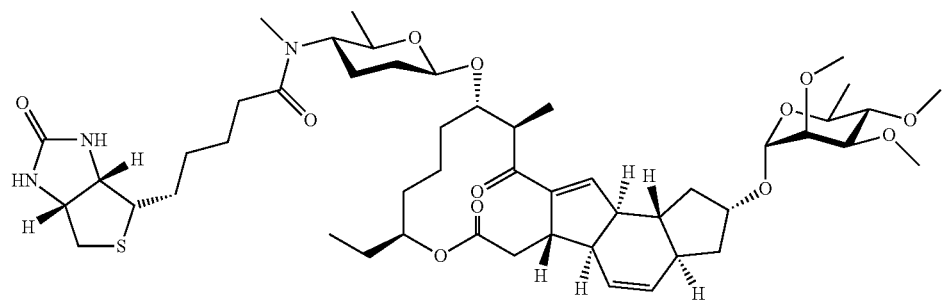
31
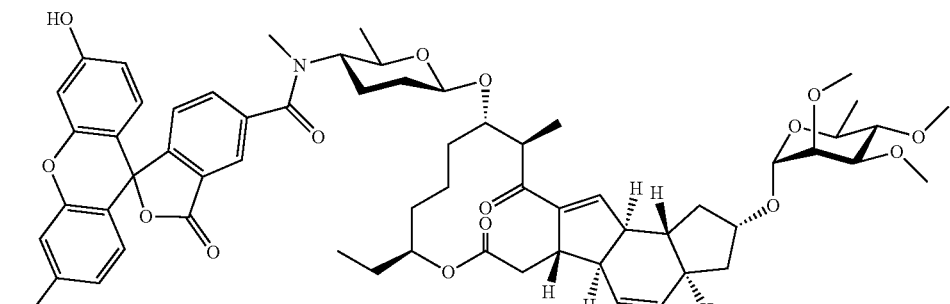
32 33
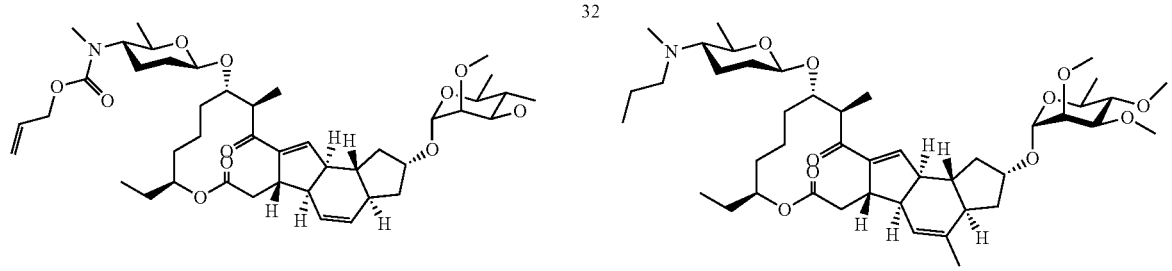
34 35
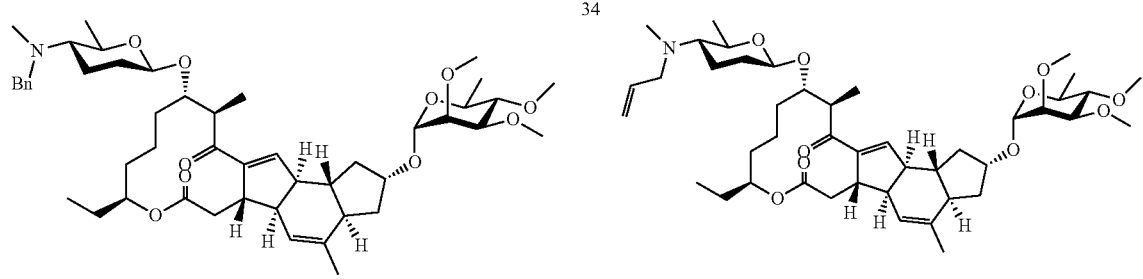
36
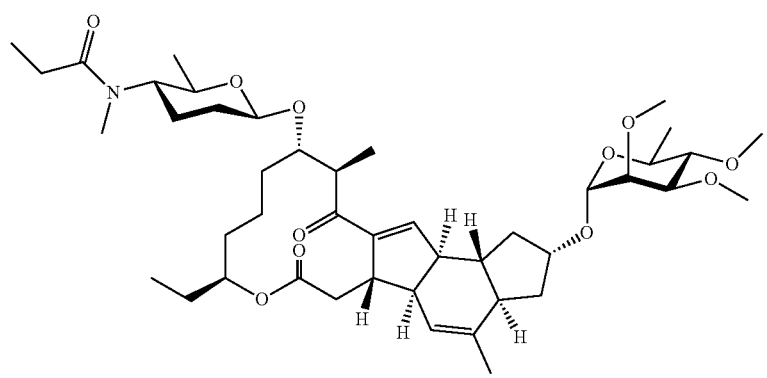

-continued
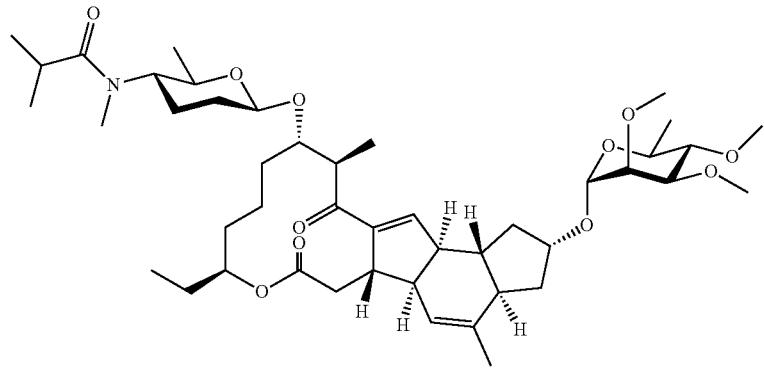
37
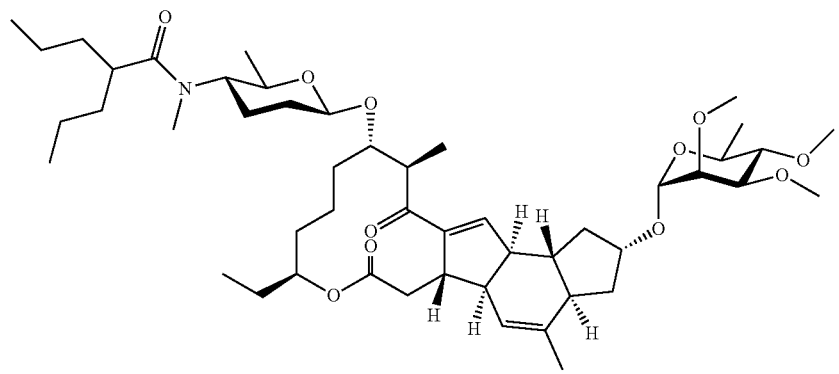
38
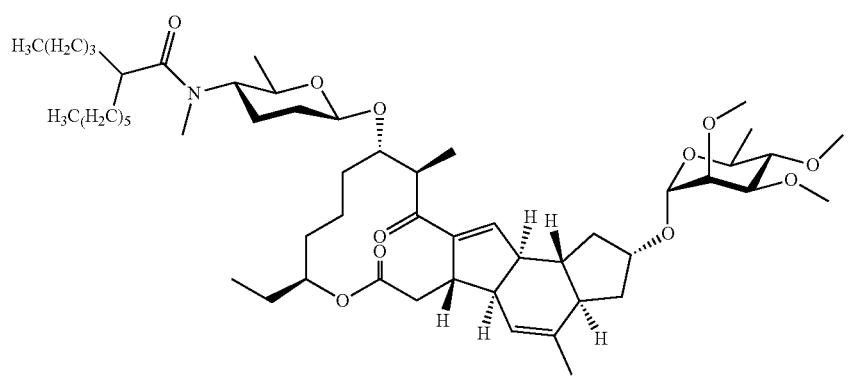
39
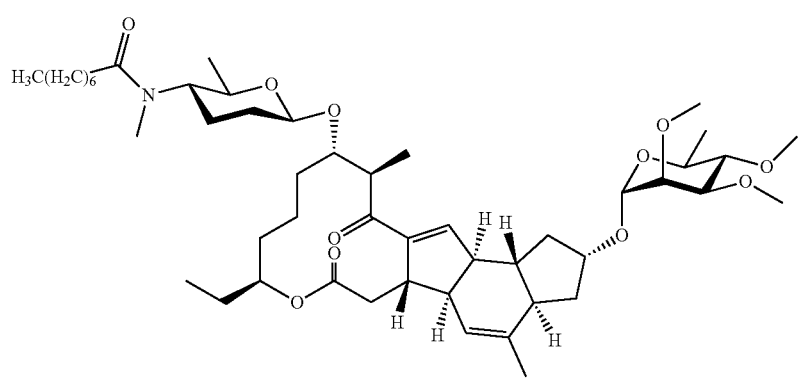
40

-continued
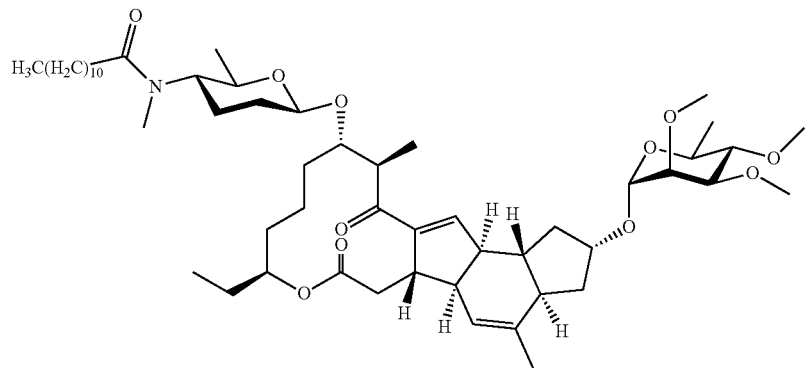
41
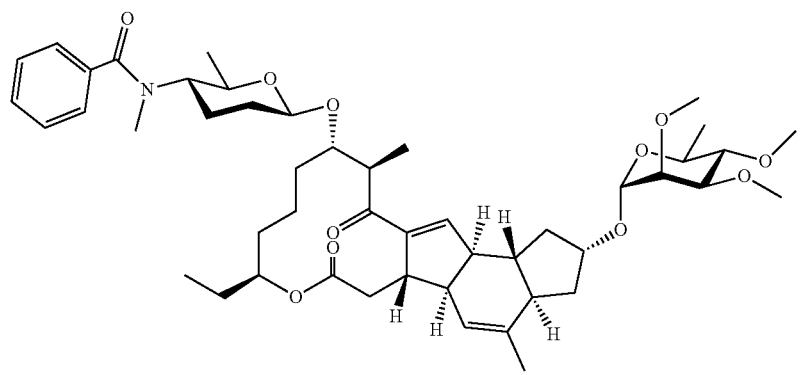
42
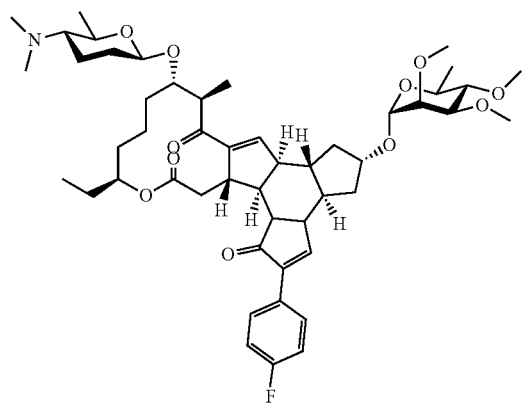
43
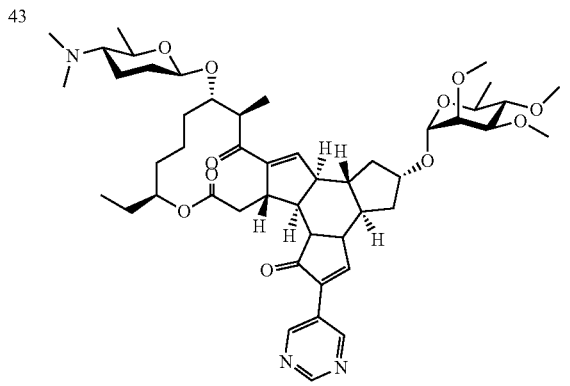
44
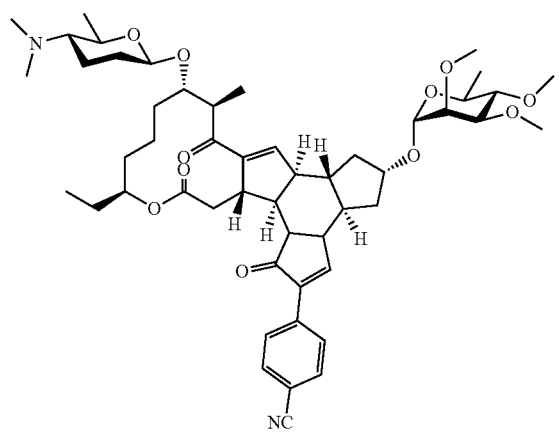
45
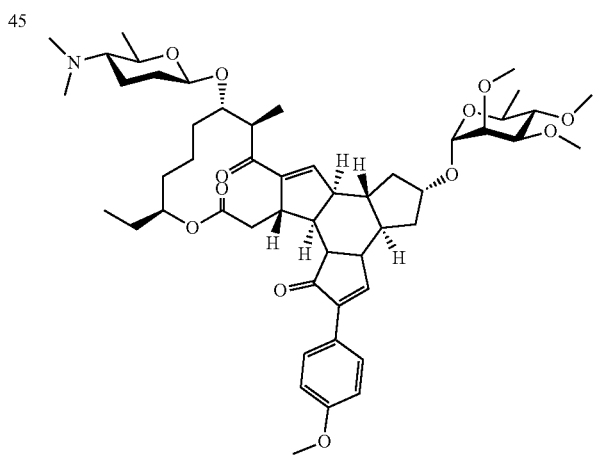
46

-continued
47
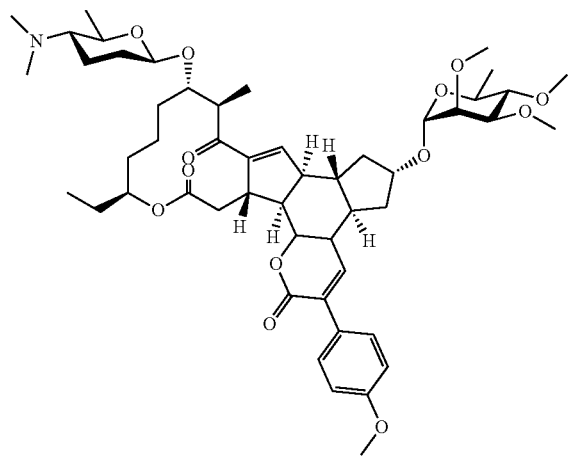
48
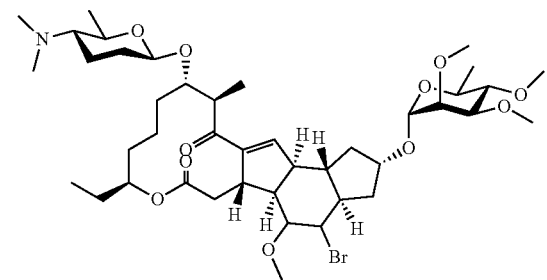
49
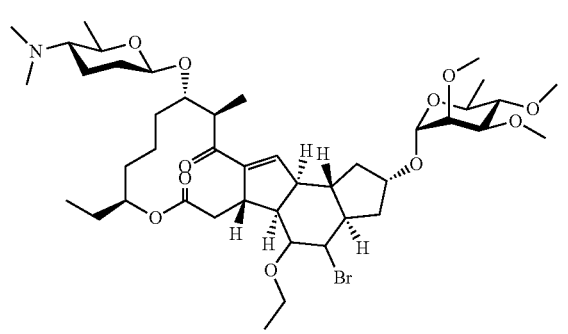
50
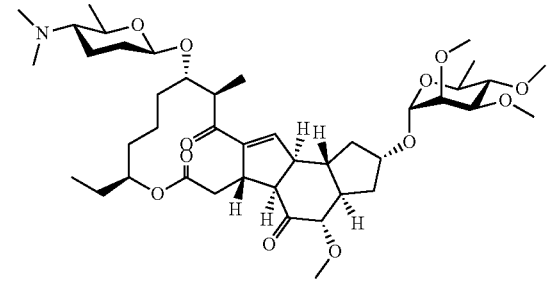
51
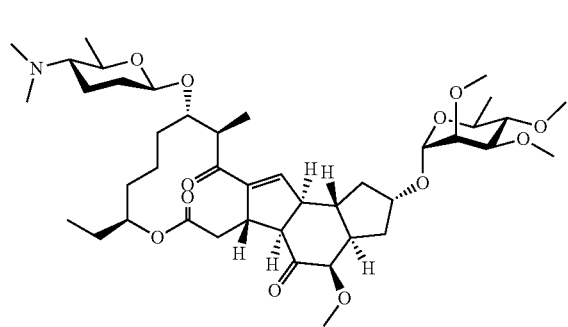
52
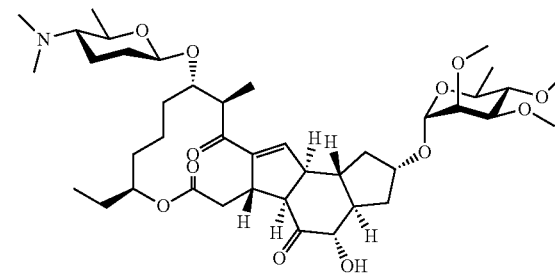
53
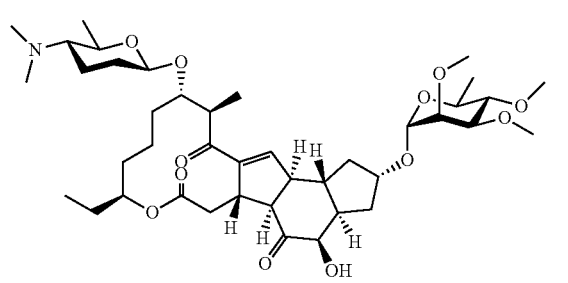
54
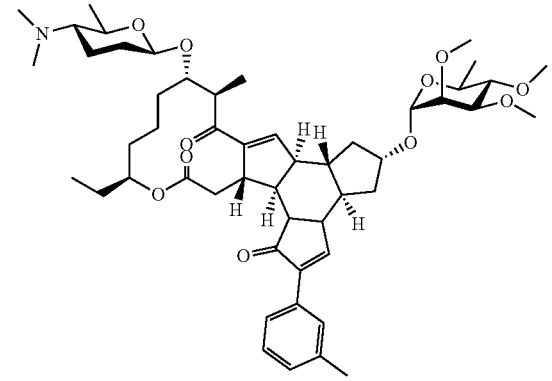

55
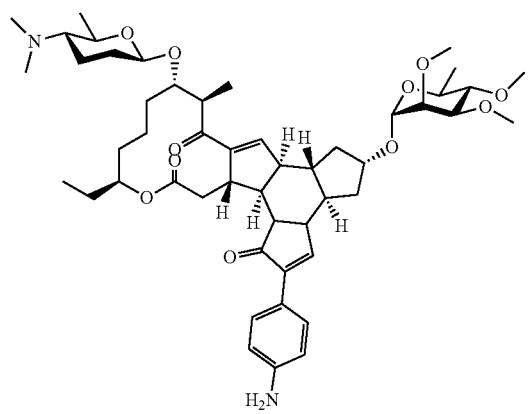
56
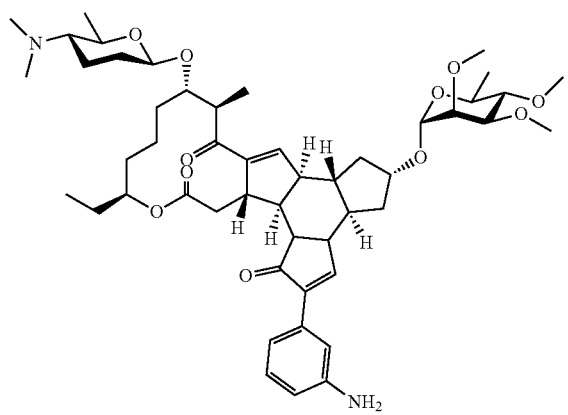
57
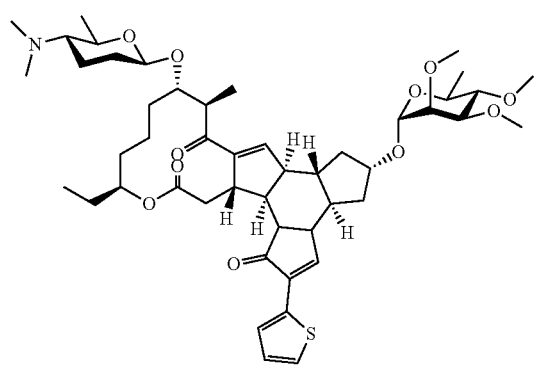
58
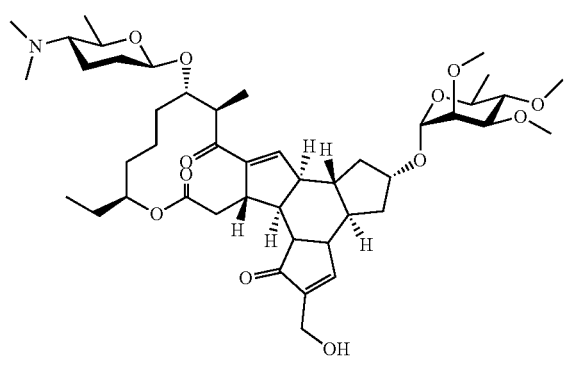
59
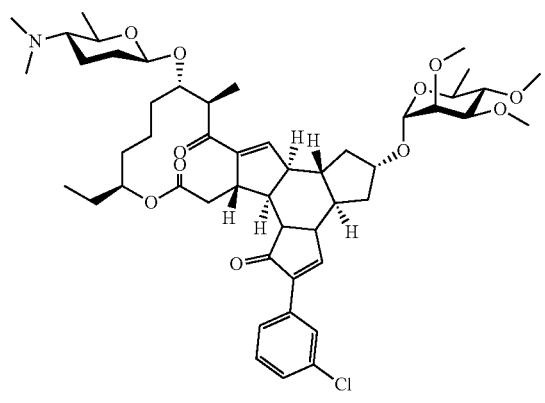
60
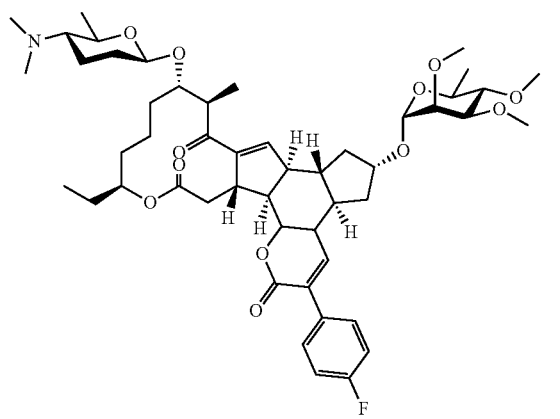
61
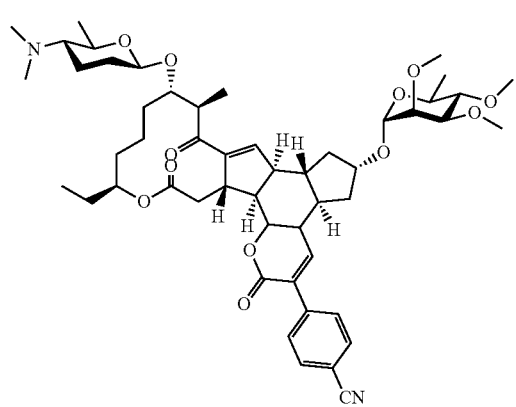
62
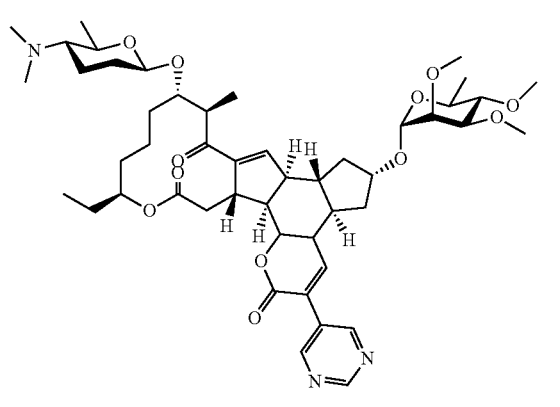

-continued
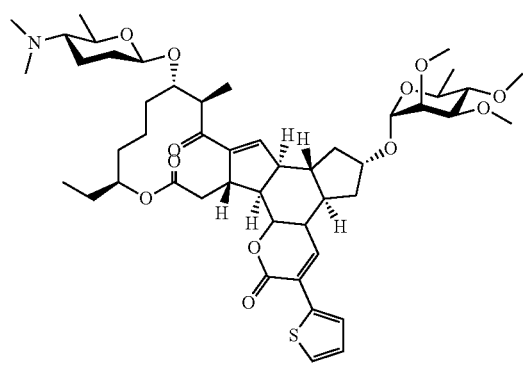
63
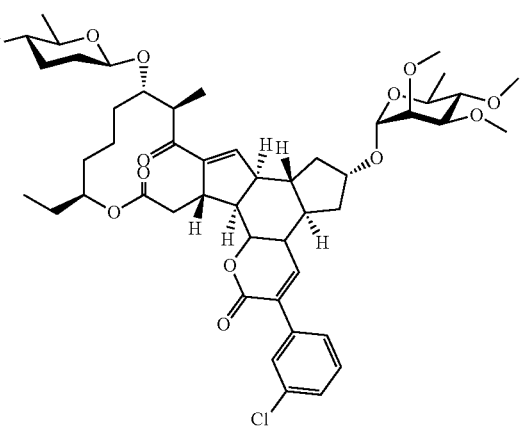
64
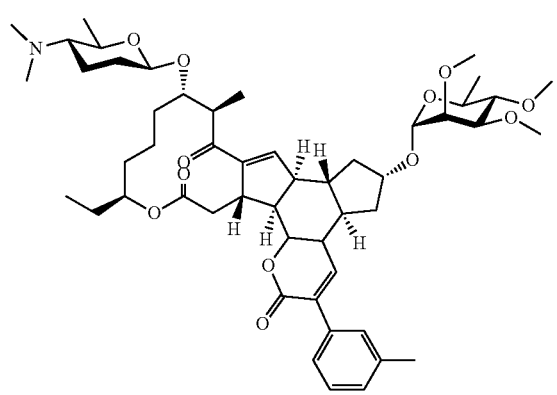
65
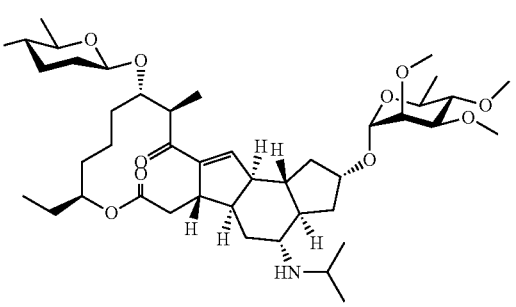
66
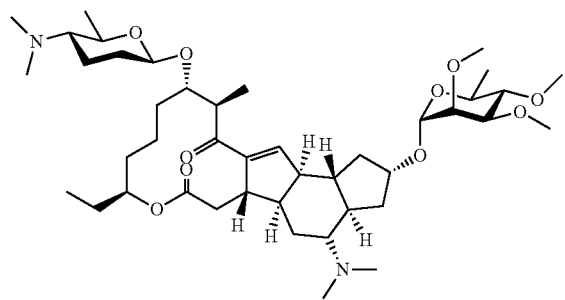
67
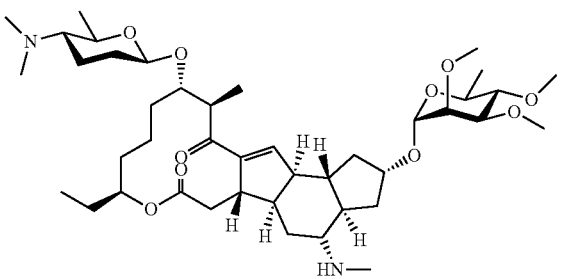
68
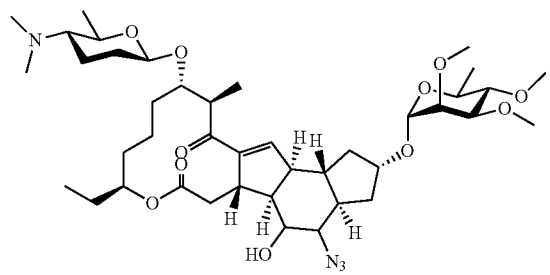
69
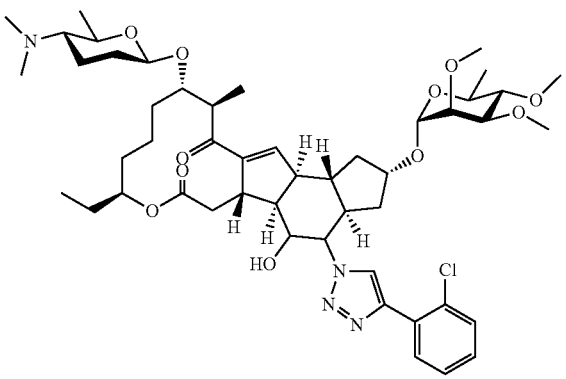
70

-continued
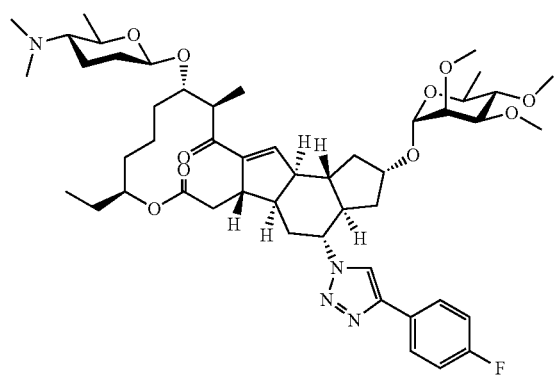
71
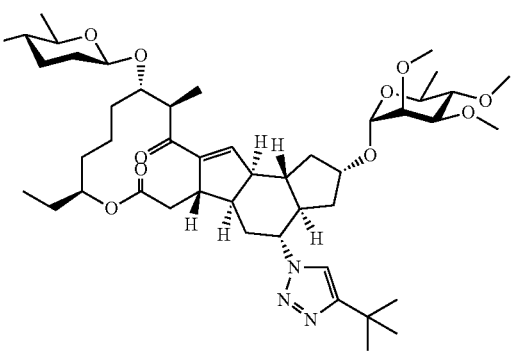
72
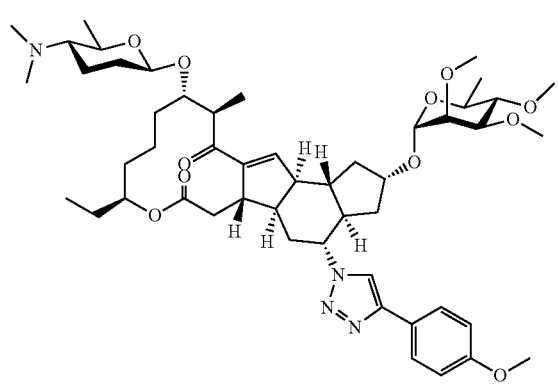
73
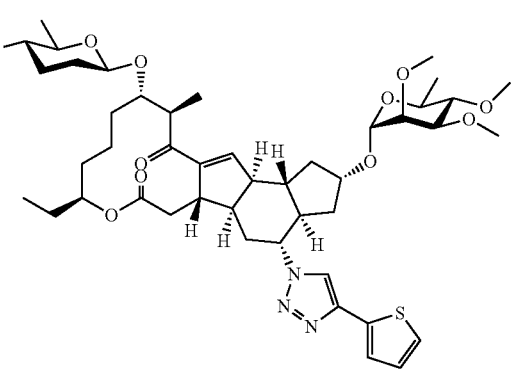
74
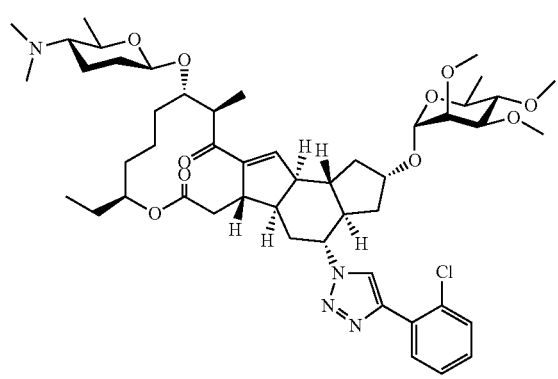
75
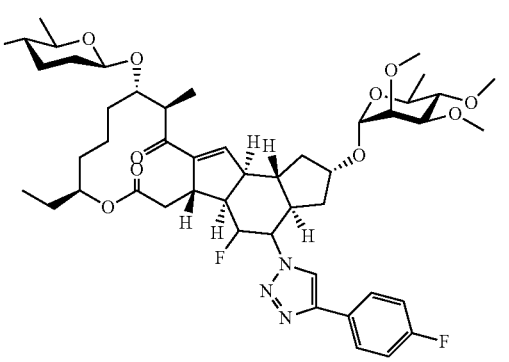
76
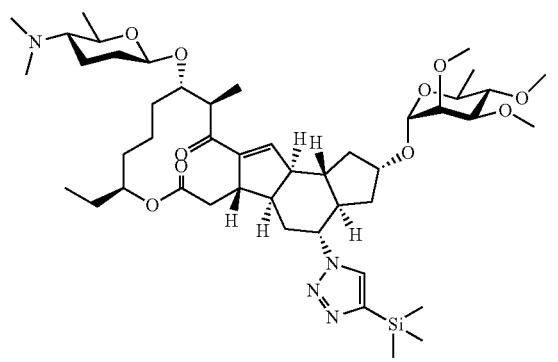
77
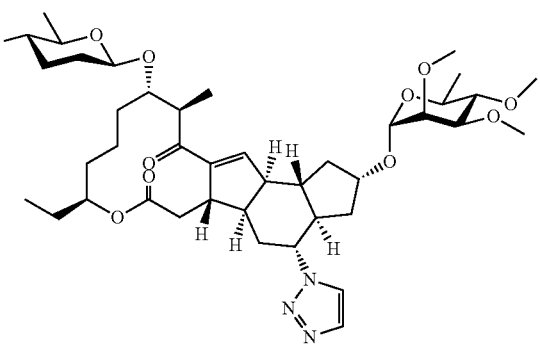
78

-continued
79
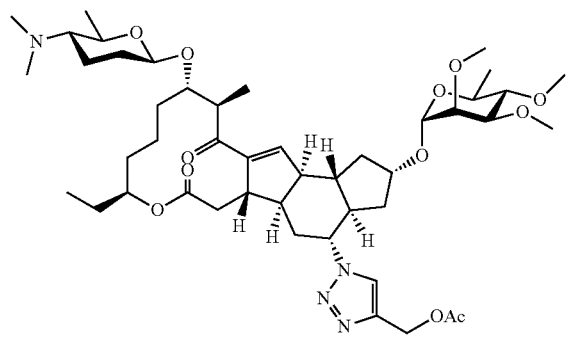
80
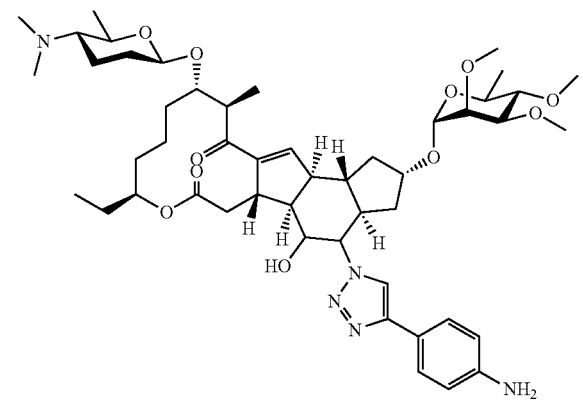
81
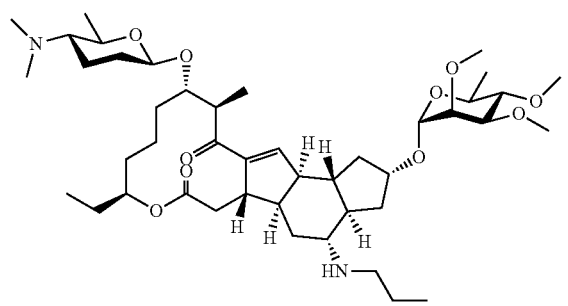
82
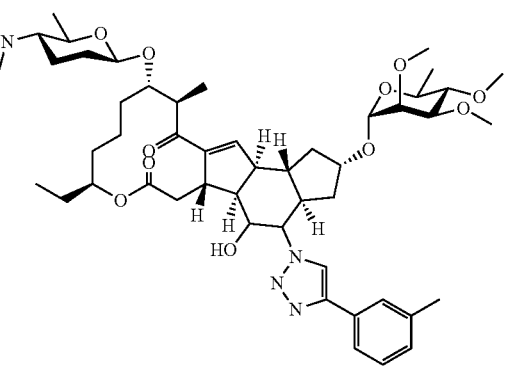
83
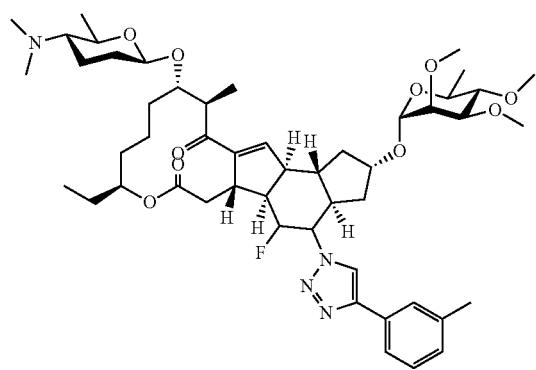
84
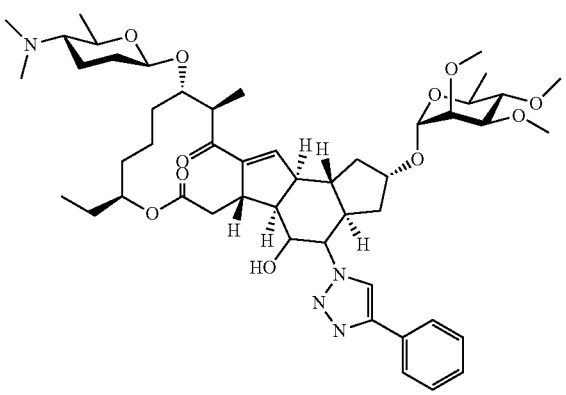
85
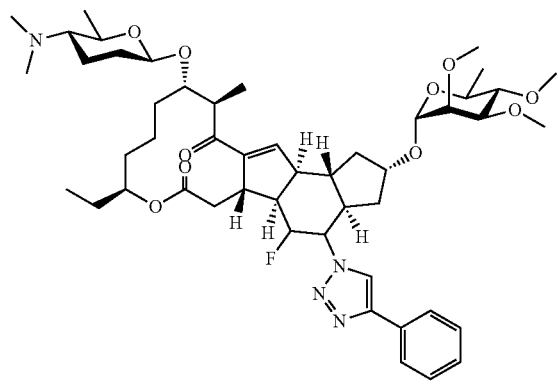
86
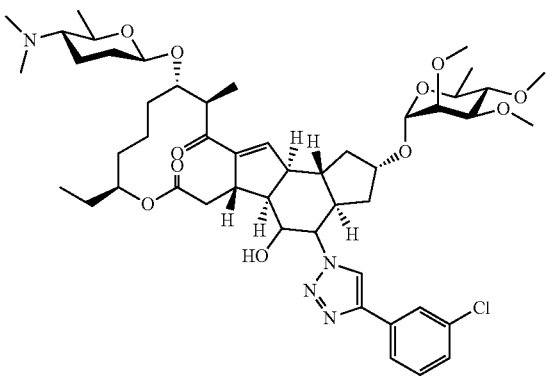

-continued
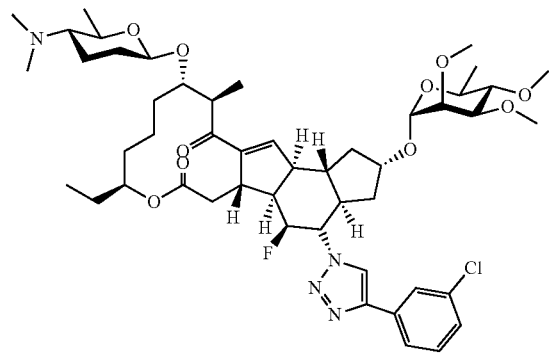
87
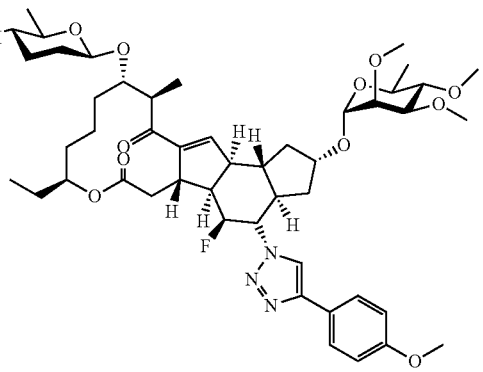
88
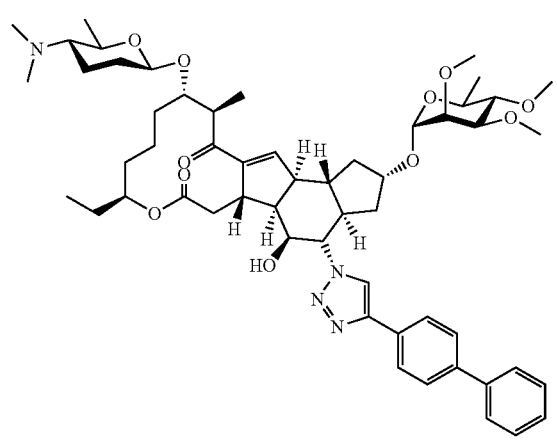
89
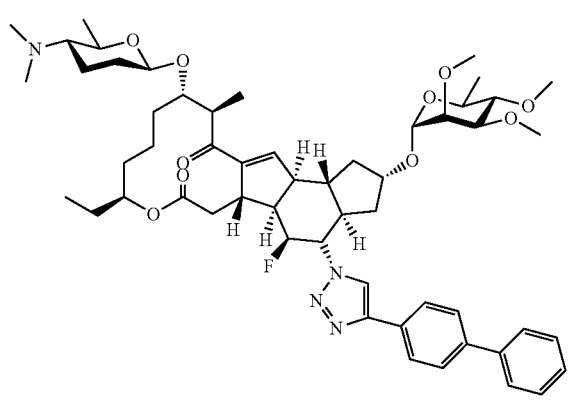
90
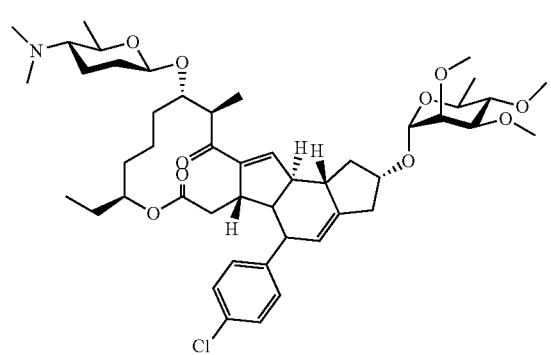
91
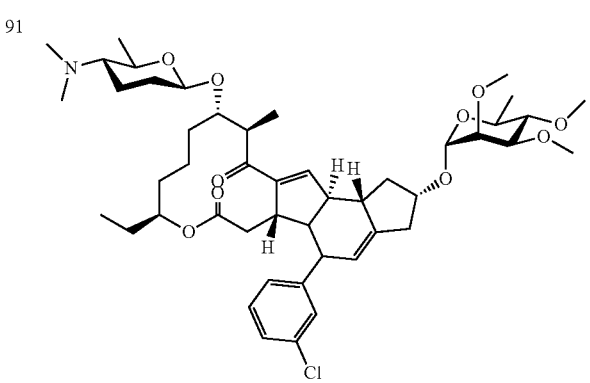
92
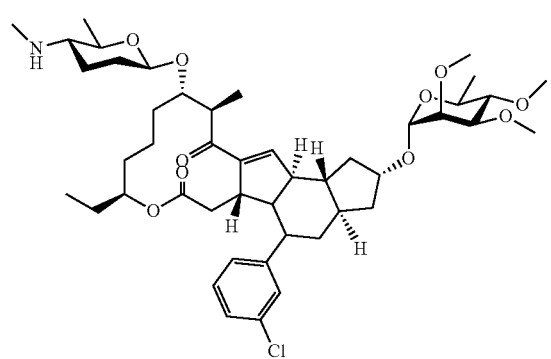
93
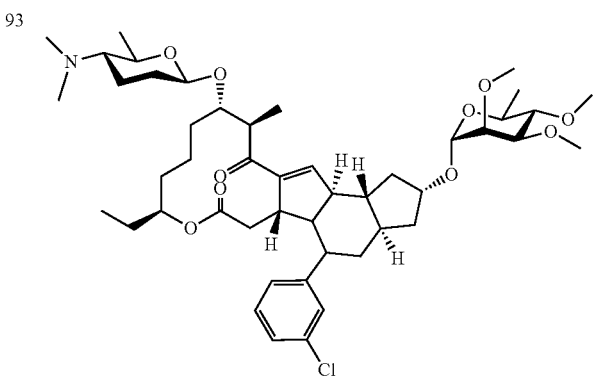
94

-continued
95
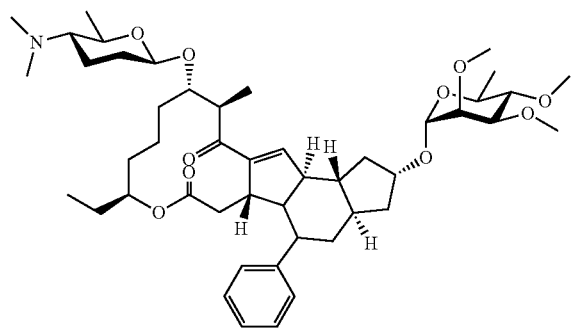
96
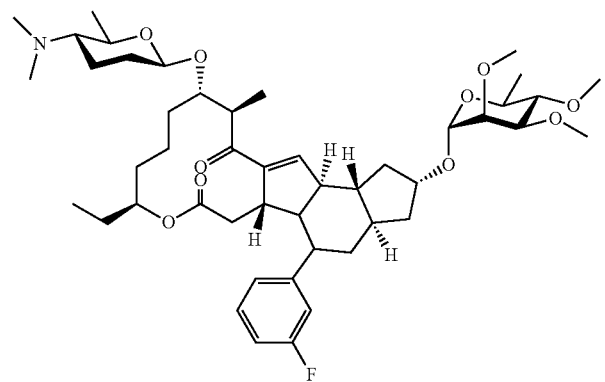
97
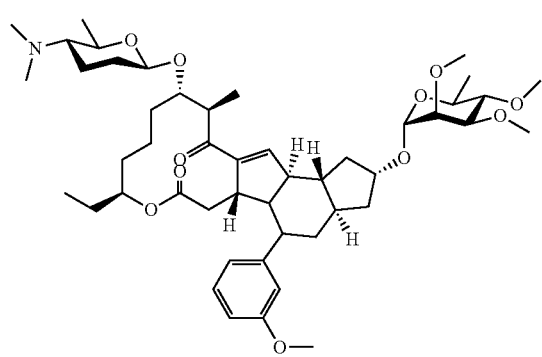
98
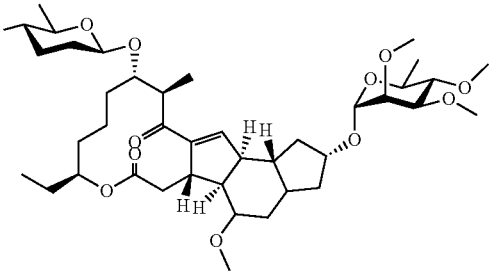
99
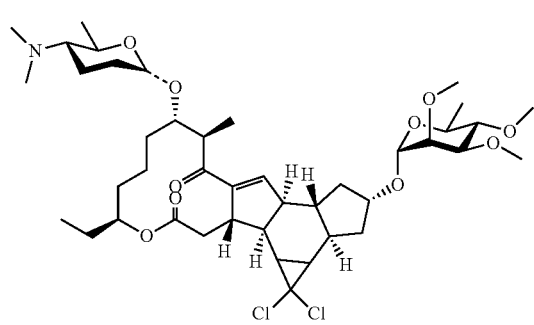
100
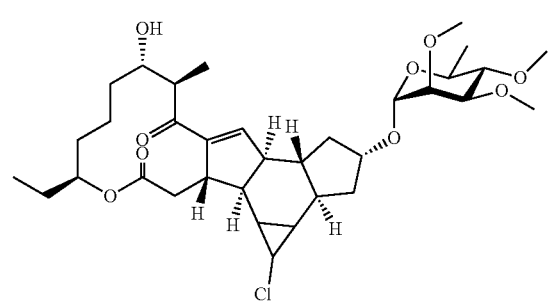
101
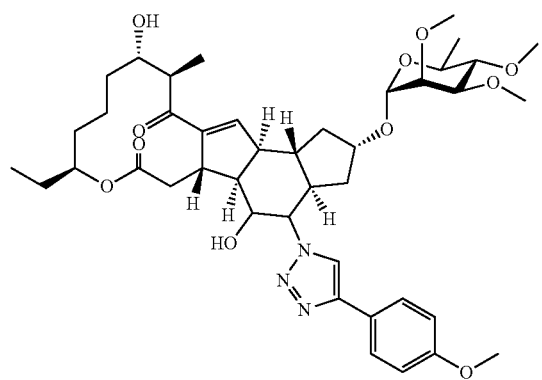
102
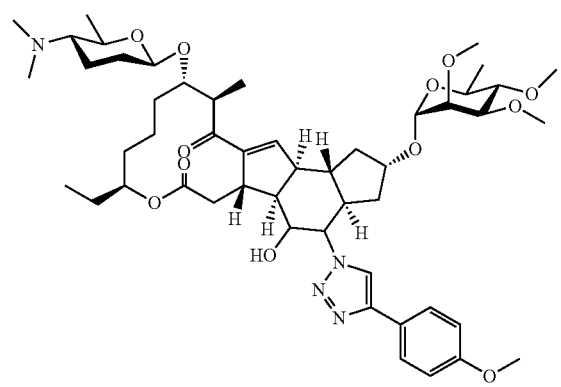

-continued
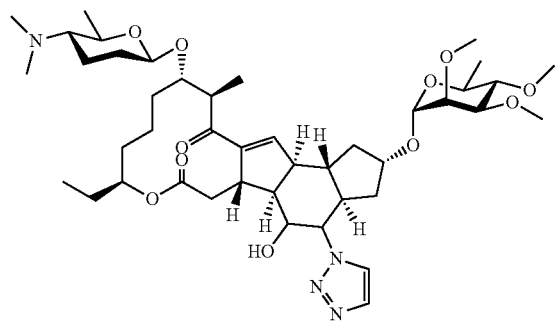
103
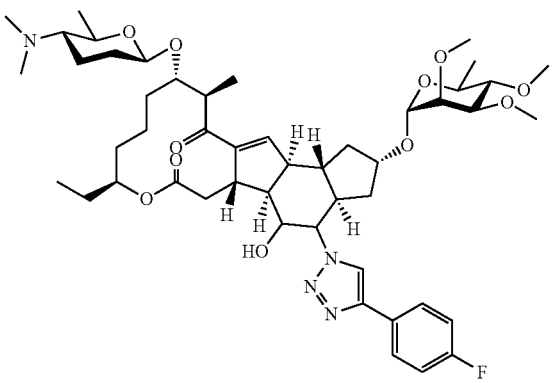
104
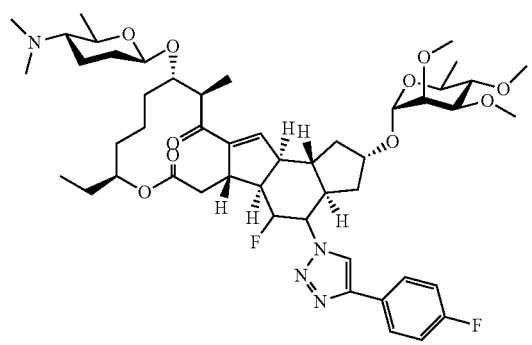
105
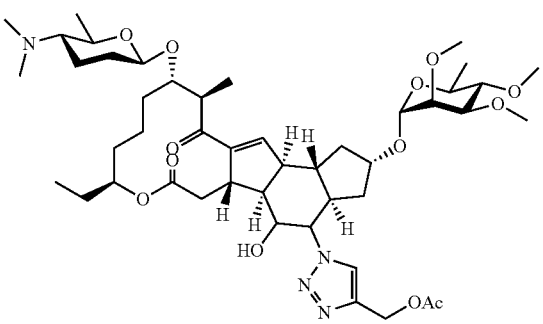
106
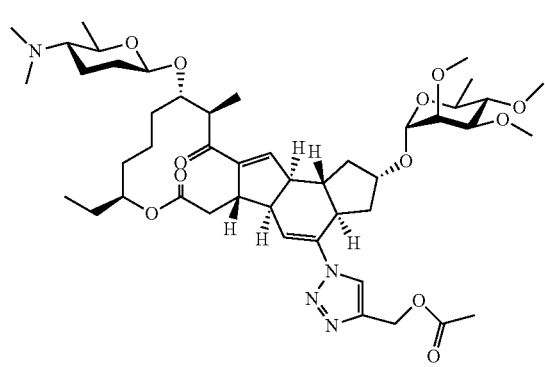
107
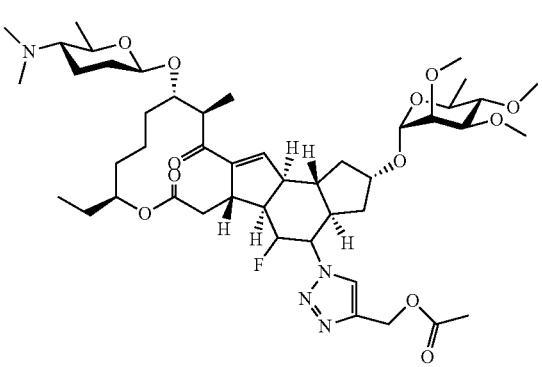
108
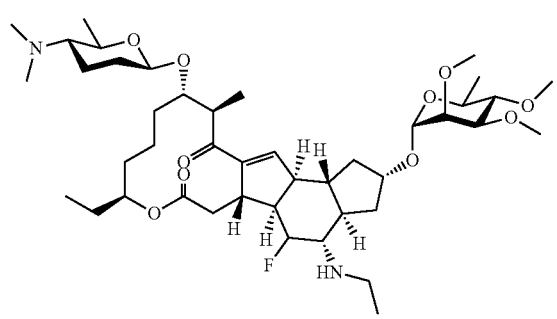
109
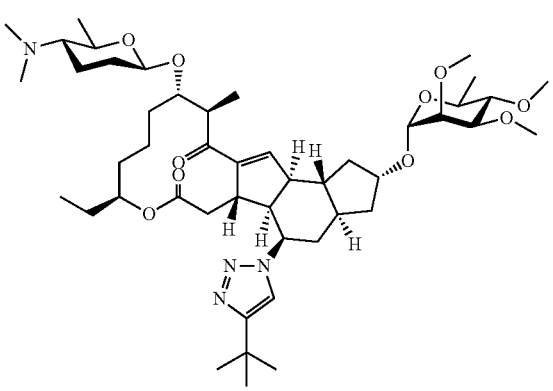
110

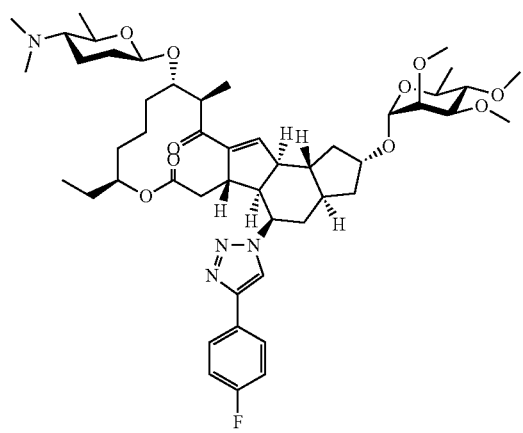
111
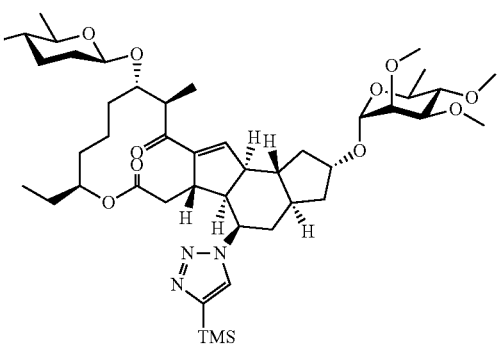
112
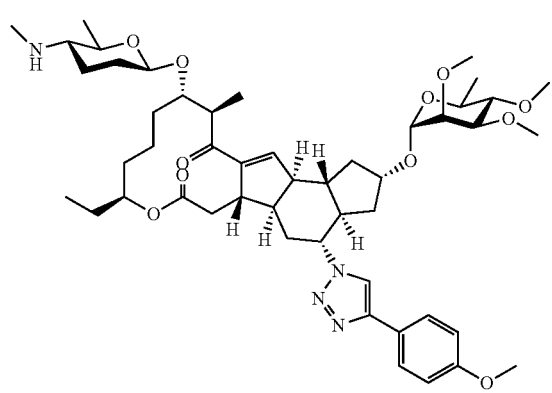
113
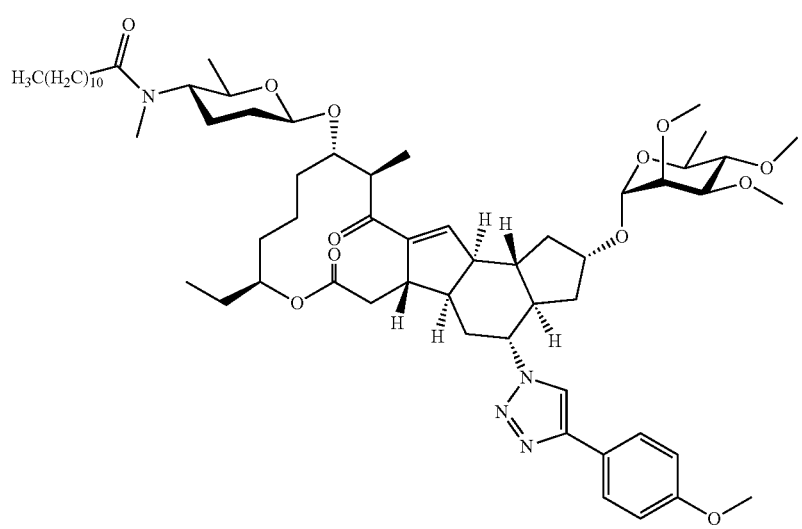
114
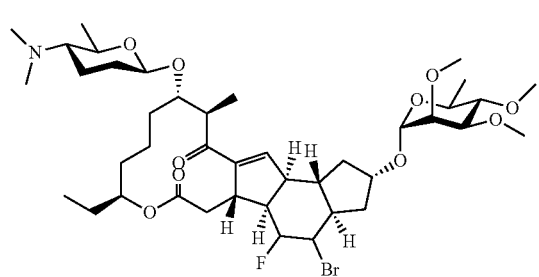
115
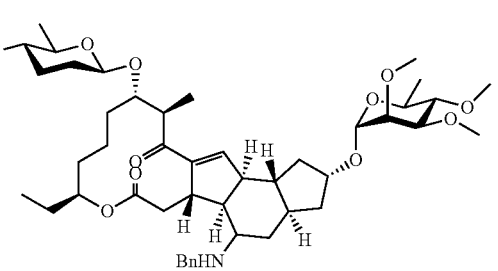
116

-continued
| | |
|---|---|
| 117 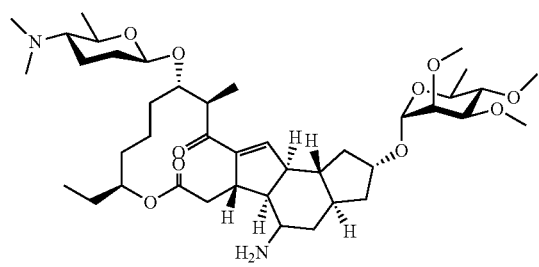 | 118 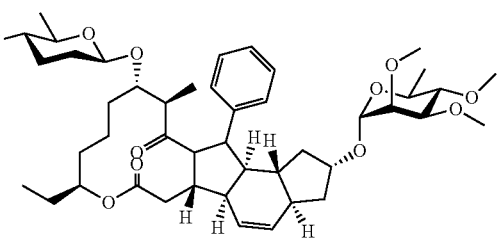 |
| 119 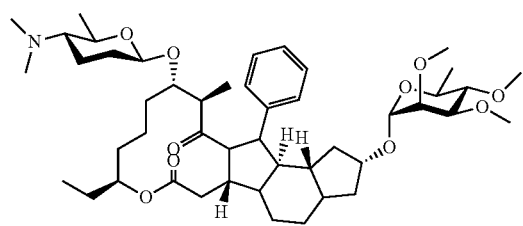 | 120 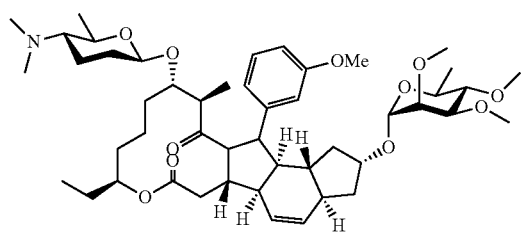 |
| 121 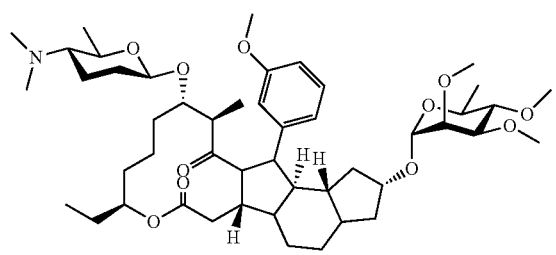 | 122 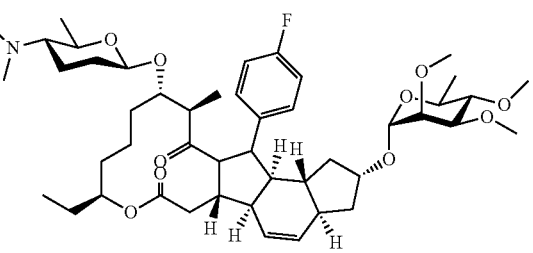 |
| 123 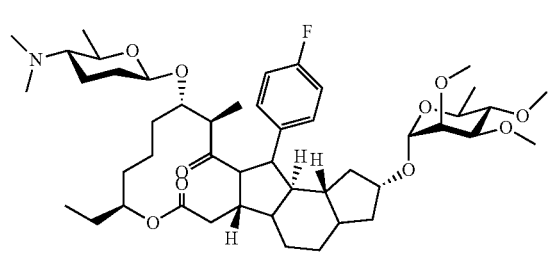 | 124 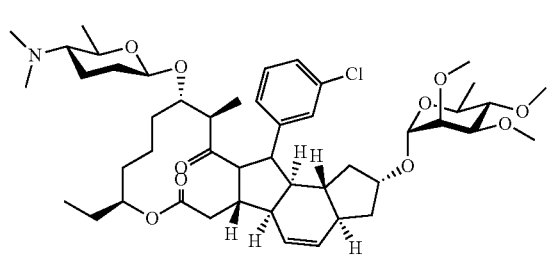 |
| 125 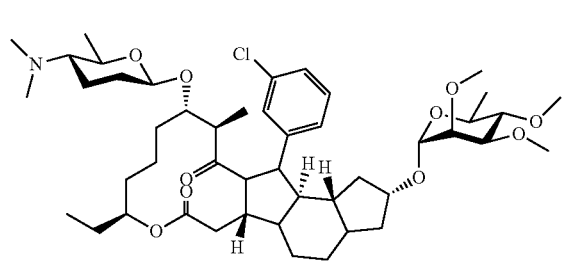 | 126 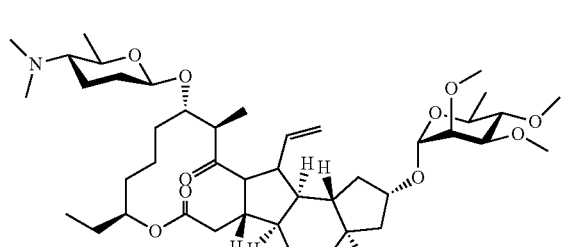 |
| 127 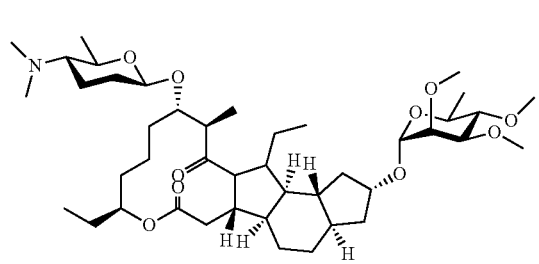 | 128 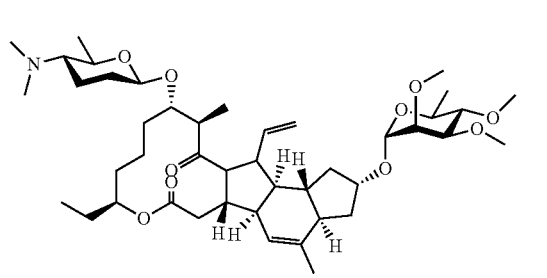 |

-continued

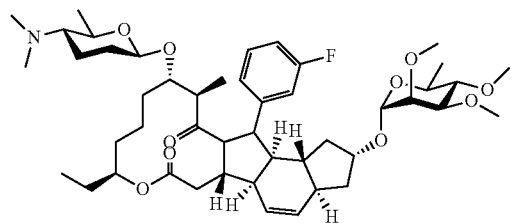

129

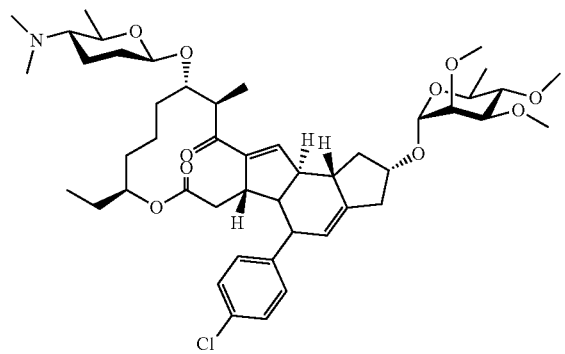

130

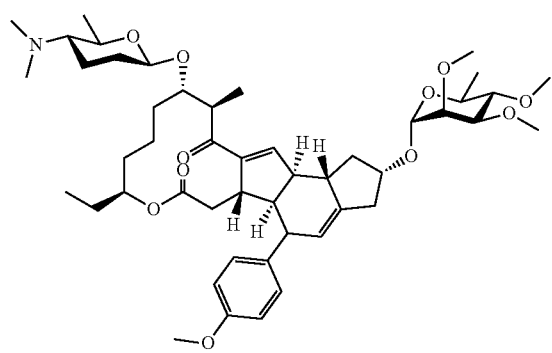

131

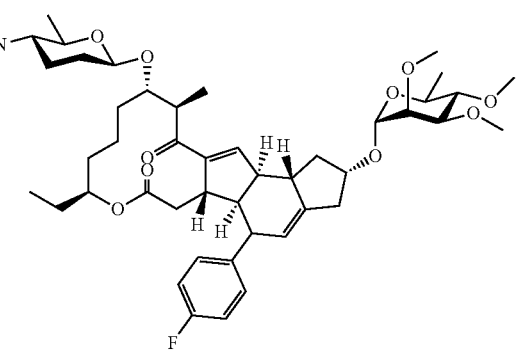

132

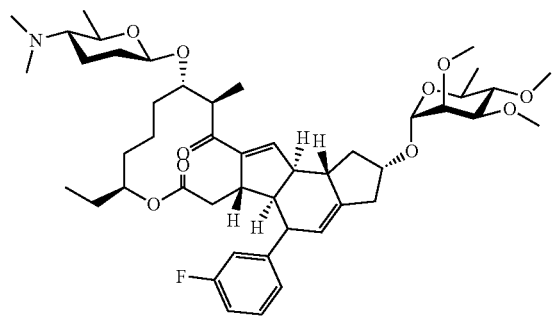

133

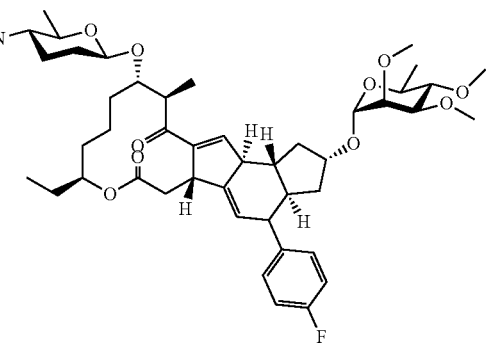

134

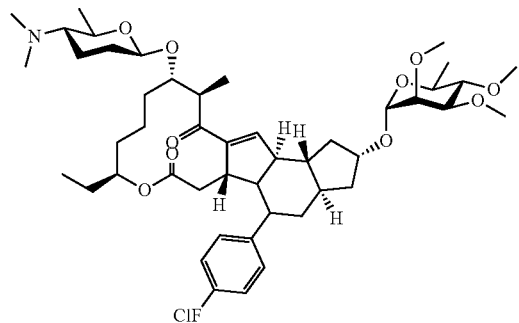

135

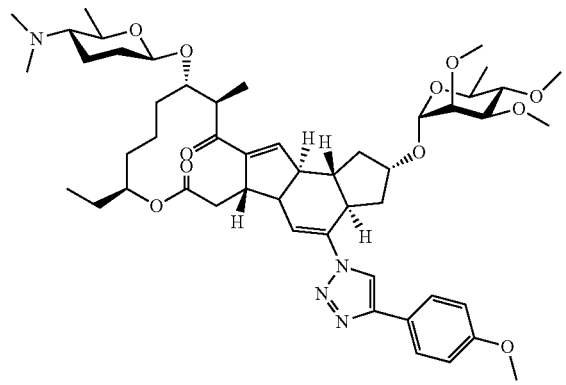

136

Where substituent groups are specified by their conventional chemical formulae, written from left to right, the structures optionally also encompass the chemically identical substituents, which would result from writing the structure from right to left, e.g., —CH$_2$O— is intended to also optionally recite —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9\text{-}10}$, oleoyl chain or the diunsaturated $C_{9\text{-}10,\ 12\text{-}13}$ linoeyl chain.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). Each of the above terms (e.g., "alkyl," "heteroalkyl," "aryl" and "heteroaryl") are meant to optionally include both substituted and unsubstituted forms of the indicated radical.

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The compounds described herein can be prepared using spinosyn precursor, spinosyn, or spinosyn analogue starting materials, such as those set forth in U.S. Pat. No. 5,362,634. As used herein, spinosyn precursors, spinosyns, or spinosyn analogue starting materials used in the synthetic methods include any tetracyclic spinosyn molecule comprising a polyketide-derived tetracyclic macrolide appended with two saccharides.

Compounds described by Formula I and pharmaceutically acceptable salts thereof can be made using the methods shown in Scheme 1, which depicts the synthesis of compounds of Formula I wherein $R^2$ is an aryl group.

Scheme 1

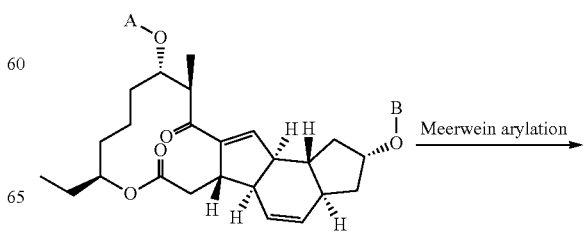

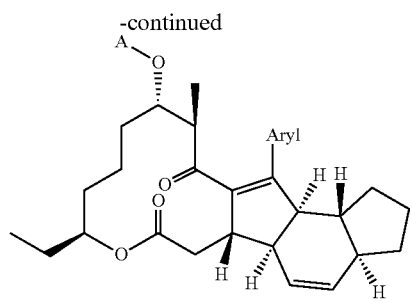

In the Meerwein acylation method (Meerwein et al., 1939, *J. Prakt. Chem.* 52:237) shown above in Scheme 1, the aryl group is added to an electron-poor alkene using an aryl diazonium salt (such as $ArN_2Br$ or $ArN_2I$), optionally supported by a metal salt (such as Cu(I)Br or KOAc) in a solvent at temperatures varying from −78° C. to the reflux temperature of solvent used. The solvent can be, for example, dichloromethane or ethyl acetate.

Compounds described by Formula I and pharmaceutically acceptable salts thereof can be made using the methods shown in Scheme 2, which depicts the synthesis of compounds of Formula I wherein $R^4$ is a substitution group (i.e., non-hydrogen).

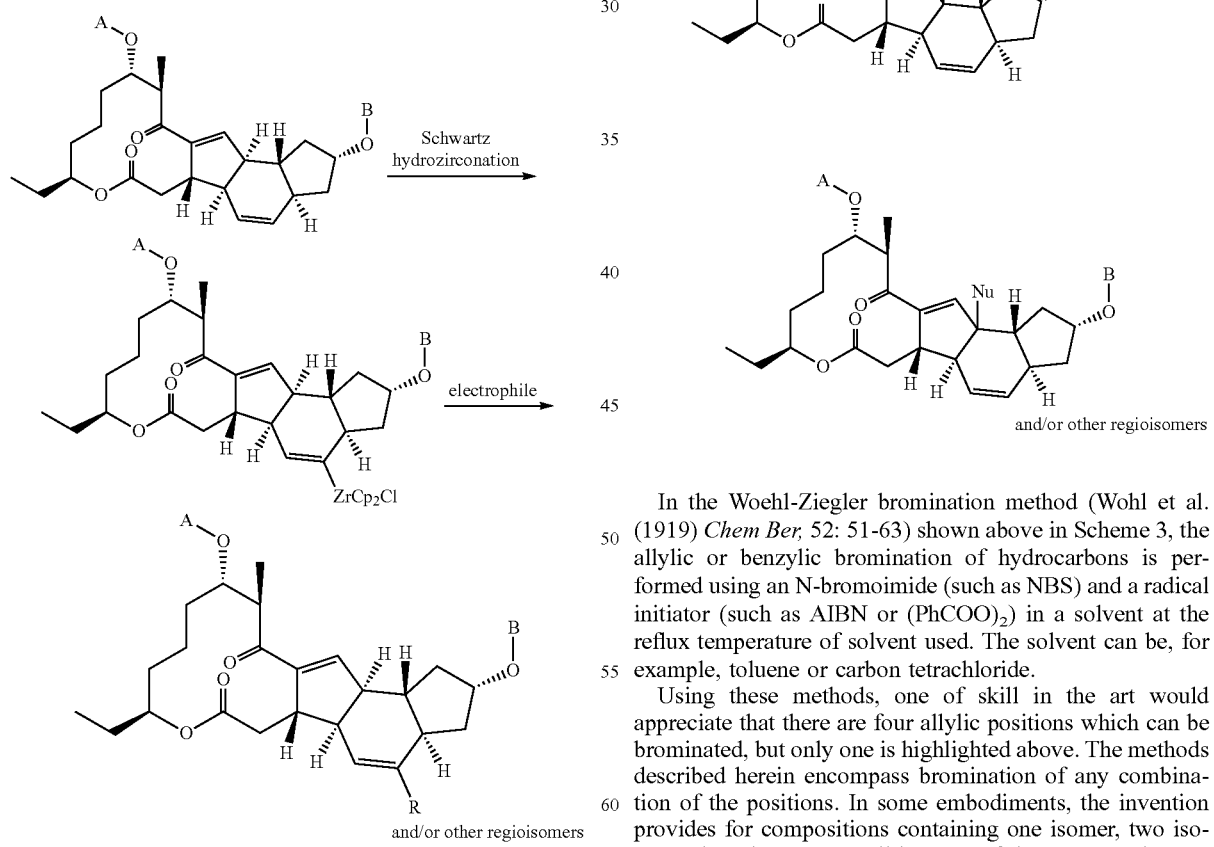

In the Schwartz hydrozirconation method (Hart et al., 2007, *J. Am. Chem. Soc.* 96 (26): 8115-8116) shown above in Scheme 2, Schwartz's reagent $(C_5H_5)_2ZrHCl$ (also called zirconocene hydrochloride or zirconocene chloride hydride) adds Zr—H across unsaturated hydrocarbons in a solvent at temperatures below 50° C. The solvent can be, for example, benzene or toluene.

Compounds described by Formula I and pharmaceutically acceptable salts thereof can be made using the methods shown in Scheme 3, which depicts the synthesis of compounds of Formula I wherein $R^5$ is a substitution group (i.e., non-hydrogen).

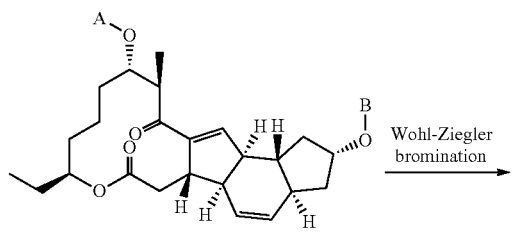

In the Woehl-Ziegler bromination method (Wohl et al. (1919) *Chem Ber*, 52: 51-63) shown above in Scheme 3, the allylic or benzylic bromination of hydrocarbons is performed using an N-bromoimide (such as NBS) and a radical initiator (such as AIBN or $(PhCOO)_2$) in a solvent at the reflux temperature of solvent used. The solvent can be, for example, toluene or carbon tetrachloride.

Using these methods, one of skill in the art would appreciate that there are four allylic positions which can be brominated, but only one is highlighted above. The methods described herein encompass bromination of any combination of the positions. In some embodiments, the invention provides for compositions containing one isomer, two isomers, three isomers, or all isomers of the compound.

Compounds described by Formula I and pharmaceutically acceptable salts thereof can be made using the methods shown in Scheme 4, which depicts the synthesis of compounds of Formula I wherein $R^3$ and $R^4$ are substitution groups (i.e., non-hydrogen).

Scheme 4

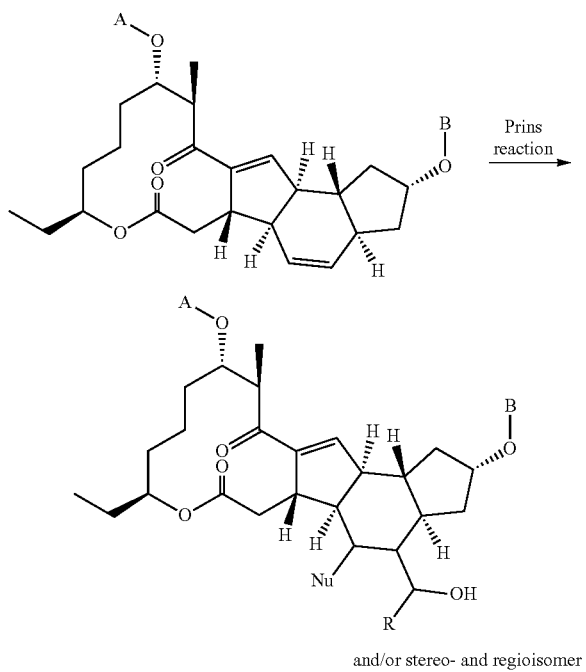

and/or stereo- and regioisomer

In the Prins reaction method (Chavre et al. (2008) *J. Org. Chem.* 73:7467-7471) shown above in Scheme 4, an aldehyde or ketone is added to an alkene or alkyne followed by capture of a nucleophile (such as water or amine) in a solvent at temperatures varying from −78° C. to the reflux temperature of solvent used. The solvent can be, for example, dichloromethane or ethyl acetate.

Compounds described by Formula I and pharmaceutically acceptable salts thereof can be made using the methods shown in Scheme 5, which depicts the synthesis of compounds of Formula I wherein $R^2$ is a substitution group (i.e., non-hydrogen).

Scheme 5

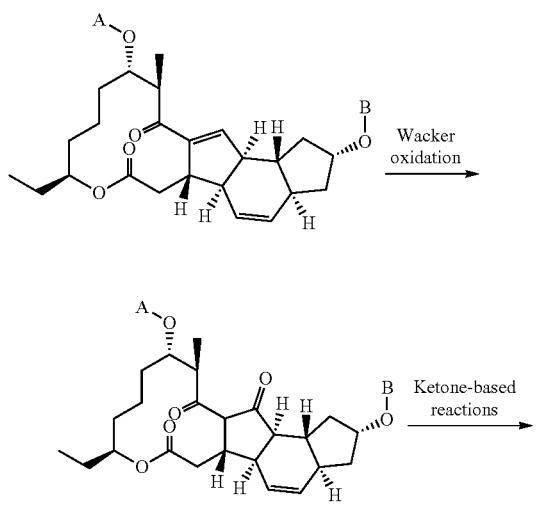

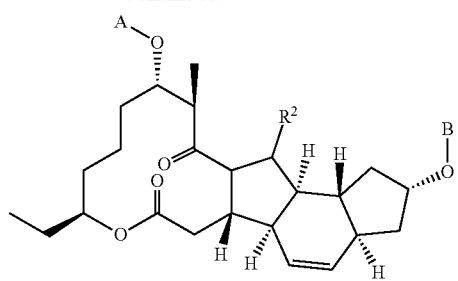

In the Wacker oxidation method (Smidt et al., 1959, Cons. elektrochem. Ind., DE 1 049 845, 1959) shown above in Scheme 5, the alkene is converted into a ketone using tetrachloropalladate(II) in a solvent at temperatures varying from −78° C. to the reflux temperature of solvent used. The solvent can be, for example, toluene or dimethylformamide.

Compounds described by Formula I and pharmaceutically acceptable salts thereof can be made using the methods shown in Scheme 6, which depicts the synthesis of compounds of Formula I wherein $R^3$ and $R^4$ combine to form an oxetane ring.

Scheme 6

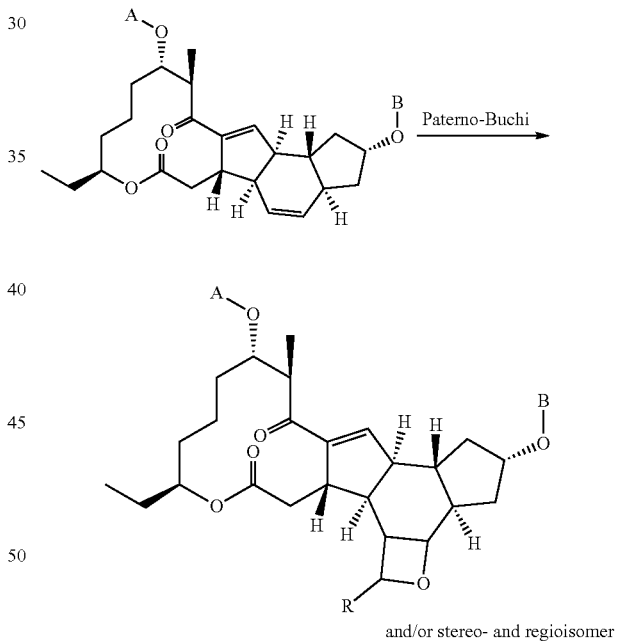

and/or stereo- and regioisomer

In the Paterno-Buchi reaction method (Büchi et al., 1998, *J Amer Chem Soc* 76(17):4327-4331) shown above in Scheme 6, a photochemical reaction is performed that forms four-membered oxetane rings from a carbonyl and an alkene in a solvent at the reflux temperature of the solvent. The solvent can be, for example, toluene or carbon tetrachloride.

Compounds described by Formula I and pharmaceutically acceptable salts thereof can be made using the methods shown in Scheme 7, which depicts the synthesis of compounds of Formula I wherein $R^3$ and $R^4$ combine to form a cyclopropyl ring.

Scheme 7

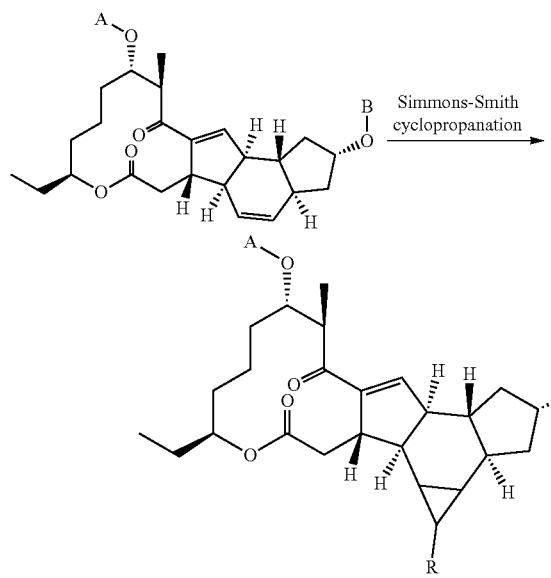

In the Simmons-Smith cyclopropanation reaction (Smith, 1958, *J. Am. Chem. Soc.* 80:5323) method shown above in Scheme 7, an organozinc carbenoid reacts with the alkene in the spinosyn compound to form a cyclopropane in a solvent at temperatures varying from −78° C. to the reflux temperature of solvent used. The solvent can be, for example, diethyl ether or ethyl acetate.

Compounds described by Formula I and pharmaceutically acceptable salts thereof can be made using the methods shown in Scheme 8, which depicts the synthesis of compounds of Formula I wherein $R^3$ and $R^4$ combine to form a cyclopentenyl ring.

Scheme 8

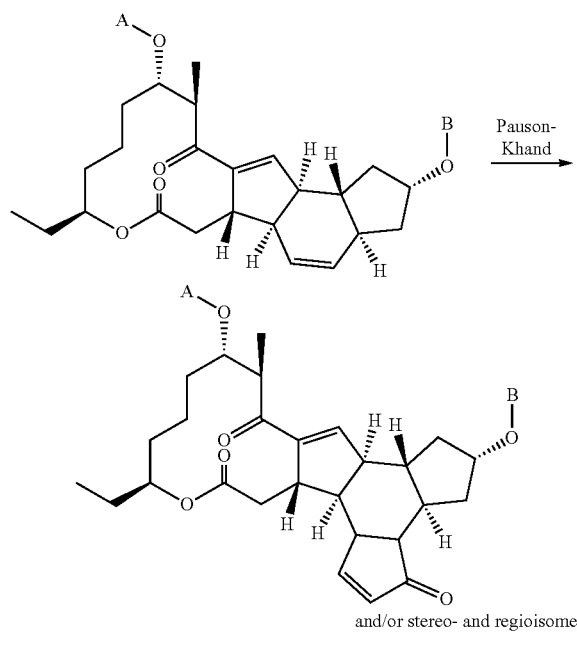

In the Pauson-Khand reaction (Pauson et al., 1977, *Ann. N.Y. Acad. Sci.* 295:2) method shown above in Scheme 8, a [2+2+1] cycloaddition is conducted between an alkyne, an alkene and carbon monoxide to form a α,β-cyclopentenone in a solvent at the reflux temperature of the solvent. The solvent can be, for example, toluene or acetone.

Compounds described by Formula I and pharmaceutically acceptable salts thereof can be made using the methods shown in Scheme 9, which depicts the synthesis of compounds of Formula I wherein $R^3$ and $R^4$ combine to form a β-lactam.

Scheme 9

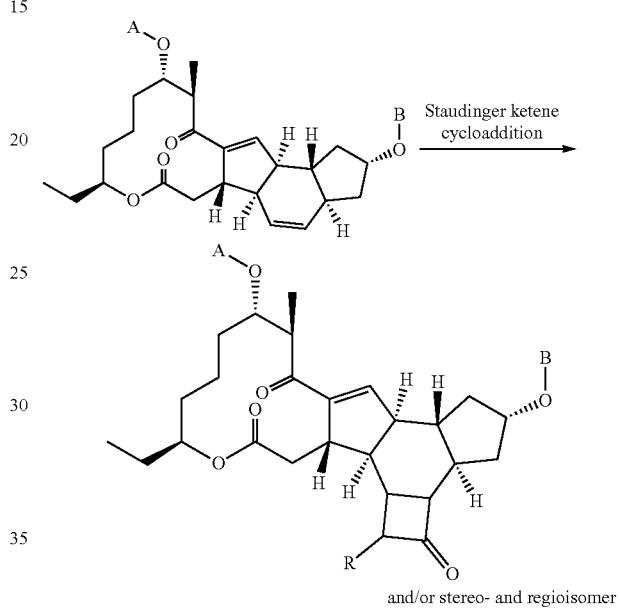

In the Staudinger ketene cycloaddition reaction (Staudinger, 1907, *Justus Liebigs Ann. Chem.* 356:51-123) method shown above in Scheme 9, an imine reacts with a ketene through a non-photochemical 2+2 cycloaddition to produce a β-lactam in a solvent (such as DCM or PhMe) at temperatures varying from 0° C. to the reflux temperature of solvent used. The solvent can be, for example, dichloromethane or toluene.

Compounds described by Formula I and pharmaceutically acceptable salts thereof can be made using the methods shown in Scheme 10, which depicts the synthesis of compounds of Formula I wherein $R^3$ and $R^4$ combine to form a cyclobutyl ring.

Scheme 10

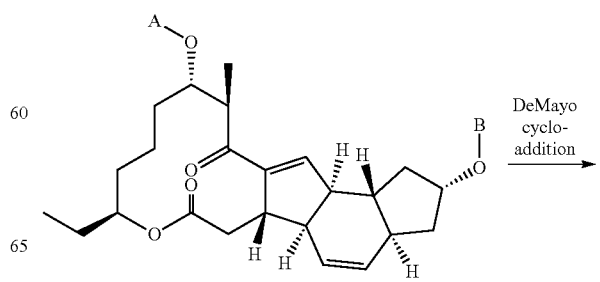

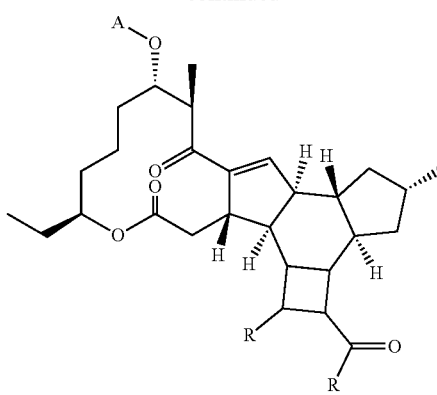

and/or stereo- and regioisomer

In the DeMayo cycloaddition reaction (DeMayo, 1972, *Can. J. Chem.* 50 (21):3465) method shown above in Scheme 10, a photochemical reaction is performed in which the enol of a 1,3-diketone reacts with an alkene in the spinosyn in a solvent at temperatures varying from −78° C. to the reflux temperature of solvent used and the resulting cyclobutane ring undergoes a retro-aldol reaction to yield a 1,5-diketone. The solvent can be, for example, diethyl ether or dichloromethane.

Compounds described by Formula I and pharmaceutically acceptable salts thereof can be made using the methods shown in Scheme 11, which depicts the synthesis of compounds of Formula I wherein $R^3$ and $R^4$ combine to form a cyclohexenyl ring.

Scheme 11

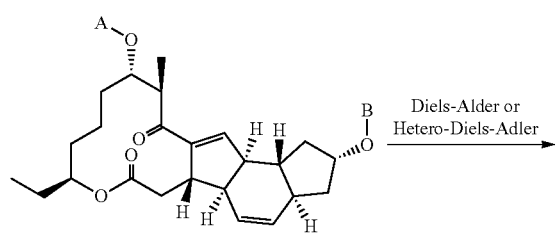

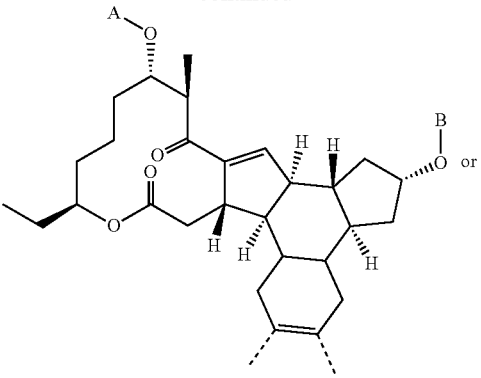

or both, and on both positions and/or stereo- and regioisomer

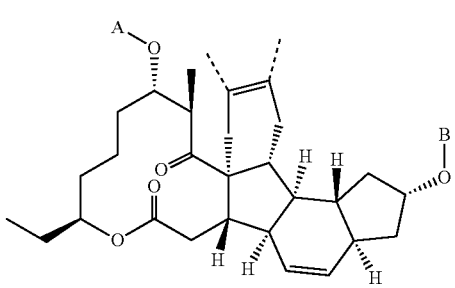

In the Diels-Alder or Hetero Diels-Alder method (Diels et al. *Liebig's Annalen der Chemie* 460:98-122) shown above in Scheme 11, a [4+2] cycloaddition occurs between a diene and an alkene in the spinosyn to form a substituted cyclohexene system in a solvent at the reflux temperature of the solvent. The solvent can be, for example, dichloromethane or toluene.

Optionally, the starting spinosyn compound can be subjected to ozonolysis to yield intermediates which then undergo aldehyde-based reactions or conjugation modification on the carboxylic acid. Optionally, the double bond between the carbons substituted with $R^1$ and $R^2$ is selectively reduced prior to ozonolysis.

The saccharide groups optionally present as A and B in the compounds according to Formula I (e.g., forosamine and rhamnose) can be modified by methods in the art and retain pesticidal activity. For example, forosamine can be replaced by certain nitrogen-containing sugars and non-sugar substituents with retention of some degree of activity (Scheme 12). See, Gaisser et al. (2002) *Chem. Comm.* 6:618-619; and Gaisser et al. (2009) *Org. Biomol. Chem.* 7:1705-1708, herein incorporated by reference. Likewise, rhamnose replacement analogs may be produced. See, Creemer et al. (2000) *J Antibiotics*, 53:171-178; Sparks et al. (2001) *Pest Manag. Sci.,* 57:896-905, herein incorporated by reference. Activity of the spinosyn derivative can be retained after changes in the structure of the rhamnose, especially certain modifications at C-2' and C-3' of the tri-O-methylrhamnose moiety.

Scheme 12

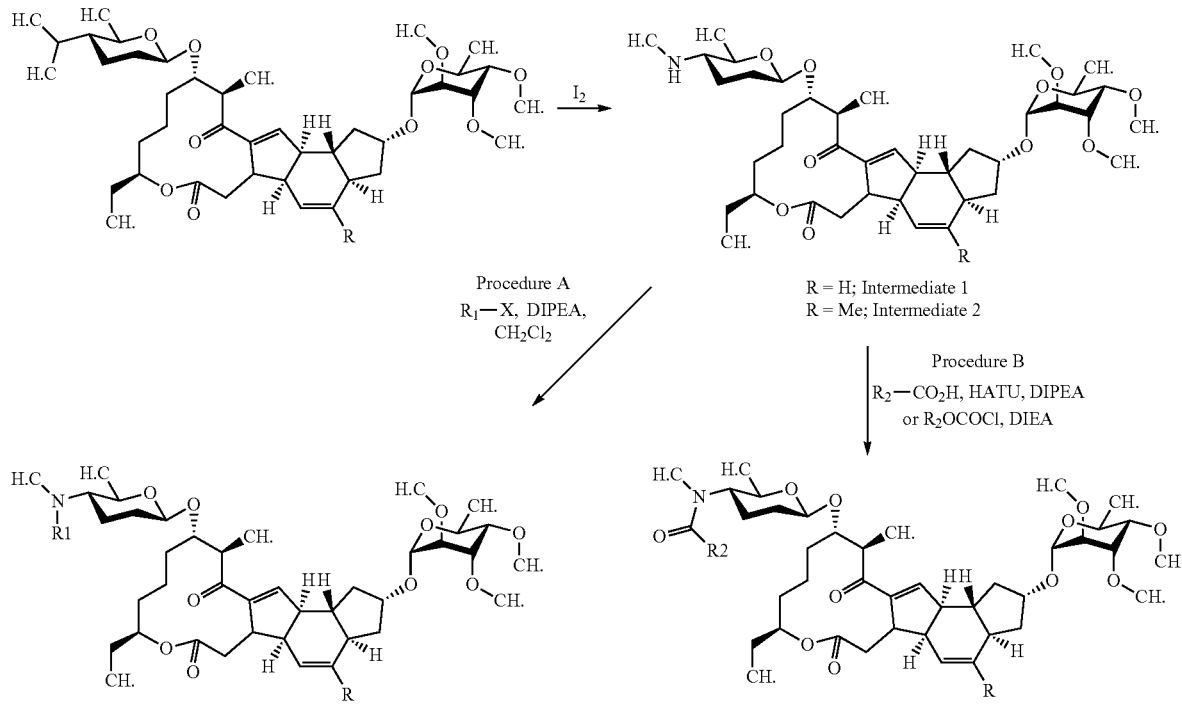

Other methods of sugar modification can be made and are well known in the art. See, Kirst et al. (2002) *Curr. Top. Med. Chem.* 2:675-699. In some embodiments, one or more of the saccharide moieties is replaced with another natural or a synthetic sugar. Synthetic sugars include modified sugars. As used herein, a "modified sugar" is covalently functionalized with a "modifying group." Useful modifying groups include, but are not limited to, water-soluble polymers, therapeutic moieties, diagnostic moieties, biomolecules and the like. Addition or removal of any saccharide moieties present on the precursor or substrate is accomplished either chemically or enzymatically.

In some embodiments, chemical deglycosylation can be used by exposure of the spinosyn compounds described herein to the compound trifluoromethanesulfonic acid, or an equivalent compound. This treatment results in the cleavage of most or all sugars except the linking sugar (N-acetylglucosamine or N-acetylgalactosamine), while leaving the remainder of the molecule intact. See, Hakimuddin et al. (1987) *Arch. Biochem. Biophys.* 259:52 and Edge et al. (1981) *Anal. Biochem.* 118:131. Enzymatic cleavage of carbohydrate moieties on peptide variants can be achieved by the use of a variety of endo- and exo-glycosidases as described by Thotakura et al. (1987) *Meth. Enzymol.* 138: 350. Chemical addition of glycosyl moieties is carried out by any art-recognized method. See, for example, U.S. Pat. Nos. 5,876,980, 6,030,815, 5,728,554, 5,922,577 and WO 2004/99231.

III. Formulations

The compounds described herein or salts thereof can be provided in a formulation or composition. The spinosyn derivatives of the invention may be prepared in compositions for control of pests. Compositions are prepared according to the procedures and formulas which are conventional in the agricultural or pest control art. The compositions may be concentrated and dispersed in water or may be used in the form of a dust, bait or granular formulation. The dispersions are typically aqueous suspensions or emulsions prepared from concentrated formulations of the compounds. The water-soluble or water-suspension or emulsifiable formulations are either solids, wettable powders, or liquids, known as emulsifiable concentrates or aqueous suspensions. Wettable powders may be agglomerated or compacted to form water dispersible granules. These granules comprise mixtures of compound, inert carriers and surfactants. The concentration of the compound is typically between about 0.1% to about 90% by weight. The inert carrier is typically attapulgite clays, montmorillonite clays and the diatomaceous earths or purified silicates.

Surfactants comprise typically about 0.5% to about 10% of the wettable powder. Surfactants include sulfonated lignins, condensed napthalene-sulfonates, the napthalene-sulfonates, alkyl-benenesulfonates, alkysulfonates or nonionic surfactants such as ethylene oxide adducts of alkylphenols or mixtures thereof. Emulsifiable concentrates of the derivatives of the invention typically range from about 50 to about 500 grams of spinosyn derivative per liter of liquid, equivalent to about 10% to about 50%, dissolved in an inert carrier which is a mixture of a water immiscible solvent and emulsifiers. Organic solvents include organics such as xylenes, and petroleum fractions such as high-boiling naphthlenic and olefinic portions of petroleum which include heavy and aromatic naphtha. Other organics may also be used such as terpenic solvents-rosin derivatives, aliphatic ketones such as cyclohexanone and complex alcohols. Emulsifiers for emulsifiable concentrates are typically mixed ionic and/or nonionic surfactants such as those mentioned herein or their equivalents.

Aqueous suspensions may be prepared containing water-insoluble spinosyn derivatives, where the compounds are dispersed in an aqueous vehicle at a concentration typically in the range of between about 5% to about 50% by weight. The suspensions are prepared by finely grinding the compound and vigorously mixing it into a vehicle of water, surfactants, and dispersants. Inert ingredients such as inorganic salts and synthetic or natural gums may also be employed to increase the density and/or viscosity of the aqueous vehicle as is desired.

Precipitated flowables may be prepared by dissolving at least one spinosyn derivative of the invention in a water-miscible solvent and surfactants or surface active polymers. When these formulations are mixed with water, the active spinosyn derivative precipitates with the surfactant controlling the size of the resulting micro-crystaline precipitate. The size of the crystal can be controlled through the selection of specific polymer and surfactant mixtures.

The spinosyn derivatives may also be applied as a granular composition that is applied to the soil. The granular composition typically contains from about 0.5% to about 10% by weight of the derivative. The spinosyn derivative is dispersed in an inert carrier which is typically clay or an equivalent substance. Generally, granular compositions are prepared by dissolving the compounds of the invention in a suitable solvent and applying it to a granular carrier which has been pre-formed to the desirable particle size. The particle size is typically between about 0.5 mm to 3 mm. The granular compositions may also be prepared by forming a dough or paste of the carrier and compound, drying the combined mixture, and crushing the dough or paste to the desired particle size.

The spinosyn derivative may also be combined with an appropriate organic solvent. The organic solvent is typically a bland petroleum oil that is widely used in the agricultural industry. These combinations are typically used as a spray. More typically, the spinosyn compounds are applied as a dispersion in a liquid carrier, where the liquid carrier is water. The compounds may also be applied in the form of an aerosol composition. The compound is dissolved in an inert carrier, which is a pressure-generating propellant mixture. The aerosol composition is packaged in a container, where the mixture is dispersed through an atomizing valve. Propellant mixtures contain either low-boiling halocarbons, which may be mixed with organic solvents or aqueous suspensions pressurized with inert gases or gaseous hydrocarbons.

The compounds may be applied to any locus inhabited by an insect or mite. Such locus typically is cotton, soybean and vegetable crops, fruit and nut trees, grape vines, houses and ornamental plants. The amount of the spinosyn derivative applied to the loci of insects and mites can be determined by those skilled in the art. Generally, the concentrations of from about 10 ppm to about 5,000 ppm provide the desired control. For crops such as soybeans and cotton, the rate of application is about 0.01 to about 1 kg/ha, where the spinosyn derivative is applied in a 5 to 50 gal/A spray formulation.

The composition can be formulated in a liquid concentrate, ready-to-use (RTU) liquid spray, dust, or solid form. The formulation chosen will depend on the use of the product.

The following general treatment methods are preferably suitable for carrying out the seed treatment, or plant propagation material treatment, according to the invention: dry treatments (preferably with addition of adhesion promoters such as, for example, liquid paraffin or talc), and, if appropriate, colorants, slurry treatments (preferably with addition of wetters, dispersants, emulsifiers, adhesives, inert fillers and colorants), aqueous liquid treatments (preferably with addition of emulsifiers, dispersants, thickeners, antifreeze agents, polymers, adhesives and colorants), solvent-based liquid treatments (with addition of solvents and colorants), emulsion treatments (with addition of emulsifiers, solvents and colorants).

The total active spinosyn derivative in the treatment formulations preferably amounts to 10 to 80% by weight. For example, the total active spinosyn compound can amount to 10% by weight, 20% by weight, 30% by weight, 40% by weight, 50% by weight, 60% by weight, 70% by weight, or 80% by weight. Generally, about 1 to about 300 g of spinosyn derivative are applied to every 100 kg of seed or plant propagation material in the form of a treatment.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex, and diet of the subject, the mode and time of administration, rate of excretion, drug combination, and severity of the particular condition. The precise dose to be employed in the formulation will also depend on the route of administration, and the seriousness of the infection, and should be decided according to the judgment of the practitioner and each subject's circumstances.

IV. Methods of Use

The spinosyn compounds described herein have insecticidal and pesticidal activity against pests, including insects, arachnids and nematodes. Therefore, the compounds and formulations as described herein can be used for controlling, inhibiting, and/or inactivating a pest of interest. The spinosyn compounds and formulations described herein provide a key source of agrichemicals with activities against crop pest species. In some instances, the compounds and formulations can be used in animal health. The spinosyn compounds and formulations described herein may possess one or more the following characteristics as compared to natural spinosyns: increased potency; reduced risk to non-target species; lower potential for environmental damage; minimal cross-resistance to other pesticides; and may overcome existing pest resistance to currently available spinosyn products.

The compounds and formulations described herein are useful in controlling or containing pests populations. The compounds and formulations exhibit potent and broad-spectrum activity against numerous commercially important insect pests. The spectrum of target insects include many species of Lepidoptera and Diptera along with some members of several other insect orders, including planthoppers, leafhoppers, spider mites and cockroaches. The compounds and formulations have potent and broad activity against many problematic larval species of Lepidoptera. Insecticidal activity is generally observed after administration of the spinosyns by a variety of delivery methods, including contact and oral feeding assays.

One skilled the art will appreciate that the compounds, formulations, and methods disclosed herein can be used to treat a variety of home and garden insect and mite pests such as, by way of non-limiting example, members of the insect order Lepidoptera including Southern armyworm, codling moth, cutworms, clothes moths, Indian meal moth, leaf rollers, corn earworm, cotton bollworm (also called Tomato fruit worm), European corn borer, imported cabbageworm, cabbage looper, pink bollworm, American bollworm, tomato hornworm, bagworms, Eastern tent caterpillar, sod webworm, diamondback moth, tomato pinworm, grape berry moth, cotton leafworm, beet armyworm, and fall armyworm; members of the order Homoptera including cotton aphid leafhoppers, plant hoppers, pear *psylla*, scale insects, whiteflies, and spittle bugs; and members of the insect order Diptera including house flies, stable flies, blow flies and mosquitoes; mites; and ants. The compounds and formulations described herein can also be used to treat members of the order Thysanoptera including melon *thrips* and Western flower *thrips*; members of the order Coleoptera, including Colorado potato beetles; members of the order Orthoptera; and Leaf miners of the orders Lepidoptera (moths and butterflies), Hymenoptera (leaf mining sawflies), Coleoptera (beetles), and Diptera (true flies). The compounds and formulations can be used to control and/or treat ants, green peach aphids, adult house flies, western tent caterpillar larvae, and two-spotted spider mites. Generally, the spinosyn compounds and formulations described herein can be active against a number of ectoparasites in a number of animals by a variety of routes. The present compounds and formulations can be used to control a wide variety of arthropod pests.

Representative pests which can be controlled by the present compounds and formulations additionally include: Arachnids, *Amblyomma americanum* (Lone-star tick), *Amblyomma maculatum* (Gulf Coast tick), *Argas persicus* (fowl tick), *Boophilus microplus* (cattle tick), *Chorioptes* spp. (mange mite), *Demodex bovis* (cattle follicle mite), *Demodex canis* (dog follicle mite), *Dermacentor andersoni* (Rocky Mountain spotted fever tick), *Dermacentor variabilis* (American dog tick), *Dermanyssus gallinae* (chicken mite), *Ixodes ricinus* (common sheep tick), *Knemidokoptes gallinae* (deplumming mite), *Knemidokoptes mutans* (scaly-leg mite), *Otobius megnini* (ear tick), *Psoroptes equi* (scab mite), *Psoroptes ovis* (scab mite), *Rhipicephalus sanguineus* (brown dog tick), *Sarcoptes scabiei* (mange mite), Insects—*Aedes* (mosquitoes), *Anopheles* (mosquitoes), *Culex* (mosquitoes), Culiseta, *Bovicola bovis* (cattle biting louse), *Callitroga homnivorax* (blowfly), *Chrysops* spp. (deer fly), *Cimex lectularius* (bed bug), *Cochliomyia* spp. (screwworm), *Ctenocephalides canis* (dog flea), *Ctenocephalides felts* (cat flea), *Culicoides* spp. (midges, sandflies, punkies, or no-see-ums), *Damalinia ovis* (sheep biting louse), *Dermatobia* spp. (warble fly), *Gasterophilus haemorrhoidalis* (nose bot fly), *Gasterophilus intestinalis* (common horse bot fly), *Gasterophilus nasalis* (chin fly), *Glossina* spp. (tsetse fly), *Haematobia irritans* (horn fly, buffalo fly), *Haematopinus asini* (horse sucking louse), *Haematopinus eurysternus* (short nosed cattle louse), *Haematopinus ovillus* (body louse), *Haematopinus suis* (hog louse), *Hydrotaea irritans* (head fly), *Hypoderma bovis* (bomb fly), *Hypoderma lineatum* (heel fly), *Linognathus ovillus* (body louse), *Linognathus pedalis* (foot louse), *Linognathus vituli* (long nosed cattle louse), *Lucilia* spp. (maggot fly), *Melophagus ovinus* (sheep ked), *Musca* spp. (house fly, face fly), *Oestrus ovis* (nose bot fly), *Pediculus* spp. (lice), *Phlebotomus* spp. (sandfly), *Phormia regina* (blowfly), *Psorophora* spp. (mosquito), *Pthirus* spp. (lice), *Reduvius* spp. (assassin bug), *Simulium* spp. (black fly), *Solenopotes capillatus* (little blue cattle louse), *Stomoxys calcitrans* (stable fly), *Tabanus* spp. (horse fly), *Tenebrio* spp. (mealworms), *Triatoma* spp. (kissing bugs). Likewise, the spinosyn derivatives are useful against pests including: from the order of the Isopoda, for example, *Oniscus asellus, Armadillidium vulgare, Porcellio scaber*; from the order of the Diplopoda, for example, *Blaniulus guttulatus*; from the order of the Chilopoda, for example, *Geophilus carpophagus, Scutigera* spp; from the order of the Symphyla, for example, *Scutigerella immaculata*; from the order of the Thysanura, for example, *Lepisma saccharina*; from the order of the Collembola, for example, *Onychiurus armatus*; from the order of the Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis, Schistocerca gregaria*; from the order of the Dermaptera, for example, *Forficula auricularia*; from the order of the Isoptera, for example, *Reticulitermes* spp.; from the order of the Anoplura, for example, *Phylloxera vastatrix, Pemphigus* spp., *Pediculus humanus corporis, Haematopinus* spp., *Linognathus* spp; from the order of the Mallophaga, for example, *Trichodectes* spp., *Damalinea* spp.; from the order of the Thysanoptera, for example, *Frankliniella occidentalis, Hercinothrips femoralis, Thrips palmi, Thrips tabaci*; from the order of the Heteroptera, for example, *Eurygaster* spp., *Dysdercus intermedius, Piesma quadrata, Cimex lectularius, Rhodnius prolixus, Triatoma* spp.; from the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima, Tortrix viridana, Cnaphalocerus* spp.; from the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Antho nomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Oulema oryzae, Lissorhoptrus oryzophilus*; from the order of the Hymenoptera, for example, *Diprion* spp., *Hoplocampa* spp., *Lasius* spp., *Monomorium pharaonis, Vespa* spp.; from the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Liriomyza* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa*; from the order of the Siphonaptera, for example, *Xenopsylla cheopis, Ceratophyllus* spp.; from the order of the Arachnida, for example, *Scorpio maurus, Latrodectus mactans*; from the order of the Acarina, for example, *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp.

Insects that can be controlled with the aid of the compounds and formulations described herein include those of the following orders: soil-dwelling insects: Diptera (for example the frit-fly, wheat-bulb fly), Coleoptera (for example *Diabrotica* (wire worm), Lepidoptera (for example dart moth), Blattophtheroidea, Myriopoda. Leaf insects: Aphidina, Coleoptera, Brachycera, Lepidotera, Homoptera, Tysanoptera, Aleurodina, Cicadina, Acasi, Cossina, Heteroptera.

Methods for controlling insect and mite pests are also provided. A method can include providing a formulation that has an effective amount of at least one spinosyn compound as described herein, at least one of an additional insecticide and miticide, and at least one of a solvent or an acceptable carrier, and administering an effective amount of the formulation to control pests. Where the formulation is a liquid, the method can further include administering an effective amount of the formulation such that an effective amount of the formulation contacts pests, plants and plant products, the vicinity of the pests, and/or the vicinity of the plants and plant products. Where the formulation is a dust or a solid, administering an effective amount of the formulation can include placing an effective amount of the composition in a vicinity of pests and/or placing an effective amount of the composition in a vicinity of plants and plant products to be protected.

An effective amount of the spinosyn compound or formulation as described herein is an amount to control or kill the target pest. The use rates vary widely and are highly impacted by the target pest, target pest size and number, host crop and crop age, climate and economic threshold or acceptable damage. In general, a typical use rate is set at about 1 ppm (1 mg a.i./kg of grain). For use on crops, between about 25 and about 200 grams per hectare (0.023 and 0.184 lbs per acre) of active ingredient is used. Turf rates are 88-450 g a.i./ha (0.078-0.4 lb ai/acre). Ornamental rates are 0.046-0.17 lb ai/100 gallons or 55-204 ppm. There is typically a positive temperature correlation that results in better activity with higher temperatures. Performance against some pests, such as leafminers and *thrips*, are positively impacted by the addition of nominal rates of penetrating surfactants such as crop oils.

All animals are subject to attack by such pests, though the problems are most severe among vertebrate hosts. Accordingly, the spinosyn compounds and formulations described herein can be used on humans, livestock animals, (cattle, sheep, pigs, goats, buffalo, water buffalo, deer, rabbits, chickens, turkeys, ducks, geese, ostriches, and the like), horses and other pleasure animals, mink and other animals grown for their fur, rats, mice, other animals used in laboratory and research settings, companion animals such as dogs and cats, fish, crustacea, and other aquatic animals. In short, the spinosyn compounds and formulations described herein are useful for treatment of the whole range of animals.

Arthropod pests are inhibited or killed on a host animal by contacting the pest with an effective amount of a spinosyn compound as described herein.

Techniques for delivering the compounds and formulations described herein are well known to those skilled in the art. In general, a present formulation comprising at least one spinosyn compound is applied to the exterior surface of an animal, whereby it contacts pests already present on the host as well as those which arrive on the host's body within the efficacy period. Typically, the spinosyn compound is formulated in a liquid formulation which is sprayed onto the animal's surface or poured onto the animal's surface. Another conventional treatment is a "dip", whereby cattle are treated by being substantially immersed in a dilute solution containing the spinosyn compound. For some hosts and pests, the formulation can be a dust, which is sprinkled onto the host, or a shampoo or cream which is employed in bathing the animal. Collars on cats and dogs can also be employed as a way of delivering the derivatives directly to the animal's surface.

The compounds and formulations described herein can also be applied to locations frequented by animals, so that pests are thereby contacted by the compound even as in direct application to the host. Application to pet bedding can be used, as well as application to carpeting. For cattle, dusting bags can be used. These are positioned in a doorway where the cattle inevitably rub against the bag and pests are contacted by the present compound.

Optionally, the present compounds and formulations can be used to control insects and arachnids which are pests in the feces of cattle and other animals. The compounds and formulations can be administered orally and the compounds travel through the intestinal tract and emerge in the feces. Control of pests in the feces indirectly protects the animals from the pests.

The formulations can include other active ingredients and/or plant or plant product treatment compounds. Optionally, the formulation can include a contact-acting insecticide and/or miticide. Exemplary contact-acting insecticides and/or miticides include those derived from fatty acids, fatty acid esters, fatty acid sugar esters, and fatty acid salts, pyrethrum extract, plant oils and their salts, vegetable oils and their salts, essential oils, mineral oils, pyrethrum extract, and combinations thereof. The contact-acting insecticide and/or miticide can also include avermectins. One skilled in the art will appreciate that the resulting spinosyn-containing compositions and formulations disclosed herein are not only pesticidally effective, but also environmentally sound and safe for human use. Further, some of the compositions and formulations can be residual in that they do not leach out of baits or easily wash off of the leaves during rain, and thus can protect against insect and mite pests during and after rainy weather. Optionally, the compositions and formulations can exhibit synergy, and result in better than expected results than just the spinosyn or the insecticide or miticide treatment alone.

The compounds and formulations described herein may be applied to the foliage of a plant which a pest might feed on. Additionally, the compounds may be used orally or topically to control pests on animals.

Oral administration may be carried out using tablets and animal feeds. For some animals, such as certain cats, administration is best accomplished by using an acceptable liquid formulation that is administered directly or added to their food ration. Especially useful methods of orally administering the spinosyn derivatives are by administering it in chewable tablets or treats and animal feeds.

The spinosyn compounds and formulations described herein are also useful for the treatment of animals to control arthropods, i.e., insects and arachnids, which are pests on animals. These arthropod pests typically attack their hosts on the external ("ecto") surface; agents which control such pests are referred to as "ectoparasiticides".

The spinosyn compounds are formulated for use as ectoparasiticides in manners known to those skilled in the art. In general, a formulation will include a compound as described herein and one or more physiologically acceptable adjuvants. Formulations include concentrated versions, in which the present active agent is present in a concentration of from 0.001 to 98.0 percent, with the remaining content being physiologically acceptable carriers. Such formulations, especially those with less than 50 percent of the present compound, can sometimes be used directly, but these formulations can also be diluted with other physiologically acceptable carriers to form more dilute treating formulations. These latter formulations can include the active agent in lesser concentrations of from 0.001 to 0.1 percent.

In another embodiment, the present compounds are usefully combined with other ectoparasiticides or with anthelmentics, the latter also known as endoparasiticides ("endo"=internal, controlling internal parasites which are typically platyhelminthes and nemathelminthes). Representative such endoparasiticides include the following: Abamectin, Albendazole, Avermectin, Bunamidine, Coumaphos, Dichlorvos, Doramectin, Epsiprantel, Febantel, Fenbendazole, Flubendazole, Ivermectin, Levamisole, Mebendazole, Milbemycin, Morantel, Moxidectin, Netobimin, Niclosamide, Nitroscanate, Oxfendazole, Oxibendazole, Piperazine, Praziquantel, Pyrantel, Ricombendazole, Tetramisole, Thiabendazole, Clorsulon, Closantel, Diamphenethide, Nitroxynil, Oxyclozanide, Rafoxanide, Triclabendazole.

Representative ectoparasiticides include the following: Abamectin, Alphamethrin, Amitraz, Avermectin, Coumaphos, Cycloprothrin, Cyfluthrin, Cyhalothrin, Cypermethrin, Cyromazine, Deltamethrin, Diazinon, Diflubenzuron, Dioxathion, Doramectin, Famphur, Fenthion, Fenvalerate, Flucythrinate, Flumethrin, Hexaflumuron, Ivermectin, Lindane, Lufenuron, Malathion, Methoprene, Metriphonate, Moxidectin, Permethrin, Phosme, Pirimiphos, Propetamphos, Propoxur, Rotenone, Temephos, Tetrachlorvinphos, Trichlorfon, Zetacypermethrin, B.t. Biotoxins and Boric Acid.

The formulations described herein can further include, in combination with the spinosyn component, one or more other compounds that have activity against the specific ectoparasite or endoparasite to be controlled, such as, for example, synthetic pyrethroids, natural pyrethins, organophosphates, organochlorines, carbamates, foramidines, avermectins, milbemycins, insect growth regulators (including chitin synthesis inhibitors, juvenile hormone analogs, and juvenile hormones), nitromethylenes, pyridines and pyrazoles. In an exemplary embodiment, the composition can include an additional contact-acting insecticide and/or miticide. The compositions can be utilized as liquid concentrates, Ready-To-Use (RTU) liquid sprays, dusts, or solids, depending upon the needs of the user. In use, the composition can be applied to the pests themselves, in the vicinity of the pests, and/or in the vicinity of plants and plant products that are to be protected.

The spinosyn compounds and formulations can be used for treating the soil, for treating seed or plant propagation material, and for drenching and irrigating plants. The following exemplary types of seed and plant propagation material can be treated: Maize, cereals (such as, for example, wheat, barley, oats, rye), rice, seed potatoes, cotton, oilseed rape, sunflower, beet (such as, for example, sugar beet), vegetable seed (such as, for example, onion, cabbage, tomato), (fodder) legumes, peanuts, soya, sorghum, and the like.

It is advantageous to apply granules comprising the active compound described herein into or onto the soil. Examples of suitable applications include broadcast, band, furrow and planting-hole application.

It is particularly advantageous to emulsify or dissolve the spinosyns or their salts in water and to use this for irrigating the plants. Examples of suitable applications are spraying onto the soil, drenching, i.e. irrigating the plants with active-compound-containing solutions, and drip irrigation, and also use in hydroponic systems, in particular in the production of vegetables and ornamentals.

Seed treatments are suitable for controlling animal pests, preferably arthropods and nematodes, in particular insects and arachnids, which are found in agriculture and in forests. They are effective against normally-sensitive and resistant species and against all or individual developmental stages.

In some embodiments, the spinosyn compounds and formulations described herein can be used for promoting or accelerating wound healing in a mammal comprising administering at least one spinosyn compound or a physiologically acceptable derivative or salt thereof, to a mammal in need thereof. In this manner, the spinosyn compounds and formulations can be used for the manufacture of a medicament for promoting or accelerating wound healing in animals, including humans. See, for example, U.S. Pat. No. 8,536,142.

As used herein the terms treatment, treat, or treating refer to a method of reducing one or more symptoms of a disease, infection, or condition. Thus in the disclosed method, treatment can refer to a 10%, 20%, 30%, 40%, 50%, 60%, 70%, 80%, 90%, or 100% reduction in the severity of one or more symptoms of the disease, infection, or condition. For example, a method for treating an infection is considered to be a treatment if there is a 10% reduction in one or more symptoms or signs of the infection in a subject as compared to a control. As used herein, control refers to the untreated condition. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, infection, condition, or symptoms of the disease, infection, or condition.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats;

mice; pigs; and goats. Non-mammals include, for example, fish and birds.

1. A spinosyn compound of the following formula:

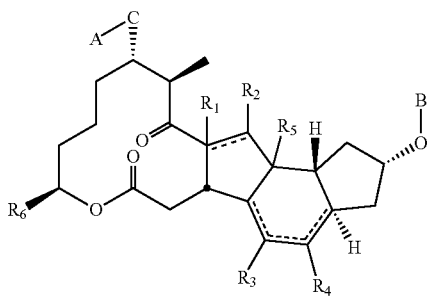

or a salt thereof, wherein:

≡ is a single bond or a double bond;

A is hydrogen or is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl;

B is selected from the group consisting of substituted or unsubstituted cycloalkyl, substituted or unsubstituted heterocycloalkyl, substituted or unsubstituted aryl, and substituted or unsubstituted heteroaryl;

C is O or NH;

$R^1$ is absent or is selected from hydrogen, hydroxyl, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;

$R^2$, $R^3$, and $R^4$ are each independently selected from hydrogen, hydroxyl, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl; and $R^5$ is hydrogen, halogen, hydroxyl, substituted or unsubstituted amino, substituted or unsubstituted thio, or substituted or unsubstituted alkoxy; and $R^6$ is substituted or unsubstituted alkyl or substituted or unsubstituted aryl, wherein optionally $R^1$ and $R^2$ or $R^3$ and $R^4$ combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl.

2. The spinosyn compound of paragraph 1, wherein A comprises forosamine.

3. The spinosyn compound of paragraph 1 or 2, wherein B comprises rhamnose or a (2R,5S)-4-ethoxy-3,5-dimethoxy-6-methyloxan-2-yl group or a (2R,5S)-3,4,5-dimethoxy-6-methyloxan-2-yl group.

4. The spinosyn compound of any of paragraphs 1-3, wherein $R^1$ is absent or is selected from substituted or unsubstituted $C_{1-6}$ alkyl and aryl, and wherein $R^2$, $R^3$, and $R^4$ are each independently selected from substituted or unsubstituted $C_{1-6}$ alkyl and aryl.

5. The spinosyn compound of any of paragraphs 1-3, wherein $R^1$ and $R^2$ combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl.

6. The spinosyn compound of any of paragraphs 1-3, wherein $R^3$ and $R^4$ combine to form a substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, and substituted or unsubstituted heteroaryl.

7. The spinosyn compound of any of paragraphs 1-4, wherein $R^5$ is hydrogen and $R^6$ is ethyl.

8. The spinosyn compound of any of paragraphs 1-4, having the formula represented by Structure I-A:

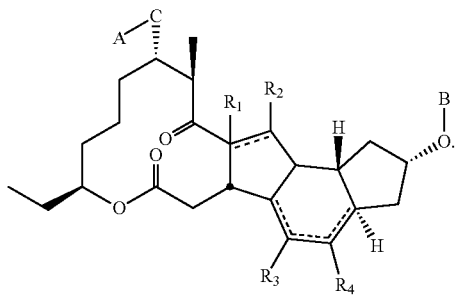

9. The spinosyn compound of any of paragraphs 1-4, wherein A is forosamine; B is 3,4,5-trimethoxyrhamnose; C is O; $R^1$ is absent; $R^2$, $R^3$, and $R^5$ are hydrogen; and $R^6$ is ethyl.

10. The spinosyn compound of any of paragraphs 1-4, having the formula represented by Structure I-B:

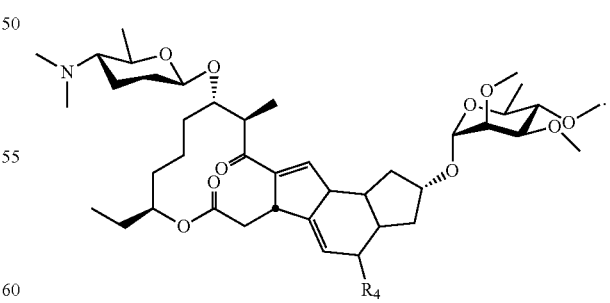

11. The spinosyn compound of any of paragraphs 1-4, wherein A is forosamine; B is 3,4,5-trimethoxyrhamnose; C is O; $R^1$ is absent; $R^2$, $R^4$, and $R^5$ are hydrogen; and $R^6$ is ethyl.

12. The spinosyn compound of any of paragraphs 1-4, having the formula represented by Structure I-C:

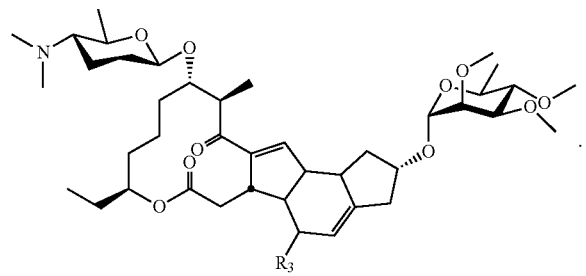

13. The spinosyn compound of any of paragraphs 1-4 or 6, wherein A is forosamine; B is 3,4,5-trimethoxyrhamnose; C is O; $R^1$ is absent, $R^2$ and $R^5$ are hydrogen, and $R^6$ is ethyl, and $R^3$ and $R^4$ join to form a cyclopentanone ring or a cyclopentenone ring optionally substituted with $R^7$, wherein $R^7$ is hydrogen, alkyl, pyridiminyl, and/or substituted or unsubstituted phenyl.

14. The spinosyn compound of paragraph 1, having the formula represented by Structure I-D:

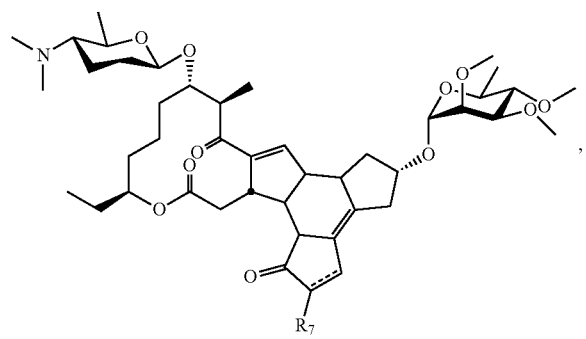

wherein $R^7$ is hydrogen, alkyl, pyridiminyl, and/or substituted or unsubstituted phenyl.

15. The spinosyn compound of any of paragraphs 1-4 or 6, wherein B is 3,4,5-trimethoxyrhamnose; C is O; $R^1$ is absent; $R^2$, $R^3$, and $R^5$ are hydrogen; and $R^4$ is hydrogen or methyl; $R^6$ is ethyl, and wherein A is a forosamine derivative comprising one or both of the methyl groups on the forosamine nitrogen group substituted with substituted or unsubstituted alkyl, substituted or unsubstituted cycloalkyl, substituted or unsubstituted heterocycloalkyl, substituted or unsubstituted alkenyl, substituted or unsubstituted aryl, substituted or unsubstituted heteroaryl, substituted or unsubstituted aldehyde, substituted or unsubstituted benzyl, or substituted or unsubstituted benzoyl.

16. The spinosyn compound of any of paragraphs 1-4, having the formula represented by Structure I-E:

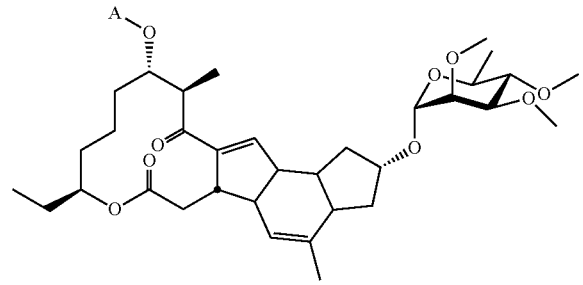

or Structure I-E':

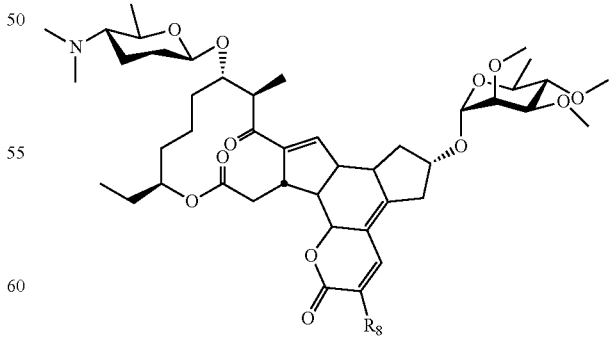

wherein A is a forosamine derivative comprising one or both of the methyl groups on the forosamine nitrogen group substituted with substituted or unsubstituted alkyl, substituted or unsubstituted cycloalkyl, substituted or unsubstituted heterocycloalkyl, substituted or unsubstituted alkenyl, substituted or unsubstituted aryl, substituted or unsubstituted heteroaryl, substituted or unsubstituted aldehyde, substituted or unsubstituted benzyl, or substituted or unsubstituted benzoyl.

17. The spinosyn compound of any of paragraphs 1-4 or 6, wherein A is forosamine; B is 3,4,5-trimethoxyrhamnose; C is O; $R^1$ is absent, $R^2$ and $R^5$ are hydrogen, $R^6$ is ethyl, and $R^3$ and $R^4$ join to form a δ-valerolactone ring optionally substituted with $R^8$, which may optionally contain a double bond, wherein $R^8$ is alkyl, substituted or unsubstituted phenyl, pyrimidinyl, or a thiophene group.

18. The spinosyn compound of any of paragraphs 1-4 or 6, having the formula represented by Structure I-F:

wherein $R^8$ is alkyl, substituted or unsubstituted phenyl, pyrimidinyl, or a thiophene group.

19. The spinosyn compound of any of paragraphs 1-4, wherein A is forosamine; B is 3,4,5-trimethoxyrhamnose; C is O; $R^1$ is absent, $R^2$ and $R^5$ are hydrogen, one of $R^3$ and $R^4$ is carbonyl, the other of $R^3$ and $R^4$ is alkoxy or hydroxyl, and $R^6$ is ethyl.

20. The spinosyn compound of any of paragraphs 1-4, having the formula represented by Structure I-G:

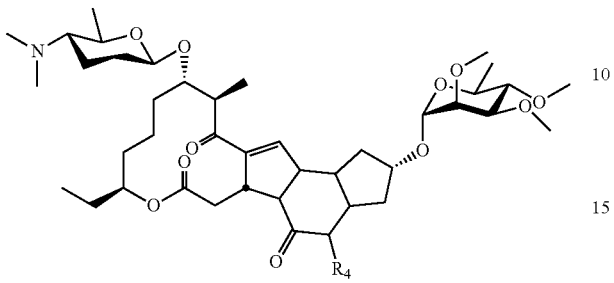

or Structure I-G':

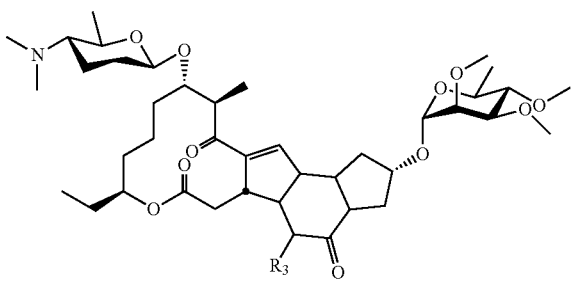

wherein the one of $R^3$ and $R^4$ that is not carbonyl is alkoxy or hydroxyl.

21. The spinosyn compound of any of paragraphs 1-4, wherein A is forosamine; B is 3,4,5-trimethoxyrhamnose; C is O; $R^1$ is absent, $R^2$ and $R^5$ are hydrogen, one of $R^3$ and $R^4$ is a substituted triazole, the other of $R^3$ and $R^4$ is selected from hydrogen, hydroxyl, and halogen and $R^6$ is ethyl, and $R^9$ is selected from alkyl, thiophene, trimethylsiloxy, $C_1$-$C_4$ methyl ester, substituted or unsubstituted phenyl, wherein the substituted phenyl may have one or more $R^9$ substitutions including but not limited to halogen, alkyl, halo alkyl, alkoxy, haloalkoxy, or ester, and wherein the substituted phenyl triazole may have one or more substitutions including but not limited to halogen, alkyl, alkoxy, phenyl, and amino.

22. The spinosyn compound of any of paragraphs 1-4, having the formula represented by Structure I-H:

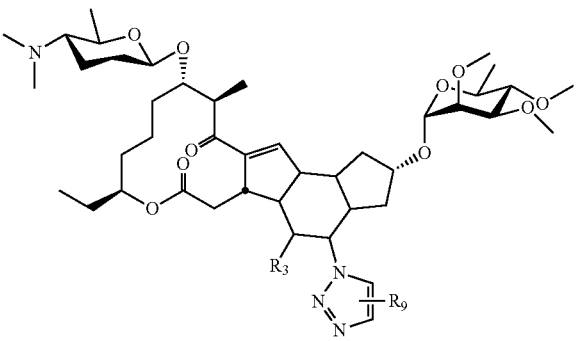

or Structure I-H':

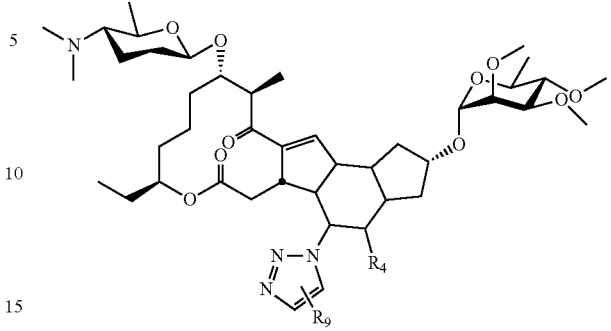

wherein the one of $R^3$ and $R^4$ that is not a substituted triazole is selected from hydrogen, hydroxyl, and halogen; and $R^9$ is selected from alkyl, thiophene, trimethylsiloxy, $C_1$-$C_4$ methyl ester, substituted or unsubstituted phenyl, wherein the substituted phenyl may have one or more $R^9$ substitutions including but not limited to halogen, alkyl, halo alkyl, alkoxy, haloalkoxy, or ester, and wherein the substituted phenyl triazole may have one or more substitutions including but not limited to halogen, alkyl, alkoxy, phenyl, and amino.

23. The spinosyn compound of any of paragraphs 1-4, wherein A is forosamine; B is 3,4,5-trimethoxyrhamnose; C is O; $R^1$, $R^3$, and $R^5$ are hydrogen, $R^4$ is hydrogen or methyl, $R^6$ is ethyl, and wherein $R^2$ is alkyl, alkenyl, or substituted or unsubstituted phenyl, wherein the substituted phenyl may have one or more substitutions including but not limited to halogen, alkyl, halo alkyl, alkoxy, haloalkoxy, or ester.

24. The spinosyn compound of any of paragraphs 1-4, having the formula represented by Structure I-I

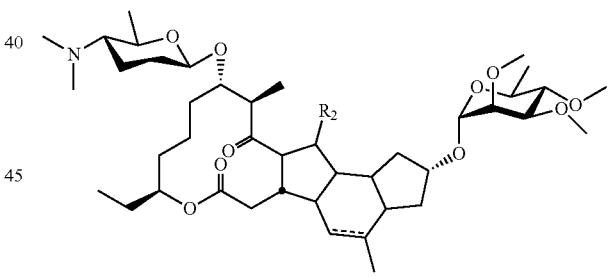

or Structure I-I':

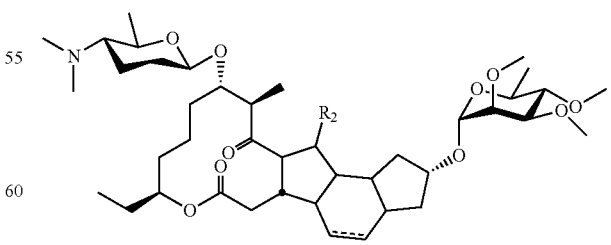

wherein $R^2$ is alkyl, alkenyl, or substituted or unsubstituted phenyl, wherein the substituted phenyl may have one or more substitutions including but not limited to halogen, alkyl, halo alkyl, alkoxy, haloalkoxy, or ester.

25. A formulation, comprising at least one spinosyn compound of any of paragraphs 1-24 and an acceptable carrier.

26. The formulation of paragraph 25, further comprising at least one additional active ingredient.

27. The formulation of paragraph 25 or 26, further comprising at least one plant or plant product treatment compound.

28. The formulation of paragraph 26, wherein the at least one additional active ingredient comprises an insecticide or a miticide.

29. The formulation of paragraph 28, wherein the insecticide is a contact-acting insecticide.

30. The formulation of paragraph 28, wherein the miticide is a contact-acting miticide.

31. A method for controlling pests, comprising contacting a pest with an effective amount of a spinosyn compound of any of paragraphs 1-24 or a formulation of any of paragraphs 25-30.

32. The method of paragraph 31, wherein the pest is an insect.

33. The method of paragraph 31, wherein the pest is an arachnid.

34. The method of paragraph 31, wherein the pest is a nematode.

35. A method for making a tetracyclic spinosyn compound, comprising using a substitution modification on a natural spinosyn or spinosyn analogue.

36. The method of paragraph 35, wherein the substitution modification is selected from the group consisting of a Meerwein arylation, a Schwartz hydrozirconation, a Woehl-Ziegler bromination, a Prius reaction, and a Wacker oxidation.

The examples below are intended to further illustrate certain aspects of the methods and compounds described herein, and are not intended to limit the scope of the claims.

EXAMPLES

Example 1: Synthesis of (2R,3aR,5bS,9S,13S,14R, 16aR,16bR)-13-{[(2R,5S,6R)-5-(dimethylamino)-6-methyloxan-2-yl]oxy}-9-ethyl-14-methyl-4-phenyl-2-{[(2R,3R,4R,5S,6S)-3,4,5-trimethoxy-6-methyloxan-2-yl]oxy}-1H,2H,3H,3aH,4H,5bH,6H, 7H,9H,10H,11H,12H,13H,14H,15H,16aH,16bH-as-indaceno[3,2-d]oxacyclododecane-7,15-dione

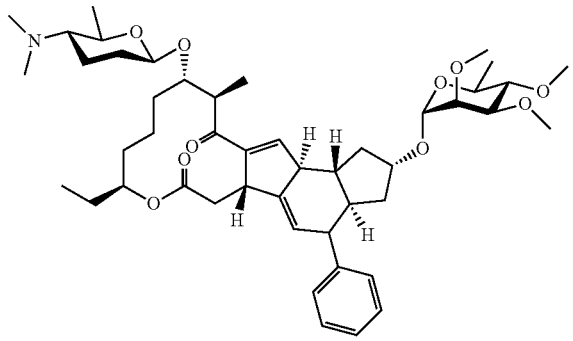

To a mixture of Spinosyn A (200 mg, 0.27 mmol) and iodo-benzene (111 mg, 0.54 mmol) in triethylamine (5 mL) was added palladium acetate (6.1 mg, 0.027 mmol) under nitrogen. The mixture was stirred at 100° C. under nitrogen overnight. The mixture was evaporated under reduced pressure to dryness. The residue was purified by preparative HPLC to give the title compound (24 mg, TFA salt, yield 10.9%) as an oil. Partial $^1$H NMR (DMSO-$d_6$, 400 MHz): δ 9.27 (s, 1H), 7.34-7.31 (m, 3H), 7.22-7.20 (m, 3H), 5.59 (s, 1H), 4.70 (s, 1H), 4.58 (d, J=9.2 Hz, 1H), 4.52-4.48 (m, 1H), 4.25-4.21 (m, 1H). LCMS: m/z 808.5 [M+H]$^+$.

Example 2: Synthesis of (2R,3aR,5bS,9S,13S,14R, 16aR,16bR)-4-(4-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5bH, 6H,7H,9H,10H,11H,12H,13H,14H,15H,16aH,16bH-as-indaceno[3,2-d]oxacyclododecane-7,15-dione

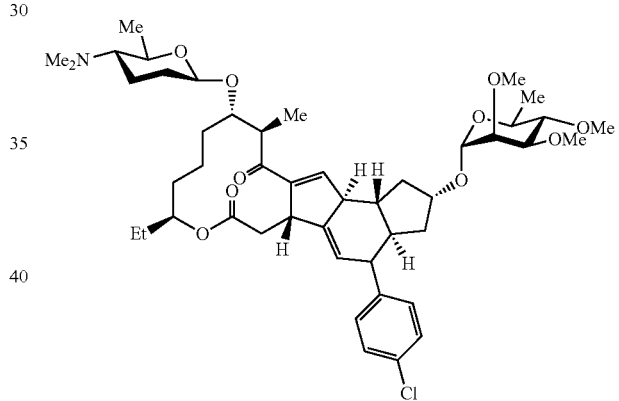

To a mixture of Spinosyn A (1.0 g, 1.37 mmol) and 1-chloro-4-iodo-benzene (980 mg, 4.11 mmol) in triethylamine (15 mL) was added palladium acetate (76 mg, 0.34 mmol) under nitrogen. The mixture was stirred at 100° C. overnight. The mixture was evaporated under reduced pressure. The residue was diluted with ethyl acetate (100 mL) and washed with brine. The organic layer was dried over anhydrous sodium sulfate, filtered, and concentrated. The residue was purified by preparative HPLC to give the title compound (60 mg, yield 5%) as a white solid. Partial $^1$H NMR (CDCl$_3$, 400 MHz): δ7.33 (d, J=8.8 Hz, 2H), 7.22 (d, J=8.4 Hz, 2H), 6.92 (s, 1H), 5.61 (s, 1H), 4.77 (s, 1H), 4.67-4.64 (m, 1H), 4.59-4.57 (m, 1H), 4.39-4.35 (m, 1H), 3.86 (s, 1H), 3.18-3.12 (m, 3H), 2.64 (dd, J=12.8, 2.8 hz, 1H), 2.50-2.44 (m, 1H), 2.20-2.15 (m, 2H), 0.85 (t, J=7.4 Hz, 3H). LCMS: m/z 842.5 [M+H]$^+$.

Example 3: Synthesis of (2S,3aR,5bS,9S,13S,14R, 16aR,16bR)-4-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5bH,6H,7H,9H,10H,11H,12H,13H,14H,15H,16aH,16bH-as-indaceno[3,2-d]oxacyclododecane-7,15-dione

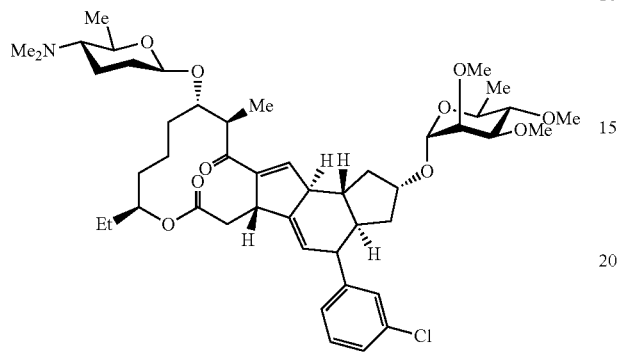

To a mixture of Spinosyn A (500 mg, 0.68 mmol) and 1-chloro-3-iodo-benzene (488 mg, 2.05 mmol) in triethylamine (10 mL) was added palladium acetate (45 mg, 0.20 mmol). The mixture was stirred at 100° C. under nitrogen overnight, cooled to room temperature, and evaporated under reduced pressure. The residue was diluted with ethyl acetate (100 mL), washed with brine, dried over anhydrous sodium sulfate, and filtered. The filtrate was concentrated and the residue was purified by preparative HPLC to give the title compound (46 mg, yield 8%) as a white solid. Partial $^1$H NMR (CDCl$_3$, 300 MHz): δ7.29-7.14 (m, 4H), 6.89 (s, 1H), 5.59 (s, 1H), 4.75 (s, 1H), 4.67-4.54 (m, 2H), 4.37-4.30 (m, 1H), 3.82 (s, 1H), 3.14-3.07 (m, 3H), 2.96-2.70 (m, 7H), 2.63 (dd, J=12.9, 2.7 Hz, 1H), 2.49-2.40 (m, 1H), 2.20-2.08 (m, 2H), 0.85 (t, J=7.5 Hz, 3H). LCMS: m/z 842.5 [M+H]$^+$.

Example 4: Synthesis of (2S,3aR,5bS,9S,13S,14R, 16aR,16bR)-13-{[(2R,5S,6R)-5-(dimethylamino)-6-methyloxan-2-yl]ozy}-9-ethyl-4-(3-fluorophenyl)-14-methyl-2-{[(2R,3R,4R,5S,6S)-3,4,5-trimethoxy-6-methyloxan-2-yl]oxy}-1H,2H,3H,3aH,4H,5bH,6H,7H,9H,10H,11H,12H,13H,14H,15H,16aH,16bH-as-indaceno[3,2-d]oxacyclododecane-7,15-dione

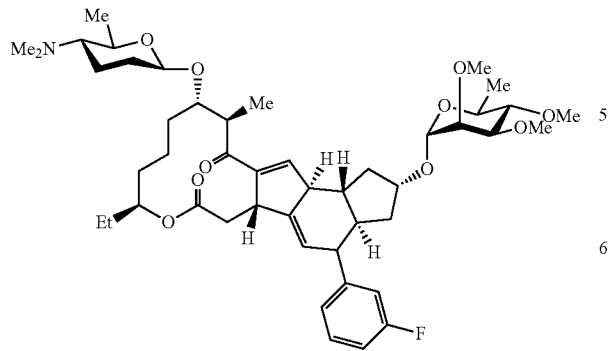

To a mixture of Spinosyn A (500 mg, 0.68 mmol) and 1-chloro-3-fluoro-benzene (453 mg, 2.05 mmol) in triethylamine (10 mL) was added palladium acetate (45 mg, 0.20 mmol). The mixture was stirred at 100° C. under nitrogen overnight, cooled to room temperature, and evaporated under reduced pressure. The residue was diluted with ethyl acetate (100 mL), washed with brine, dried over anhydrous sodium sulfate, and filtered. The filtrate was evaporated in vacuum and the residue was purified by preparative HPLC to give the title compound (40 mg, yield 7%) as a white solid. Partial $^1$H NMR (CDCl$_3$, 300 MHz): δ7.32-7.25 (m, 1H), 7.06-6.88 (m, 4H), 5.60 (s, 1H), 4.75 (s, 1H), 4.67-4.54 (m, 2H), 4.37-4.30 (m, 1H), 3.83-3.82 (m, 1H), 3.18-3.07 (m, 3H), 2.20-2.11 (m, 2H), 0.85 (t, J=7.5 Hz, 3H). LCMS: m/z 826.5 [M+H]$^+$.

Example 5: Synthesis of (2R,3aR,5bS,9S,13S,14R, 16aR,16bR)-13-{[(2R,5S,6R)-5-(dimethylamino)-6-methyloxan-2-yl]oxy}-9-ethyl-4-(4-methoxyphenyl)-14-methyl-2-{[(2R,3R,4R,5S,6S)-3,4,5-trimethoxy-6-methyloxan-2-yl]oxy}-1H,2H,3H,3aH,4H,5bH,6H,7H,9H,10H,11H,12H,13H,14H,15H,16aH,16bH-as-indaceno[3,2-d]oxacyclododecane-7,15-dione

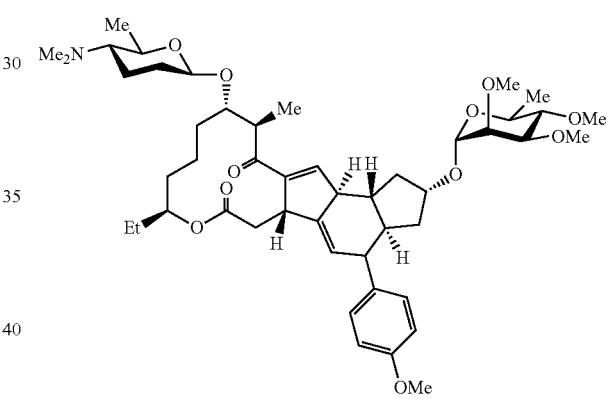

To a solution of bipicoline (70 mg, 0.38 mmol) in dimethylformamide (10 mL) was added palladium acetate (62 mg, 0.27 mmol) under nitrogen. The mixture was stirred for 30 min at room temperature, followed by the addition of Spinosyn A (1.0 g, 1.37 mmol) and 4-methoxyphenylboronic acid (312 mg, 2.06 mmol). The flask was charged with O$_2$ and the reaction mixture was allowed to stir at room temperature for 2 days under O$_2$ (balloon). The reaction mixture was diluted with water (30 mL) and extracted with ethyl acetate (3×50 mL). The combined organic phase was washed with brine (30 mL), dried over anhydrous sodium sulfate, filtered, and concentrated. The residue was purified by preparative HPLC to afford the title compound (110 mg, 13% yield) as a beige solid. Partial $^1$H NMR (400 MHz, Acetone-d$_6$): δ7.13 (s, 1H), 7.07 (d, J=8.4 Hz, 2H), 6.76 (d, J=8.4 Hz, 2H), 5.49 (s, 1H), 4.61 (s, 1H), 4.49-4.43 (m, 1H), 4.36 (d, J=8.4 Hz, 1H), 4.23-4.16 (m, 1H), 3.66 (s, 3H), 3.65-3.62 (m, 1H), 3.06-3.02 (m, 1H), 2.86 (t, J=9.6 Hz, 1H), 3.75-3.71 (m, 1H), 2.72 (dd, J=12.8, 3.2 Hz, 1H), 2.44-2.39 (m, 1H), 0.99 (d, J=6.4 Hz, 3H), 0.77-0.73 (m, 1H), 0.69 (t, J=7.6 Hz, 3H); LC-MS: m/z 838.5 [M+H]$^+$.

Examples 6 and 7: Synthesis of (2S,3aR,4R,5aR, 5bS,9S,13S,14R,16aR,16bS)-13-{[(2R,5S,6R)-5-(dimethylamino)-6-methyloxan-2-yl]oxy}-9-ethyl-4-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione (Example 6), and (2R,3aR,5S,5aR,5bS,9S,13S,14R,16aR,16bR)-13-{[(2R,5S,6R)-5-(dimethylamino)-6-methyloxan-2-yl]oxy}-9-ethyl-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H, 14H,15H,16aH,16bH-as-indaceno[3,2-d]oxacyclododecane-7,15-dione (Example 7)

To a solution of Spinosyn A (10.0 g, 13.66 mmol) in tetrahydrofuran (250 mL) was added $BH_3 \cdot SMe_2$ (10 M, 10.0 mL, 0.1 mol) at room temperature. The resulting mixture was stirred at room temperature overnight. The reaction solution was quenched with water (40 mL) and extracted with dichloromethane (200 mL×2). The organics were dried over sodium sulfate, filtered, and concentrated in vacuum. The residue was dissolved in acetonitrile (200 mL) and water (20 mL), treated with $H_2O_2$ (30% in water, 20 mL) and aqueous NaOH (3 M, 10 mL). The mixture was stirred at r.t. for 2 h, and then quenched with aqueous $NaHSO_3$ (15 mL) at 0° C. The mixture was extracted with dichloromethane (2×200 mL), washed with brine (100 mL), dried over sodium sulfate, filtered and concentrated in vacuum. The residue was purified by column chromatography on silica gel (methanol/dichloromethane=1/20) to afford a mixture of isomers (5.9 g), 0.5 g of the which was further purified by preparative HPLC to afford the title compounds as white solids.

Example 6 (25 mg)

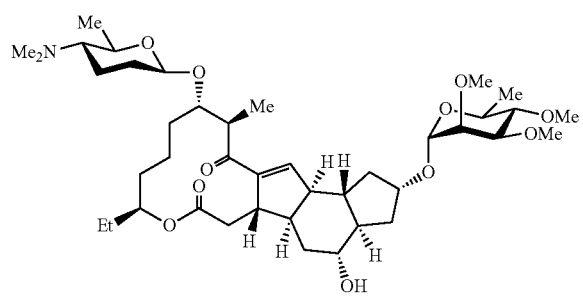

Partial $^1$H NMR ($CDCl_3$, 400 MHz): δ 6.83 (s, 1H), 4.84 (s, 1H), 4.66 (m, 1H), 4.51 (d, J=8.8 Hz, 1H), 4.26 (m, 1H).

Example 7 (40 mg)

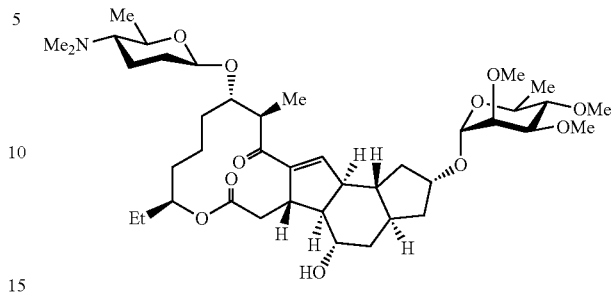

Partial $^1$H NMR ($CDCl_3$, 400 MHz): δ 6.84 (s, 1H), 4.83 (s, 1H), 4.66 (m, 1H), 4.42 (d, J=8.4 Hz, 1H), 4.24 (m, 1H), 4.08 (d, J=0.4 Hz, 1H), 3.00 (m, 1H).

Example 8: Synthesis of (2S,3aR,4S,5aR,5bS,9S, 13S,14R,16aR,16bS)-13-{[(2R,5S,6R)-5-(dimethylamino)-6-methyloxan-2-yl]oxy}-9-ethyl-4-hydroxy-14-methyl-2-{[(2R,3R,4R,5S,6S)-3,4,5-trimethoxy-6-methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-7,15-dione

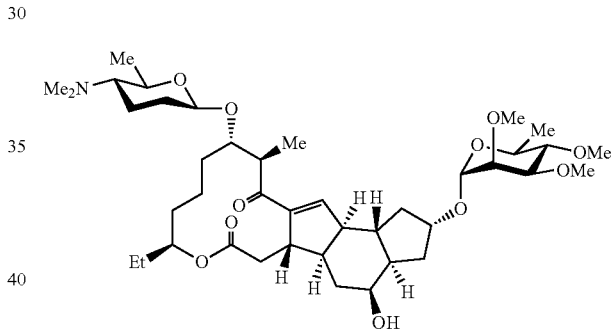

Step 1—To a solution of Spinosyn A (3.0 g, 4.1 mmol) in dichloromethane (100 mL) was added m-CPBA (2.18 g, 12.3 mmol) at 0° C. The resulting mixture was stirred at 0° C. for 1 hour and at room temperature for 1.5 hours. To the mixture was added saturated aqueous $NaHSO_3$ (100 mL) and the mixture was stirred at room temperature for 2 hours. The organic layer was separated and the aqueous was extracted with dichloromethane (100 mL×2). The combined organic phase was washed with brine (300 mL), dried over anhydrous sodium sulfate, concentrated and the residue was purified by column chromatography on silica gel (dichloromethane/methanol=40/1) to give 2.35 g, of a white solid. Partial $^1$H NMR (400 MHz, $CDCl_3$): δ6.58 (s, 1H), 4.85 (1H, s), 4.67-4.65 (m, 1H), 4.43-4.41 (m, 1H), 4.26-4.21 (m, 1H), 3.64-3.52 (m, 1H), 3.27-3.18 (m, 2H), 3.12 (t, J=9.6 Hz, 1H), 2.61-2.56 (m, 1H), 2.43 (dd, J=13.6, 2.4 Hz, 1H), 0.82 (t, J=7.2 Hz, 3H). LCMS: m/z 748.0 [M+H]$^+$.

Step 2—To a solution of PhSeSePh (1.5 g, 4.7 mmol) in ethanol (150 mL) was added sodium borohydride (358 mg, 9.4 mmol) and the mixture was stirred at room temperature for 30 minutes. The white solid from step 1 above was added (2.3 g, 3.1 mmol) and the resulting mixture was stirred at room temperature overnight. The reaction mixture was quenched with water (100 mL) and concentrated under reduced pressure. The residue was extracted with ethyl acetate (100 mL×3). The combined organic phase was washed with brine (300 mL), dried over anhydrous sodium sulfate, concentrated, and the residue was purified by column chromatography on silica gel (dichloromethane/methanol=10/1) to give 1.75 g of a white solid. Partial $^1$H NMR (400 MHz, CDCl$_3$): δ7.64-7.62 (m, 2H), 7.30-7.28 (m, 3H), 6.73 (s, 1H), 4.83 (1H, s), 4.65-4.63 (m, 1H), 4.44-4.42 (m, 1H), 4.26-4.23 (m, 1H), 4.15-4.13 (m, 1H), 3.66-3.63 (m, 1H), 3.31-3.25 (m, 2H), 3.13-3.07 (m, 2H), 3.01 (dd, J=13.6, 4.8 Hz, 1H), 2.94-2.89 (m, 1H), 2.43 (dd, J=13.6, 2.4 Hz, 1H), 2.35-2.28 (m, 7H), 0.82 (t, J=7.2 Hz, 3H). LCMS: m/z 905.9 [M+H]$^+$.

Step 3—A mixture of the white solid from step 2 above (749 mg, 0.83 mmol), Ph$_3$SnH (871 mg, 2.5 mmol), and azobisisobutyronitrile (AIBN; 6 mg, 0.04 mmol) in toluene (40 mL) was stirred at 130° C. for 0.5 hours. The mixture was quenched with water (100 mL). The organic layer was separated and the aqueous was extracted with ethyl acetate (100 mL×2). The combined organic layer was washed with brine (300 mL), dried over anhydrous sodium sulfate and concentrated. The residue was purified by preparative TLC (dichloromethane/methanol=10/1) to give the title compound (390 mg, 63%) as a white solid. Partial $^1$H NMR (400 MHz, CDCl$_3$): δ6.81 (s, 1H), 4.84 (1H, s), 4.64-4.60 (m, 1H), 4.48-4.45 (m, 1H), 4.24-4.21 (m, 1H), 4.15-4.14 (m, 1H), 3.30-3.27 (m, 2H), 3.14-3.07 (m, 2H), 1.16 (d, J=6.9, 3H), 0.81 (t, J=7.2 Hz, 3H). LCMS: m/z 750.5 [M+H]$^+$.

Example 9 and 10: (2S,3aR,5aR,5bS,9S,13S,14R,16aR,16bS)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-4,7,15-trione (9), and (2R,3aS,5aR,5bS,9S,13S,14R,16aR,16bR)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-5,7,15-trione (10)

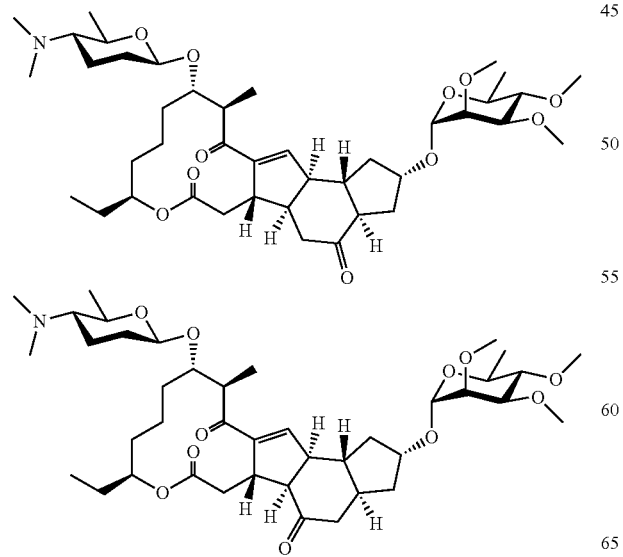

To a solution of the mixture of Examples 6 and 7 (2.0 g, 2.7 mmol) in dichloromethane (20 mL) was added Dess-Martin reagent (4.0 g, 10.3 mmol). The mixture was stirred at room temperature overnight. The reaction was quenched with saturated aqueous sodium bicarbonate (50 mL) and extracted with dichloromethane (3×30 mL). The combined organic phase was washed with brine (30 mL), dried with sodium sulfate and concentrated to give the crude product which was purified by prep-HPLC to give compound Example 9 (150 mg) and Example 10 (100 mg) as white solid.

Example 9: Partial $^1$H NMR (CDCl$_3$, 400 MHz): 6.68 (s, 1H), 4.82 (s, 1H), 4.68 (br, 1H), 4.41-4.39 (m, 1H), 4.26-4.23 (m, 1H), 3.71-3.60 (m, 1H), 3.34-3.19 (m, 3H), 3.12-2.86 (m, 3H), 2.64-2.58 (m, 1H), 2.48-2.36 (m, 3H), 2.31-2.22 (m, 9H), 2.11-1.73 (m, 6H), 0.80-0.76 (t, J=8 Hz, 3H). LC-MS: m/z 748.3[M+H]$^+$.

Example 10: Partial $^1$H NMR (CDCl$_3$, 400 MHz): 6.60 (s, 1H), 4.83 (s, 1H), 4.67-4.60 (m, 1H), 4.41-4.28 (m, 2H), 3.95-3.85 (m, 1H), 3.67-3.64 (m, 1H), 3.30-3.26 (m, 1H), 3.14-3.09 (m, 1H), 3.00-2.95 (m, 1H), 2.78-2.72 (m, 1H), 2.46-2.36 (m, 2H), 2.30-2.19 (m, 8H), 2.04-1.93 (m, 3H), 1.15-0.99 (m, 5H), 0.82-0.78 (t, J=7.8 Hz, 3H). LC-MS: m/z 748.3[M+H]$^+$.

Example 11: Synthesis of (2S,3aR,4S,5aR,5bS,9S,13S,14R,16aR,16bS)-13-{[(2R,5S,6R)-5-(dimethylamino)-6-methyloxan-2-yl]oxy}-4-ethoxy-9-ethyl-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

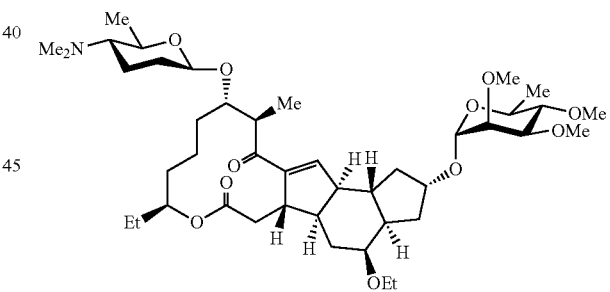

To a mixture of Example 8 (437 mg, 0.58 mmol), EtI (2.7 g, 17.4 mmol), and silver acetate (390 mg, 2.3 mmol) in dimethylformamide (5 mL) was added t-BuOK (261 mg, 2.3 mmol). The resulting mixture was stirred at room temperature for 4 days. The mixture was diluted with dichloromethane (20 mL) and filtered. The filtrate was concentrated and the residue was purified by preparative TLC (dichloromethane/methanol=10/1) to give the title compound (13 mg, yield 3%) as a white solid. Partial $^1$H NMR (400 MHz, CDCl$_3$): δ6.81 (s, 1H), 4.84 (1H, s), 4.63-4.60 (m, 1H), 4.45-4.43 (m, 1H), 4.22-4.20 (m, 1H), 3.65-3.44 (m, 16H), 3.34-3.22 (m, 3H), 3.16-3.08 (m, 2H), 2.74-2.72 (m, 1H), 2.59-2.54 (m, 1H), 2.10-1.90 (m, 3H), 1.12 (t, J=7.2 Hz, 3H), 0.81 (t, J=7.6 Hz, 3H). LCMS: m/z 778.5 [M+H]$^+$.

Example 12: Synthesis of (2S,5aR,5bS,9S,13S,14R, 16aS,16bS)-13-{[(2R,5S,6R)-5-(dimethylamino)-6-methyloxan-2-yl]oxy}-9-ethyl-14-methyl-5-phenyl-2-{[(2R,3R,4R,5S,6S)-3,4,5-trimethoxy-6-methyloxan-2-yl]oxy}-1H,2H,3H,5H,5aH,5bH,6H, 7H,9H,10H,11H,12H,13H,14H,15H,16aH,16bH-as-indaceno[3,2-d]oxacyclododecane-7,15-dione

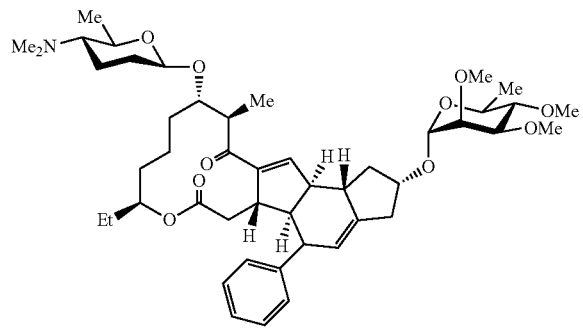

To a solution of bis(aryl)acenaphthequinonediimine (BIAN, 149 mg, 0.38 mol) in dimethylformamide (10 mL) was added palladium acetate (62 mg, 0.27 mmol) and the system was charged with nitrogen 3 times. The mixture was stirred for 30 min at room temperature, followed by the addition of Spinosyn A (1.0 g, 1.37 mmol) and phenylboronic acid (251 mg, 2.06 mmol). The flask was charged with $O_2$ and the reaction mixture was allowed to stir at room temperature for 2 days under $O_2$ (balloon). The reaction mixture was diluted with water (30 mL) and extracted with ethyl acetate (50 mL×3). The combined organic phase was washed with brine (30 mL), dried over anhydrous sodium sulfate, filtered, and concentrated. The residue was purified by preparative HPLC to afford the title compound (80 mg, 9.9% yield) as a yellow solid. $^1$H NMR (400 MHz, Acetone-$d_6$): δ 7.42-7.26 (m, 5H), 7.15 (s, 1H), 5.73 (s, 1H), 4.92 (s, 1H), 4.68 (d, J=8.8 Hz, 1H), 4.60-4.54 (m, 1H), 4.35-4.30 (m, 1H), 4.01-3.95 (m, 1H), 3.64-3.60 (m, 2H), 3.58 (s, 1H), 2.68-2.63 (m, 1H), 2.31 (dd, J=12.8, 3.2 Hz, 1H), 1.84-1.78 (m, 1H), 0.75 (t, J=7.4 Hz, 3H). LCMS: m/z 808.5 [M+H]$^+$.

Example 13: Synthesis of (1S,2R,6R,8S,10R,11S, 15R,16S,20S)-4,4-dichloro-16-{[(2R,5S,6R)-5-(dimethylamino)-6-methyloxan-2-yl]oxy}-20-ethyl-15-methyl-8-{[(2R,3R,4R,5S,6S)-3,4,5-trimethoxy-6-methyloxan-2-yl]oxy}-21-oxapentacyclo[11.10.0.0$^2$,$^{11}$.0$^3$,$^5$.0$^6$,$^{10}$]tricos-12-ene-14,22-dione

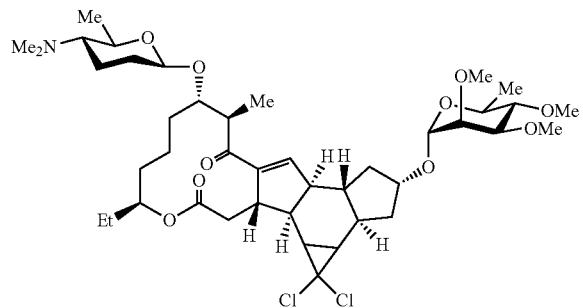

To a cold solution of triethyl benzylammonium chloride (15 mg) in 15 mL of chloroform in a three-necked flask was added Spinosyn A (500 mg, 0.68 mmol). The mixture was stirred for 10 minutes, and a 50% sodium hydroxide solution (820 mg) was added in carefully over 5 minutes. The resulting mixture was stirred at 10° C. for 1 hour, and then stirred at room temperature overnight. The mixture was diluted with water and extracted with ethyl acetate (80 mL). The organic layer was washed with brine, dried over sodium sulfate, filtered and concentrated in vacuo to give an oil which was further purified by preparative HPLC to afford the title compound (162 mg, 27.5%) as a white solid. Partial $^1$H NMR (DMSO-$d_6$, 400 MHz): g 7.00 (s, 1H), 5.35 (m, 2H), 4.88-4.84 (m, 1H), 4.80 (s, 1H), 4.59-4.57 (m, 1H), 4.52-4.50 (m, 1H), 4.26-4.21 (m, 1H), 3.73-3.69 (m, 1H). LC-MS: m/z 862.4 [M+H]$^+$.

Example 14: Synthesis of (4S,5R,7R,9S,12R,13S, 17S,21S,22R)-21-{[(2R,5S,6R)-5-(dimethylamino)-6-methyloxan-2-yl]oxy}-17-ethyl-22-methyl-7-{[(2R,3R,4R,5S,6S)-3,4,5-trimethoxy-6-methyloxan-2-yl]oxy}-16-oxapentacyclo[11.10.0.0$^1$,$^3$.0$^4$,$^{12}$.0$^5$,$^9$] tricos-10-ene-15,23-dione

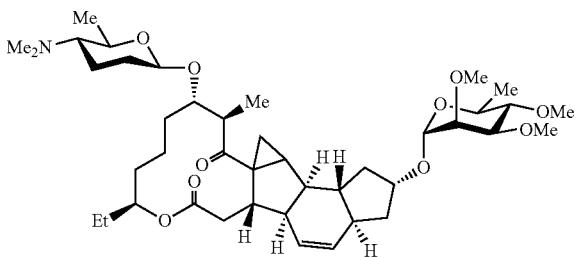

A solution of trimethylsulfoxonium iodide (90 mg, 0.41 mmol) in dry dimethylsulfoxide (DMSO, 2 mL) was treated with sodium hydride (60% in mineral, 14 mg, 0.35 mmol). The mixture was stirred at room temperature for 2 hours. To this mixture was added a solution of Spinosyn A (200 mg, 0.27 mmol) in DMSO/tetrahydrofuran (4 mL, 1/1, v/v). The resulting mixture was stirred for another 2 hours and was then concentrated. The residue was purified by preparative HPLC to afford the title compound (140 mg, yield 68.9%) as a white solid. Partial $^1$H NMR (Acetone-$d_6$, 300 MHz): δ 5.85 (m, 2H), 4.82 (s, 1H), 4.53-4.51 (m, 1H), 4.49-4.41 (m, 1H), 4.37-4.32 (m, 1H), 3.01 (t, J=9.6 Hz, 1H), 0.83 (t, J=7.5 Hz, 3H). LCMS: m/z 746.5 [M+H]$^+$.

General Procedure for Pauson-Khand Reaction on Spinsyn Derivatives

Example 15: Synthesis of (1S,2R,8R,10S,12R,13S, 17R,18S,22S)-18-{[(2R,5S,6R)-5-(dimethylamino)-6-methyloxan-2-yl]oxy}-22-ethyl-5-(4-fluorophenyl)-17-methyl-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione

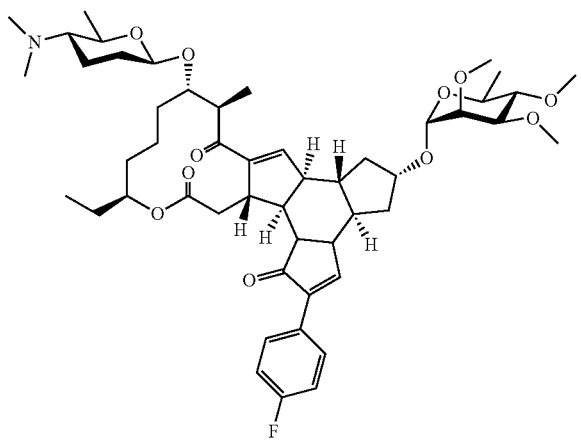

To a solution of 1-ethynyl-4-fluoro-benzene (331 mg, 2.73 mmol) in toluene (50 mL) was added dicobalt octacarbonyl (0.93 g, 2.72 mmol) under nitrogen. The resulting mixture was stirred at room temperature for 1 hour. A solution of Spinosyn A (1.0 g, 1.37 mmol) in toluene (10 mL) was added. The resulting mixture was charged with carbon monoxide and heated at 110° C. for 36 hours under carbon monoxide atmosphere. The reaction solution was quenched with water (50 mL) and extracted with dichloromethane (50 mL×2). The combined organic layer was dried over potassium carbonate, filtered, and concentrated. The residue was purified by column chromatography on silica gel (methanol/dichloromethane=2/100) and chiral preparative HPLC to afford the title compound (100 mg, 7.9%) as a white solid. Partial $^1$H NMR (CDCl$_3$, 400 MHz): δ 7.73-7.68 (m, 3H), 7.07 (t, J=8.8 Hz, 2H), 6.71 (s, 1H), 4.85 (s, 1H), 4.67-4.58 (m, 1H), 4.44-4.36 (m, 2H), 3.77-3.67 (m, 2H), 3.60-3.55 (m, 13H), 3.20-3.08 (m, 2H), 2.97-2.88 (m, 2H), 2.73-2.65 (m, 1H), 2.55-2.39 (m, 3H), 2.25 (s, 6H), 2.20-2.12 (m, 1H), 2.01-1.9 (m, 24H), 1.34-1.18 (m, 12H), 1.14-1.03 (m, 1H), 0.80 (t, J=7.6 Hz, 3H); LC-MS: m/z 879.8 [M+H]$^+$.

Example 16: Synthesis of (1S,2R,8R,10S,12R,13S, 17R,18S,22S)-18-{[(2R,5S,6R)-5-(dimethylamino)-6-methyloxan-2-yl]oxy}-22-ethyl-17-methyl-5-(pyrimidin-5-yl)-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione

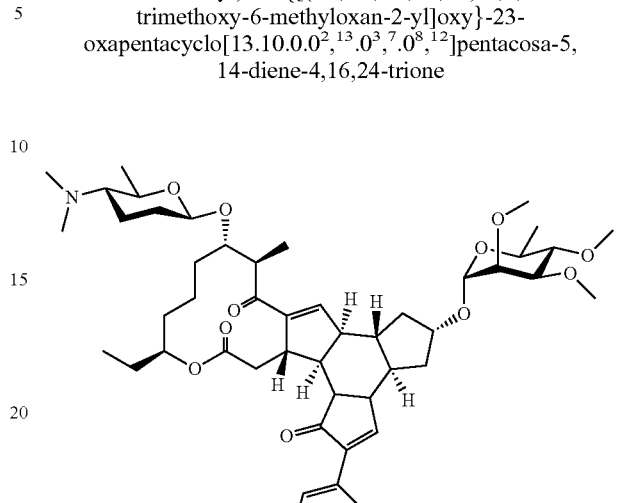

According to the general procedures as outlined for Example 15, 30 mg of Example 16 was obtained as a white solid from 1.0 g of Spinosyn A using 1-ethynyl-pyrimidine. $^1$HNMR (CDCl$_3$, 400 MHz): δ 9.19 (s, 1H), 9.08 (s, 2H), 7.91 (s, 1H), 6.71 (s, 1H), 4.86 (s, 1H), 4.68-4.58 (m, 1H), 4.46-4.37 (m, 2H), 3.75-3.68 (m, 2H), 3.60-3.36 (m, 15H), 3.21-3.10 (m, 2H), 2.99-2.90 (m, 2H), 2.84-2.77 (m, 1H), 2.54-2.47 (m, 3H), 2.26-2.16 (m, 8H), 2.02-1.03 (m, 36H), 0.80 (t, J=7.6 Hz, 3H); LC-MS: m/z 863.8 [M+H]$^+$.

Example 17: Synthesis of 4-[(1S,2R,8R,10S,12R, 13S,17R,18S,22S)-18-{[(2R,5S,6R)-5-(dimethylamino)-6-methyloxan-2-yl]oxy}-22-ethyl-17-methyl-4,16,24-trioxo-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-dien-5-yl]benzonitrile

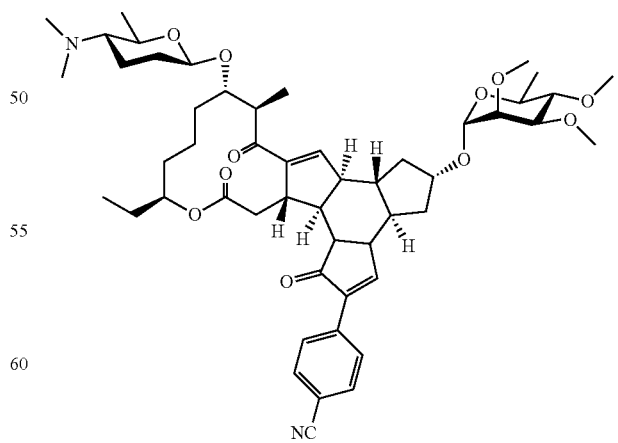

According to the general procedures as outlined for compound Example 15, 40 mg of example 15 was obtained as a white solid from 1.0 g of Spinosyn A using 1-ethynyl- 4-cyano-benzene. ¹HNMR (CDCl₃, 400 MHz): δ 7.85 (d, J=8.4 Hz, 3H), 7.67 (d, J=8.4 Hz, 2H), 6.71 (s, 1H), 4.85 (s, 1H), 4.67-4.59 (m, 1H), 4.45-4.37 (m, 2H), 3.75-3.68 (m, 2H), 3.58-3.36 (m, 15H), 3.19-3.09 (m, 2H), 2.98-2.89 (m, 2H), 2.78-2.71 (m, 1H), 2.55-2.41 (m, 3H), 2.28-2.14 (m, 8H), 2.02-1.03 (m, 24H), 0.80 (t, J=7.6 Hz, 3H); LC-MS: m/z 886.8 [M+H]⁺.

Example 18: Synthesis of (1S,2R,8R,10S,12R,13S, 17R,18S,22S)-18-{[(2R,5S,6R)-5-(dimethylamino)- 6-methyloxan-2-yl]oxy}-22-ethyl-17-methyl-5-phe- nyl-10-{[(2R,3R,4R,5S,6S)-3,4,5-trimethoxy-6- methyloxan-2-yl]oxy}-23-oxapentacyclo[13.10.0.0², ¹³.0³,⁷.0⁸,¹²]pentacosa-5,14-diene-4,16,24-trione

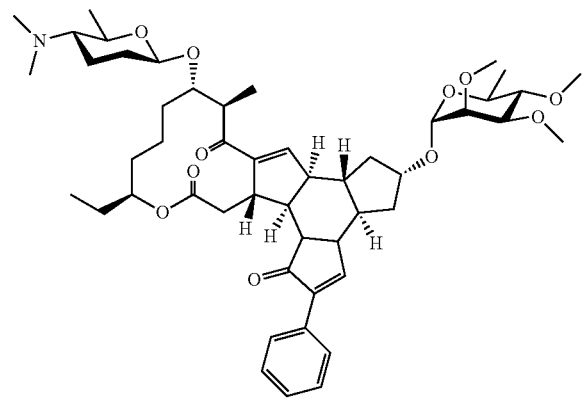

According to the general procedures as outlined for compound Example 15, 40 mg of Example 18 was obtained as a white solid from 1.0 g of Spinosyn A using 1-ethynyl-benzene. Partial ¹H-NMR (CDCl₃, 400 MHz) δ 7.72-7.70 (m, 3H), 7.41-7.34 (m, 3H), 6.72 (s, 1H), 4.86 (s, 1H), 4.65-4.62 (m, 1H), 4.45-4.39 (m, 2H), 3.74-3.69 (m, 2H), 3.39-3.33 (m, 1H), 3.18-3.10 (m, 2H), 2.95-2.90 (m, 2H), 2.70-2.68 (m, 1H), 2.54 (dd, J=13.6, 2.8 Hz, 1H), 2.48-2.42 (m, 2H), 2.27 (s, 6H), 2.19-2.13 (m, 1H), 0.80 (t, J=8.0 Hz, 3H); LC-MS: m/z 861.9 [M+H]⁺.

Example 19: Synthesis of (1S,2R,8R,10S,12R,13S, 17R,18S,22S)-18-{[(2R,5S,6R)-5-(dimethylamino)- 6-methyloxan-2-yl]oxy}-22-ethyl-17-methyl-5-phe- nyl-10-{[(2R,3R,4R,5S,6S)-3,4,5-trimethoxy-6- methyloxan-2-yl]oxy}-23-oxapentacyclo[13.10.0.0², ¹³.0³,⁷.0⁸,¹²]pentacosane-4,16,24-trione

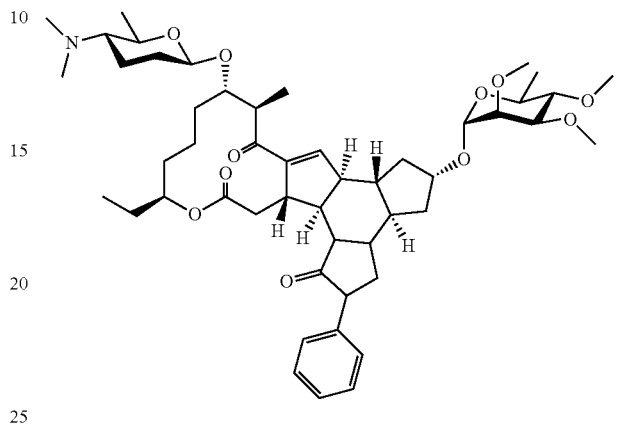

A mixture of Example 18 (100 mg, 0.12 mmol) and palladium on carbon (10 mg) in methanol (10 mL) was stirred under hydrogen at room temperature overnight. The mixture was filtered through Celite and washed with methanol (50 mL). The filtrate was concentrated and purified by preparative HPLC to afford the title compound (10 mg, 12.5% yield) as a white solid. ¹HNMR (CDCl₃, 400 MHz): δ 7.35-7.19 (m, 5H), 4.89-4.79 (m, 2H), 4.44-4.29 (m, 2H), 3.93-3.86 (m, 1H), 3.58-3.39 (m, 19H), 3.12 (t, J=9.2 Hz, 1H), 2.47-1.17 (m, 42H), 0.87 (t, J=7.6 Hz, 3H); LC-MS: m/z 865.9 [M+H]⁺.

Intermediate 1: Synthesis of (2R,5bS,9S,13S,14R, 16aS,16bR)-9-ethyl-14-methyl-13-{[(2R,5S,6R)-6- methyl-5-(methylamino)oxan-2-yl]oxy}-2-{[(2R,3R, 4R,5S,6S)-3,4,5-trimethoxy-6-methyloxan-2-yl] oxy}-1H,2H,3H,3aH,5aH,5bH,6H,7H,9H,10H,11H, 12H,13H,14H,15H,16aH,16bH-as-indaceno[3,2-d] oxacyclododecane-7,15-dione

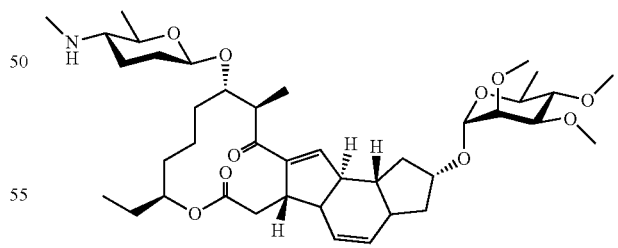

A mixture of Spinosyn A (10.0 g, 13.7 mmol) and sodium acetate (5.6 g, 68.5 mmol) in 80% methanol-water (200 mL) was heat to 47° C. under nitrogen. Then I₂ (5.2 g, 20.6 mmol) was added in one portion and the pH was adjusted to keep between 8-9 by addition of 1N NaOH. After 2.5 h, the reaction was complete as monitored by LC-MS. The reaction was cooled to r.t., quenched with saturated ammonium chloride solution (400 mL) and extracted with ethyl acetate (3×200 mL). The combined organic phase was washed with brine (200 mL), dried over anhydrous sodium sulfate, filtered and concentrated. The residue was purified by prep-HPLC to afford mono des-N-methyl spinosyn A (6.0 g, 61.2% yield) as a white solid. Partial $^1$H NMR (400 MHz, CDCl$_3$): δ 6.77 (s, 1H), 5.88 (d, J=10.0 Hz, 1H), 5.80 (m, 1H), 4.85 (d, J=1.6 Hz, 1H), 4.70-4.64 (m, 1H), 4.46 (dd, J=9.2, 1.6 Hz, 1H), 4.34-4.29 (m, 1H), 3.31-3.24 (m, 2H), 3.15-3.09 (m, 2H), 3.03-3.01 (m, 1H), 2.90-2.84 (m, 1H), 2.42 (s, 3H), 2.39 (m, 1H), 2.29-2.23 (m, 1H), 2.18-2.11 (m, 3H), 1.95-1.90 (m, 2H), 0.96-0.86 (m, 1H), 0.82 (t, J=7.6 Hz, 3H); LCMS: m/z 717.9 [M+H]$^+$.

Example 20: Synthesis of (2R,3aS,5aR,5bS,9S,13S,14R,16aS,16bR)-9-ethyl-14-methyl-13-{[(2R,5S,6R)-6-methyl-5-[methyl(propyl)amino]oxan-2-yl]oxy}-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

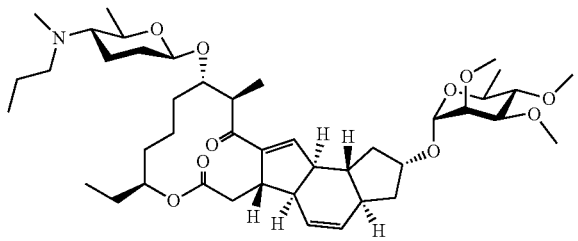

To a solution of Intermediate 1 (300 mg, 0.42 mol) and DIPEA (108 mg, 0.84 mmol) in dichloromethane (10 mL) was added n-PrBr (78 mg, 0.63 mmol). The mixture was then stirred at r.t. overnight. The solvent was removed under reduced pressure, and the residue was purified by prep-HPLC to afford the title compound (100 mg, 32.1% yield) as a white solid. Partial $^1$H NMR (400 MHz, Acetone-d$_6$): δ 7.05 (s, 1H), 5.92-5.85 (m, 2H), 4.83 (d, J=1.6 Hz, 1H), 4.68-4.63 (m, 1H), 4.47 (dd, J=9.2, 1.6 Hz, 1H), 4.33 (q, J=6.4 Hz, 1H), 3.07 (dd, J=13.2, 4.8 Hz, 1H), 2.90-2.84 (m, 1H), 2.79-2.76 (m, 1H), 2.48-2.32 (m, 4H), 2.20-2.14 (m, 6H), 2.00-1.91 (m, 2H), 1.83-1.78 (m, 2H), 1.12 (d, J=6.8 Hz, 3H), 0.96-0.91 (m, 1H), 0.87 (t, J=7.6 Hz, 3H), 0.81 (t, J=7.6 Hz, 3H); LCMS: m/z 759.9 [M+H]$^+$.

Example 21: Synthesis of (2R,3aS,5aR,5bS,9S,13S,14R,16aS,16bR)-13-{[(2R,5S,6R)-5-[benzyl(methyl)amino]-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

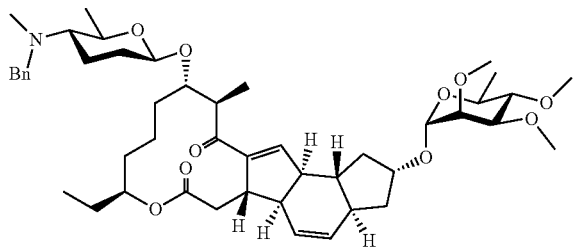

Example 21 was prepared using the common Intermediate 1, procedure A. To a solution of Intermediate 1 (300 mg, 0.42 mol) and DIPEA (108 mg, 0.84 mmol) in dichloromethane (10 mL) was added BnBr (108 mg, 0.63 mmol). The mixture was then stirred at r.t. overnight. The solvent was removed under reduced pressure, and the residue was purified by prep-HPLC to afford the title compound (80 mg, 23.6% yield) as a white solid. Partial $^1$H NMR (400 MHz, Acetone-d$_6$): δ 7.35-7.27 (m, 4H), 7.24-7.21 (m, 1H), 7.05 (s, 1H), 5.92-5.85 (m, 2H), 4.84 (d, J=1.6 Hz, 1H), 4.68-4.63 (m, 1H), 4.47 (dd, J=9.2, 1.6 Hz, 1H), 4.33 (q, J=6.4 Hz, 1H), 3.74-3.66 (m, 2H), 3.57-3.30 (m, 16H), 3.07 (dd, J=13.2, 4.8 Hz, 1H), 3.02 (t, J=9.2 Hz, 1H), 2.92-2.89 (m, 1H), 2.80-2.75 (m, 1H), 2.78 (d, J=12.8 Hz, 3H), 2.45 (dd, J=13.2, 2.8 Hz, 1H), 2.39-2.25 (m, 2H), 2.18-2.12 (m, 4H), 0.98-0.87 (m, 1H), 0.80 (t, J=7.6 Hz, 3H); LCMS: m/z 807.9 [M+H]$^+$.

Example 22: Synthesis of (2R,3aS,5aR,5bS,9S,13S,14R,16aS,16bR)-9-ethyl-14-methyl-13-{[(2R,5S,6R)-6-methyl-5-[methyl(prop-2-en-1-yl)amino]oxan-2-yl]oxy}-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

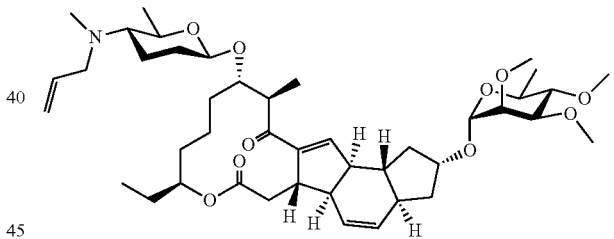

Example 22 was prepared using the method of Example 20. To a solution of Intermediate 1 (300 mg, 0.42 mol) and DIPEA (108 mg, 0.84 mmol) in dichloromethane (10 mL) was added allyl bromide (76 mg, 0.63 mmol). The mixture was then stirred at r.t. overnight. The solvent was removed under reduced pressure, and the residue was purified by prep-HPLC to afford the title compound (100 mg, 31.5% yield) as a white solid. $^1$H NMR (400 MHz, Acetone-d$_6$): δ 7.05 (s, 1H), 5.92-5.74 (m, 3H), 5.17 (d, J=16.8 Hz, 1H), 5.05 (d, J=10.4 Hz, 1H), 4.83 (d, J=1.6 Hz, 1H), 4.68-4.63 (m, 1H), 4.47 (dd, J=9.2, 1.6 Hz, 1H), 4.33 (q, J=6.4 Hz, 1H), 2.78 (d, J=13.6 Hz, 4H), 2.45 (dd, J=13.2, 2.8 Hz, 1H), 2.39-2.33 (m, 1H), 2.27-2.14 (m, 6H), 2.00-1.91 (m, 2H), 1.12 (d, J=6.8 Hz, 3H), 0.96-0.91 (m, 1H), 0.81 (t, J=7.6 Hz, 3H); LCMS: m/z 757.9 [M+H]$^+$.

Example 23: Synthesis of N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methylpropanamide

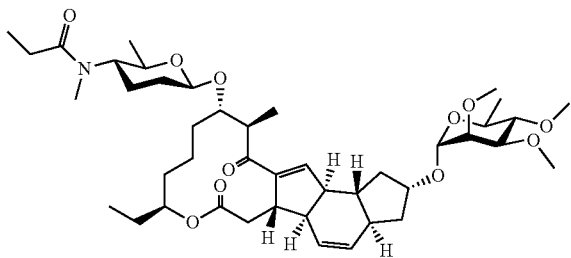

Example 23 was prepared using Intermediate 1, following Procedure B. To a stirred solution of propionic acid (56 mg, 0.63 mmol) and DIPEA (108 mg, 0.84 mmol) in DMF (10 mL) was added HATU (319 mg, 0.84 mmol) and Intermediate 1 (300 mg, 0.42 mol). The mixture was then stirred at r.t. overnight. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (120 mg, 37.0% yield) as a white solid. Partial $^1$H NMR (400 MHz, Acetone-$d_6$): δ 6.94 (s, 1H), 5.79-5.73 (m, 2H), 4.70 (d, J=1.6 Hz, 1H), 4.54-4.50 (m, 1H), 4.47-4.41 (m, 1H), 4.20 (q, J=6.4 Hz, 1H), 3.73-3.69 (m, 1H), 2.94 (dd, J=13.2, 4.8 Hz, 1H), 2.86 (t, J=9.2 Hz, 1H), 2.83-2.80 (m, 1H), 2.36-2.18 (m, 4H), 2.06-1.97 (m, 1H), 1.87-1.80 (m, 2H), 0.94-0.88 (m, 5H), 0.85-0.75 (m, 1H), 0.67 (t, J=7.6 Hz, 3H); LCMS: m/z 774.0 [M+H]$^+$.

Example 24: Synthesis of N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N,2-dimethylpropanamide

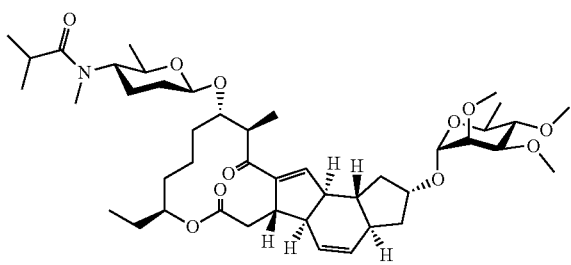

Example 24 was prepared using the Intermediate 1, following Procedure B. To a stirred solution of isobutyric acid (56 mg, 0.63 mmol) and DIPEA (108 mg, 0.84 mmol) in DMF (10 mL) was added HATU (319 mg, 0.84 mmol) and Intermediate 1 (300 mg, 0.42 mol). The mixture was then stirred at r.t. overnight. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (100 mg, 30.3% yield) as a white solid. Partial $^1$H NMR (400 MHz, Acetone-$d_6$): δ 7.09 (s, 1H), 5.94-5.88 (m, 2H), 4.85 (d, J=1.6 Hz, 1H), 4.69-4.56 (m, 2H), 4.35 (q, J=6.4 Hz, 1H), 3.92-3.82 (m, 1H), 3.08 (dd, J=13.2, 4.8 Hz, 1H), 3.04 (t, J=9.2 Hz, 1H), 2.98-2.81 (m, 5H), 2.75 (s, 1H), 2.52-2.46 (m, 1H), 2.41-2.35 (m, 1H), 2.22-2.14 (m, 1H), 1.00-0.93 (m, 1H), 0.82 (t, J=7.6 Hz, 3H); LCMS: m/z 787.9 [M+H]$^+$.

Example 25: Synthesis of N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methyl-2-propylpentanamide

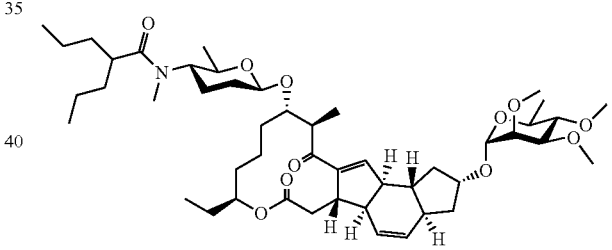

Example 25 was prepared using Intermediate 1, following Procedure B. To a stirred solution of 2-propylpentanoic acid (91 mg, 0.63 mmol) and DIPEA (108 mg, 0.84 mmol) in DMF (10 mL) was added HATU (319 mg, 0.84 mmol) and Intermediate 1 (300 mg, 0.42 mol). The mixture was then stirred at r.t. overnight. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (100 mg, 28.2% yield) as a white solid. Partial $^1$H NMR (400 MHz, Acetone-$d_6$): δ 7.07 (s, 1H), 5.92-5.86 (m, 2H), 4.83 (d, J=1.6 Hz, 1H), 4.69-4.56 (m, 2H), 4.35 (q, J=6.4 Hz, 1H), 3.92-3.82 (m, 1H), 3.60-3.30 (m, 16H), 3.07 (dd, J=13.2, 4.8 Hz, 1H), 3.02 (t, J=9.2 Hz, 1H), 2.49-2.44 (m, 1H), 2.39-2.33 (m, 1H), 2.21-2.17 (m, 1H), 0.81 (t, J=7.6 Hz, 3H); LCMS: m/z 843.9 [M+H]$^+$.

Example 26: Synthesis of N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-2-butyl-N-methyloctanamide

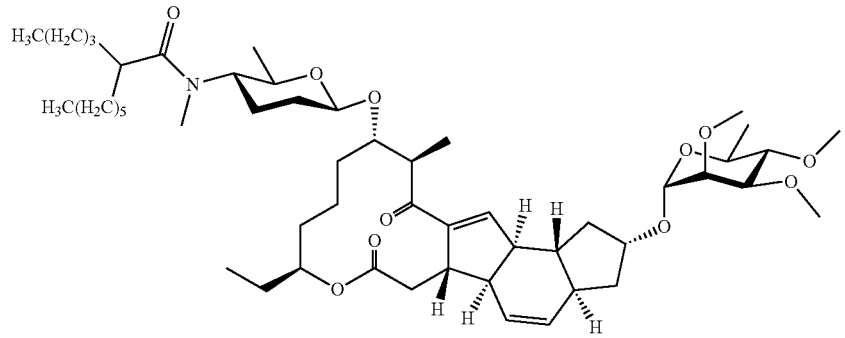

Example 26 was prepared using the Intermediate 1, following Procedure B. To a stirred solution of 2-butyloctanoic acid (126 mg, 0.63 mmol) and DIPEA (108 mg, 0.84 mmol) in DMF (10 mL) was added HATU (319 mg, 0.84 mmol) and Intermediate 1 (300 mg, 0.42 mol). The mixture was then stirred at r.t. overnight. The reaction mixture was diluted with water (10 mL) and extracted with ethyl acetate (3×20 mL). The combined organic phase was washed with brine (50 mL), dried over anhydrous sodium sulfate, filtered and concentrated. The residue was purified by prep-HPLC to afford the title compound (120 mg, 32.6% yield) as a white solid. Partial $^1$H NMR (400 MHz, Acetone-$d_6$): δ 6.94 (s, 1H), 5.79-5.73 (m, 2H), 4.70 (d, J=1.6 Hz, 1H), 4.56-4.43 (m, 2H), 4.20 (q, J=6.4 Hz, 1H), 3.77-3.68 (m, 1H), 2.94 (dd, J=13.2, 4.8 Hz, 1H), 2.89 (t, J=9.2 Hz, 1H), 2.84-2.61 (m, 8H), 2.35-2.31 (m, 1H), 2.27-2.20 (m, 1H), 2.07-1.97 (m, 1H), 0.82-0.72 (m, 7H), 0.68 (t, J=7.6 Hz, 3H); LCMS: m/z 901.5 [M+H]$^+$.

Example 27: Synthesis of N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH as-indaceno[3,2-d]oxacyclododecan-13-yl]oxy}-2-methyloxan-3-yl]-N-methyloctanamide

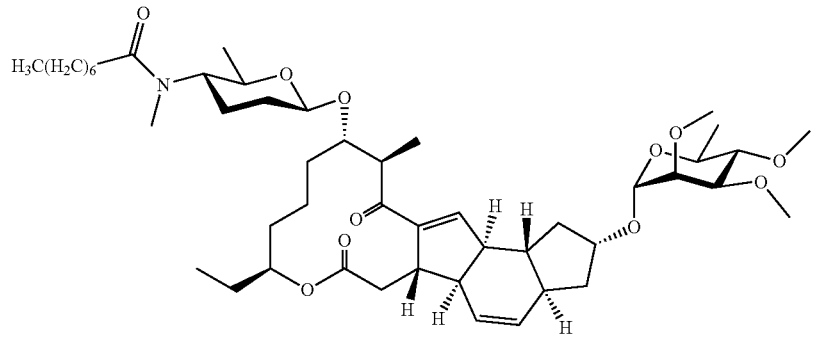

Example 27 was prepared using Intermediate 1, following Procedure B. To a stirred solution of n-caprylic acid (91 mg, 0.63 mmol) and DIPEA (108 mg, 0.84 mmol) in DMF (10 mL) was added HATU (319 mg, 0.84 mmol) and Intermediate 1 (300 mg, 0.42 mmol). The mixture was then stirred at r.t. overnight. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (115 mg, 32.5% yield) as a white solid. Partial $^1$H NMR (400 MHz, Acetone-d$_6$): δ 6.94 (s, 1H), 5.79-5.73 (m, 2H), 4.70 (d, J=1.6 Hz, 1H), 4.56-4.43 (m, 2H), 4.19 (q, J=6.4 Hz, 1H), 3.73-3.68 (m, 1H), 3.47-3.16 (m, 16H), 2.95 (dd, J=13.2, 4.8 Hz, 1H), 2.89 (t, J=9.2 Hz, 1H), 2.78-2.72 (m, 3H), 0.35-2.31 (m, 1H), 2.26-2.16 (m, 3H), 0.67 (t, J=7.6 Hz, 3H); LCMS: m/z 843.9 [M+H]$^+$.

Example 28: Synthesis of N-[(2R,3S,6R)-6-{[(2R, 3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH, 5aH,5bH,6H,7H,9H,10H,11H,12H,13H,14H,15H, 16aH,16bH-as-indaceno[3,2-d]oxacyclododecan-13-yl]oxy}-2-methyloxan-3-yl]-N-methyldodecanamide

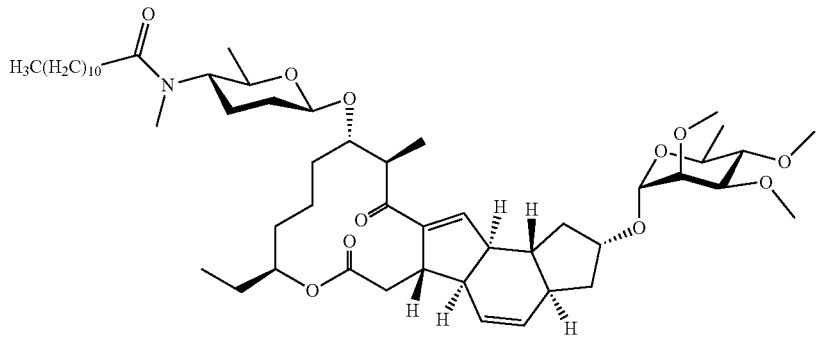

Example 28 was prepared using Intermediate 1, following Procedure B. To a stirred solution of lauric acid (126 mg, 0.63 mmol) and DIPEA (108 mg, 0.84 mmol) in DMF (10 mL) was added HATU (319 mg, 0.84 mmol) and Intermediate 1 (300 mg, 0.42 mol). The mixture was then stirred at r.t. overnight. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (120 mg, 31.8% yield) as a white solid. Partial $^1$H NMR (400 MHz, Acetone-d$_6$): δ 6.94 (s, 1H), 5.79-5.72 (m, 2H), 4.70 (d, J=1.6 Hz, 1H), 4.57-4.41 (m, 2H), 4.20 (q, J=6.4 Hz, 1H), 3.73-3.64 (m, 1H), 2.94 (dd, J=13.2, 4.8 Hz, 1H), 2.87 (t, J=9.2 Hz, 1H), 2.83-2.65 (m, 5H), 2.60 (s, 1H), 2.35-2.31 (m, 1H), 2.28-2.14 (m, 3H), 2.06-1.97 (m, 1H), 1.06-0.93 (m, 9H), 0.67 (t, J=7.6 Hz, 3H); LCMS: m/z 901.4 [M+H]$^+$.

Example 29: Synthesis of N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methylbenzamide

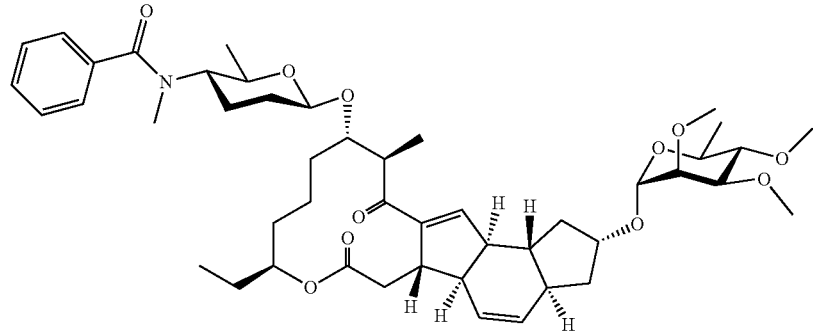

Example 29 was prepared using the Intermediate 1, following Procedure B. To a solution of Intermediate 1 (300 mg, 0.42 mol) and DIPEA (108 mg, 0.84 mmol) in dichloromethane (10 mL) was added benzoyl chloride (89 mg, 0.63 mmol). The mixture was then stirred at r.t. overnight. The reaction mixture was diluted with water (30 mL) and extracted with dichloromethane (3×30 mL). The combined organic phase was washed with brine (100 mL), dried over anhydrous sodium sulfate, filtered and concentrated. The residue was purified by prep-HPLC to afford the title compound (100 mg, 29.0% yield) as a white solid. Partial $^1$H NMR (400 MHz, Acetone-$d_6$): δ 7.33-7.23 (m, 5H), 6.95-6.91 (m, 2H), 5.80-5.70 (m, 2H), 4.70 (s, 1H), 4.55-4.40 (m, 2H), 4.20-4.16 (m, 1H), 3.75-3.70 (m, 1H), 2.97-2.67 (m, 8H), 2.60 (s, 1H), 2.35-2.29 (m, 1H), 2.28-2.22 (m, 1H), 2.03-1.96 (m, 1H), 1.12-0.92 (m, 9H), 0.82-0.73 (m, 1H), 0.70-0.63 (m, 3H); LCMS: m/z 822.0 [M+H]$^+$.

Example 30: Synthesis of 5-[(3aS,4S,6aR)-2-oxo-hexahydro-1H-thieno[3,4-d]imidazol-4-yl]-N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methylpentanamide

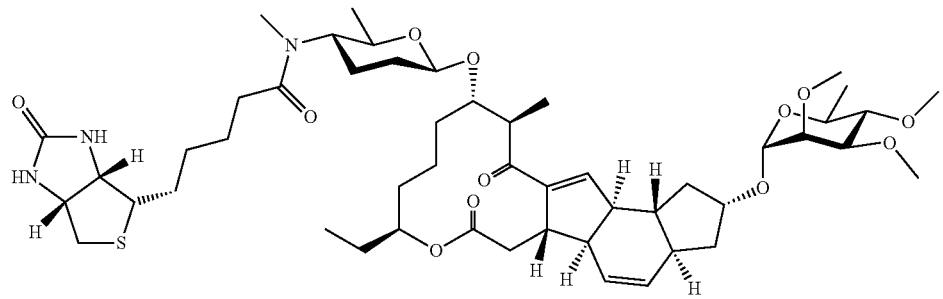

Example 30 was prepared using Intermediate 1, following Procedure B. To a stirred solution of D-biotin (205 mg, 0.84 mmol) and DIPEA (144 mg, 1.12 mmol) in DMF (20 mL) was added HATU (424 mg, 1.12 mmol) and Intermediate 1 (400 mg, 0.56 mol). The mixture was then stirred at r.t. overnight. The reaction mixture was diluted with water (20 mL) and extracted with ethyl acetate (3×30 mL). The combined organic phase was washed with brine (100 mL), dried over anhydrous sodium sulfate, filtered and concentrated. The residue was purified by prep-HPLC to afford the title compound (200 mg, 37.9% yield) as a white solid. Partial $^1$H NMR (400 MHz, Acetone-d$_6$): δ 7.07 (s, 1H), 6.15 (d, J=6.8 Hz, 1H), 5.93-5.87 (m, 3H), 4.83 (d, J=1.6 Hz, 1H), 4.67-4.64 (m, 1H), 4.61-4.49 (m, 2H), 4.35-4.30 (m, 2H), 3.86-3.78 (m, 1H), 3.26-3.20 (m, 1H), 2.74-2.69 (m, 2H), 2.48-2.35 (m, 4H), 0.96-0.88 (m, 1H), 0.81 (t, J=7.6 Hz, 3H); LCMS: m/z 943.8 [M+H]$^+$.

Example 31: Synthesis of N-[(2R,3S,6R)-6-{[(2R, 3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-3',6'-dihydroxy-N-methyl-3-oxo-3H-spiro[2-benzofuran-1,9'-xanthene]-5-carboxamide

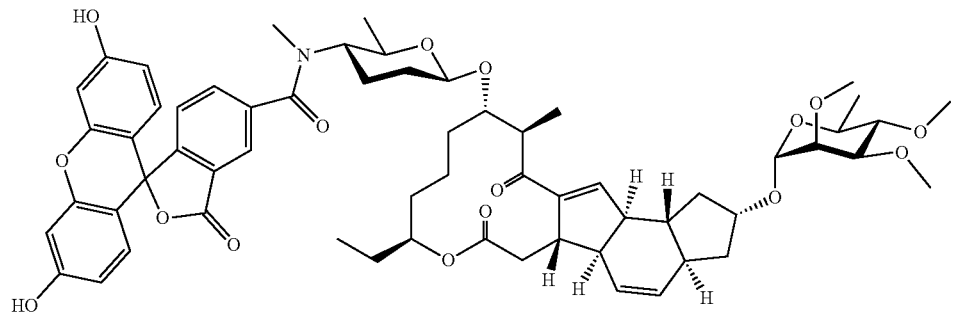

Example 31 was prepared using Intermediate 1, following Procedure B. To a stirred solution of 5-carboxyfluorescein (318 mg, 0.84 mmol) and DIPEA (144 mg, 1.12 mmol) in DMF (20 mL) was added HATU (424 mg, 1.12 mmol) and Intermediate 1 (400 mg, 0.56 mol). The mixture was then stirred at r.t. overnight. The reaction mixture was diluted with water (20 mL) and extracted with ethyl acetate (3×30 mL). The combined organic phase was washed with brine (100 mL), dried over anhydrous sodium sulfate, filtered and concentrated. The residue was purified by prep-HPLC to afford the title compound (90 mg, 15.0% yield) as a yellow solid. Partial $^1$H NMR (400 MHz, Acetone-d$_6$): δ 9.14 (brs, 1H), 7.95 (d, J=11.6 Hz, 1H), 7.84-7.78 (m, 1H), 7.37 (t, J=4.0 Hz, 1H), 7.07 (d, J=12.0 Hz, 1H), 6.76-6.72 (m, 4H), 6.64-6.61 (m, 2H), 5.92-5.85 (m, 2H), 4.83 (s, 1H), 4.69-4.55 (m, 2H), 4.33 (s, 1H), 4.01-3.91 (m, 1H), 2.46 (d, J=12.8 Hz, 1H), 2.40-2.34 (m, 1H), 2.19-1.87 (m, 6H), 0.96-0.77 (m, 5H); LCMS: m/z 1075.7 [M+H]$^+$.

Example 32: Synthesis of prop-2-en-1-yl N-[(2R,3S,6R)-6-{[(2R,3aS,5aR,5bS,9S,13S,14R,16aS,16bR)-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methylcarbamate

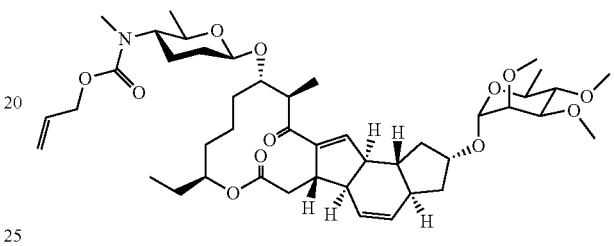

Example 32 was prepared using Intermediate 1, following Procedure A. To a solution of Intermediate 1 (1.0 g, 1.39 mmol) in dichloromethane (10 mL) was added DIEA (0.48 mL, 2.78 mmol) and Alloc-Cl (0.22 mL, 2.09 mmol) at 0° C. The resulting mixture was stirred at r.t. for 3 h. The mixture was treated with H$_2$O and extracted with dichloromethane (3×50 mL). The combined organic phase was washed with brine (30 mL), dried over anhydrous sodium sulfate, filtered and concentrated. The residue was purified by silica gel column chromatography (petroleum ether/ethyl acetate=3/1) to afford the title compound (792 mg, 71% yield) as a white solid. Partial $^1$H NMR (CDCl$_3$, 400 MHz): δ 6.77 (s, 1H), 5.96-5.79 (m, 3H), 5.29 (d, J=13.2 Hz, 2H), 5.21 (d, J=10.0 Hz, 1H), 4.85 (s, 1H), 4.68-4.58 (m, 3H), 4.47 (d, J=8.8 Hz, 1H), 4.34-4.29 (m, 1H), 3.65-3.62 (m, 2H), 3.56 (s, 3H), 3.50 (s, 6H), 3.46 (dd, J=9.2, 2.8 Hz, 1H), 3.32-3.28 (m, 1H), 3.15-3.09 (m, 2H), 3.02-3.01 (m, 1H), 2.90-2.85 (m, 1H), 2.79 (s, 3H), 2.41 (d, J=12.4 Hz, 1H), 2.30-2.16 (m, 2H), 2.00-1.90 (m, 2H), 1.28 (d, J=6.4 Hz, 3H), 0.82 (t, J=7.6 Hz, 3H); LC-MS: m/z 819 [M+NH$_4$]$^+$.

Intermediate 2: Synthesis of (2S,5bS,9S,13S,14R, 16aS,16bS)-9-ethyl-4,14-dimethyl-13-{[(2R,5S,6R)-6-methyl-5-(methylamino)oxan-2-yl]oxy}-2-{[(2R, 3R,4R,5S,6S)-3,4,5-trimethoxy-6-methyloxan-2-yl]oxy}-1H,2H,3H,3aH,5aH,5bH,6H,7H,9H,10H,11H, 12H,13H,14H,15H,16aH,16bH-as-indaceno[3,2-d]oxacyclododecane-7,15-dione

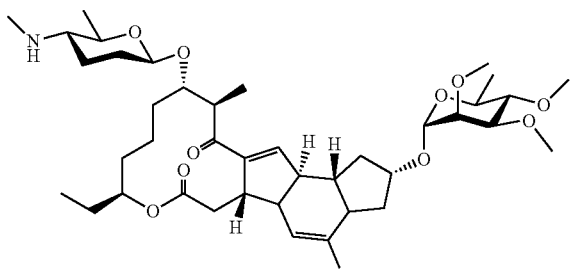

A mixture of Spinosyn D (5 g, 6.7 mmol) and sodium acetate (2.7 g, 33.5 mmol) in 80% methanol-water (100 mL) was heated to 47° C. under nitrogen. Iodine (2.6 g, 10.1 mmol) was added in one portion, and the pH was maintained between 8-9 by addition of 1N NaOH. After 2.5 h, the reaction was complete as monitored by LC-MS. The reaction was cooled to r.t., quenched with saturated ammonium chloride solution (100 mL) and extracted with ethyl acetate (3×100 mL). The combined organic phase was washed with brine (200 mL), dried over anhydrous sodium sulfate, filtered and concentrated. The residue was purified by prep-HPLC to afford the title compound (3.0 g, 61.2% yield) as a white solid. Partial $^1$H NMR (400 MHz, CDCl$_3$): δ 6.76 (s, 1H), 5.48 (s, 1H), 4.86 (d, J=1.6 Hz, 1H), 4.69-4.63 (m, 1H), 4.46 (dd, J=9.2, 1.6 Hz, 1H), 4.32-4.28 (m, 1H), 3.66-3.40 (m, 15H), 3.30-3.24 (m, 2H), 3.15-3.10 (m, 2H), 2.99-2.95 (m, 1H), 2.80-2.75 (m, 1H), 2.43 (s, 3H), 2.39 (dd, J=13.2, 3.2 Hz, 1H), 2.30-2.10 (m, 4H), 1.95-1.90 (m, 2H), 1.73 (s, 3H), 1.03-0.96 (m, 1H), 0.81 (t, J=7.6 Hz, 3H); LCMS: m/z 732.2 [M+H]$^+$.

Example 33: (2S,3aR,5aS,5bS,9S,13S,14R,16aS, 16bS)-9-ethyl-4,14-dimethyl-13-{[(2R,5S,6R)-6-methyl-5-[methyl(propyl)amino]oxan-2-yl]oxy}-2-{ [(2R,3R,4R,5S,6S)-3,4,5-trimethoxy-6-methyloxan-2-yl]oxy}-1H,2H,3H,3aH,5aH,5bH,6H,7H,9H,10H, 11H,12H,13H,14H,15H,16aH,16bH-as-indaceno[3, 2-d]oxacyclododecane-7,15-dione

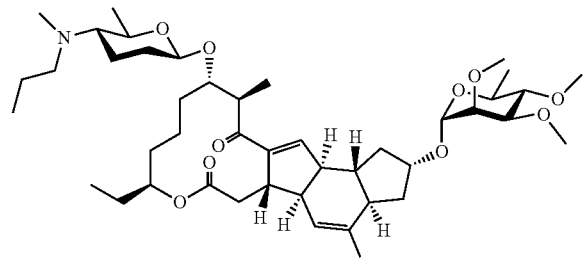

Following Procedure A: To a solution of Intermediate 2 (100 mg, 0.14 mol) and DIPEA (36 mg, 0.28 mmol) in dichloromethane (5 mL) was added n-PrBr (26 mg, 0.21 mmol). The mixture was then stirred at r.t. for overnight. The solvent was removed under reduced pressure and the residue was purified by prep-HPLC to afford the title compound (37 mg, 34.7% yield) as a white solid. Partial $^1$H NMR (400 MHz, Acetone-d$_6$): δ 7.03 (s, 1H), 5.54 (s, 1H), 4.84 (d, J=1.6 Hz, 1H), 4.68-4.63 (m, 1H), 4.47 (dd, J=9.2, 1.6 Hz, 1H), 4.33 (q, J=6.4 Hz, 1H), 3.07 (dd, J=13.2, 4.8 Hz, 1H), 3.02 (t, J=9.2 Hz, 1H), 2.92-2.89 (m, 1H), 2.80-2.75 (m, 3H), 2.45-2.33 (m, 4H), 2.18-2.12 (m, 6H), 2.00-1.91 (m, 2H), 0.96-0.91 (m, 1H), 0.87 (t, J=7.6 Hz, 3H), 0.81 (t, J=7.6 Hz, 3H); LCMS: m/z 773.9 [M+H]$^+$.

Example 34: Synthesis of (2S,3aR,5aS,5bS,9S,13S, 14R,16aS,16bS)-13-{[(2R,5S,6R)-5-[benzyl(methyl) amino]-6-methyloxan-2-yl]oxy}-9-ethyl-4,14-dimethyl-2-{[(2R,3R,4R,5S,6S)-3,4,5-trimethoxy-6-methyloxan-2-yl]oxy}-1H,2H,3H,3aH,5aH,5bH,6H, 7H,9H,10H,11H,12H,13H,14H,15H,16aH,16bH-as-indaceno[3,2-d]oxacyclododecane-7,15-dione

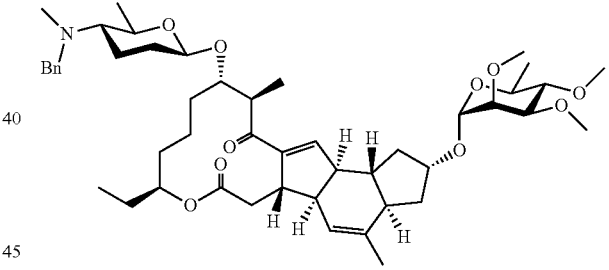

Example 34 was prepared using Intermediate 2 and Procedure A. To a solution of Intermediate 2 (100 mg, 0.14 mol) and DIPEA (36 mg, 0.28 mmol) in dichloromethane (5 mL) was added BnBr (36 mg, 0.21 mmol). The mixture was then stirred at r.t. for overnight. The solvent was removed under reduced pressure and the residue was purified by prep-HPLC to afford the title compound (30 mg, 26.1% yield) as a white solid. Partial $^1$H NMR (400 MHz, Acetone-d$_6$): δ 7.35-7.27 (m, 4H), 7.24-7.21 (m, 1H), 7.05 (s, 1H), 5.54 (s, 1H), 4.84 (d, J=1.6 Hz, 1H), 4.68-4.63 (m, 1H), 4.47 (dd, J=9.2, 1.6 Hz, 1H), 4.33 (q, J=6.4 Hz, 1H), 3.74-3.66 (m, 2H), 3.07 (dd, J=13.2, 4.8 Hz, 1H), 3.02 (t, J=9.2 Hz, 1H), 2.92-2.89 (m, 1H), 2.80-2.75 (m, 4H), 2.45 (dd, J=13.2, 2.8 Hz, 1H), 2.39-2.25 (m, 2H), 2.18-2.12 (m, 4H), 0.98-0.87 (m, 1H), 0.80 (t, J=7.6 Hz, 3H); LCMS: m/z 821.9 [M+H]$^+$.

Example 35: Synthesis of (2S,3aR,5aS,5bS,9S,13S, 14R,16aS,16bS)-9-ethyl-4,14-dimethyl-13-{[(2R,5S, 6R)-6-methyl-5-[methyl(prop-2-en-1-yl)amino] oxan-2-yl]oxy}-2-{[(2R,3R,4R,5S,6S)-3,4,5-trimethoxy-6-methyloxan-2-yl]oxy}-1H,2H,3H,3aH, 5aH,5bH,6H,7H,9H,10H,11H,12H,13H,14H,15H, 16aH,16bH-as-indaceno[3,2-d]oxacyclododecane-7, 15-dione

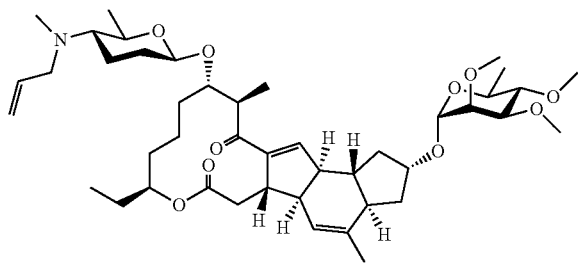

Example 35 was prepared using Intermediate 2 and Procedure A. To a solution of Intermediate 2 (100 mg, 0.14 mol) and DIPEA (36 mg, 0.28 mmol) in dichloromethane (5 mL) was added allyl bromide (25 mg, 0.21 mmol). The mixture was then stirred at r.t. overnight. The solvent was removed under reduced pressure, and the residue was purified by prep-HPLC to afford the title compound (35 mg, 33.2% yield) as a white solid. Partial $^1$H NMR (400 MHz, Acetone-d$_6$): δ 7.04 (s, 1H), 5.84-5.74 (m, 1H), 5.54 (s, 1H), 5.17 (d, J=16.8 Hz, 1H), 5.05 (d, J=10.4 Hz, 1H), 4.83 (d, J=1.6 Hz, 1H), 4.68-4.63 (m, 1H), 4.47 (dd, J=9.2, 1.6 Hz, 1H), 4.33 (q, J=6.4 Hz, 1H), 3.15-2.95 (m, 4H), 2.92-2.86 (m, 1H), 2.80-2.75 (m, 4H), 2.45 (dd, J=13.2, 2.8 Hz, 1H), 2.39-2.33 (m, 1H), 2.00-1.91 (m, 2H), 1.83-1.78 (m, 2H), 1.74 (s, 3H), 0.96-0.91 (m, 1H), 0.81 (t, J=7.6 Hz, 3H); LCMS: m/z 771.9 [M+H]$^+$.

Example 36: Synthesis of N-[(2R,3S,6R)-6-{[(2S, 3aR,5aS,5bS,9S,13S,14R,16aS,16bS)-9-ethyl-4,14-dimethyl-7,15-dioxo-2-{[(2R,3R,4R,5S,6S)-3,4,5-trimethoxy-6-methyloxan-2-yl]oxy}-1H,2H,3H,3aH, 5aH,5bH,6H,7H,9H,10H,11H,12H,13H,14H,15H, 16aH,16bH-as-indaceno[3,2-d]oxacyclododecan-13-yl]oxy}-2-methyloxan-3-yl]-N-methylpropanamide

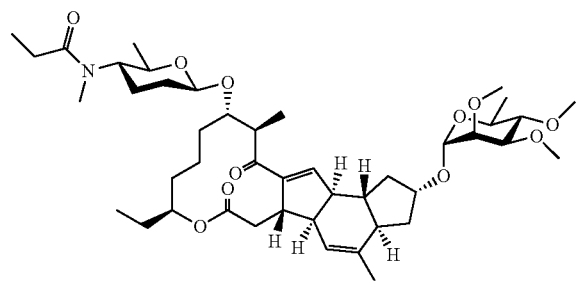

Example 36 was prepared using Intermediate 2 and Procedure B: To a stirred solution of propionic acid (19 mg, 0.21 mmol) and DIPEA (36 mg, 0.28 mmol) in DMF (5 mL) was added HATU (106 mg, 0.28 mmol) and Intermediate 2 (100 mg, 0.14 mol). The mixture was then stirred at r.t. overnight. The reaction mixture was diluted with water (10 mL) and extracted with ethyl acetate (3×20 mL). The combined organic phase was washed with brine (50 mL), dried over anhydrous sodium sulfate, filtered and concentrated. The residue was purified by prep-HPLC to afford the title compound (35 mg, 31.8% yield) as a white solid. Partial $^1$H NMR (400 MHz, Acetone-d$_6$): δ 6.93 (s, 1H), 5.41 (s, 1H), 4.72 (d, J=1.6 Hz, 1H), 4.52-4.48 (m, 1H), 4.45-4.40 (m, 1H), 4.19 (q, J=6.4 Hz, 1H), 3.74-3.70 (m, 1H), 2.94 (dd, J=13.2, 4.8 Hz, 1H), 2.86 (t, J=9.2 Hz, 1H), 2.83-2.60 (m, 6H), 2.36-2.18 (m, 4H), 2.06-1.97 (m, 1H), 0.85-0.75 (m, 1H), 0.67 (t, J=7.6 Hz, 3H); LCMS: m/z 788.1 [M+H]$^+$.

Example 37: Synthesis of N-[(2R,3S,6R)-6-{[(2S, 3aR,5aS,5bS,9S,13S,14R,16aS,16bS)-9-ethyl-4,14-dimethyl-7,15-dioxo-2-{[(2R,3R,4R,5S,6S)-3,4,5-trimethoxy-6-methyloxan-2-yl]oxy}-1H,2H,3H,3aH, 5aH,5bH,6H,7H,9H,10H,11H,12H,13H,14H,15H, 16aH,16bH-as-indaceno[3,2-d]oxacyclododecan-13-yl]oxy}-2-methyloxan-3-yl]-N,2-dimethylpropanamide

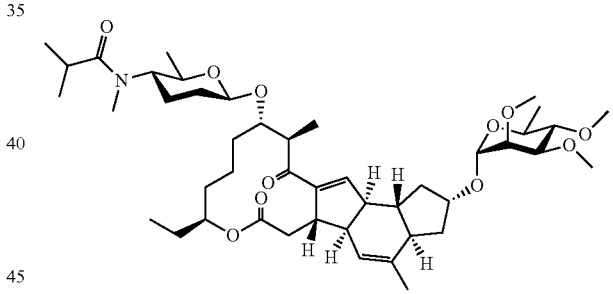

Example 37 was prepared using Intermediate 2 and Procedure B. To a stirred solution of isobutyric acid (19 mg, 0.21 mmol) and DIPEA (36 mg, 0.28 mmol) in DMF (5 mL) was added HATU (106 mg, 0.28 mmol) and Intermediate 2 (100 mg, 0.14 mol). The mixture was then stirred at r.t. overnight. The reaction mixture was diluted with water (10 mL) and extracted with ethyl acetate (3×20 mL). The combined organic phase was washed with brine (50 mL), dried over anhydrous sodium sulfate, filtered and concentrated. The residue was purified by prep-HPLC to afford the title compound (32 mg, 29.2% yield) as a white solid. Partial $^1$H NMR (400 MHz, Acetone-d$_6$): δ 6.93 (s, 1H), 5.42 (s, 1H), 4.72 (d, J=1.6 Hz, 1H), 4.53-4.41 (m, 2H), 4.19 (q, J=6.4 Hz, 1H), 3.75-3.66 (m, 1H), 2.33-2.27 (m, 1H), 2.27-2.20 (m, 1H), 2.08-2.01 (m, 1H), 1.88-1.61 (m, 7H), 0.67 (t, J=7.6 Hz, 3H); LCMS: m/z 801.9 [M+H]$^+$.

Example 38: N-[(2R,3S,6R)-6-{[(2S,3aR,5aS,5bS,
9S,13S,4R,16aS,16bS)-9-ethyl-4,14-dimethyl-7,15-
dioxo-2-{[(2R,3R,4R,5S,6S)-3,4,5-trimethoxy-6-
methyloxan-2-yl]oxy}-1H,2H,3H,3aH,5aH,5bH,6H,
7H,9H,10H,11H,12H,13H,14H,15H,16aH,16bH-as-
indaceno[3,2-d]oxacyclododecan-13-yl]oxy}-2-
methyloxan-3-yl]-N-methyl-2-propylpentanamide

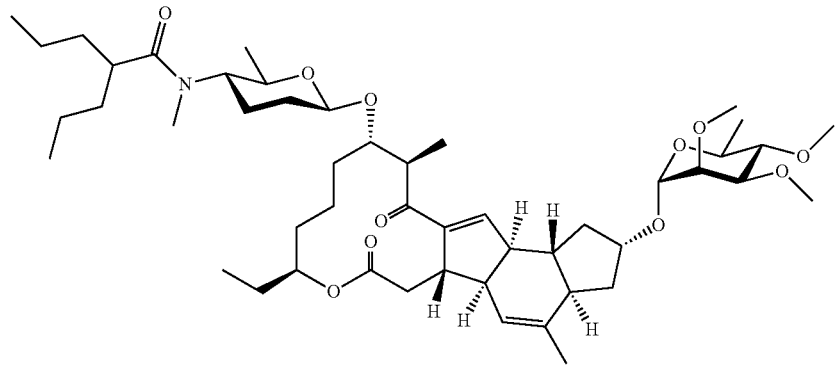

Example 38 was prepared using Intermediate 2 and Procedure B. To a stirred solution of 2-propylpentanoic acid (30 mg, 0.21 mmol) and DIPEA (36 mg, 0.28 mmol) in DMF (5 mL) was added HATU (106 mg, 0.28 mmol) and Intermediate 2 (100 mg, 0.14 mol). The mixture was then stirred at r.t. overnight. The reaction mixture was diluted with water (10 mL) and extracted with ethyl acetate (3×20 mL). The combined organic phase was washed with brine (50 mL), dried over anhydrous sodium sulfate, filtered and concentrated. The residue was purified by prep-HPLC to afford the title compound (35 mg, 28.5% yield) as a white solid. Partial $^1$H NMR (400 MHz, Acetone-d$_6$): δ 7.06 (s, 1H), 5.55 (s, 1H), 4.85 (d, J=1.6 Hz, 1H), 4.67-4.55 (m, 2H), 4.32 (q, J=6.4 Hz, 1H), 3.90-3.82 (m, 1H), 3.08 (dd, J=13.2, 4.8 Hz, 1H), 3.02 (t, J=9.2 Hz, 1H), 2.97-2.75 (m, 7H), 2.49-2.44 (m, 1H), 2.39-2.33 (m, 1H), 2.05-1.75 (m, 7H), 0.90-0.65 (m, 6H), 0.80 (t, J=7.6 Hz, 3H); LCMS: m/z 857.9 [M+H]$^+$.

Example 39: Synthesis of N-[(2R,3S,6R)-6-{[(2S,
3aR,5aS,5bS,9S,13S,14R,16aS,16bS)-9-ethyl-4,14-
dimethyl-7,15-dioxo-2-{[(2R,3R,4R,5S,6S)-3,4,5-
trimethoxy-6-methyloxan-2-yl]oxy}-1H,2H,3H,3aH,
5aH,5bH,6H,7H,9H,10H,11H,12H,13H,14H,15H,
16aH,16bH-as-indaceno[3,2-d]oxacyclododecan-13-
yl]oxy}-2-methyloxan-3-yl]-2-butyl-N-
methyloctanamide

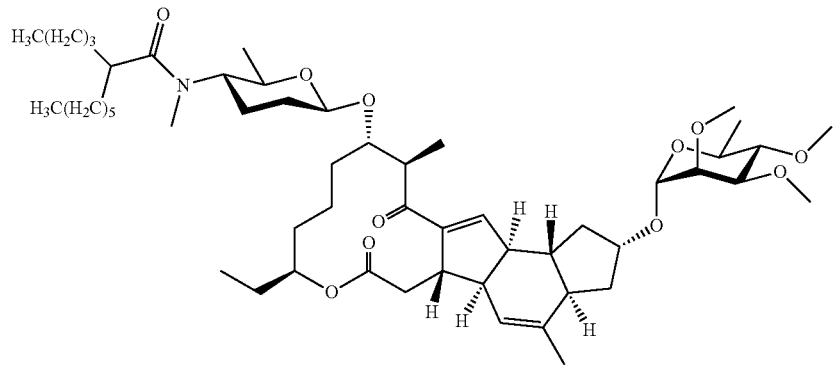

Example 39 was prepared using Intermediate 2 and Procedure B. To a stirred solution of 2-butyloctanoic acid (42 mg, 0.21 mmol) and DIPEA (36 mg, 0.28 mmol) in DMF (5 mL) was added HATU (106 mg, 0.28 mmol) and Intermediate 2 (100 mg, 0.14 mol). The mixture was then stirred at r.t. overnight. The reaction mixture was diluted with water (30 mL) and extracted with ethyl acetate (3×50 mL). The combined organic phase was washed with brine (100 mL), dried over anhydrous sodium sulfate, filtered and concentrated. The residue was purified by prep-HPLC to afford the title compound (115 mg, 30.7% yield) as a white solid. Partial $^1$H NMR (400 MHz, Acetone-d$_6$): δ 6.93 (s, 1H), 5.41 (s, 1H), 4.72 (d, J=1.6 Hz, 1H), 4.54-4.42 (m, 2H), 4.19 (q, J=6.4 Hz, 1H), 3.77-3.68 (m, 1H), 2.95 (dd, J=13.2, 4.8 Hz, 1H), 2.89 (t, J=9.2 Hz, 1H), 2.84-2.61 (m, 7H), 2.33-2.29 (m, 1H), 2.09-2.01 (m, 1H), 0.82-0.72 (m, 7H), 0.67 (t, J=7.6 Hz, 3H); LCMS: m/z 915.5 [M+H]$^+$.

Example 40: Synthesis of N-[(2R,3S,6R)-6-{[(2S,3aR,5aS,5bS,9S,13S,14R,16aS,16bS)-9-ethyl-4,14-dimethyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methyloctanamide

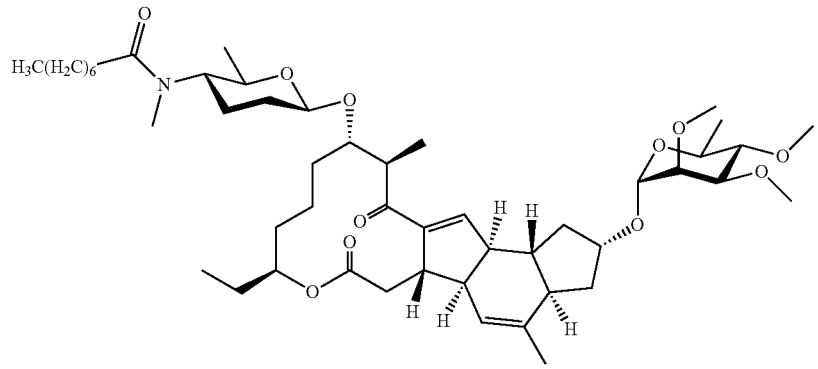

Example 40 was prepared using Intermediate 2 and Procedure B. To a stirred solution of n-caprylic acid (30 mg, 0.21 mmol) and DIPEA (26 mg, 0.28 mmol) in DMF (5 mL) was added HATU (106 mg, 0.28 mmol) and Intermediate 2 (100 mg, 0.14 mmol). The mixture was then stirred at r.t. overnight. The reaction mixture was diluted with water (10 mL) and extracted with ethyl acetate (3×20 mL). The combined organic phase was washed with brine (50 mL), dried over anhydrous sodium sulfate, filtered and concentrated. The residue was purified by prep-HPLC to afford the title compound (95 mg, 27.0% yield) as a white solid. $^1$H NMR (400 MHz, Acetone-d$_6$): δ 6.92 (s, 1H), 5.41 (s, 1H), 4.72 (d, J=1.6 Hz, 1H), 4.52-4.40 (m, 2H), 4.19 (q, J=6.4 Hz, 1H), 3.73-3.68 (m, 1H), 3.47-3.18 (m, 17H), 2.95 (dd, J=13.2, 4.8 Hz, 1H), 2.89 (t, J=9.2 Hz, 1H), 0.67 (t, J=7.6 Hz, 3H); LCMS: m/z 857.9 [M+H]$^+$.

Example 41: Synthesis of N-[(2R,3S,6R)-6-{[(2S,3aR,5aS,5bS,9S,13S,14R,16aS,16bS)-9-ethyl-4,14-dimethyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methyldodecanamide

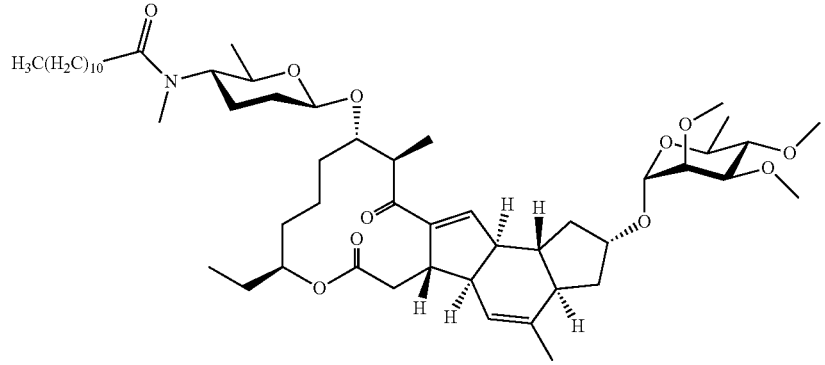

Example 41 was prepared using Intermediate 2 and Procedure B. To a stirred solution of lauric acid (42 mg, 0.21 mmol) and DIPEA (36 mg, 0.28 mmol) in DMF (5 mL) was added HATU (106 mg, 0.28 mmol) and Intermediate 2 (100 mg, 0.14 mol). The mixture was then stirred at r.t. overnight. The reaction mixture was diluted with water (10 mL) and extracted with ethyl acetate (3×20 mL). The combined organic phase was washed with brine (50 mL), dried over anhydrous sodium sulfate, filtered and concentrated. The residue was purified by prep-HPLC to afford the title compound (105 mg, 28.1% yield) as a white solid. Partial $^1$H NMR (400 MHz, Acetone-$d_6$): δ 6.93 (s, 1H), 5.42 (s, 1H), 4.73 (d, J=1.6 Hz, 1H), 4.52-4.41 (m, 2H), 4.19 (q, J=6.4 Hz, 1H), 3.73-3.65 (m, 1H), 2.95 (dd, J=13.2, 4.8 Hz, 1H), 2.89 (t, J=9.2 Hz, 1H), 2.68-2.63 (m, 3H), 2.60 (s, 1H), 2.33-2.17 (m, 3H), 2.09-2.01 (m, 1H), 1.22-1.16 (m, 21H), 0.77-0.74 (m, 3H), 0.68 (t, J=7.6 Hz, 3H); LCMS: m/z 916.4 [M+H]$^+$.

Example 42: Synthesis of N-[(2R,3S,6R)-6-{[(2S,3aR,5aS,5bS,9S,13S,14R,16aS,16bS)-9-ethyl-4,14-dimethyl-7,15-dioxo-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecan-13-yl]oxy}-2-methyloxan-3-yl]-N-methylbenzamide

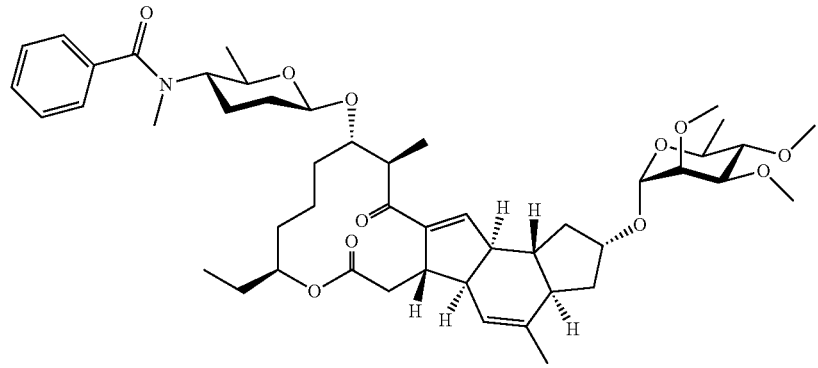

Example 42 was prepared using Intermediate 2 and Procedure B. To a solution of Intermediate 2 (100 mg, 0.14 mol) and DIPEA (36 mg, 0.28 mmol) in dichloromethane (5 mL) was added benzoyl chloride (30 mg, 0.21 mmol). The mixture was then stirred at r.t. overnight. The reaction mixture was diluted with water (10 mL) and extracted with dichloromethane (3×10 mL). The combined organic phase was washed with brine (30 mL), dried over anhydrous sodium sulfate, filtered and concentrated. The residue was purified by prep-HPLC to afford the title compound (30 mg, 26.3% yield) as a white solid. Partial $^1$H NMR (400 MHz, Acetone-d$_6$): 7.33-7.23 (m, 5H), 6.94-6.90 (m, 2H), 5.40 (s, 1H), 4.72 (s, 1H), 4.52-4.40 (m, 2H), 4.20-4.16 (m, 1H), 3.75-3.70 (m, 1H), 2.96-2.86 (m, 2H), 2.78-2.60 (m, 6H), 2.33-2.20 (m, 2H), 2.06-1.96 (m, 1H), 1.90-1.70 (m, 4H), 1.60 (s, 3H), 0.70-0.63 (m, 3H); LCMS: m/z 836.0 [M+H]$^+$.

Intermediate 3: Synthesis of (9H-fluoren-9-yl) methyl N-[(2R,3S,6R)-6-{[(2R,3aS,5aR,5bS,9S,13S, 14R,16aS,16bR)-9-ethyl-14-methyl-7,15-dioxo-2-{ [(2R,3R,4R,5S,6S)-3,4,5-trimethoxy-6-methyloxan-2-yl]oxy}-1H,2H,3H,3aH,5aH,5bH,6H,7H,9H,10H, 11H,12H,13H,14H,15H,16aH,16bH-as-indaceno[3, 2-d]oxacyclododecan-13-yl]oxy}-2-methyloxan-3-yl]-N-methylcarbamate Intermediate 3 was prepared using Intermediate 1, procedure A. To a solution of Intermediate 1 (5.0 g, 6.97 mmol) in dichloromethane (20 mL) was added DIEA (1.58 mL, 9.06 mmol) and Fmoc-Cl (1.99 g, 7.67 mmol) at 0° C. The resulting mixture was stirred at r.t. for 3 h. The mixture was quenched with water and extracted with dichloromethane (3×50 mL). The combined organic phase was washed with brine (30 mL), dried over anhydrous sodium sulfate, filtered and concentrated. The residue was purified by silica gel column chromatography (petroleum ether/ethyl acetate=3/1) to afford the title compound (5.4 g, 83% yield) as a white solid. Partial $^1$H NMR (CDCl$_3$, 400 MHz): δ7.77 (d, J=7.6 Hz, 1H), 7.60-7.55 (m, 2H), 7.40 (t, J=7.6 Hz, 2H), 7.33-7.28 (m, 2H), 6.78 (d, J=6.8 Hz, 1H), 5.91-5.81 (m, 2H), 4.86 (s, 1H), 4.72-4.67 (m, 1H), 4.48-4.42 (m, 2H), 4.34-4.21 (m, 2H), 3.56 (s, 3H), 3.50 (s, 6H), 3.32-3.28 (m, 1H), 3.15-3.03 (m, 1H), 2.89-2.87 (m, 1H), 2.74 (d, J=5.6 Hz, 3H), 2.42-2.38 (m, 1H), 2.30-2.18 (m, 2H), 1.96-1.90 (m, 2H), 1.18 (d, J=6.8 Hz, 3H), 1.12 (d, J=5.6 Hz, 3H), 0.82 (t, J=7.6 Hz, 3H); LC-MS: m/z 958 [M+NH$_4$]$^+$.

Intermediate 4: Synthesis of prop-2-en-1-yl N-[(2R, 3S,6R)-6-{[(2R,3aS,5aR,5bS,9S,13S,14R,16aS, 16bR)-9-ethyl-14-methyl-7,15-dioxo-2-{[(2R,3R, 4R,5S,6S)-3,4,5-trimethoxy-6-methyloxan-2-yl] oxy}-1H,2H,3H,3aH,5aH,5bH,6H,7H,9H,10H,11H, 12H,13H,14H,15H,16aH,16bH-as-indaceno[3,2-d] oxacyclododecan-13-yl]oxy}-2-methyloxan-3-yl]-N-methylcarbamate

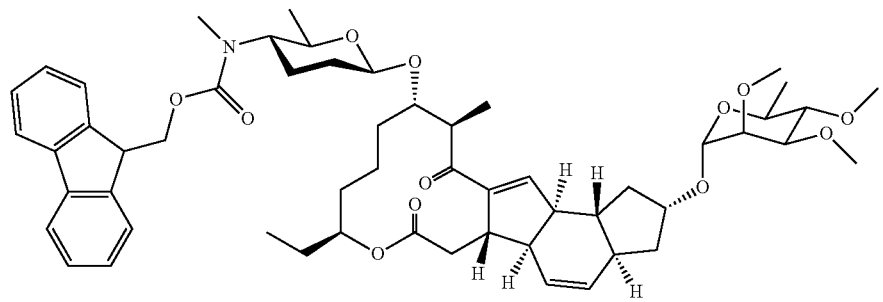

Intermediate 4 was prepared using Intermediate 1, procedure A. To a solution of Intermediate 1 (1.0 g, 1.39 mmol) in dichloromethane (10 mL) was added DIEA (0.48 mL, 2.78 mmol) and Alloc-Cl (0.22 mL, 2.09 mmol) at 0° C. The resulting mixture was stirred at rt. for 3 h. The mixture was treated with water and extracted with dichloromethane (3×50 mL). The combined organic phase was washed with brine (30 mL), dried over anhydrous sodium sulfate, filtered and concentrated. The residue was purified by silica gel column chromatography (petroleum ether/ethyl acetate=3/1) to afford the title compound (792 mg, 71% yield) as a white solid. Partial $^1$H NMR (CDCl$_3$, 400 MHz): δ6.77 (s, 1H), 5.96-5.79 (m, 3H), 5.29 (d, J=13.2 Hz, 2H), 5.21 (d, J=10.0 Hz, 1H), 4.85 (s, 1H), 4.68-4.58 (m, 3H), 4.47 (d, J=8.8 Hz, 1H), 4.34-4.29 (m, 1H), 3.65-3.62 (m, 2H), 3.56 (s, 3H), 3.50 (s, 6H), 3.46 (dd, J=9.2, 2.8 Hz, 1H), 3.32-3.28 (m, 1H), 3.15-3.09 (m, 2H), 3.02-3.01 (m, 1H), 2.90-2.85 (m, 1H), 2.79 (s, 3H), 2.41 (d, J=12.4 Hz, 1H), 2.30-2.16 (m, 2H), 2.00-1.90 (m, 2H), 1.28 (d, J=6.4 Hz, 3H), 0.82 (t, J=7.6 Hz, 3H); LC-MS: m/z 819 [M+NH$_4$]$^+$.

Intermediates 5 and 6: Synthesis of (1S,2R,3R,6S, 7R,9S,11R,12S,16R,17S,21S)-5,5-dichloro-21-ethyl-16-methyl-4,15,23-trioxo-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-en-17-yl acetate, and (1S,2R,3R,6S,7R,9S,11R,12S,16R,17S,21S)-4,4-dichloro-21-ethyl-16-methyl-5,15,23-trioxo-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-en-17-yl acetate

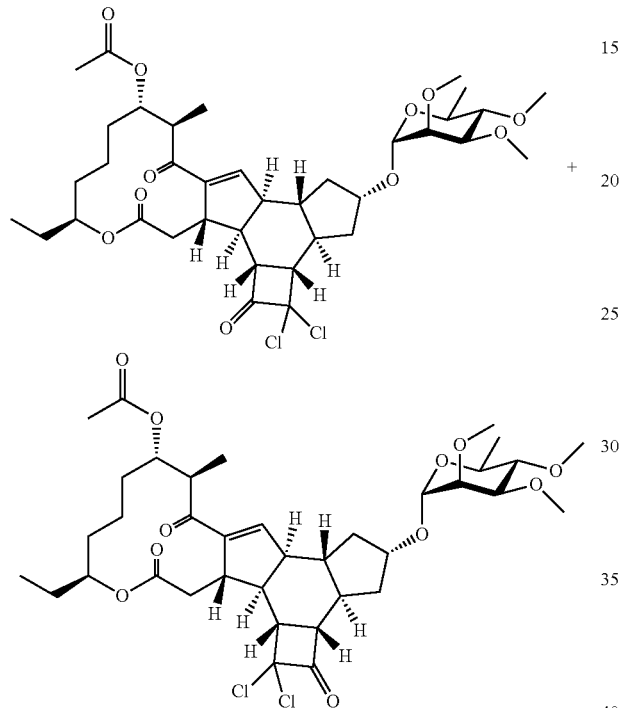

A mixture of Spinosyn A (10 g, 13.7 mmol) and sulfuric acid (0.1 N, 300 mL) was stirred at reflux overnight. After cooling to room temperature, the mixture was filtered and washed with 5% sodium bicarbonate, then brine. The solid was dried in vacuo to dryness to afford the product (6.1 g, yield 75.0%) as a white solid. LCMS: m/z 591.0 [M+H]$^+$.

To a solution of the product (6.1 g, 10.3 mmol) in dichloromethane (100 mL) was added Ac$_2$O (2.1 g, 20.5 mmol) and Triethylamine (2.3 g, 22.5 mmol). The mixture was stirred at 40° C. for 18 h. The mixture was quenched with aqueous 5% sodium bicarbonate solution (80 mL) and extracted with dichloromethane (100 mL×3). The combined organic phase was dried over sodium sulfate and concentrated. The residue was purified by column chromatography on silica gel (dichloromethane/methanol=100/1-20/1) to afford the intermediate product as a mixture of regioisomers (5.9 g, yield 92.1%) as a yellow solid. LCMS: m/z 650.2 [M+NH$_4$]$^+$.

To a solution of intermediate products (5.9 g, 9.3 mmol) in tetrahydrofuran (60 mL) was added Zinc-Cu couple (2.2 g, 17.1 mmol) under nitrogen. After stirred for 10 min at 0° C., trichloro-acetyl chloride (3.4 g, 18.66 mmol) in tetrahydrofuran (10 mL) and POCl$_3$ (1.85 g, 12.13 mmol) in tetrahydrofuran (10 mL) was added over 1.5 h. Then the mixture was heated to reflux for overnight. The mixture was quenched with aqueous 5% sodium bicarbonate solution (80 mL) and extracted with EA (100 mL×4). The combined organic phase was dried over sodium sulfate and concentrated. The residue was purified by column chromatography on silica gel (petroleum ether/ethyl acetate=6/1-1/1) to afford the crude mixture of the title compounds Intermediates 5 and 6 (3.2 g, yield 46.2%) as a yellow oil. LCMS: m/z 760.1 [M+NH$_4$]$^+$.

Intermediates 7 and 8: Synthesis of (1S,2R,3S,6S, 7R,9R,11R,12S,16R,17S,21S)-21-ethyl-16-methyl-4,15,23-trioxo-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-en-17-yl acetate and (1S,2R,3R,6S,7R,9S,11R,12S,16R,17S,21S)-21-ethyl-16-methyl-5,15,23-trioxo-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-en-17-yl acetate

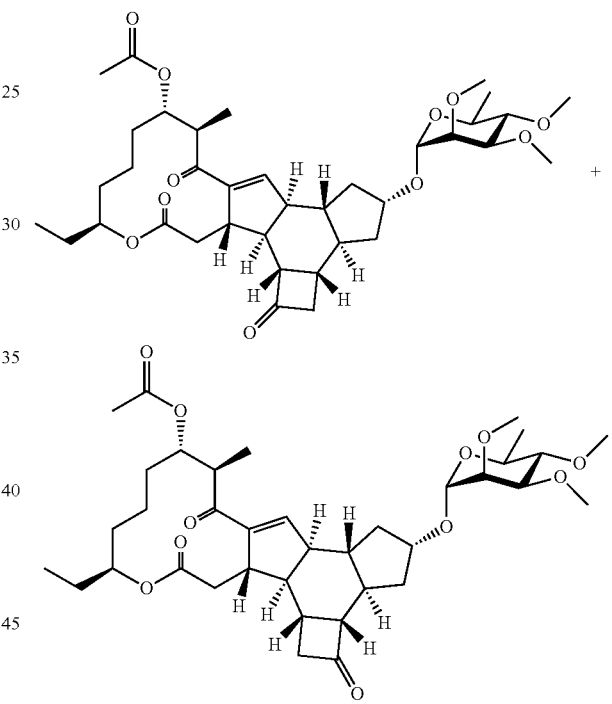

To the crude mixture of Intermediates 5 and 6 (3.2 g, 4.3 mmol) in methanol (40 mL) was added Zinc-Cu couple (1.22 g, 9.48 mmol) and ammonium chloride (0.34 g, 6.5 mmol). The mixture was stirred at 65° C. for 3 h. The mixture was quenched with aqueous 5% sodium bicarbonate solution (80 mL) and extracted with ethyl acetate (100 mL×2). The combined organic phase was dried over sodium sulfate and concentrated. The residue was purified by prep-HPLC and followed by prep-Chiral column to afford Intermediate 7 (960 mg) and Intermediate 8 (230 mg) as a white solid.

Intermediate 7: Partial $^1$H NMR (CDCl$_3$, 400 MHz): δ 6.77 (s, 1H), 5.05-5.00 (m, 1H), 4.86 (s, 1H), 4.73-4.70 (m, 1H), 4.36-4.32 (m, 1H), 3.59-3.34 (m, 16H), 3.17-3.09 (m, 2H), 3.00 (br, 1H), 2.75-2.67 (m, 2H), 2.41-2.23 (m, 3H), 2.10 (s, 3H), 2.08-2.05 (m, 1H), 1.15 (d, 6.8 Hz, 1H), 0.97-0.92 (m, 1H), 0.84 (t, J=7.2 Hz, 3H); LCMS: m/z 692.2 [M+NH$_4$]$^+$.

Intermediate 8: Partial $^1$H NMR (CDCl$_3$, 400 MHz): δ 6.79 (s, 1H), 5.11-5.08 (m, 1H), 4.86 (s, 1H), 4.68-4.66 (m, 1H), 4.38-4.33 (m, 1H), 3.60-3.47 (m, 13H), 3.35-3.12 (m, 5H), 2.98-2.94 (m, 1H), 2.71-2.63 (m, 2H), 2.50-2.39 (m, 2H), 2.30-2.24 (m, 1H), 2.16-2.11 (m, 4H), 1.99-1.95 (m, 1H), 0.85 (t, J=7.2 Hz, 3H); LCMS: m/z 692.2 [M+NH$_4$]$^+$.

Intermediates 9 and 10: Synthesis of (1S,2R,8R,10S,12R,13R,17R,18S,22S)-22-ethyl-17-methyl-5,16,24-trioxo-10-{[(2R,3R,4R,5S,6S)-3,4,5-trimethoxy-6-methyloxan-2-yl]oxy}-4,23-dioxapentacyclo[13.10.0.0$^{2,13}$.0$^{3,7}$.0$^{8,12}$]pentacos-14-en-18-yl acetate (Intermediate 9), and (1S,2R,8R,10S,12S,13S,17R,18S,22S)-22-ethyl-17-methyl-5,16,24-trioxo-10-{[(2R,3R,4R,5S,6S)-3,4,5-trimethoxy-6-methyloxan-2-yl]oxy}-6,23-dioxapentacyclo[13.10.0.0$^{2,13}$.0$^{3,7}$.0$^{8,12}$]pentacos-14-en-18-yl acetate (Intermediate 10)

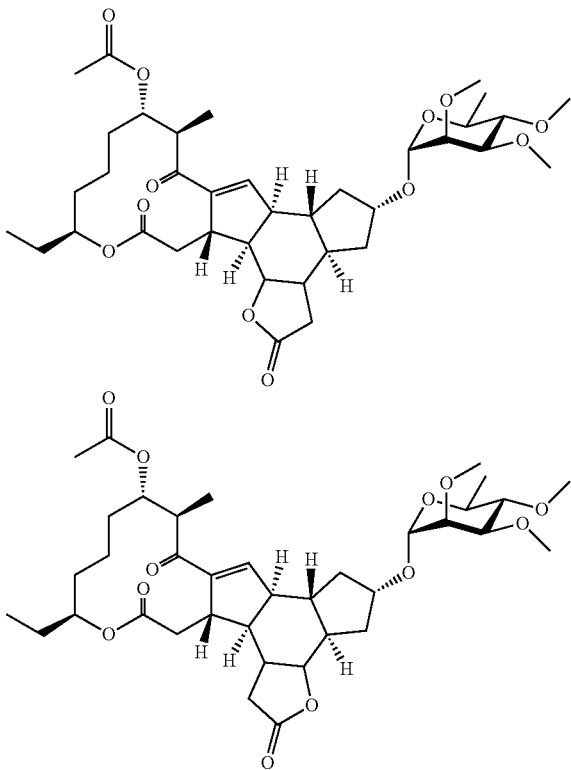

To a mixture of Intermediate 7 and Intermediate 8 (1.5 g, 2.22 mmol) in dichloromethane (30 mL) were added m-CPBA (1.14 g, 6.66 mmol) and Na$_2$HPO$_4$ (0.63 g, 4.44 mmol) at 0° C. The resulting mixture was stirred at r.t. for 48 h. To the mixture was added saturated aqueous Na$_2$SO$_3$ (30 mL) and the mixture was stirred at r.t. for 2 h. The organic layer was separated and the aqueous was extracted with dichloromethane (60 mL×2). The combined organic phase was washed with brine (50 mL), dried over anhydrous sodium sulfate, filtered and concentrated. The residue was purified by prep-HPLC and prep-Chiral column to afford Intermediate 9 (360 mg) and Intermediate 10 (90 mg) as white solids.

Intermediate 9: Partial $^1$H NMR (CDCl$_3$, 400 MHz): δ 6.76 (s, 1H), 5.06-5.02 (m, 1H), 4.83 (s, 1H), 4.71-4.67 (m, 1H), 4.48 (t, J=6.8 Hz, 1H), 4.36-4.32 (m, 1H), 3.27 (s, 1H), 3.15-2.98 (m, 4H), 2.81-2.75 (m, 1H), 2.50-2.33 (m, 4H), 2.08 (s, 3H), 2.04-1.98 (m, 1H), 0.83 (t, J=7.2 Hz, 3H); LCMS: m/z 707.9 [M+NH$_4$]$^+$.

Intermediate 10: Partial $^1$H NMR (CDCl$_3$, 400 MHz): δ 6.74 (s, 1H), 5.09-5.06 (m, 1H), 4.86 (s, 1H), 4.68-4.65 (m, 1H), 4.41-4.34 (m, 2H), 3.28-3.23 (m, 1H), 3.14 (t, J=9.2 Hz, 1H), 3.00-2.92 (m, 2H), 2.82-2.72 (m, 2H), 2.50-2.33 (m, 4H), 2.27-2.22 (m, 1H), 2.09 (s, 3H), 2.06-1.98 (m, 1H), 0.84 (t, J=7.2 Hz, 3H); LCMS: m/z 707.9 [M+NH$_4$]$^+$.

Intermediate 11: Synthesis of (1S,2R,3S,6S,7R,9R,11R,12S,16R,17S,21S)-21-ethyl-17-hydroxy-16-methyl-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-ene-4,15,23-trione

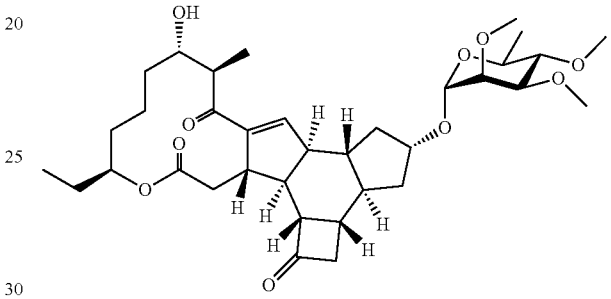

To a solution of Intermediate 7 (500 mg, 0.74 mmol) in methanol (4 mL) was added potassium carbonate (200 mg, 1.48 mmol). After stirred at r.t. for 2 h, the reaction was quenched with saturated aqueous ammonium chloride and was extracted with ethyl acetate (60 mL×2). The organic layer was washed with brine, dried over anhydrous sodium sulfate and concentrated. The residue was purified by prep-HPLC to afford the title compound (220 mg, yield 47.0%) as a white solid.

Partial $^1$H NMR (CDCl$_3$, 400 MHz): δ 6.78 (s, 1H), 4.86 (s, 1H), 4.77-4.71 (m, 1H), 4.37-4.32 (m, 1H), 3.72-3.68 (m, 1H), 3.00-2.97 (m, 1H), 2.74-2.66 (m, 2H), 2.40-2.23 (m, 3H), 2.08-2.03 (m, 1H), 0.84 (t, J=7.2 Hz, 3H); LCMS: m/z 649.9 [M+NH$_4$]$^+$.

Intermediate 12: Synthesis of (1S,2R,3R,6S,7R,9S,11R,12S,16R,17S,21S)-21-ethyl-17-hydroxy-16-methyl-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-ene-5,15,23-trione

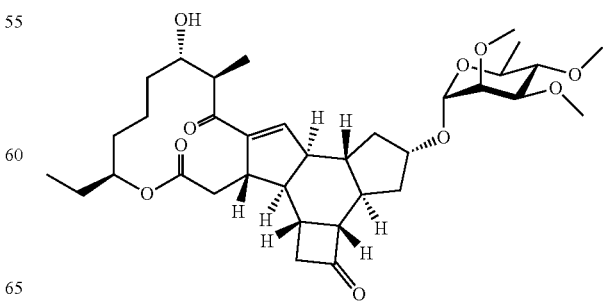

To a solution of Intermediate 8 (230 mg, 0.34 mmol) in methanol (2 mL) was added potassium carbonate (94 mg, 0.68 mmol). After stirring at r.t. for 2 h, the reaction was quenched with saturated aqueous ammonium chloride (10 mL) and was extracted with ethyl acetate (30 mL×2). The combined organic layers were washed with brine, dried over anhydrous sodium sulfate and concentrated. The residue was purified by prep-HPLC to afford the title compound (80 mg, yield 37.2%) as a white solid. Partial $^1$H NMR (CDCl$_3$, 400 MHz): δ 6.78 (s, 1H), 4.86 (s, 1H), 4.72-4.65 (m, 1H), 4.38-4.32 (m, 1H), 3.86-3.83 (m, 1H), 2.97 (dd, J=13.4, 5.0 Hz, 1H), 2.73-2.65 (m, 2H), 2.50-2.40 (m, 2H), 2.32-2.22 (m, 1H), 2.16-2.11 (m, 1H), 2.00-1.94 (m, 1H), 0.86 (t, J=7.2 Hz, 3H); LCMS: m/z 649.9 [M+NH$_4$]$^+$.

Intermediates 13 and 14: Synthesis of (1S,2R,3S,6S,7R,9R,11R,12S,16R,21S)-21-ethyl-16-methyl-9-{[(2R,3R,4R,5S,6S)-3,4,5-trimethoxy-6-methyl-oxan-2-yl]oxy}-22-oxapentacyclo[12.10.0.0$^{2,12}$.0$^{3,6}$.0$^{7,11}$]tetracos-13-ene-4,15,17,23-tetrone (Intermediate 13), and (1S,2R,3R,6S,7R,9S,11R,12S,16R,21S)-21-ethyl-16-methyl-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-ene-5,15,17,23-tetrone (Intermediate 14)

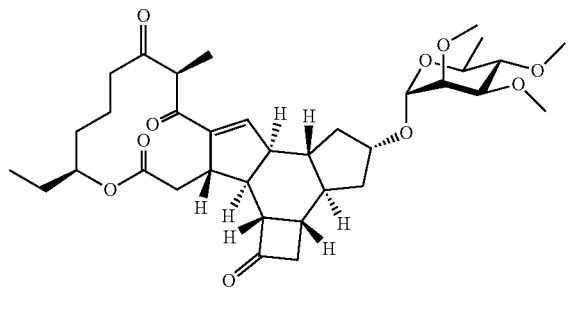

To a solution of Intermediate 11 (200 mg, 0.3 mmol) in dichloromethane (15 mL), was added DMP (200 mg, 0.45 mmol). After stirred at r.t. for 2 h, the reaction was quenched with saturated aqueous Na$_2$SO$_3$ (20 mL). The aqueous layer was extracted with dichloromethane (30 mL). The combined organic layers were washed with brine, dried over anhydrous sodium sulfate, and concentrated. The residue was purified by prep-HPLC to give the title compound Intermediate 13 (89 mg, yield 44%) as a white solid. Partial $^1$H NMR (CDCl$_3$, 400 MHz): δ 6.90 (s, 1H), 4.85-4.81 (m, 2H), 4.32-4.18 (m, 2H), 3.74-3.69 (m, 1H), 3.54-3.39 (m, 14H), 3.27-3.08 (m, 2H), 3.16 (t, J=9.6 Hz, 1H); 2.91-2.86 (m, 2H), 2.64-2.51 (m, 3H), 2.41-2.20 (m, 4H), 2.05-2.00 (m, 1H), 0.84 (t, J=7.6 Hz, 3H); LCMS: m/z 647.9 [M+NH$_4$]$^+$.

Intermediate 14 was prepared from Intermediate 12 under the similar procedure as described for the synthesis of intermediate 13.

Intermediate 14: Partial $^1$H NMR (CDCl$_3$, 400 MHz): δ 6.93 (s, 1H), 4.91-4.85 (m, 2H), 4.36-4.21 (m, 2H), 3.59-3.41 (m, 14H), 3.30-3.21 (m, 2H), 3.15 (t, J=9.4 Hz, 1H); 2.96-2.93 (m, 2H), 2.69-2.56 (m, 3H), 2.45-2.25 (m, 4H), 2.08-2.00 (m, 1H), 0.84 (t, J=7.6 Hz, 3H); LCMS: 712/z 648.0 [M+NH$_4$]$^+$.

Intermediate 15: Synthesis of (1S,2R,3S,6S,7R,9R,11R,12S,16R,17S,21S)-17-{[(2R,5S,6R)-5-(dimethylamino)-6-methyloxan-2-yl]oxy}-21-ethyl-16-methyl-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-ene-4,15,23-trione

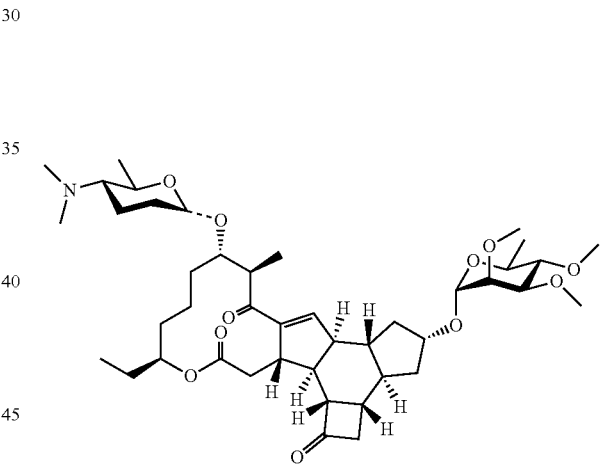

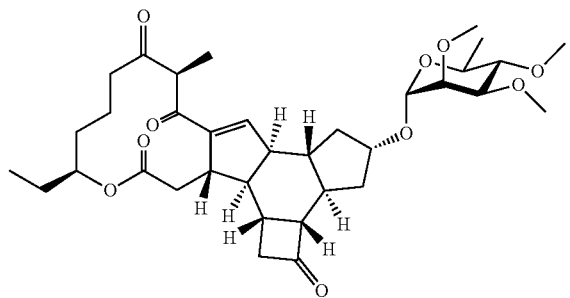

To the mixture of compound Intermediate 11 (180 mg, 0.28 mmol) and AgOTf (430 mg, 1.68 mmol) in dichloromethane (10 mL) was added thioforosamine (140 mg, 0.55 mmol) at 0° C. over 2 h. The mixture was stirred at r.t. for 18 h. The mixture was concentrated and the residue was purified by column chromatography and then by prep-HPLC to afford the title compound (α/β mixture, 7 mg, yield 2.7%) as yellow oil.

Partial $^1$H NMR (CDCl$_3$, 400 MHz): δ 6.81 and 6.77 (s, 1H), 4.87 and 4.90 (s, 1H), 4.73-4.68 (m, 1H), 4.37-4.33 (m, 1H), 3.93-3.87 (m, 1H), 3.42-3.24 (m, 4H), 3.18-3.00 (m, 3H), 2.87-2.68 (m, 2H); LCMS: m/z 773.9 [M+H]$^+$.

Intermediates 16 and 17: Synthesis of (1S,2R,8R,10S,12R,13R,17R,18S,22S)-22-ethyl-18-hydroxy-17-methyl-10-{[(2R,3R,4R,5S,6S)-3,4,5-trimethoxy-6-methyloxan-2-yl]oxy}-4,23-dioxapentacyclo[13.10.0.0$^{2,13}$.0$^{3,7}$.0$^{8,12}$]pentacos-14-ene-5,16,24-trione (Intermediate 16), and (1S,2R,8R,10S,12R,13R,17R,18S,22S)-22-ethyl-17-methyl-5,16,24-trioxo-10-{[(2R,3R,4R,5S,6S)-3,4,5-trimethoxy-6-methyloxan-2-yl]oxy}-4,23-dioxapentacyclo[13.10.0.0$^{2,13}$.0$^{3,7}$.0$^{8,12}$]pentacos-14-en-18-yl acetate (Intermediate 17)

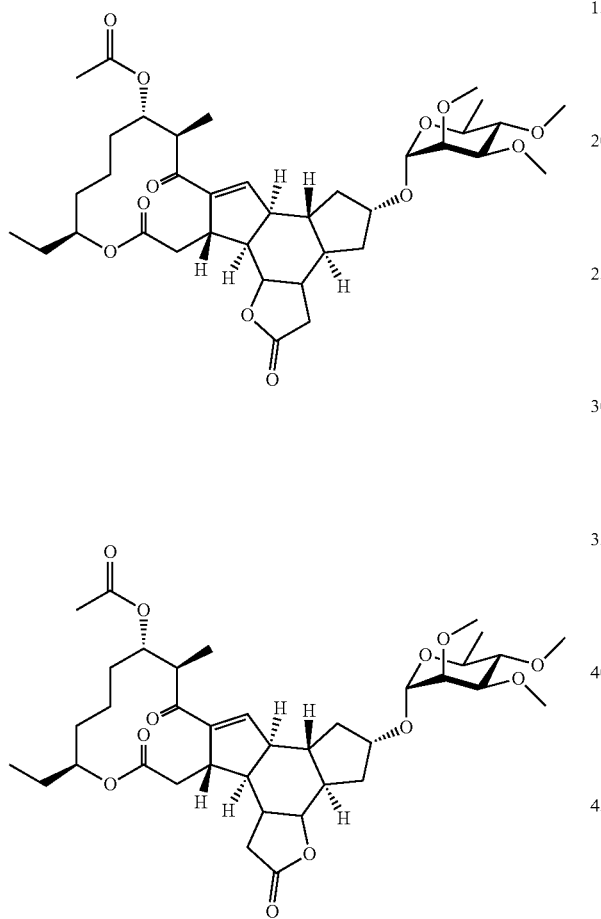

To a solution of Intermediate 9 (500 mg, 0.72 mmol) in methanol (20 mL) was added potassium carbonate (220 mg, 1.6 mmol). After stirred at r.t. for 16 h, the reaction was quenched with saturated aqueous ammonium chloride and was extracted with dichloromethane (100 mL). The organic layers was washed with brine, dried over anhydrous sodium sulfate and concentrated. The residue was purified by prep-HPLC to afford Intermediate 16 (130 mg, yield 27.8%) as a white solid. Partial $^1$H NMR (CDCl$_3$, 400 MHz): δ 6.78 (s, 1H), 4.86 (s, 1H), 4.77-4.71 (m, 1H), 4.51 (t, J=6.4 Hz, 1H), 4.40-4.36 (m, 1H), 3.82-3.76 (m, 1H), 3.03 (dd, J=14.0, 5.2 Hz, 1H), 2.83-2.76 (m, 1H), 2.48-2.32 (m, 4H), 2.07-2.00 (m, 1H), 0.87 (t, J=7.2 Hz, 3H); LCMS: m/z 666.3 [M+NH$_4$]$^+$.

Intermediate 17 was prepared from Intermediate 10 under the similar procedure as described for the synthesis of compound Intermediate 16. Partial $^1$H NMR (CDCl$_3$, 400 MHz): 6.73 (s, 1H), 4.86 (s, 1H), 4.69-4.65 (m, 1H), 4.40-4.35 (m, 2H), 3.83-3.80 (m, 1H), 3.31-3.21 (m, 2H), 3.14 (t, J=9.4 Hz, 1H), 2.98-2.91 (m, 2H), 2.82-2.76 (m, 2H), 2.49-2.33 (m, 4H), 2.05-2.00 (m, 1H), 0.85 (t, J=7.6 Hz, 3H); LCMS: m/z 666.3 [M+NH$_4$]$^+$.

Example 43: Synthesis of (1S,2R,8R,10S,12R,13S,17R,18S,22S)-18-{[(2R,5S,6R)-5-(dimethylamino)-6-methyloxan-2-yl]oxy}-22-ethyl-5-(4-fluorophenyl)-17-methyl-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione

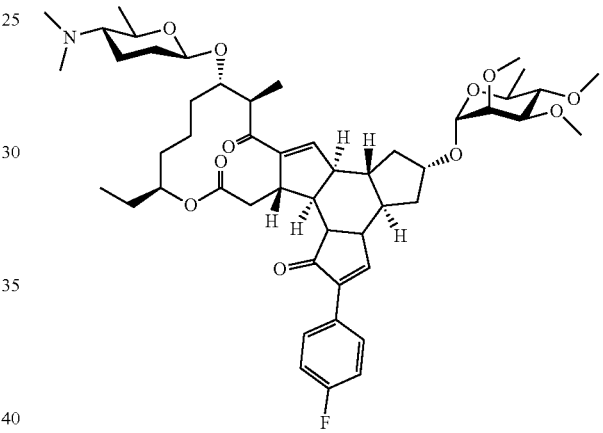

To a solution of 1-Ethynyl-4-fluoro-benzene (331 mg, 2.73 mmol) in toluene (50 mL) was added dicobalt octacarbonyl (0.93 g, 2.72 mmol) under nitrogen. The resulting mixture was stirred at r.t. for 1 h. A solution of Spinosyn A (1.0 g, 1.37 mmol) in toluene (10 mL) was added. The resulting mixture was charged with carbon monoxide and heated to 110° C. for 36 h under a carbon monoxide atmosphere. The reaction solution was cooled, quenched with water (50 mL) and extracted with dichloromethane (50 mL×2). The combined organic layer was dried over potassium carbonate, filtered and concentrated. The residue was purified by column chromatography on silica gel (methanol/dichloromethane=2/100) and chiral prep-HPLC to afford the title compound (100 mg, yield 7.9%) as a white solid. Partial $^1$H NMR (CDCl$_3$, 400 MHz): δ 7.73-7.68 (m, 3H), 7.07 (t, J=8.8 Hz, 2H), 6.71 (s, 1H), 4.85 (s, 1H), 4.67-4.58 (m, 1H), 4.44-4.36 (m, 2H), 3.77-3.67 (m, 2H), 3.60-3.55 (m, 13H), 3.20-3.08 (m, 2H), 2.97-2.88 (m, 2H), 2.73-2.65 (m, 1H), 2.55-2.39 (m, 3H), 2.25 (s, 6H), 2.20-2.12 (m, 1H), 2.01-1.9 (m, 24H), 1.34-1.18 (m, 12H), 1.14-1.03 (m, 1H), 0.80 (t, J=7.6 Hz, 3H); LC-MS: m/z 879.8 [M+H]$^+$.

Example 44: (1S,2R,8R,10S,12R,13S,17R,18S, 22S)-18-{[(2R,5S,6R)-5-(dimethylamino)-6-methyloxan-2-yl]oxy}-22-ethyl-17-methyl-5-(pyrimidin-5-yl)-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione

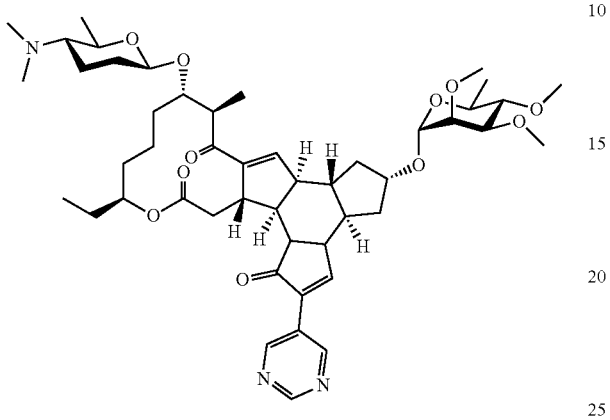

According to the general procedures as outlined for Example 43, 30 mg of Example 44 was obtained as a white solid from 1.0 g of Spinosyn A. $^1$HNMR (CDCl$_3$, 400 MHz): δ 9.19 (s, 1H), 9.08 (s, 2H), 7.91 (s, 1H), 6.71 (s, 1H), 4.86 (s, 1H), 4.68-4.58 (m, 1H), 4.46-4.37 (m, 2H), 3.75-3.68 (m, 2H), 3.60-3.36 (m, 15H), 3.21-3.10 (m, 2H), 2.99-2.90 (m, 2H), 2.84-2.77 (m, 1H), 2.54-2.47 (m, 3H), 2.26-2.16 (m, 8H), 2.02-1.03 (m, 36H), 0.80 (t, J=7.6 Hz, 3H); LC-MS: m/z 863.8 [M+H]$^+$.

Example 45: Synthesis of 4-[(1S,2R,8R,10S,12R, 13S,17R,18S,22S)-18-{[(2R,5S,6R)-5-(dimethylamino)-6-methyloxan-2-yl]oxy}-22-ethyl-17-methyl-4,16,24-trioxo-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-dien-5-yl]benzonitrile

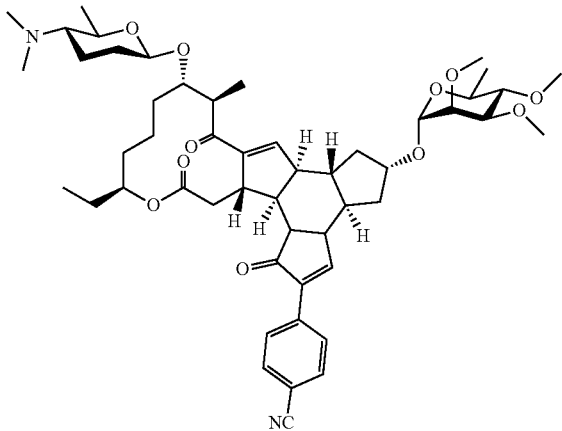

According to the general procedures as outlined for Example 43, 40 mg of Example 45 was obtained as a white solid from 1.0 g of Spinosyn A $^1$HNMR (CDCl$_3$, 400 MHz): δ 7.85 (d, J=8.4 Hz, 3H), 7.67 (d, J=8.4 Hz, 2H), 6.71 (s, 1H), 4.85 (s, 1H), 4.67-4.59 (m, 1H), 4.45-4.37 (m, 2H), 3.75-3.68 (m, 2H), 3.58-3.36 (m, 15H), 3.19-3.09 (m, 2H), 2.98-2.89 (m, 2H), 2.78-2.71 (m, 1H), 2.55-2.41 (m, 3H), 2.28-2.14 (m, 8H), 2.02-1.03 (m, 24H), 0.80 (t, J=7.6 Hz, 3H); LC-MS: m/z 886.8 [M+H]$^+$.

Intermediate 18: Synthesis of (1S,2R,8R,10S,12R, 13R,17R,18S,22S)-18-[(tert-butyldimethylsilyl)oxy]-22-ethyl-17-methyl-10-{[(2R,3R,4R,5S,6S)-3,4,5-trimethoxy-6-methyloxan-2-yl]oxy}-4,23-dioxapentacyclo[13.10.0.0$^{2,13}$.0$^{3,7}$.0$^{8,12}$]pentacos-14-ene-5,16,24-trione

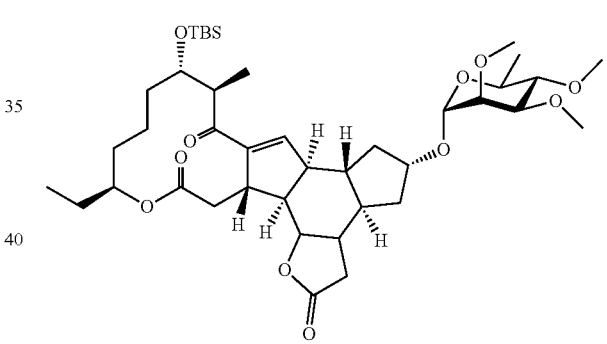

To a solution of Intermediate 16 (50 mg, 0.07 mmol) in dichloromethane (6 mL) was added TBSOTf (101.8 mg, 0.38 mmol) and 2,6-Dimethyl-pyridine(66 mg, 0.62 mmol). The mixture was stirred at r.t. for 3 h. The mixture was extracted with dichloromethane (20 mL×3) and washed with brine. The organic layer was dried over sodium sulfate, and filtered. The filtrate was concentrated and purified by pre-HPLC to afford the title compound as a white solid (45.8 mg, 85.9%). $^1$H NMR (CDCl$_3$, 400 MHz): δ6.73 (s, 1H), 4.82 (s, 1H), 4.70-4.60 (m, 1H), 4.42 (t, J=8.6 Hz, 1H), 4.35-4.33 (m, 1H), 3.90-3.86 (m, 1H), 3.60-3.43 (m, 11H), 3.36-3.09 (m, 4H), 3.00-2.70 (m, 3H), 2.51-2.31 (m, 4H), 2.04-1.96 (m, 1H), 1.81-1.61 (m, 4H), 1.58-0.96 (m, 15H), 0.90 (s, 9H), 0.82 (t, J=7.6 Hz, 3H), 0.07-0.08 (d, J=4.8 Hz, 6H). LCMS: m/z 780.3 [M+1]$^+$ Intermediates 19 and 20: Synthesis of (1S,2R,8R,10S,12S,13S,17R,18S,22S)-22-ethyl-17-methyl-5,16,24-trioxo-10-{[(2R,3R,4R,5S,6S)-3,4,5-trimethoxy-6-methyloxan-2-yl]oxy}-23-oxa-6-azapentacyclo[13.10.0.0$^{2,13}$.0$^{3,7}$.0$^{8,12}$]pentacos-14-en-18-yl acetate (19), and (1S,2R,8R,10S,12R,13R,17R,18S,22S)-22-ethyl-17-methyl-5,16,24-trioxo-10-{[(2R,3R,4R,5S,6S)-3,4,5-trimethoxy-6-methyloxan-2-yl]oxy}-23-oxa-4-azapentacyclo[13.10.0.0$^{2,13}$.0$^{3,7}$.0$^{8,12}$]pentacos-14-en-18-yl acetate (20)

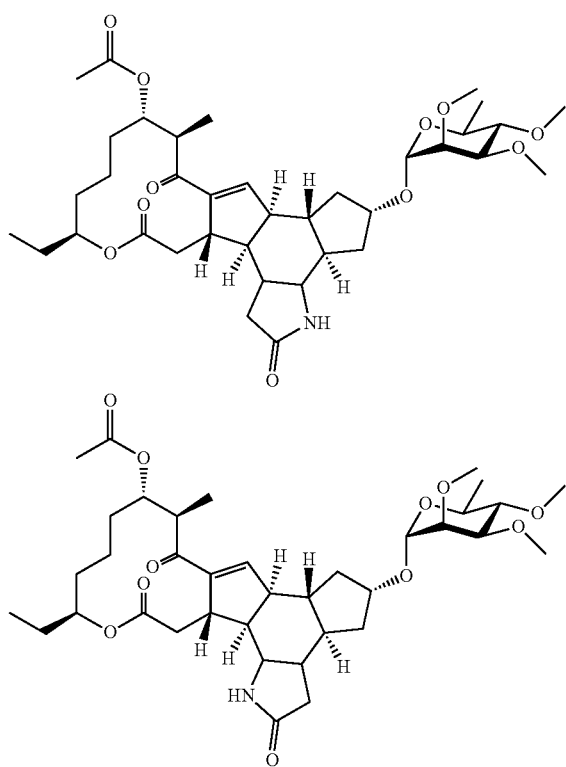

A mixture of compound Intermediates 7 and 8, (50 mg, 0.07 mmol) and O-(mesitylsulfonyl)hydroxylamine (17 mg, 0.08 mmol) in dichloromethane (5 mL) was stirred at room temperature for 10 h. The solution was concentrated and purified by chiral pre-HPLC to afford the title compounds Intermediate 19 (17.0 mg, yield 35.4%) and intermediate 20 (8.8 mg, yield 18.5%) as white solids. Intermediate 19 $^1$H NMR (CDCl$_3$, 400 MHz): δ 6.76 (s, 1H), 5.68 (s, 1H), 5.08-5.02 (m, 1H), 4.83 (s, 1H), 4.68-4.61 (m, 1H), 4.36-4.29 (m, 1H), 3.57-3.40 (m, 15H), 3.15-2.97 (m, 4H), 2.83-2.76 (m, 1H), 2.58-2.51 (m, 1H), 2.47-2.35 (m, 2H), 2.28-2.15 (m, 2H), 2.08 (s, 3H), 2.03-1.98 (m, 1H),1.80-1.25 (m, 20H), 1.19-1.08 (m, 5H), 0.82 (t, J=7.6 Hz, 3H); LCMS: m/z 689.9 [M+1]$^+$.

Intermediate 20: $^1$H NMR (CDCl$_3$, 400 MHz): δ 6.76 (s, 1H), 5.57 (s, 1H), 5.06-5.00 (m, 1H), 4.81 (s, 1H), 4.74-4.66 (m, 1H), 4.33-4.26 (m, 1H), 3.58-3.36 (m, 17H), 3.29-3.22 (m, 1H), 3.16-3.03 (m, 3H), 2.86-2.79 (m, 1H), 2.47-2.19 (m, 4H), 2.07 (s, 3H), 1.99-1.92 (m, 1H), 1.69-1.10 (m, 3H), 1.05-0.93 (m, 1H), 0.81 (t, J=7.6 Hz, 3H); LCMS: m/z 689.9 [M+1]$^+$.

Intermediate 21: Synthesis of (1S,2R,3S,6S,7R,9R,11R,12S,16R,17S,21S)-21-ethyl-4-hydroxy-16-methyl-15,23-dioxo-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-en-17-yl acetate

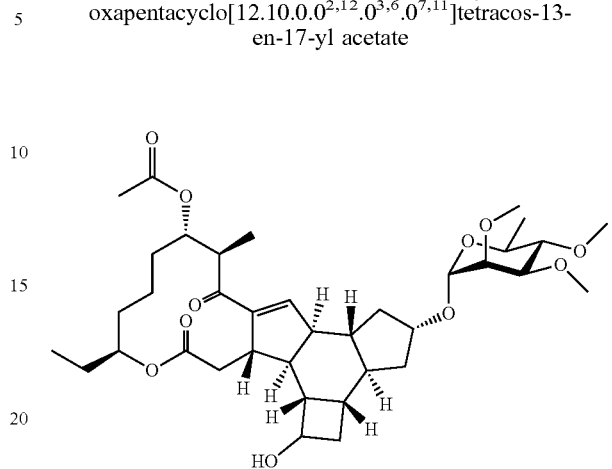

To a solution of Intermediate 7 (300 mg, 0.44 mmol) in methanol (10 mL) was added NaBH$_4$ (33 mg, 0.88 mmol) at 0° C. The mixture was stirred at 0° C. for 1.5 h before it was quenched by addition of acetone (3 mL). The mixture was stirred for another 15 min. The solvent was evaporated and the residue was dissolved in dichloromethane (90 mL) and washed with water. The organic layer was dried over sodium sulfate, filtered and concentrated. The residue was purified by prep-HPLC afford the title compound as a white solid (90 mg, 30%). $^1$H NMR (CDCl$_3$, 400 MHz): δ 6.74 (s, 1H), 5.08-5.03 (m, 1H), 4.82 (s, 1H), 4.69-4.60 (m, 1H), 4.45-4.37 (m, 1H), 4.30-4.24 (m, 1H), 3.60-3.45 (m, 14H), 3.27-3.19 (m, 1H), 3.16-3.08 (m, 2m), 2.96 (brs, 1H), 2.82-2.68 (m, 2H), 2.60-2.52 (m, 1H), 2.39-2.29 (m, 2H), 2.07 (s, 3H), 1.98-1.84 (m, 2H), 1.80 (d, J=6.0 Hz, 1H), 1.76-1.45 (m, 14H), 1.37-1.11 (m, 11H), 1.04-0.92 (m, 1H), 0.83 (t, J=7.4 Hz, 3H). LCMS: m/z 693.9 [M+1]$^+$ Intermediate 22: Synthesis of (1S,2R,3S,6S,7R,9R,11R,12S,16R,17S,21S)-4-(benzylamino)-21-ethyl-16-methyl-15,23-dioxo-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-en-17-yl acetate

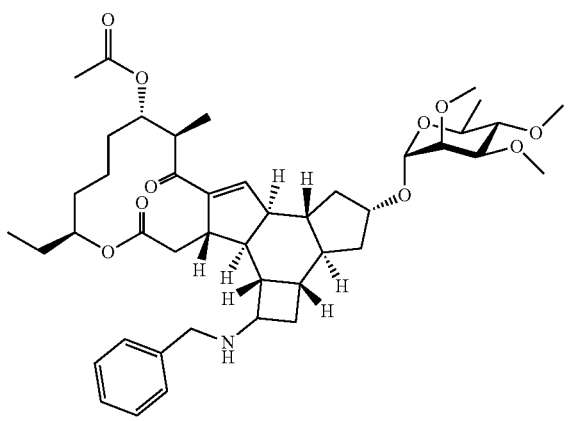

To a solution of Intermediate 7 (150 mg, 0.22 mmol) in dichloromethane (5 mL) was added 1 drop of HOAc, and Benzylamine (357 mg, 3.3 mmol). The mixture was stirred at r.t. overnight. sodium cyanoborohydride (48.51 mg, 0.77 mmol) was added and the mixture was stirred for 2 h before it was diluted with water (30 mL), and extracted with dichloromethane (30 mL×3). The organic layer was dried over sodium sulfate, and filtered. The filtrate was concentrated and purified by pre-HPLC to afford the title compound as a white solid (15.2 mg, 9%). $^1$HNMR (CDCl$_3$, 400 MHz): 7.59 (d, J=7.2 Hz, 2H), 7.40-7.32 (m, 3H), 6.78 (s, 1H), 5.05-4.98 (m, 1H), 4.81 (s, 1H), 4.67-4.58 (m, 1H), 4.31-4.22 (m, 1H), 4.03 (d, J=13.2 Hz, 1H), 3.58-3.38 (m, 12H), 3.35-3.19 (m, 3H), 3.12 (t, J=9.4 Hz, 1H), 2.98-2.83 (m, 2H), 2.63-2.47 (m, 2H), 2.29-2.16 (m, 2H), 2.07 (s, 3H), 2.00-1.90 (m, 4H), 1.81-1.09 (m, 21H), 0.80 (t, J=7.2 Hz, 3H), 0.74-0.62 (m, 1H). LCMS: m/z 765.9 [M+1]$^+$ mg, 5%). $^1$H NMR (CDCl$_3$, 400 MHz): δ7.15 (t, J=8.0 Hz, 2H), 6.80 (s, 1H), 6.69 (t, J=7.4 Hz, 1H), 6.60 (d, J=7.6 Hz, 2H), 5.03-4.97 (m, 1H), 4.85 (s, 1H), 4.65-4.57 (m, 1H), 4.32-4.25 (m, 1H), 3.82-3.73 (m, 1H), 3.60-3.47 (m, 13H), 3.39-3.30 (m, 1H), 3.22-3.09 (m, 2H), 2.90-2.79 (m, 2H), 2.73-2.65 (m, 1H), 2.39-2.20 (m, 4H), 2.10-1.96 (m, 5H), 1.88-1.40 (m, 13H), 1.37-1.18 (m, 11H), 0.85-0.72 (m, 4H). LCMS: m/z 751.9 [M+1]$^+$ Intermediate 24: Synthesis of (1S,2R,3S,6S,7R,9R,11R,12S,16R,17S,21S)-21-ethyl-16-methyl-4-(methylamino)-15,23-dioxo-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-en-17-yl acetate Intermediate 23: Synthesis of (1S,2R,3S,6S,7R,9R,11R,12S,16R,17S,21S)-21-ethyl-16-methyl-15,23-dioxo-4-(phenylamino)-9-{[(2R,3R,4R,5S,6S)-3,4,5-trimethoxy-6-methyloxan-2-yl]oxy}-22-oxapentacyclo[12.10.0.0$^{2,12}$.0$^{3,6}$.0$^{7,11}$]tetracos-13-en-17-yl acetate

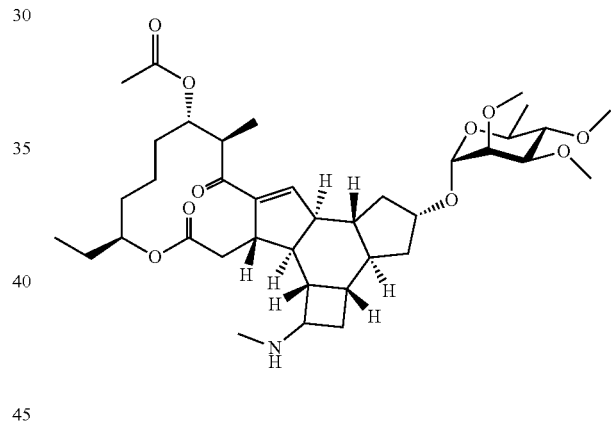

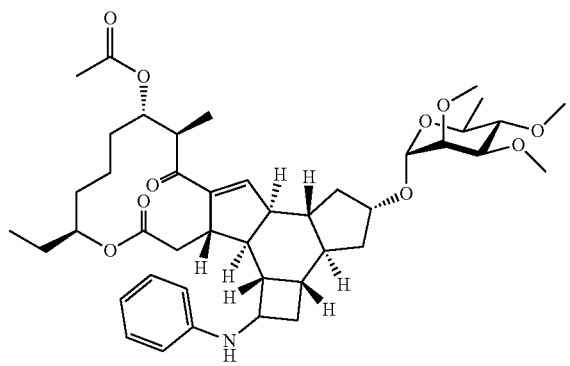

To a solution of Intermediate 7 (300 mg, 0.4 mmol) in dichloromethane (10 mL) was added 1 drop of HOAc, and aniline (621 mg, 6.67 mmol). The mixture was stirred overnight. sodium cyanoborohydride (63 mg, 1.0 mmol) was added and the mixture was stirred at r.t. under nitrogen for 5 h before it was diluted with water (30 mL) and extracted with dichloromethane (20 mL×3). The organic layer was dried over sodium sulfate and filtered. The filtrate was concentrated and purified by pre-HPLC and Chiral-Pre-HPLC to afford the title compound as a white solid. (17.1

To a solution of Intermediate 7 (300 mg, 0.44 mmol) in dichloromethane (10 mL) was added 1 drop of HOAc, then aniline (621 mg, 6.67 mmol). The mixture was stirred overnight. sodium cyanoborohydride (63 mg, 1.0 mmol) was added and the mixture was stirred at r.t. under nitrogen for 5 h before it was diluted with water (30 mL) and extracted with dichloromethane (20 mL×3). The organic layer was dried over sodium sulfate and filtered. The filtrate was concentrated and purified by pre-HPLC and Chiral-Pre-HPLC to afford the title compound as a white solid. (8.1 mg, 2%). $^1$H NMR (CDCl$_3$, 400 MHz): δ 6.80 (s, 1H), 5.04-4.98 (m, 1H), 4.82 (s, 1H), 4.64-4.59 (m, 1H), 4.26-4.23 (m, 1H), 3.60-3.43 (m, 13H), 3.37-3.10 (m, 4H), 2.93-2.80 (m, 2H), 2.71-2.41 (m, 26H), 2.30-2.19 (m, 1H), 2.10-1.93 (m, 12H), 1.62-1.40 (m, 9H), 1.36-1.07 (m, 13H), 0.81 (t, J=7.6 Hz, 3H), 0.76-0.65 (m, 1H). LCMS: m/z 689.9 [M+1]$^+$ Example 46: Synthesis of (1S,2R,8R,10S,12R,13S, 17R,18S,22S)-18-{[(2R,5S,6R)-5-(dimethylamino)-6-methyloxan-2-yl]oxy}-22-ethyl-5-(4-methoxyphenyl)-17-methyl-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione

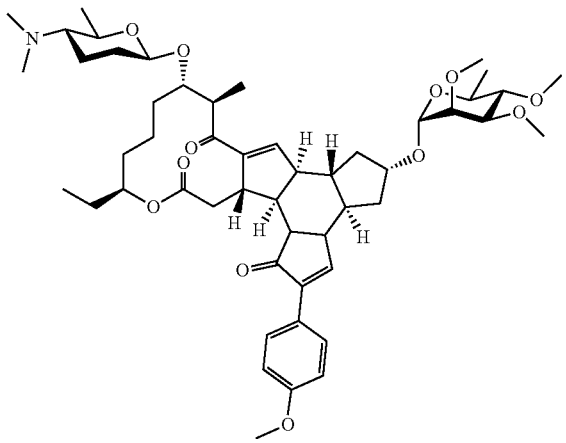

According to the general procedure as outlined for Example 15, Example 46 was obtained as a white solid from 1.0 g of Spinosyn A using 1-ethynyl-4-methoxy-benzene. (100 mg, yield 8%) as a white solid. Partial $^1$H NMR (CDCl$_3$, 400 MHz): δ 7.69 (d, J=8.4 Hz, 2H), 7.63 (d, J=2.4 Hz, 1H), 6.91 (d, J=8.4 Hz, 2H), 6.72 (s, 1H), 4.86 (s, 1H), 4.66-4.61 (m, 1H), 4.44-4.38 (m, 2H), 3.83 (s, 3H), 3.72-3.70 (m, 2H), 3.39-3.33 (m, 1H), 3.18-3.10 (m, 2H), 2.95-2.90 (m, 2H), 2.70-2.68 (m, 1H), 2.54 (dd, J=14.0, 3.2 Hz, 1H), 2.46-2.41 (m, 2H), 2.25 (s, 6H), 2.19-2.13 (m, 1H), 0.80 (t, J=7.6 Hz, 1H); LC-MS: m/z 891.9 [M+H]$^+$.

Representative Procedure for Baeyer-Villiger Oxidation of Cyclopentenones

Example 47: Synthesis of (1R,2S,6S,10S,11R,15R, 16R,18S,20R)-10-{[(2R,5S,6R)-5-(dimethylamino)-6-methyloxan-2-yl]oxy}-6-ethyl-23-(4-methoxyphenyl)-11-methyl-18-{[(2R,3R,4R,5S,6S)-3,4,5-trimethoxy-6-methyloxan-2-yl]oxy}-5,25-dioxapentacyclo[13.11.0.0$^{2,13}$.0$^{16,20}$.0$^{21,26}$]hexacosa-13,22-diene-4,12,24-trione

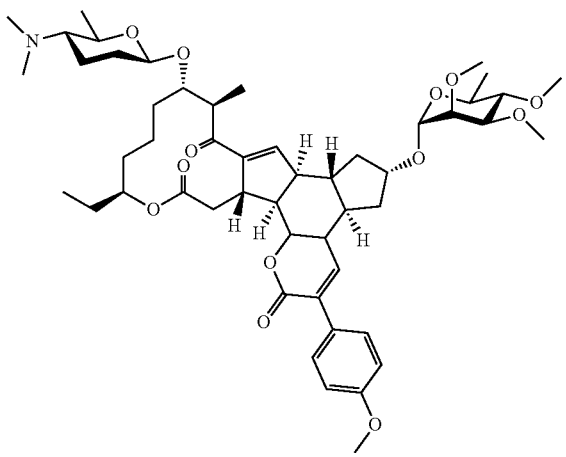

A mixture of Example 46 (60 mg, 0.07 mmol), m-CPBA (35 mg, 0.20 mmol) and Na$_2$HPO$_4$ (19 mg, 0.13 mmol) in dichloromethane (20 mL) was stirred at r.t. overnight. The reaction solution was concentrated in vacuum, the residue was purified by prep-TLC (methanol/dichloromethane=9/100) and prep-HPLC to afford the title compound Example 47 (15 mg, yield 24.6%) as a white solid. Partial $^1$H NMR (DMSO-d$_6$, 300 MHz): δ 8.00 (s, 1H), 7.76 (d, J=7.2 Hz, 2H), 7.16 (s, 1H), 6.97 (d, J=7.8 Hz, 2H), 4.83 (s, 1H), 4.75-4.70 (m, 1H), 4.55-4.47 (m, 1H), 4.31-4.22 (m, 2H), 3.78 (s, 3H); LC-MS: m/z 907.8 [M+H]$^+$.

Example 48: (2S,3aR,5aR,5bS,9S,13S,14R,16aR, 16bS)-4-bromo-13-{[(2R,5S,6R)-5-(dimethylamino)-6-methyloxan-2-yl]oxy}-9-ethyl-5-methoxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

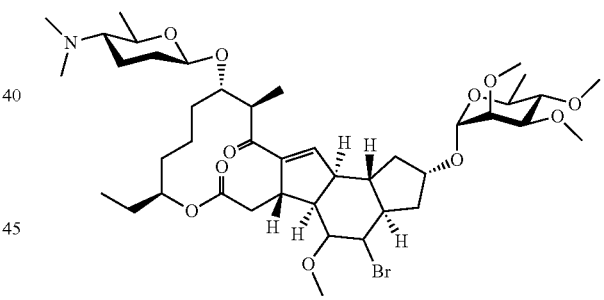

To a solution of Spinosyn A (2.0 g, 2.7 mmol) in methanol (60 ml) were added NH$_4$Br (295 mg, 3.0 mmol) and oxone (1.85 g, 3.0 mmol). The mixture was stirred at room temperature for overnight. The reaction mixture was filtered and the solvent was evaporated under reduced pressure. The residue was purified by flash column (MeCN: water=2:3 to 19:1) to give the title compound (225 mg, yield 9.7%) as a white solid. Partial $^1$H NMR (DMSO-d$_6$, 400 MHz): δ7.12 (s, 1H), 4.79 (s, 1H), 4.73 (s, 1H), 4.57-4.53 (m, 1H), 4.42 (d, J=9.6 Hz, 1H), 4.16-4.12 (m, 1H), 3.85 (s, 1H), 2.96-2.91 (m, 3H), 2.68-2.63 (m, 1H), 2.35-2.31 (m, 1H), 0.74 (t, J=7.6 Hz, 3H). LCMS: m/z 841.8 [M+H]$^+$ Example 49: (2S,3aR,5aR,5bS,9S,13S,14R,16aR, 16bS)-4-bromo-13-{[(2R,5S,6R)-5-(dimethyl-amino)-6-methyloxan-2-yl]oxy}-5-ethoxy-9-ethyl-14-methyl-2-{[(2R,3R,4R,5S,6S)-3,4,5-trimethoxy-6-methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-7,15-dione

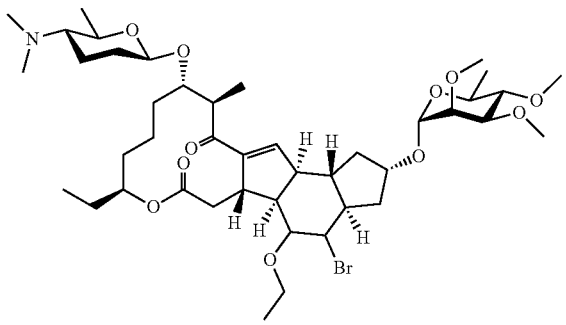

To a solution of Spinosyn A (2.0 g, 2.7 mmol) and NBS (578 mg, 3.2 mmol) in ethanol (20 mL) was added dropwise 5N HCl aqueous (0.58 mL, 2.9 mmol). The mixture was stirred at room temperature for overnight. The mixture was concentrated and the residue was purified by flash column (MeCN/water 30%-95%) to give the crude product which was further purified by prep-HPLC to afford the title compound (41 mg, yield 1.7%) as a white solid. Partial $^1$H NMR (DMSO-$d_6$, 300 MHz): δ 7.11 (s, 1H), 4.79 (s, 1H), 4.67 (s, 1H), 4.56-4.52 (m, 1H), 4.41 (d, J=9.0 Hz, 1H), 4.16-4.12 (m, 1H), 3.94 (s, 1H), 2.97-2.89 (m, 3H), 2.69-2.64 (m, 1H), 2.14 (s, 6H), 0.74 (t, J=7.2 Hz, 3H). LCMS: m/z 855.8, 857.8 [M+H]$^+$.

Intermediate 25: (2S,3aR,5aR,5bS,9S,13S,14R, 16aR,16bS)-4-bromo-13-{[(2R,5S,6R)-5-(dimethyl-amino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5H,5aH, 5bH,6H,7H,9H,10H,-11H,12H,13H,14H,15H,16aH, 16bH-as-indaceno[3,2-d]oxacyclododecane-5,7,15-trione

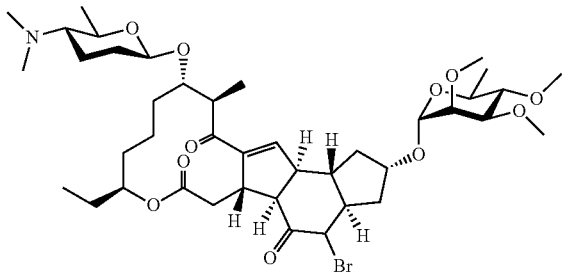

To a solution of Spinosyn A (5.0 g, 6.8 mmol) in dimethyl sulfoxide (DMSO, 50 mL) was added dropwise 10 mL of water and concentrated SULFURIC ACID (670 mg, 6.8 mmol). The mixture was then cooled to 0° C. and N-bromosuccinimide (NBS; 1.2 g, 6.8 mmol) was added. After stirring for 30 minutes at 0° C., ethyl acetate (200 mL) and saturated aqueous sodium bicarbonate (150 mL) were added. The organic layer was washed with water and brine, dried over sodium sulfate, filtered and concentrated in vacuo to give a white solid (5.5 g, 97.1%) which was used in the next chemical step without further purification.

To a solution of this white solid (5.5 g, 6.6 mmol) in dichloromethane (100 mL) at 0° C. was added Dess-Martin periodinane (3.1 g, 7.3 mmol). The mixture was stirred at room temperature overnight. The mixture was then washed with saturated sodium bicarbonate (30 mL), saturated $Na_2SO_3$ (20 mL), and brine. The organic layer was dried over sodium sulfate, filtered, and concentrated in vacuo to give an oil which was purified by silica gel column chromatography (using a dichloromethane (dichloromethane) to methanol (methanol) gradient of from 50/1 to 15/1) to afford the title compound (2.1 g, 38.6%) as a white solid.

Examples 50 and 51: (2S,3aR,4S,5aR,5bS,9S,13S, 14R,16aR,16bS)-13-{[(2R,5S,6R)-5-(dimethyl-amino)-6-methyloxan-2-yl]oxy}-9-ethyl-4-methoxy-14-methyl-2-{[(2R,3R,4R,5S,6S)-3,4,5-trimethoxy-6-methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-5,7,15-trione, and (2S,3aR,4R,5aR,5bS,9S,13S,14R,16aR, 16bS)-13-{[(2R,5S,6R)-5-(dimethylamino)-6-methyloxan-2-yl]oxy}-9-ethyl-4-methoxy-14-methyl-2-{[(2R,3R,4R,5S,6S)-3,4,5-trimethoxy-6-methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-5,7,15-trione

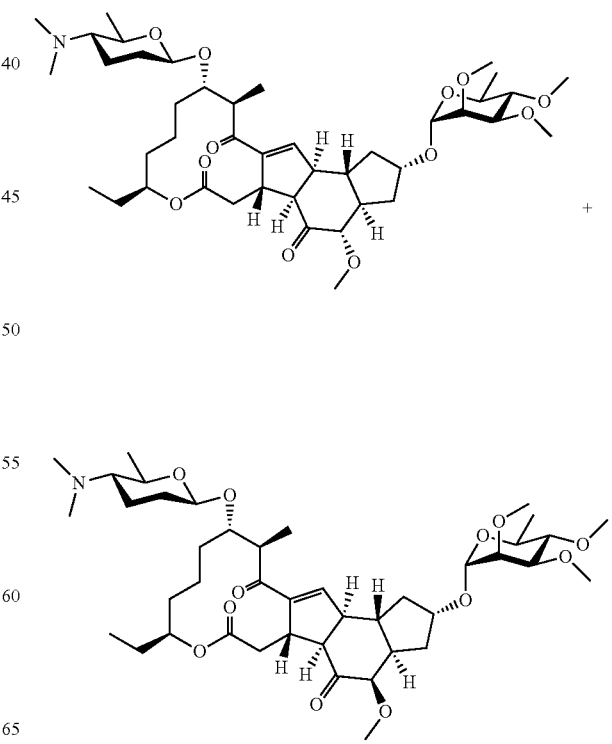

To a solution of Intermediate 25 (500 mg, 0.60 mmol) in methanol (5 mL) was added sodium formate (206 mg, 3.0 mmol). The mixture was then heated to reflux for 20 hr and allowed to cool. The mixture was portioned between ethyl acetate and saturated sodium bicarbonate (50 mL/30 mL), the organic was isolated and washed with brine, dried over sodium sulfate, filtered and concentrated in vacuo to give an oil, which was further purified by Prep-HPLC afford Example 50 (110 mg) and Example 51 (106 mg).

Example 50: Partial $^1$H NMR (DMSO-$d_6$, 300 MHz): δ 7.10 (s, 1H), 4.79 (s, 1H), 4.60-4.53 (m, 1H), 4.41 (d, J=6.9 Hz, 1H), 4.25-4.22 (m, 1H), 3.65 (d, J=10.5 Hz, 1H), 0.74 (t, J=7.2 Hz, 3H). LC-MS: m/z 777.9 [M+H]$^+$.

Example 51: Partial $^1$H NMR (DMSO-$d_6$, 300 MHz): δ 7.05 (s, 1H), 4.82 (s, 1H), 4.56-4.53 (m, 1H), 4.42 (d, J=10.5 Hz, 1H), 4.19-4.16 (m, 1H), 3.71 (d, J=5.4 Hz, 1H), 0.74 (t, J=7.2 Hz, 3H). LC-MS: m/z 777.9 [M+H]$^+$.

Example 52: (2S,3aR,4S,5aR,5bS,9S,13S,14R,16aR,16bS)-13-{[(2R,5S,6R)-5-(dimethylamino)-6-methyloxan-2-yl]oxy}-9-ethyl-4-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-5,7,15-trione

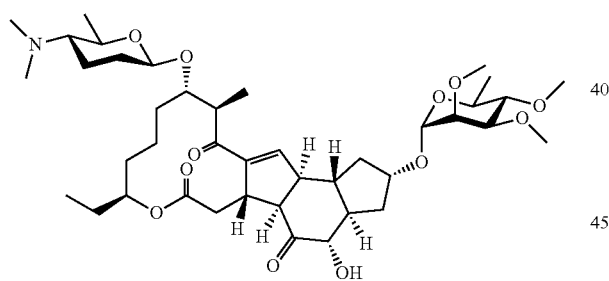

A solution of LiOH.water (101 mg, 2.42 mmol) in water (3 mL) was added to a solution of Intermediate 25 (2.0 g, 2.42 mmol) in DMF (20 mL) at 0° C. The mixture was stirred at 0° C. for 1 h. The mixture was diluted with ethyl acetate (150 mL) and water (80 mL). The separated organic layer was washed with brine, dried over sodium sulfate, filtered and concentrated. The residue was purified by prep-HPLC to afford the title compound (1.0 g, 54.1%). Partial $^1$H NMR (DMSO-$d_6$, 300 MHz): δ 7.13 (s, 1H), 5.15 (d, J=4.2 Hz, 1H), 4.79 (s, 1H), 4.63-4.57 (m, 1H), 4.41 (d, J=8.4 Hz, 1H), 4.27-4.22 (m, 1H), 3.85-3.82 (m, 1H), 3.05-2.865 (m, 3H), 2.35-2.27 (m, 2H), 0.74 (t, J=7.5 Hz, 3H). LC-MS: m/z 763.9 [M+H]$^+$.

Example 53: (2S,3aR,4R,5aR,5bS,9S,13S,14R,16aR,16bS)-13-{[(2R,5S,6R)-5-(dimethylamino)-6-methyloxan-2-yl]oxy}-9-ethyl-4-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-5,7,15-trione

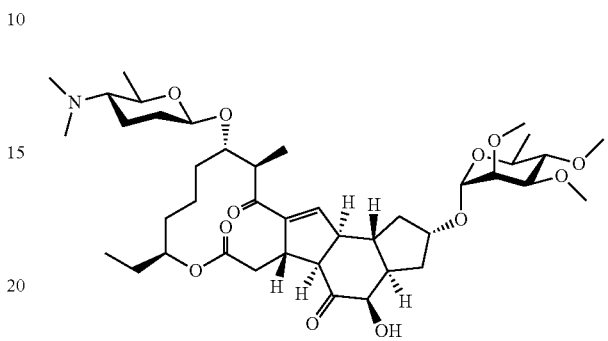

To a solution of Intermediate 25 (500 mg, 0.60 mmol) in methanol (5 mL) was added sodium formate (206 mg, 3.0 mmol). The mixture was then heated to reflux for 20 hr and allowed to cool. The mixture was diluted with ethyl acetate (50 mL) and saturated aqueous sodium bicarbonate (30 mL). The separated organic layer was isolated, washed with brine, dried over sodium sulfate, then filtered and concentrated. The residue was further purified by prep-HPLC afford the title compound (43 mg) as white solid. Partial $^1$H NMR (DMSO-$d_6$, 400 MHz): δ 6.99 (s, 1H), 5.22 (br, 1H), 4.82 (s, 1H), 4.56-4.63 (m, 1H), 4.42 (d, J=8.4 Hz, 1H), 4.17-4.16 (m, 1H), 4.08-4.06 (m, 1H), 3.82 (m, 1H), 2.96 (t, J=9.2 Hz, 1H), 2.73-2.68 (m, 1H), 0.74 (t, J=7.2 Hz, 3H). LC-MS: m/z 763.9 [M+H]$^+$.

Example 54: (1S,2R,8R,10S,12R,13S,17R,18S,22S)-18-{[(2R,5S,6R)-5-(dimethylamino)-6-methyloxan-2-yl]oxy}-22-ethyl-17-methyl-5-(3-methylphenyl)-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione

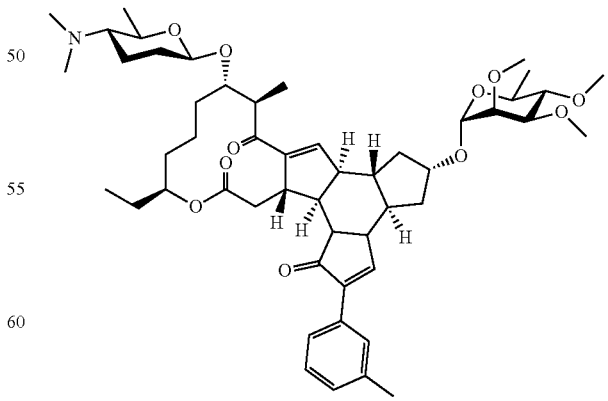

According to the general procedure as outlined for Example 15, 40 mg of the title compound was obtained as a white solid from 1.0 g of Spinosyn A.

Partial $^1$H NMR (CDCl$_3$, 400 MHz): δ 7.69 (d, J=2.4 Hz, 1H), 7.54 (s, 1H), 7.49 (d, J=7.2 Hz, 1H), 7.31-7.24 (m, 1H), 7.15 (d, J=7.2 Hz, 1H), 6.71 (s, 1H), 4.86 (s, 1H), 4.68-4.58 (m, 1H), 4.44-4.38 (m, 2H), 3.77-3.69 (m, 2H), 3.19-3.09 (m, 2H), 2.98-2.69 (m, 2H), 2.73-2.65 (m, 1H), 2.58-2.51 (m, 1H), 2.49-2.40 (m, 2H), 2.37 (s, 3H), 2.29-2.11 (m, 8H), 0.80 (t, J=7.4 Hz, 3H); LC-MS: m/z 875.9 [M+H]$^+$.

Example 55: (1S,2R,8R,10S,12R,13S,17R,18S, 22S)-5-(4-aminophenyl)-18-{[(2R,5S,6R)-5-(dimethylamino)-6-methyloxan-2-yl]oxy}-22-ethyl-17-methyl-10-{[(2R,3R,4R,5S,6S)-3,4,5-trimethoxy-6-methyloxan-2-yl]oxy}-23-oxapentacyclo[13. 10.0.0$^{2,13}$.0$^{3,7}$.0$^{8,12}$]pentacosa-5,14-diene-4,16,24-trione

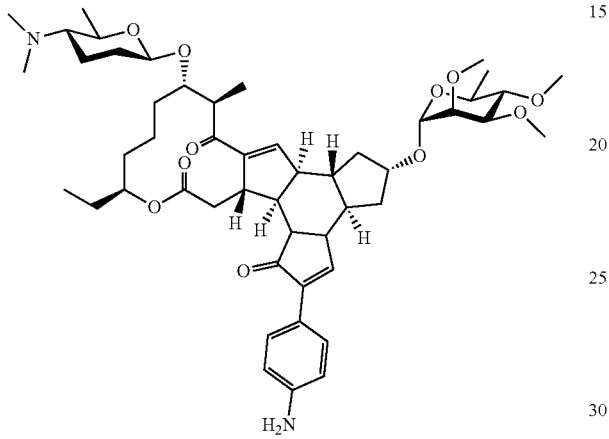

According to the general procedure as outlined for Example 15, 50 mg of the title compound was obtained as a white solid from 1.0 g of Spinosyn A.

Partial $^1$H NMR (CDCl$_3$, 400 MHz): δ 7.58-7.56 (m, 3H), 6.71-6.67 (m, 3H), 4.86 (s, 1H), 4.67-4.61 (m, 1H), 4.44-4.37 (m, 2H), 3.73-3.71 (m, 2H), 3.17-2.57 (m, 5H), 2.67-2.37 (m, 5H), 0.80 (t, J=7.4 Hz, 3H); LC-MS: m/z 876.8 [M+H]$^+$.

Example 56: (1S,2R,8R,10S,12R,13S,17R,18S, 22S)-5-(3-aminophenyl)-18-{[(2R,5S,6R)-5-(dimethylamino)-6-methyloxan-2-yl]oxy}-22-ethyl-17-methyl-10-{[(2R,3R,4R,5S,6S)-3,4,5-trimethoxy-6-methyloxan-2-yl]oxy}-23-oxapentacyclo[13. 10.0.0$^{2,13}$.0$^{3,7}$.0$^{8,12}$]pentacosa-5,14-diene-4,16,24-trione

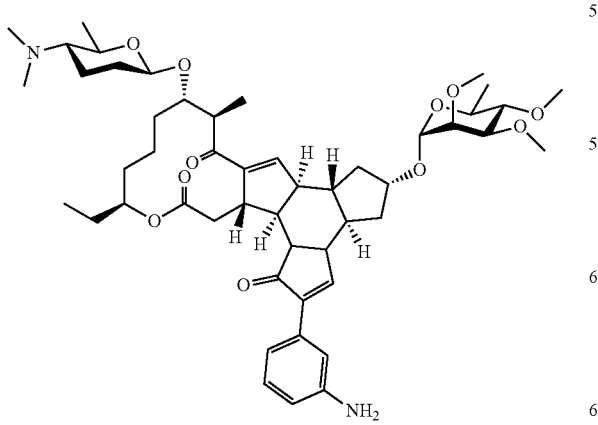

According to the general procedure as outlined for Example 15, 40 mg of the title compound was obtained as a white solid from 1.0 g of Spinosyn A.

Partial $^1$H NMR (CDCl$_3$, 400 MHz): δ 7.68 (d, J=2.4 Hz, 1H), 7.18-7.14 (m, 2H), 7.04 (d, J=8.0 Hz, 1H), 6.71 (s, 1H), 6.67-6.64 (m, 1H), 4.85 (s, 1H), 4.67-4.61 (m, 1H), 4.44-4.40 (m, 2H), 3.72-3.70 (m, 4H), 3.17-3.08 (m, 2H), 2.96-2.88 (m, 2H), 2.71-2.64 (m, 1H), 2.58-2.50 (m, 1H), 2.47-2.40 (m, 2H), 0.80 (t, J=7.2 Hz, 3H); LC-MS: m/z 876.9 [M+H]$^+$.

Example 57: (1S,2R,8R,10S,12R,13S,17R,18S, 22S)-18-{[(2R,5S,6R)-5-(dimethylamino)-6-methyloxan-2-yl]oxy}-22-ethyl-17-methyl-5-(thiophen-2-yl)-10-{[(2R,3R,4R,5S,6S)-3,4,5-trimethoxy-6-methyloxan-2-yl]oxy}-23-oxapentacyclo[13. 10.0.0$^{2,13}$.0$^{3,7}$.0$^{8,12}$]pentacosa-5,14-diene-4,16,24-trione

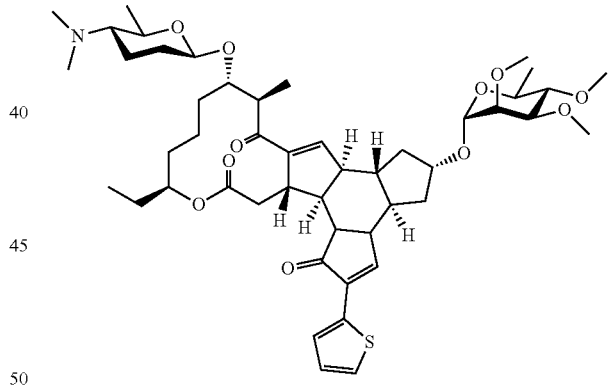

According to the general procedure as outlined for Example 15, 40 mg of the title compound was obtained as a white solid from 1.0 g of Spinosyn A. Partial $^1$HNMR (CDCl$_3$, 400 MHz): δ 7.66 (d, J=2.8 Hz, 1H), 7.63 (d, J=2.8 Hz, 1H), 7.32 (dd, J=5.2 Hz, J=1.2 Hz, 1H), 7.06 (dd, J=5.2 Hz, J=2.7 Hz, 1H), 6.70 (s, 1H), 4.86 (s, 1H), 4.65-4.62 (m, 1H), 4.46-4.36 (m, 2H), 3.75-3.68 (m, 2H), 3.19-3.08 (m, 2H), 2.96-2.87 (m, 2H), 2.75-2.68 (m, 1H), 2.59-2.51 (m, 1H), 2.49-2.40 (m, 2H), 2.30 (s, 6H), 2.21-2.12 (m, 1H), 0.79 (t, J=7.2 Hz, 3H); LC-MS: m/z 868.3 [M+H]$^+$.

Example 58: (1S,2R,8R,10S,12R,13S,17R,18S,22S)-18-{[(2R,5S,6R)-5-(dimethylamino)-6-methyloxan-2-yl]oxy}-22-ethyl-5-(hydroxymethyl)-17-methyl-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione

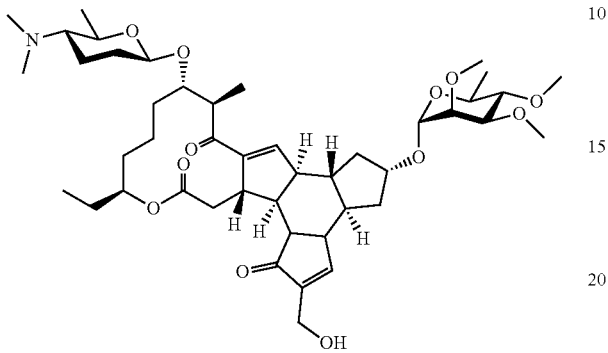

According to the general procedure as outlined for Example 15, 30 mg of the title compound was obtained as a white solid from 1.0 g of Spinosyn A. Partial $^1$HNMR (CDCl$_3$, 400 MHz): 7.42 (s, 1H), 6.69 (s, 1H), 4.84 (s, 1H), 4.68-4.59 (m, 1H), 4.46-4.37 (m, 4H), 3.74-3.68 (m, 1H), 3.64 (s, 1H), 3.17-3.07 (m, 2H), 2.94-2.80 (m, 2H), 2.66-2.58 (m, 1H), 2.55-2.47 (m, 1H), 2.46-2.38 (m, 1H), 2.15-2.07 (m, 1H), 0.80 (t, J=7.2 Hz, 3H); LC-MS: m/z 815.8 [M+H]$^+$.

Example 59: (1S,2R,8R,10S,12R,13S,17R,18S,22S)-5-(3-chlorophenyl)-18-{[(2R,5S,6R)-5-(dimethylamino)-6-methyloxan-2-yl]oxy}-22-ethyl-17-methyl-10-{[(2R,3R,4R,5S,6S)-3,4,5-trimethoxy-6-methyloxan-2-yl]oxy}-23-oxapentacyclo[13.10.0.0$^{2,13}$.0$^{3,7}$.0$^{8,12}$]pentacosa-5,14-diene-4,16,24-trione

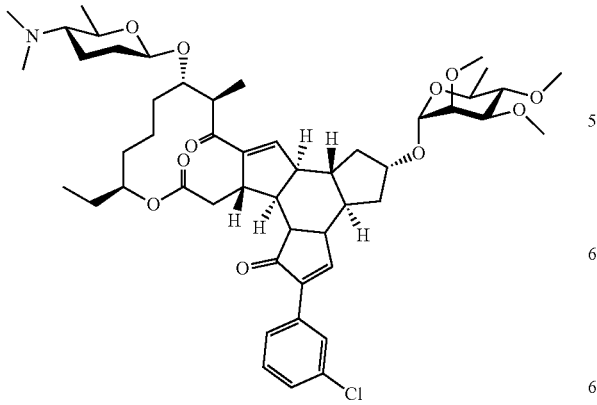

According to the general procedure as outlined for Example 15, 50 mg of the title compound was obtained as a white solid from 1.0 g of Spinosyn A. Partial $^1$HNMR (CDCl$_3$, 400 MHz): 7.75 (d, J=2.4 Hz, 1H), 7.72 (s, 1H), 7.65-7.61 (m, 1H), 7.33-7.30 (m, 2H), 6.71 (s, 1H), 4.86 (s, 1H), 4.67-4.59 (m, 1H), 4.45-4.37 (m, 2H), 3.75-3.68 (m, 2H), 3.19-3.09 (m, 2H), 2.97-2.90 (m, 2H), 2.74-2.67 (m, 1H), 2.58-2.40 (m, 3H), 2.27 (s, 7H), 2.19-2.12 (m, 1H), 0.80 (t, J=7.2 Hz, 3H); LC-MS: m/z 895.8 [M+H]$^+$.

Example 60: (1R,2S,6S,10S,11R,15R,16R,18S,20R)-10-{[(2R,5S,6R)-5-(dimethylamino)-6-methyloxan-2-yl]oxy}-6-ethyl-23-(4-fluorophenyl)-11-methyl-18-{[(2R,3R,4R,5S,6S)-3,4,5-trimethoxy-6-methyloxan-2-yl]oxy}-5,25-dioxapentacyclo[13.11.0.0$^{2,13}$.0$^{16,20}$.0$^{21,26}$]hexacosa-13,22-diene-4,12,24-trione

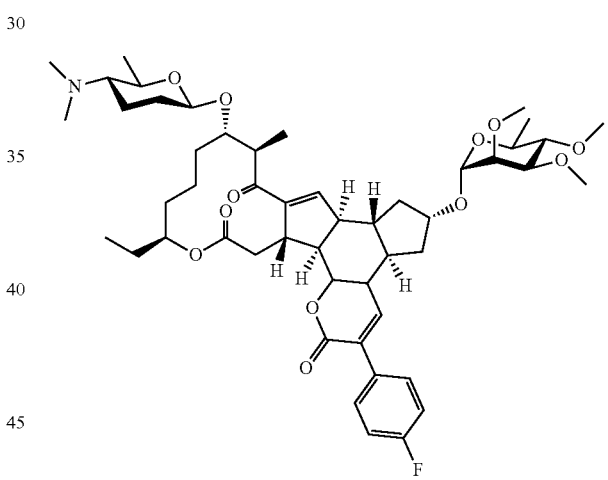

According to the general procedure for Example 47, Example 15 (70 mg, 0.08 mmol), m-CPBA (27 mg, 0.16 mmol) and Na$_2$HPO$_4$ (22.3 mg, 0.16 mmol) provided the title compound (50 mg, yield 49%) as a white solid. Partial $^1$H NMR (CDCl$_3$, 400 MHz): δ 7.73-7.67 (m, 3H), 7.07 (t, J=8.8 Hz, 2H), 6.72 (s, 1H), 4.86 (s, 1H), 4.82-4.76 (m, 1H), 4.69-4.59 (m, 1H), 4.43-4.35 (m, 2H), 3.79-3.70 (m, 2H), 3.58-3.32 (m, 14H), 3.25-3.07 (m, 9H), 2.96-2.87 (m, 2H), 2.73-2.65 (m, 1H), 2.58-2.52 (m, 1H), 2.48-2.38 (m, 2H), 2.31-2.09 (m, 3H), 0.80 (t, J=7.2 Hz, 3H); LC-MS: m/z 895.8 [M+H]$^+$.

Example 61: 4-[(1R,2S,6S,10S,11R,15R,16R,18S,20R)-10-{[(2R,5S,6R)-5-(dimethylamino)-6-methyloxan-2-yl]oxy}-6-ethyl-11-methyl-4,12,24-trioxo-18-{[(2R,3R,4R,5S,6S)-3,4,5-trimethoxy-6-methyloxan-2-yl]oxy}-5,25-dioxapentacyclo[13.11.0.0²,¹³.0¹⁶,²⁰.0²¹,²⁶]hexacosa-13,22-dien-23-yl]benzonitrile

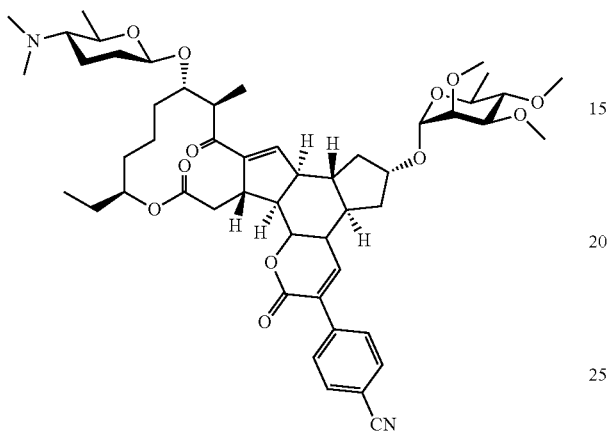

According to the general procedure for Example 47, Example 17 (30 mg, 0.03 mmol), m-CPBA (5.8 mg, 0.06 mmol) and Na₂HPO₄ (4.8 mg, 0.06 mmol provided the title compound (12.5 mg, yield 23.1%) as a white solid. Partial ¹H NMR (CDCl₃, 400 MHz): δ 7.88-7.82 (m, 3H), 7.67 (d, J=8.4 Hz, 3H), 6.72 (s, 1H), 4.86 (s, 1H), 4.81-4.75 (m, 1H), 4.68-4.59 (m, 1H), 4.45-4.34 (m, 2H), 3.79-3.69 (m, 2H), 2.98-2.87 (m, 2H), 2.78-2.71 (m, 1H), 2.55-2.41 (m, 3H), 0.80 (t, J=7.6 Hz, 3H); LC-MS: m/z 902.8 [M+H]⁺.

Example 62: (1R,2S,6S,10S,11R,15R,16R,18S,20R)-10-{[(2R,5S,6R)-5-(dimethylamino)-6-methyloxan-2-yl]oxy}-6-ethyl-11-methyl-23-(pyrimidin-5-yl)-18-{[(2R,3R,4R,5S,6S)-3,4,5-trimethoxy-6-methyloxan-2-yl]oxy}-5,25-dioxapentacyclo[13.11.0.0²,¹³.0¹⁶,²⁰.0²¹,²⁶]hexacosa-13,22-diene-4,12,24-trione

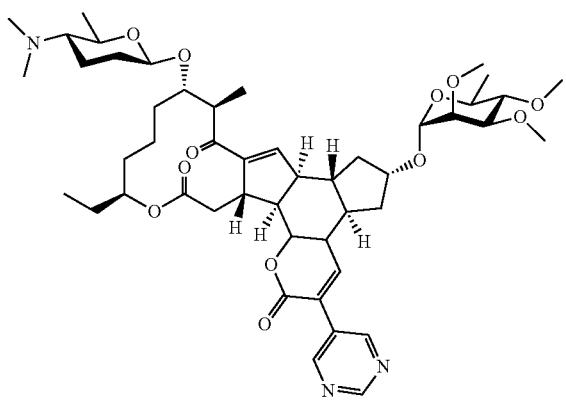

According to the general procedure for Example 47, Example 16 (30 mg, 0.03 mmol), m-CPBA (12 mg, 0.07 mmol) and Na₂HPO₄ (10 mg, 0.07 mmol) provided the title compound (8.2 mg, yield 31%) as a white solid. Partial ¹H NMR (CDCl₃, 400 MHz): δ 9.20 (s, 1H), 9.11 (s, 2H), 7.93 (s, 1H), 6.72 (s, 1H), 4.86 (s, 1H), 4.82-4.76 (m, 1H), 4.69-4.61 (m, 1H), 4.45-4.38 (m, 1H), 4.32-4.25 (m, 1H), 4.06-3.97 (m, 1H), 3.79-3.71 (m, 2H), 3.23-3.10 (m, 3H), 0.81 (t, J=7.6 Hz, 3H); LC-MS: m/z 880.8 [M+H]⁺.

Example 63: (1R,2S,6S,10S,11R,15R,16R,18S,20R)-10-{[(2R,5S,6R)-5-(dimethylamino)-6-methyloxan-2-yl]oxy}-6-ethyl-11-methyl-23-(thiophen-2-yl)-18-{[(2R,3R,4R,5S,6S)-3,4,5-trimethoxy-6-methyloxan-2-yl]oxy}-5,25-dioxapentacyclo[13.11.0.0²,¹³.0¹⁶,²⁰.0²¹,²⁶]hexacosa-13,22-diene-4,12,24-trione

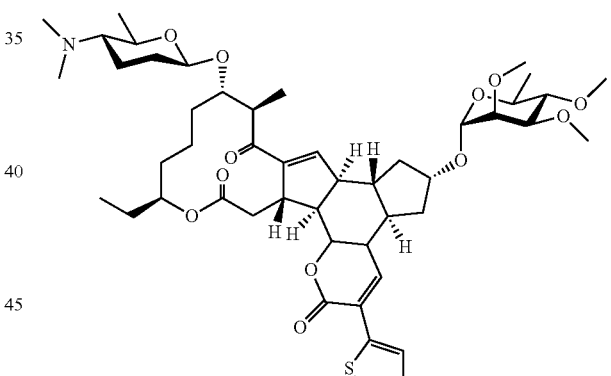

According to the general procedure for Example 47. Example 57 (30 mg, 0.03 mmol), m-CPBA (11.9 mg, 0.07 mmol) and Na₂HPO₄ (9.8 mg, 0.07 mmol) provided the title compound (11.0 mg, yield 36%) as a white solid. Partial ¹H NMR (CDCl₃, 400 MHz): δ 7.64 (dd, J=12.8 Hz, 3.6 Hz, 2H) 7.32 (d, J=4.8 Hz, 7.07 (dd, J=4.8 Hz, 4.0 Hz, 1H), 6.71 (s, 1H), 4.86 (s, 1H), 4.80-4.75 (m, 1H), 4.67-4.59 (m, 1H), 4.43-4.35 (m, 2H), 3.78-3.71 (m, 2H), 2.95-2.87 (m, 2H), 2.75-2.68 (m, 1H), 2.60-2.53 (m, 1H), 2.48-2.38 (m, 2H), 2.32-2.08 (m, 3H), 0.81 (t, J=7.6 Hz, 3H); LC-MS: m/z 883.8 [M+H]⁺.

143

Example 64: (1R,2S,6S,10S,11R,15R,16R,18S,20R)-23-(3-chlorophenyl)-10-{[(2R,5S,6R)-5-(dimethylamino)-6-methyloxan-2-yl]oxy}-6-ethyl-11-methyl-18-{[(2R,3R,4R,5S,6S)-3,4,5-trimethoxy-6-methyloxan-2-yl]oxy}-5,25-dioxapentacyclo[13.11.0.0$^{2,13}$.0$^{16,20}$.0$^{21,26}$]hexacosa-13,22-diene-4,12,24-trione

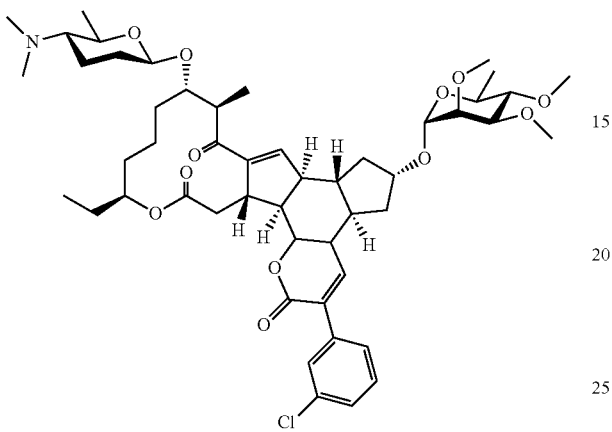

According to the general procedure for Example 47, Example 59 (50 mg, 0.05 mmol), m-CPBA (19.2 mg, 0.11 mmol) and Na$_2$HPO$_4$ (15.8 mg, 0.11 mmol) provided the title compound (17.5 mg, yield 34.4%) as a white solid. Partial $^1$H NMR (CDCl$_3$, 400 MHz): δ 7.74 (d, J=2.4 Hz, 1H), 7.72 (s, 1H), 7.65-7.60 (m, 1H), 7.32-7.30 (m, 2H), 6.71 (s, 1H), 4.86 (s, 1H), 4.81-4.75 (m, 1H), 4.68-4.61 (m, 1H), 4.44-4.35 (m, 2H), 3.79-3.72 (m, 2H), 3.41-3.32 (m, 1H), 2.96-2.88 (m, 2H), 2.74-2.67 (m, 1H), 2.58-2.52 (m, 1H), 2.49-2.40 (m, 2H), 2.33-2.09 (m, 3H), 0.81 (t, J=7.6 Hz, 3H); LC-MS: m/z 911.8 [M+H]$^+$.

Example 65: (1R,2S,6S,10S,11R,15R,16R,18S,20R)-10-{[(2R,5S,6R)-5-(dimethylamino)-6-methyloxan-2-yl]oxy}-6-ethyl-11-methyl-23-(3-methylphenyl)-18-{[(2R,3R,4R,5S,6S)-3,4,5-trimethoxy-6-methyloxan-2-yl]oxy}-5,25-dioxapentacyclo[13.11.0.0$^{2,13}$.0$^{16,20}$.0$^{21,26}$]hexacosa-13,22-diene-4,12,24-trione

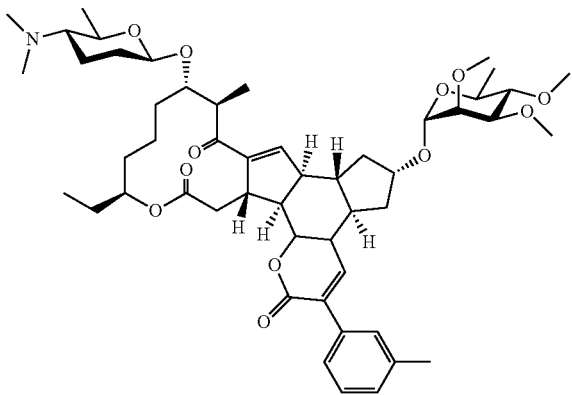

144

According to the general procedure for Example 47, Example 54 (45 mg, 0.05 mmol), m-CPBA (17.2 mg, 0.1 mmol) and Na$_2$HPO$_4$ (14.2 mg, 0.1 mmol) provided the title compound (15.8 mg, yield 35.4%) as a white solid. Partial $^1$H NMR (CDCl$_3$, 400 MHz): δ 7.69 (d, J=2.4 Hz, 1H), 7.53 (s, 1H), 7.48 (d, J=8.0 Hz, 1H), 7.29-7.27 (m, 1H), 7.15 (d, J=7.6 Hz, 1H), 6.72 (s, 1H), 4.86 (s, 1H), 4.81-4.75 (m, 1H), 4.68-4.59 (m, 1H), 4.41-4.37 (m, 2H), 3.80-3.73 (m, 2H), 3.58-3.43 (m, 15H), 3.23-3.08 (m, 10H), 2.96-2.85 (m, 2H), 2.72-2.65 (m, 1H), 2.59-2.53 (m, 1H), 2.48-2.39 (m, 2H), 2.32-2.23 (m, 1H), 2.20-2.09 (m, 2H), 0.81 (t, J=7.6 Hz, 3H); LC-MS: m/z 892.1 [M+H]$^+$.

Intermediate 26: (2S,3aR,4S,5aR,5bS,9S,13S,14R,16aR,16bS)-13-{[(2R,5S,6R)-5-(dimethylamino)-6-methyloxan-2-yl]oxy}-9-ethyl-14-methyl-7,15-dioxo-2-{[(2R,3R,4R,5S,6S)-3,4,5-trimethoxy-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecan-4-yl methanesulfonate

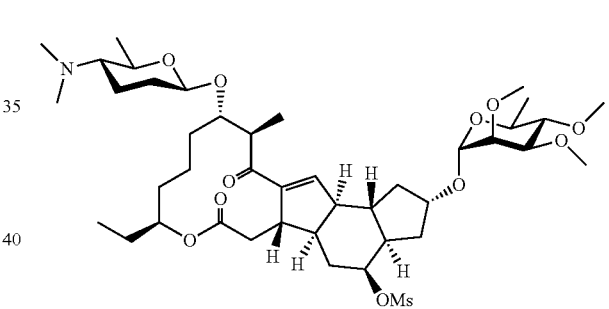

A mixture of Example 8 (3.7 g, 5.0 mmol) and triethylamine (6.3 mL, 45 mmol) in dichloromethane (300 mL) was cooled to 0° C. Methanesulfonyl chloride (1.7 g, 15.0 mmol) was added dropwise. The resulting mixture was stirred at rt for 24 h. The reaction mixture was quenched with saturated aqueous sodium bicarbonate (300 mL). The organic phase was separated and washed with brine (300 mL), dried over anhydrous sodium sulfate, filtered and concentrated. The residue was purified by column chromatography on silica gel (dichloromethane/methanol=100/1 to 30/1) to afford the title compound (3.2 g, 78% yield) as a yellow solid. Partial $^1$H NMR (CDCl$_3$, 400 MHz): δ 6.79 (s, 1H), 5.12-5.09 (m, 1H), 4.83 (d, J=1.6 Hz, 1H), 4.66-4.62 (m, 1H), 4.44-4.42 (m, 1H), 4.26-4.24 (m, 1H), 3.00 (s, 3H), 2.69-2.64 (m, 1H), 2.24 (s, 6H), 0.81 (t, J=7.6 Hz, 3H). LCMS: m/z 828.5 [M+H]$^+$.

Intermediate 27: (2S,3aR,4R,5aR,5bS,9S,13S,14R,
16aR,16bS)-4-azido-13-{[(2R,5S,6R)-5-(dimethyl-
amino)-6-methyloxan-2-yl]oxy}-9-ethyl-14-methyl-
2-{[(2R,3R,4R,5S,6S)-3,4,5-trimethoxy-6-
methyloxan-2-yl]oxy}-1H,2H,3H,3aH,4H,5H,5aH,
5bH,6H,7H,9H,10H,11H,12H,13H,14H,15H,16aH,
16bH-as-indaceno[3,2-d]oxacyclododecane-7,15-
dione

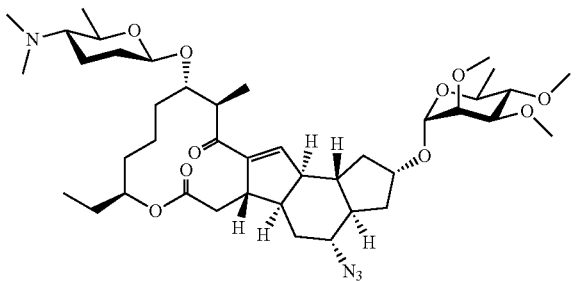

A mixture of Intermediate 26 (2.0 g, 2.4 mmol) and sodium azide (1.0 g, 14.5 mmol) in DMF (50 mL) was stirred at 60° C. for 2 h. The reaction mixture was diluted with water (150 mL) and extracted with ethyl acetate (100 mL×3). The combined organic layer was washed with water (200 mL×3), dried over anhydrous sodium sulfate, filtered and concentrated. The residue was purified by column chromatography on silica gel (dichloromethane/methanol=100/1 to 30/1) to afford compound 3 (1.67 g, 89% yield) as a yellow solid. LCMS: m/z 774.9 [M+H]$^+$.

Intermediate 28: (2S,3aR,4R,5aR,5bS,9S,13S,14R,
16aR,16bS)-4-amino-13-{[(2R,5S,6R)-5-(dimethyl-
amino)-6-methyloxan-2-yl]oxy}-9-ethyl-14-methyl-
2-{[(2R,3R,4R,5S,6S)-3,4,5-trimethoxy-6-
methyloxan-2-yl]oxy}-1H,2H,3H,3aH,4H,5H,5aH,
5bH,6H,7H,9H,10H,11H,12H,13H,14H,15H,16aH,
16bH-as-indaceno[3,2-d]oxacyclododecane-7,15-
dione

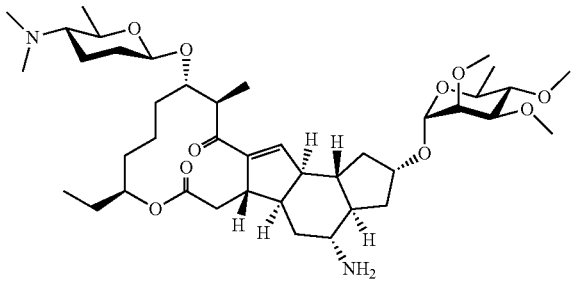

A mixture of Intermediate 27 (100 mg, 0.12 mmol) and palladium on carbon (20 mg) in methanol (20 mL) was stirred under 50 psi of H$_2$ at 40° C. for 4 h. The mixture was filtered through Celite and washed with methanol (50 ml). The filtrate was concentrated under reduced pressure to give a residue, which was purified by prep-HPLC to afford the title compound (50 mg, 50% yield) as a white solid (3.2 g, 78% yield) as a yellow solid. Partial $^1$H NMR (CDCl$_3$, 400 MHz): δ 6.79 (s, 1H), 5.12-5.09 (m, 1H), 4.83 (d, J=1.6 Hz, 1H), 4.66-4.62 (m, 1H), 4.44-4.42 (m, 1H), 4.26-4.24 (m, 1H), 3.00 (s, 3H), 2.69-2.64 (m, 1H), 2.24 (s, 6H), 0.81 (t, J=7.6 Hz, 3H). LCMS: m/z 828.5 [M+H]$^+$.

Example 66: (2S,3aR,4R,5aR,5bS,9S,13S,14R,
16aR,16bS)-13-{[(2R,5S,6R)-5-(dimethylamino)-6-
methyloxan-2-yl]oxy}-9-ethyl-14-methyl-4-[(pro-
pan-2-yl)amino]-2-{[(2R,3R,4R,5S,6S)-3,4,5-
trimethoxy-6-methyloxan-2-yl]oxy}-1H,2H,3H,3aH,
4H,5H,5aH,5bH,6H,7H,9H,10H,11H,12H,13H,14H,
15H,16aH,16bH-as-indaceno[3,2-d]
oxacyclododecane-7,15-dione A mixture of Intermediate 28 (350 mg, 0.47 mmol), acetone (81 mg, 1.4 mmol) and acetic acid (1 drop) in tetrahydrofuran (50 mL) was stirred at room temperature for 0.5 h. Sodium triacetoxyborohydride (496 mg, 2.34 mmol) was added. The resulting mixture was stirred at r.t for 2 h. The reaction mixture was quenched with saturated aqueous sodium bicarbonate (150 mL) and extracted with ethyl acetate (100 mL×3). The combined organic layer was washed with brine (200 mL), dried over anhydrous sodium sulfate, filtered and concentrated. The residue was purified by prep-HPLC to afford the title compound (36 mg, 7% yield) as a yellow solid. Partial $^1$H NMR (CDCl$_3$, 400 MHz): δ 6.83 (s, 1H), 4.82 (d, J=1.2 Hz, 1H), 4.67-4.63 (m, 1H), 4.42 (d, J=7.2 Hz, 1H), 4.25-4.21 (m, 1H), 3.64-3.55 (m, 1H), 3.28-3.24 (m, 1H), 3.17-3.08 (m, 2H), 2.99 (br, 1H), 2.98-2.91 (m, 2H), 2.59-2.55 (m, 1H), 2.44-2.35 (m, 2H), 2.24 (s, 6H), 1.17 (d, J=6.8 Hz, 1H), 1.06 (d, J=6.4 Hz, 1H), 1.02 (d, J=6.4 Hz, 1H), 0.92-0.87 (m, 1H), 0.81 (t, J=7.2 Hz, 3H). LCMS: m/z 790.9 [M+H]$^+$.

Example 67: (2S,3aR,4R,5aR,5bS,9S,13S,14R, 16aR,16bS)-4-(dimethylamino)-13-{[(2R,5S,6R)-5- (dimethylamino)-6-methyloxan-2-yl]oxy}-9-ethyl- 14-methyl-2-{[(2R,3R,4R,5S,6S)-3,4,5-trimethoxy- 6-methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-7,15- dione

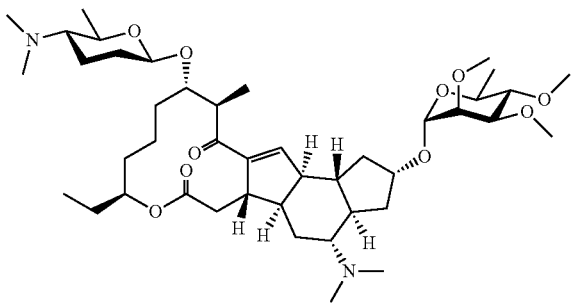

A mixture of Intermediate 28 (350 mg, 0.47 mmol), formic acid (190 mg, 2.34 mmol; 37% w in water) and acetic acid (1 drop) in tetrahydrofuran (50 mL) was stirred at room temperature for 0.5 h. Sodium triacetoxyborohydride (496 mg, 2.34 mmol) was added. The resulting mixture was stirred at r.t for 2 h. The reaction mixture was quenched with saturated aqueous sodium bicarbonate (150 mL) and extracted with ethyl acetate (100 mL×3). The combined organic layer was washed with brine (200 mL), dried over anhydrous sodium sulfate, filtered and concentrated. The residue was purified by prep-HPLC to afford the title compound (115 mg, 31% yield) as a yellow solid. Partial $^1$H NMR (CDCl$_3$, 400 MHz): δ 6.81 (s, 1H), 4.83 (s, 1H), 4.66-4.63 (m, 1H), 4.43-4.41 (m, 1H), 4.26-4.21 (m, 1H), 3.66-3.61 (m, 1H), 3.28-3.24 (m, 1H), 3.15-3.08 (m, 2H), 3.00-2.94 (m, 2H), 2.60-2.55 (m, 1H), 2.31 (s, 1H), 2.23 (s, 1H), 1.17 (d, J=6.8 Hz, 3H), 0.93-0.89 (m, 1H), 0.81 (t, J=7.2 Hz, 3H). LCMS: m/z 776.9 [M+H]$^+$.

Example 68: (2S,3aR,4R,5aR,5bS,9S,13S,14R, 16aR,16bS)-13-{[(2R,5S,6R)-5-(dimethylamino)-6- methyloxan-2-yl]oxy}-9-ethyl-14-methyl-4-(methyl- amino)-2-{[(2R,3R,4R,5S,6S)-3,4,5-trimethoxy-6- methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-7,15- dione

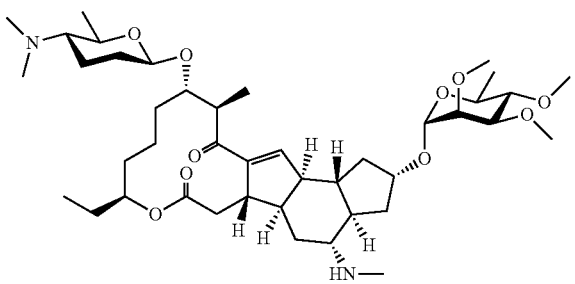

To a mixture of Intermediate 26 (600 mg, 0.72 mmol) and potassium carbonate (501 mg, 3.6 mmol) in DMF (15 mL) was added methylamine (5 mL, 30 mmol, 27% w in ethanol). The resulting mixture was then stirred at 70° C. for 3 h in a microwave reactor. The reaction mixture was quenched with water (50 mL), and extracted with ethyl acetate (50 mL×3). The combined organic layer was washed with water (100 mL×2), dried over anhydrous sodium sulfate, filtered and concentrated. The residue was purified by prep-HPLC to afford the title compound (40 mg, 7% yield) as a white solid. Partial $^1$H NMR (CDCl$_3$, 400 MHz): δ 6.82 (s, 1H), 4.82 (d, J=0.8 Hz, 1H), 4.67-4.63 (m, 1H), 4.42 (d, J=7.2 Hz, 1H), 4.26-4.23 (m, 1H), 3.65-3.60 (m, 1H), 3.29-3.24 (m, 1H), 3.16-3.10 (m, 2H), 3.01-2.93 (m, 2H), 2.62-2.57 (m, 1H), 2.45 (s, 3H), 2.37 (d, J=13.2, 2.8 Hz, 1H), 2.24 (s, 6H), 1.17 (d, J=6.4 Hz, 1H), 0.94-0.88 (m, 1H), 0.81 (t, J=7.2 Hz, 3H). LCMS: m/z 762.9 [M+H]$^+$.

Example 69: (2S,3aR,5aR,5bS,9S,13S,14R,16aR, 16bS)-4-azido-13-{[(2R,5S,6R)-5-(dimethylamino)- 6-methyloxan-2-yl]oxy}-9-ethyl-5-hydroxy-14- methyl-2-{[(2R,3R,4R,5S,6S)-3,4,5-trimethoxy-6- methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-7,15- dione

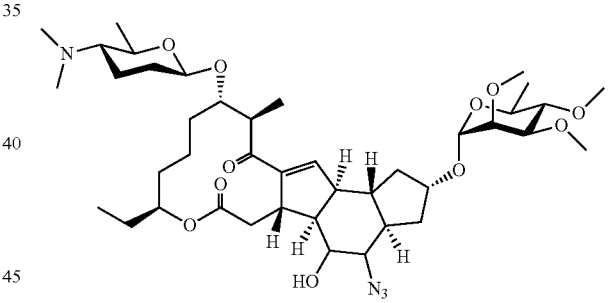

To a solution of Spinosyn A (3.0 g, 4.1 mmol) in dichloromethane (100 mL) was added m-CPBA (2.18 g, 12.3 mmol) at 0° C. The resulting mixture was stirred at 0° C. for 1 hour and at room temperature for 1.5 hours. To the mixture was added saturated aqueous NaHSO$_3$ (100 mL) and the mixture was stirred at room temperature for 2 hours. The organic layer was separated and the aqueous was extracted with dichloromethane (100 mL×2). The combined organic phase was washed with brine (300 mL), dried over anhydrous sodium sulfate, concentrated and the residue was purified by column chromatography on silica gel (dichloromethane/methanol=40/1) to give 2.35 g, of a white solid. Partial $^1$H NMR (400 MHz, CDCl$_3$): δ6.58 (s, 1H), 4.85 (1H, s), 4.67-4.65 (m, 1H), 4.43-4.41 (m, 1H), 4.26-4.21 (m, 1H), 3.64-3.52 (m, 1H), 3.27-3.18 (m, 2H), 3.12 (t, J=9.6

Hz, 1H), 2.61-2.56 (m, 1H), 2.43 (dd, J=13.6, 2.4 Hz, 1H), 0.82 (t, J=7.2 Hz, 3H). LCMS: m/z 748.0 [M+H]⁺.

A mixture of the above intermediate (7 g, 9.0 mmol) and Sodium azide (3.5 g, 54.3 mmol) in DMF (60 mL) was stirred at 60° C. for 2 h. The reaction mixture was cooled to r.t and filtered through the kieselguhr. The filtrate was poured into saturated aq sodium bicarbonate (100 mL). The mixture was extracted with ethyl acetate (3×100 mL). The combined organic layer was dried over sodium sulfate, filtered and concentrated. The residue was purified by flash to afford compound 1 (4.5 g, 63% yield) as a white solid. LCMS: m/z 791.9 [M+H]⁺.

Example 70: (2S,3aR,5aR,5bS,9S,13S,14R,16aR,16bS)-4-[4-(2-chlorophenyl)-1H-1,2,3-triazol-1-yl]-13-{[(2R,5S,6R)-5-(dimethylamino)-6-methyloxan-2-yl]oxy}-9-ethyl-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

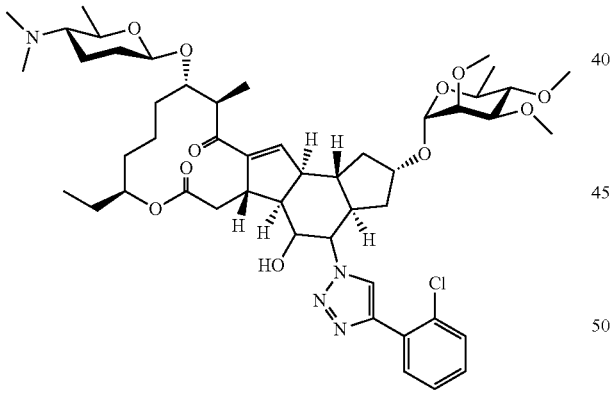

A mixture of Example 69 (300 mg, 0.38 mmol), 1-Chloro-2-ethynyl-benzene (260 mg, 1.9 mmol), copper sulfate (12 mg, 0.076 mmol) and sodium ascorbate (15 mg, 0.076 mmol) in t-butanol/H₂O (3 mL/1.5 mL) was stirred at 100° C. for 17 h in a sealed tube. The reaction mixture was filtered through kieselguhr, and the filtrate was concentrated. The residue was purified by prep-HPLC to afford the title compound (50 mg, 14% yield) as a white solid. Partial ¹H NMR (CDCl₃, 400 MHz): δ 8.42 (s, 1H), 8.23 (dd, J=1.6, 8.0 Hz, 1H), 7.45 (dd, J=0.8, 8.0 Hz, 2H), 7.40-7.36 (m, 1H), 6.88 (s, 1H), 4.72 (s, 1H), 4.67-4.64 (m, 1H), 4.53 (dd, J=2.4, 11.6 Hz, 1H), 4.44-4.40 (m, 2H), 4.29-4.24 (m, 1H), 3.65-3.61 (m, 1H), 3.55-3.43 (m, 17H), 3.28-3.22 (m, 4H), 3.17-3.07 (m, 2H), 3.00-2.95 (m, 1H), 2.81-2.73 (m, 1H), 2.40-2.21 (m, 11H), 1.99-1.97 (m, 1H), 1.87-1.74 (m, 7H), 0.81 (t, J=7.2 Hz, 3H). LCMS: m/z 893.1 [M+H]⁺.

Example 71: (2S,3aR,4R,5aR,5bS,9S,13S,14R,16aR,16bS)-13-{[(2R,5S,6R)-5-(dimethylamino)-6-methyloxan-2-yl]oxy}-9-ethyl-4-[4-(4-fluorophenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

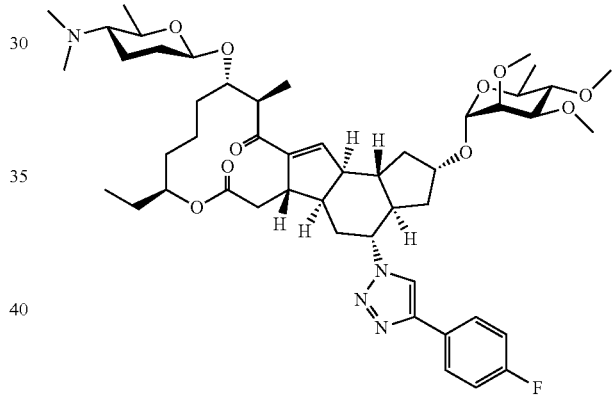

A mixture of Intermediate 27 (250 mg, 0.32 mmol), 1-ethynyl-4-fluoro-benzene (194 mg, 1.6 mmol), copper sulfate (10 mg, 0.06 mmol) and sodium ascorbate (13 mg, 0.06 mmol) in t-butanol/H₂O (3 mL/1.5 mL) was stirred at 100° C. for 17 h in a sealed tube. The reaction mixture was filtered through kieselguhr, and the filtrate was concentrated. The residue was purified by prep-HPLC to afford the title compound (130 mg, 45% yield) as a white solid. Partial ¹H NMR (CDCl₃, 400 MHz): δ 7.84-7.80 (m, 2H), 7.76 (s, 1H), 7.15-7.11 (m, 2H), 6.85 (s, 1H), 4.70 (d, J=0.8 Hz, 1H), 4.69-4.64 (m, 1H), 4.43 (d, J=8.8 Hz, 1H), 4.36 (dt, J=10.8, 4.4 Hz, 1H), 4.28-4.25 (m, 1H), 3.65-3.60 (m, 1H), 3.30-3.24 (m, 2H), 3.18 (dd, J=13.6, 5.2 Hz, 1H), 3.11-3.06 (m, 2H), 2.79-2.74 (m, 1H), 2.24 (s, 6H), 2.00-1.97 (m, 1H), 1.20 (d, J=6.8 Hz, 1H), 1.16-1.10 (m, 1H), 0.81 (t, J=7.2 Hz, 3H). LCMS: m/z 894.9 [M+H]⁺.

Example 72: (2S,3aR,4R,5aR,5bS,9S,13S,14R, 16aR,16bS)-4-(4-tert-butyl-1H-1,2,3-triazol-1-yl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H, 3H,3aH,4H,5H,5aH,5bH,6H,7H,9H,10H,11H,12H, 13H,14H,15H,16aH,16bH-as-indaceno[3,2-d]oxacyclododecane-7,15-dione

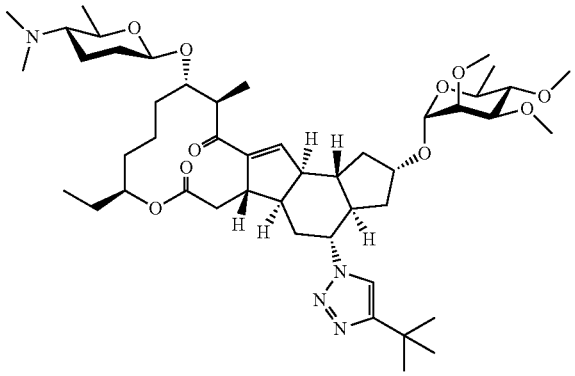

A mixture of Intermediate 27 (250 mg, 0.32 mmol), 3,3-Dimethyl-but-1-yne (132 mg, 1.6 mmol), copper sulfate (10 mg, 0.065 mmol) and sodium ascorbate (13 mg, 0.065 mmol) in t-butanol/H$_2$O (3 mL/1.5 mL) was stirred at 100° C. for 17 h in a sealed tube. The reaction mixture was filtered through kieselguhr and the filtrate was concentrated. The residue was purified by prep-HPLC to afford the title compound (110 mg, 40% yield) as a white solid. Partial $^1$H NMR (CDCl$_3$, 400 MHz): δ 6.84 (s, 1H), 4.72 (d, J=1.6 Hz, 1H), 4.67-4.64 (m, 1H), 4.42 (d, J=7.2 Hz, 1H), 4.29-4.21 (m, 2H), 3.65-3.60 (m, 1H), 3.30-3.20 (m, 2H), 3.17 (dd, J=13.2, 4.8 Hz, 1H), 3.13-3.04 (m, 1H), 2.74-2.70 (m, 1H), 2.23 (s, 6H), 1.99-1.96 (m, 1H), 1.35 (s, 9H), 1.19 (d, J=6.8 Hz, 3H), 1.12-1.05 (m, 1H), 0.80 (t, J=7.6 Hz, 3H). LCMS: m/z 857.0 [M+H]$^+$.

Example 73: (2S,3aR,4R,5aR,5bS,9S,13S,14R, 16aR,16bS)-13-{[(2R,5S,6R)-5-(dimethylamino)-6-methyloxan-2-yl]oxy}-9-ethyl-4-[4-(4-methoxyphenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H, 10H,11H,12H,13H,14H,15H,16aH,16bH-as-indaceno[3,2-d]oxacyclododecane-7,15-dione

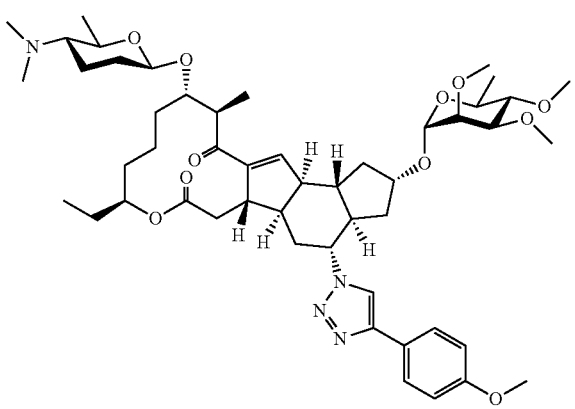

A mixture of Intermediate 27 (250 mg, 0.32 mmol), 1-Ethynyl-4-methoxy-benzene (213 mg, 1.6 mmol), copper sulfate (10 mg, 0.065 mmol) and sodium ascorbate (13 mg, 0.065 mmol) in t-butanol/H$_2$O (3 mL/1.5 mL) was stirred at 100° C. for 17 h in a sealed tube. The reaction mixture was filtered through kieselguhr, and the filtrate was concentrated. The residue was purified by prep-HPLC to afford the title compound (121 mg, 41% yield) as a white solid. Partial $^1$H NMR (CDCl$_3$, 400 MHz): δ 7.79-7.77 (m, 2H), 7.72 (s, 1H), 6.98-6.96 (m, 2H), 6.85 (s, 1H), 4.70 (d, J=1.2 Hz, 1H), 4.70-4.66 (m, 1H), 4.43 (d, J=7.2 Hz, 1H), 4.36 (dt, J=11.2, 4.8 Hz, 1H), 4.28-4.23 (m, 1H), 3.85 (s, 1H), 3.66-3.60 (m, 1H), 3.31-3.21 (m, 2H), 3.18 (dd, J=13.6, 4.8 Hz, 1H), 3.11-3.06 (m, 2H), 2.78-2.73 (m, 1H), 2.24 (s, 6H), 1.99-1.97 (m, 1H), 1.20 (d, J=6.4 Hz, 3H), 1.14-1.09 (m, 1H), 0.81 (t, J=7.6 Hz, 3H). LCMS: m/z 907.4 [M+H]$^+$.

Example 74: (2S,3aR,4R,5aR,5bS,9S,13S,14R, 16aR,16bS)-13-{[(2R,5S,6R)-5-(dimethylamino)-6-methyloxan-2-yl]oxy}-9-ethyl-14-methyl-4-[4-(thiophen-2-yl)-1H-1,2,3-triazol-1-yl]-2-{[(2R,3R,4R,5S, 6S)-3,4,5-trimethoxy-6-methyloxan-2-yl]oxy}-1H, 2H,3H,3aH,4H,5H,5aH,5bH,6H,7H,9H,10H,11H, 12H,13H,14H,15H,16aH,16bH-as-indaceno[3,2-d]oxacyclododecane-7,15-dione

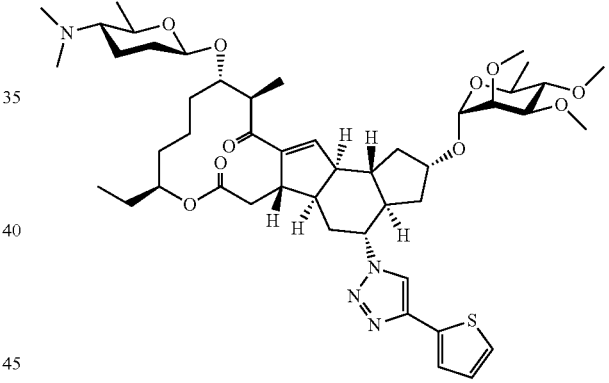

A mixture of Intermediate 27 (250 mg, 0.32 mmol), 2-Ethynyl-thiophene (174 mg, 1.6 mmol), copper sulfate (10 mg, 0.065 mmol) and sodium ascorbate (13 mg, 0.065 mmol) in t-butanol/H$_2$O (3 mL/1.5 mL) was stirred at 100° C. overnight in a sealed tube. The reaction mixture was filtered through kieselguhr, and the filtrate was concentrated. The residue was purified by prep-HPLC to afford the title compound (116 mg, 40% yield) as a white solid. Partial $^1$H NMR (CDCl$_3$, 400 MHz): δ 7.71 (s, 1H), 7.40 (dd, J=3.6, 0.8 Hz, 1H), 7.31 (dd, J=5.2, 1.2 Hz, 1H), 7.09 (dd, J=5.2, 3.6 Hz, 1H), 6.85 (s, 1H), 4.71 (d, J=1.2 Hz, 1H), 4.70-4.65 (m, 1H), 4.42 (d, J=6.8 Hz, 1H), 4.36 (dt, J=10.8, 4.8 Hz, 1H), 4.27-4.24 (m, 1H), 3.65-3.61 (m, 1H), 3.29-3.23 (m, 2H), 3.18 (d, J=14.0, 4.8 Hz, 1H), 3.11-3.06 (m, 2H), 2.78-2.73 (m, 1H), 2.24 (s, 6H), 1.99-1.96 (m, 1H), 1.67 (dd, J=13.6, 6.8 Hz, 1H), 1.20 (d, J=6.4 Hz, 3H), 1.14-1.09 (m, 1H), 0.81 (t, J=7.6 Hz, 3H). LCMS: m/z 883.4 [M+H]$^+$.

153

Example 75: (2S,3aR,4R,5aR,5bS,9S,13S,14R, 16aR,16bS)-4-[4-(2-chlorophenyl)-1H-1,2,3-triazol-1-yl]-13-{[(2R,5S,6R)-5-(dimethylamino)-6-methyloxan-2-yl]oxy}-9-ethyl-14-methyl-2-{[(2R,3R,4R, 5S,6S)-3,4,5-trimethoxy-6-methyloxan-2-yl]oxy}-1H,2H,3H,3aH,4H,5H,5aH,5bH,6H,7H,9H,10H, 11H,12H,13H,14H,15H,16aH,16bH-as-indaceno[3, 2-d]oxacyclododecane-7,15-dione

154

Example 76: (2S,3aR,5aR,5bS,9S,13S,14R,16aR, 16bS)-13-{[(2R,5S,6R)-5-(dimethylamino)-6-methyloxan-2-yl]oxy}-9-ethyl-5-fluoro-4-[4-(4-fluorophenyl)-1H-1,2,3-triazol-1-yl]-14-methyl-2-{[(2R, 3R,4R,5S,6S)-3,4,5-trimethoxy-6-methyloxan-2-yl]oxy}-1H,2H,3H,3aH,4H,5H,5aH,5bH,6H,7H,9H, 10H,11H,12H,13H,14H,15H,16aH,16bH-as-indaceno[3,2-d]oxacyclododecane-7,15-dione

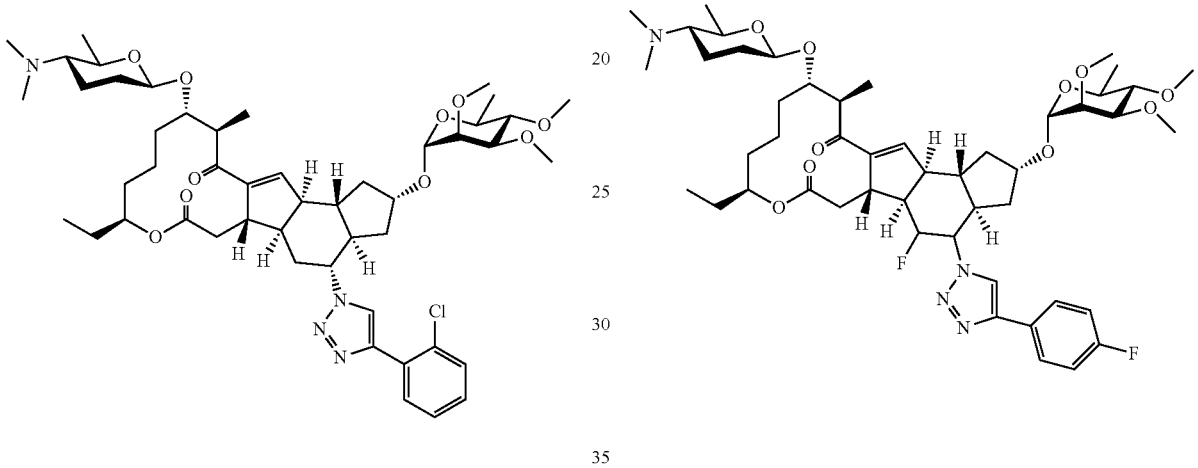

A mixture of Intermediate 27 (145 mg, 0.19 mmol), 1-chloro-2-ethynyl-benzene (128 mg, 0.94 mmol), copper sulfate (6 mg, 0.04 mmol) and sodium ascorbate (8 mg, 0.04 mmol) in t-butanol/H$_2$O (2 mL/1 mL) was stirred at 100° C. for 17 h in a sealed tube. The reaction mixture was filtered through kieselguhr, and the filtrate was concentrated. The residue was purified by prep-HPLC to afford the title compound (26 mg, 15% yield) as a white solid. Partial $^1$H NMR (CDCl$_3$, 400 MHz): δ 8.28 (dd, J=8.0, 1.6 Hz, 1H), 8.23 (s, 1H), 7.46 (dd, J=8.0, 1.2 Hz, 1H), 7.41-7.37 (m, 1H), 7.31-7.28 (m, 1H), 6.87 (s, 1H), 4.72 (s, 1H), 4.69-4.66 (m, 1H), 4.44-4.37 (m, 2H), 4.28-4.25 (m, 1H), 3.65-3.61 (m, 1H), 3.32-3.26 (m, 2H), 3.18 (dd, J=13.6, 4.8 Hz, 1H), 3.11-3.07 (m, 2H), 2.79-2.74 (m, 1H), 2.24 (s, 6H), 2.00-1.97 (m, 1H), 1.69 (dd, J=13.2, 6.0 Hz, 1H), 1.21 (d, J=7.2 Hz, 3H), 1.17-1.10 (m, 1H), 0.81 (t, J=7.6 Hz, 3H). LCMS: m/z 910.9 [M+H]$^+$.

The hydroxyl triazole was prepared from Example 69 according to the representative procedure. To a solution of the hydroxyl triazole (150 mg, 0.16 mmol) in dichloromethane (10 mL) was was added DAST (53.1 mg, 0.33 mmol) at −78° C. under nitrogen. After stirred at −78° C. for 30 min, the mixture was warmed to room temperature and quenched with aqueous sodium bicarbonate (10 mL). After stirred for 15 min, the mixture was extracted with dichloromethane (10 mL×3). The combined organic layer was washed with brine, dried over sodium sulfate, filtered and concentrated. The residue was purified by prep-HPLC to afford Example 76 (40 mg, yield 50%) as a white solid. Partial $^1$H NMR (CDCl$_3$, 400 MHz): δ7.84-7.81 (m, 2H), 7.78 (s, 1H), 7.15-7.11 (m, 2H), 6.81 (s, 1H), 5.27-5.16 (m, 1H), 4.74-4.68 (m, 2H), 4.43-4.29 (m, 3H), 3.31-3.99 (m, 5H), 2.63-2.21 (m, 16H), 0.82 (t, J=7.2 Hz, 3H). LCMS: m/z 914.1 [M+H]$^+$.

Example 77: (2S,3aR,4R,5aR,5bS,9S,13S,14R, 16aR,16bS)-13-{[(2R,5S,6R)-5-(dimethylamino)-6-methyloxan-2-yl]oxy}-9-ethyl-14-methyl-2-{[(2R, 3R,4R,5S,6S)-3,4,5-trimethoxy-6-methyloxan-2-yl] oxy}-4-[4-(trimethylsilyl)-1H-1,2,3-triazol-1-yl]-1H, 2H,3H,3aH,4H,5H,5aH,5bH,6H,7H,9H,10H,11H, 12H,13H,14H,15H,16aH,16bH-as-indaceno[3,2-d] oxacyclododecane-7,15-dione

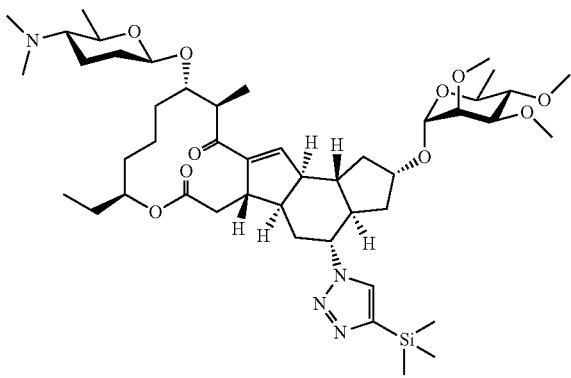

A mixture of Intermediate 27 (300 mg, 0.39 mmol), ethynyl-trimethyl-silane (190 mg, 1.9 mmol), copper sulfate (12 mg, 0.08 mmol) and sodium ascorbate (15 mg, 0.08 mmol) in t-butanol/$H_2O$ (3 mL/1.5 mL) was stirred at 100° C. for 17 h in a sealed tube. The reaction mixture was filtered through kieselguhr, and the filtrate was concentrated. The residue was purified by prep-HPLC to afford the title compound (135 mg, 40% yield) as a white solid. Partial $^1$H NMR (CDCl$_3$, 400 MHz): δ 7.54 (s, 1H), 6.85 (s, 1H), 4.72 (d, J=0.8 Hz, 1H), 4.69-4.65 (m, 1H), 4.42 (d, J=7.2 Hz, 1H), 4.34 (td, J=10.8, 4.8 Hz, 1H), 4.27-4.22 (m, 1H), 3.66-3.60 (m, 1H), 3.17 (dd, J=13.6, 4.8 Hz, 1H), 2.77-2.72 (m, 1H), 2.24 (s, 6H), 2.01-1.97 (m, 1H), 1.20 (d, J=7.6 Hz, 1H), 1.15-1.06 (m, 1H), 0.81 (t, J=7.6 Hz, 3H), 0.33 (s, 9H). LCMS: m/z 872.9 [M+H]$^+$.

Example 78: (2S,3aR,4R,5aR,5bS,9S,13S,14R, 16aR,16bS)-13-{[(2R,5S,6R)-5-(dimethylamino)-6-methyloxan-2-yl]oxy}-9-ethyl-14-methyl-4-(1H-1,2, 3-triazol-1-yl)-2-{[(2R,3R,4R,5S,6S)-3,4,5-trimethoxy-6-methyloxan-2-yl]oxy}-1H,2H,3H,3aH, 4H,5H,5aH,5bH,6H,7H,9H,10H,11H,12H,13H,14H, 15H,16aH,16bH-as-indaceno[3,2-d] oxacyclododecane-7,15-dione

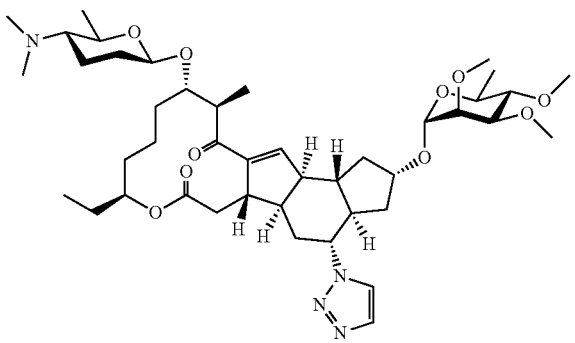

To a solution of Example 77 (300 mg, 0.39 mmol) in tetrahydrofuran (10 mL) was added TBAF (1M in tetrahydrofuran, 0.6 mL, 0.6 mmol). The resulting mixture was stirred at 65° C. overnight. The reaction mixture was concentrated. The residue was purified by prep-HPLC to afford the title compound (19 mg, 20% yield) as a white solid. Partial $^1$H NMR (CDCl$_3$, 400 MHz): δ 7.75 (s, 1H), 7.60 (s, 1H), 6.85 (s, 1H), 4.70 (s, 1H), 4.68-4.64 (m, 1H), 4.43 (d, J=7.2 Hz, 1H), 4.37 (dt, J=10.8, 4.8 Hz, 1H), 4.27-4.22 (m, 1H), 3.66-3.61 (m, 1H), 3.29-3.24 (m, 2H), 3.18 (dd, J=13.6, 4.8 Hz, 1H), 2.77-2.72 (m, 1H), 2.24 (s, 6H), 2.00-1.97 (m, 1H), 1.20 (d, J=7.2 Hz, 1H), 1.14-1.07 (m, 1H), 0.81 (t, J=7.6 Hz, 3H). LCMS: m/z 800.9 [M+H]$^+$.

Example 79: {1-[(2S,3aR,4R,5aR,5bS,9S,13S,14R, 16aR,16bS)-13-{[(2R,5S,6R)-5-(dimethylamino)-6-methyloxan-2-yl]oxy}-9-ethyl-14-methyl-7,15-dioxo-2-{[(2R,3R,4R,5S,6S)-3,4,5-trimethoxy-6-methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecan-4-yl]-1H-1,2,3-triazol-4-yl}methyl acetate

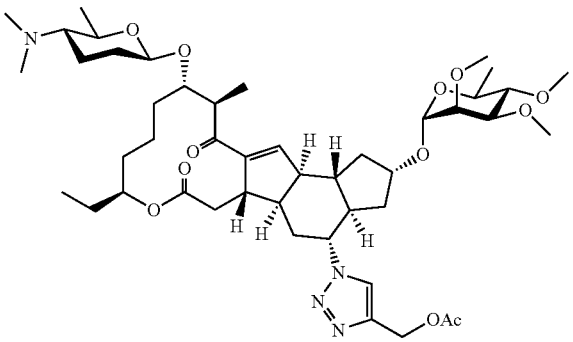

A mixture of Intermediate 27 (145 mg, 0.19 mmol), prop-2-ynyl acetate (92 mg, 0.94 mmol), copper sulfate (6 mg, 0.04 mmol) and sodium ascorbate (8 mg, 0.04 mmol) in t-butanol/$H_2O$ (2 mL/1 mL) was stirred at 100° C. for 17 h in a sealed tube. The reaction mixture was filtered through kieselguhr and the filtrate was concentrated. The residue was purified by prep-HPLC to afford the title compound (40 mg, 24% yield) as a white solid. Partial $^1$H NMR (CDCl$_3$, 400 MHz): δ 7.63 (s, 1H), 6.84 (s, 1H), 5.23 (s, 2H), 4.72 (s, 1H), 4.68-4.65 (m, 1H), 4.43 (d, J=7.2, Hz, 1H), 4.31-4.24 (m, 2H), 3.64-3.61 (m, 1H), 3.29-3.23 (m, 2H), 3.18 (dd, J=13.2, 5.2 Hz, 1H), 3.12-3.04 (m, 2H), 2.76-2.72 (m, 1H), 2.24 (s, 6H), 2.00-1.97 (m, 1H), 1.20 (d, J=6.8 Hz, 3H), 1.12-1.07 (m, 1H), 0.81 (t, J=7.6 Hz, 3H). LCMS: m/z 872.9 [M+H]$^+$.

Example 80: (2S,3aR,5aR,5bS,9S,13S,14R,16aR,16bS)-4-[4-(4-aminophenyl)-1H-1,2,3-triazol-1-yl]-13-{[(2R,5S,6R)-5-(dimethylamino)-6-methyloxan-2-yl]oxy}-9-ethyl-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

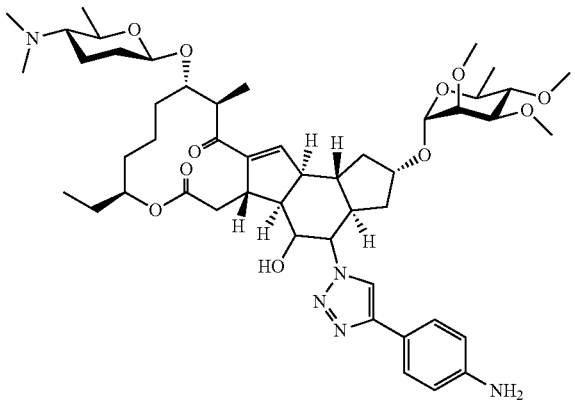

A mixture of Example 69 (300 mg, 0.38 mmol), 4-ethynylaniline (222 mg, 1.9 mmol), copper sulfate (12 mg, 0.076 mmol) and sodium ascorbate (15 mg, 0.076 mmol) in t-butanol/H$_2$O (3 mL/1.5 mL) was stirred at 100° C. for 17 h in a sealed tube. The reaction mixture was filtered through kieselguhr and the filtrate was concentrated. The residue was purified by prep-HPLC to afford the title compound (50 mg, 8.7% yield) as a white solid. Partial $^1$H NMR (CDCl$_3$, 400 MHz): δ 7.87 (s, 1H), 7.62 (d, J=8.4 Hz, 2H), 6.86 (s, 1H), 6.74 (d, J=8.8 Hz, 2H), 4.70-4.63 (m, 2H), 4.45-4.42 (m, 2H), 4.34 (s, 1H), 4.25-4.23 (m, 1H), 3.65-3.58 (m, 1H), 3.55-3.43 (m, 17H), 3.28-3.22 (m, 3H), 3.14-3.07 (m, 2H), 2.98-2.95 (m, 1H), 2.73-2.68 (m, 1H), 2.38-2.21 (m, 11H), 2.01-1.97 (m, 1H), 1.88-1.82 (m, 5H), 1.53-1.06 (m, 31H), 0.81 (t, J=7.6 Hz, 3H), LCMS: m/z 908.7 [M+H]$^+$.

Example 81: (2S,3aR,4R,5aR,5bS,9S,13S,14R,16aR,16bS)-13-{[(2R,5S,6R)-5-(dimethylamino)-6-methyloxan-2-yl]oxy}-9-ethyl-14-methyl-4-(propylamino)-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

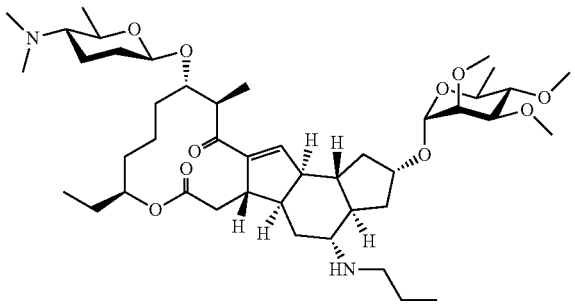

A mixture of Intermediate 28 (105 mg, 0.14 mmol), propionaldehyde (24 mg, 0.42 mmol) and Acetic acid (1 drop) in tetrahydrofuran (10 mL) was stirred at room temperature for 17 h. Sodium tris(acetoxy)borohydride (148 mg, 0.7 mmol) was added and the resulting mixture was stirred at r.t for another 3 h. The reaction mixture was quenched with saturated aqueous sodium bicarbonate (100 mL) and extracted with ethyl acetate (100 mL×2). The combined organic layer was washed with brine (200 mL), dried over anhydrous sodium sulfate, filtered and concentrated. The residue was purified by prep-HPLC to afford the title compound (30 mg, 27% yield) as a yellow solid. Partial $^1$H NMR (CDCl$_3$, 400 MHz): δ 6.84 (s, 1H), 4.82 (d, J=1.2 Hz, 1H), 4.67-4.63 (m, 1H), 4.42 (d, J=7.2 Hz, 1H), 4.25-4.22 (m, 1H), 3.64-3.60 (m, 1H), 3.29-3.24 (m, 1H), 3.17-3.08 (m, 2H), 2.99-2.95 (m, 2H), 2.24 (s, 6H), 1.17 (d, J=6.4 Hz, 1H), 0.93 (t, J=7.2 Hz, 1H), 0.93-0.87 (m, 1H), 0.81 (t, J=7.6 Hz, 3H). LCMS: m/z 791.1 [M+H]$^+$.

Example 82: (2S,3aR,5aR,5bS,9S,13S,14R,16aR,16bS)-13-{[(2R,5S,6R)-5-(dimethylamino)-6-methyloxan-2-yl]oxy}-9-ethyl-5-hydroxy-14-methyl-4-[4-(3-methylphenyl)-1H-1,2,3-triazol-1-yl]-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

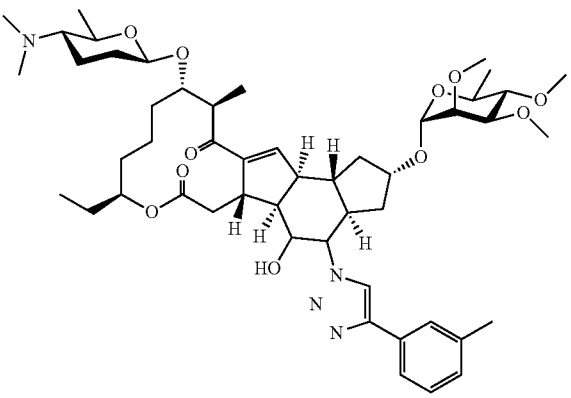

A mixture of Example 69 (300 mg, 0.38 mmol), 1-ethynyl-3-methyl-benzene (220 mg, 1.9 mmol), copper sulfate (12 mg, 0.07 mmol) and sodium ascorbate (15 mg, 0.07 mmol) in t-butanol/H$_2$O (3 mL/1.5 mL) was stirred at 100° C. for 17 h in a sealed tube. The reaction mixture was filtered through kieselguhr and the filtrate was concentrated. The residue was purified by prep-HPLC to afford the title compound (20 mg, 8.7% yield) as a white solid. Partial $^1$H NMR (CDCl$_3$, 400 MHz): δ 8.00 (s, 1H), 7.71 (s, 1H), 7.63 (d, J=4.8 Hz, 1H), 7.34 (t, J=7.6 Hz, 1H), 7.16 (d, J=7.2 Hz, 1H), 6.87 (s, 1H), 4.71-4.63 (m, 2H), 4.51-4.41 (m, 1H), 4.38 (s, 1H), 4.28-4.25 (m, 1H), 3.64-3.60 (m, 1H), 3.55-3.41 (m, 13H), 3.31-3.22 (m, 3H), 3.16-3.07 (m, 2H), 3.01-2.92 (m, 2H), 2.76-2.71 (m, 1H), 2.43-2.27 (m, 5H), 1.99-1.97 (m, 1H), 1.88-1.78 (m, 2H), 0.821 (t, J=7.2 Hz, 3H), LCMS: m/z 907.7 [M+H]$^+$.

Examples 83: (2S,3aR,5aR,5bS,9S,13S,14R,16aR,16bS)-13-{[(2R,5S,6R)-5-(dimethylamino)-6-methyloxan-2-yl]oxy}-9-ethyl-5-fluoro-14-methyl-4-[4-(3-methylphenyl)-1H-1,2,3-triazol-1-yl]-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione Representative Procedure for Hydroxy Triazole Formation Using Example 69

Example 84: (2S,3aR,5aR,5bS,9S,13S,14R,16aR,16bS)-13-{[(2R,5S,6R)-5-(dimethylamino)-6-methyloxan-2-yl]oxy}-9-ethyl-5-hydroxy-14-methyl-4-(4-phenyl-M-1,2,3-triazol-1-yl)-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

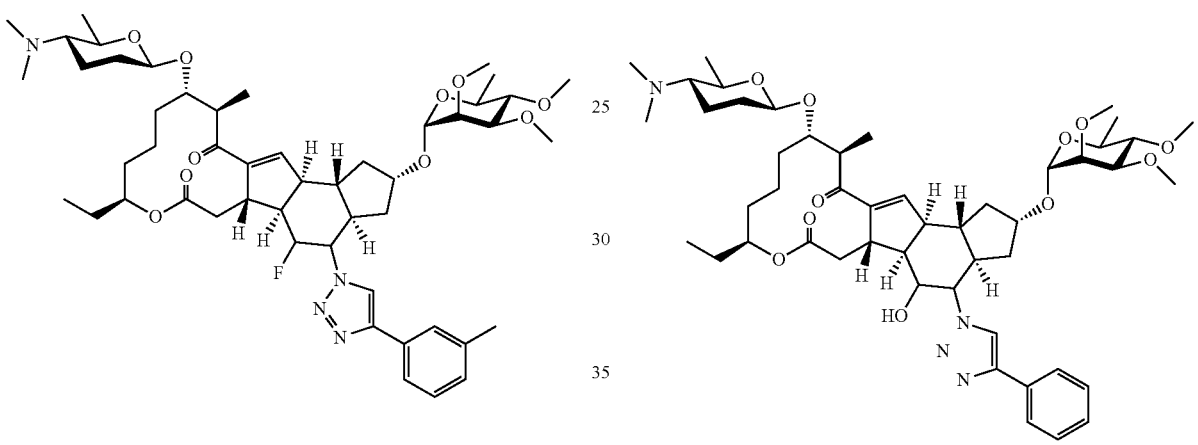

Example 82 (950 mg, 1.05 mmol) in dichloromethane (10 mL) was cooled at −78° C. under nitrogen. Then DAST (844 mg, 5.2 mmol) was added dropwise. The mixture was stirred at −78° C. for 30 mins, then the mixture was allowed to warm up to room temperature. To the mixture was added sodium bicarbonate (aq 10 mL), and the reaction was extracted with dichloromethane (10 mL×3). The combined organic phase was washed with brine, dried over anhydrous sodium sulfate, filtered and concentrated. The crude product was further purified by prep-HPLC to afford Example 83 (200 mg, yield 21%). Partial $^1$H NMR (CDCl$_3$, 400 MHz): δ7.89 (s, 1H), 7.71 (s 1H), 7.63 (d, J=7.6 Hz, 1H), 7.34-7.32 (m, 1H), 7.17 (d, J=7.6 Hz, 1H), 6.79 (s, 1H), 6.18 (m, 1H), 4.82 (d, J=1.2 Hz 1H), 4.73-4.32 (m, 1H), 4.43 (d, J=7.6 Hz 1H), 4.36-4.33 (m, 1H), 3.95-3.80 (m, 1H), 3.34-3.09 (m, 6H), 2.47-2.21 (m, 15H), 0.83 (t, J=7.6 Hz, 3H). LCMS: m/z 890.1 [M+H]$^+$.

A mixture of Example 69 (300 mg, 0.38 mmol), phenylacetylene (220 mg, 1.9 mmol), copper sulfate (12 mg, 0.07 mmol) and sodium ascorbate (15 mg, 0.07 mmol) in t-butanol/H$_2$O (3 mL/1.5 mL) was stirred at 100° C. for 17 h in a sealed tube. The reaction mixture was filtered through kieselguhr, and the filtrate was concentrated. The residue was purified by prep-HPLC to afford the title compound (80 mg, 23% yield) as a white solid. Partial $^1$H NMR (CDCl$_3$, 400 MHz): δ 8.02 (s, 1H), 7.86 (d, J=8.0 Hz, 2H), 7.45 (t, J=7.6 Hz, 2H), 7.36-7.33 (m, 2H), 6.87 (s, 1H), 4.71-4.63 (m, 2H), 4.51-4.41 (m, 1H), 4.38 (s, 1H), 4.28-4.23 (m, 1H), 3.64-3.41 (m, 15H), 3.29-2.96 (m, 6H), 2.76-2.71 (m, 1H), 2.38-2.21 (m, 9H), 2.00-1.05 (m, 34H), 0.81 (t, J=7.6 Hz, 3H), LCMS: m/z 893.1 [M+H]$^+$.

Examples 85: (2S,3aR,5aR,5bS,9S,13S,14R,16aR,16bS)-13-{[(2R,5S,6R)-5-(dimethylamino)-6-methyloxan-2-yl]oxy}-9-ethyl-5-fluoro-14-methyl-4-(4-phenyl-1H-1,2,3-triazol-1-yl)-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione Example 86: (2S,3aR,5aR,5bS,9S,13S,14R,16aR,16bS)-4-[4-(3-chlorophenyl)-1H-1,2,3-triazol-1-yl]-13-{[(2R,5S,6R)-5-(dimethylamino)-6-methyloxan-2-yl]oxy}-9-ethyl-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

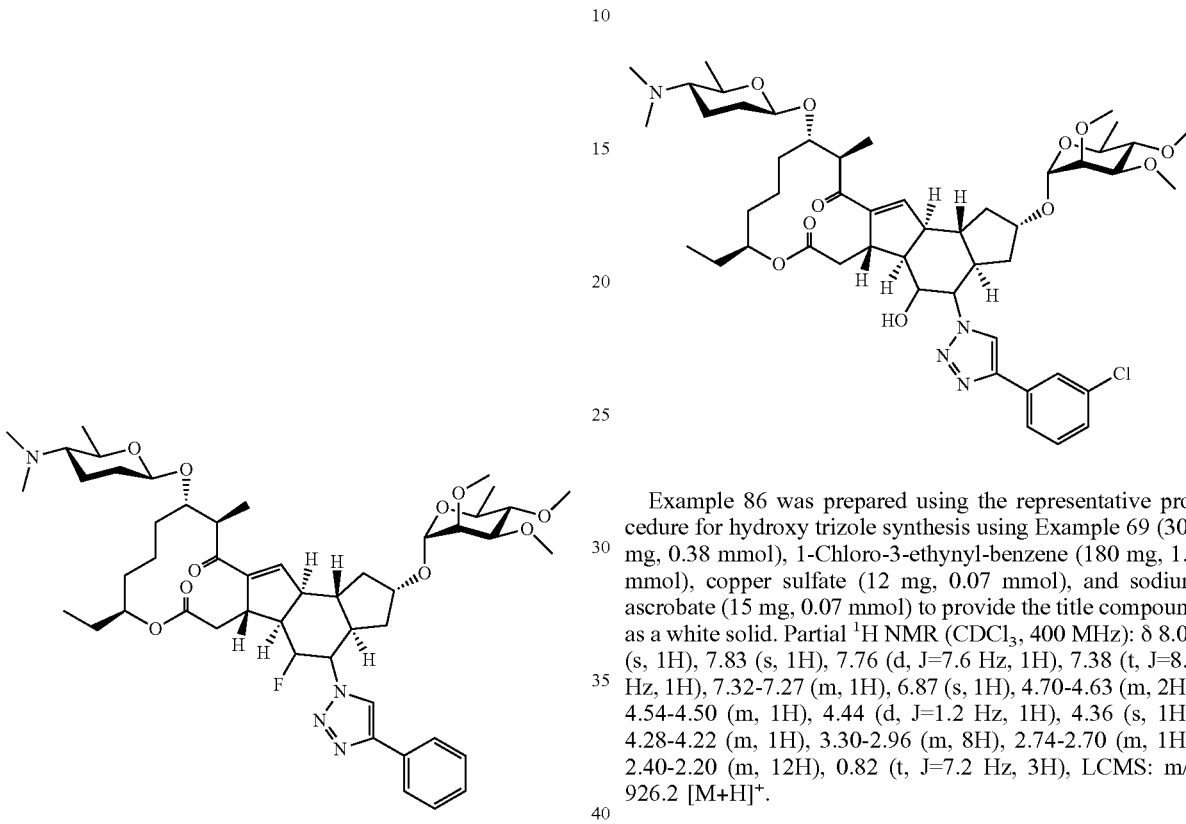

Example 86 was prepared using the representative procedure for hydroxy trizole synthesis using Example 69 (300 mg, 0.38 mmol), 1-Chloro-3-ethynyl-benzene (180 mg, 1.9 mmol), copper sulfate (12 mg, 0.07 mmol), and sodium ascrobate (15 mg, 0.07 mmol) to provide the title compound as a white solid. Partial $^1$H NMR (CDCl$_3$, 400 MHz): δ 8.06 (s, 1H), 7.83 (s, 1H), 7.76 (d, J=7.6 Hz, 1H), 7.38 (t, J=8.0 Hz, 1H), 7.32-7.27 (m, 1H), 6.87 (s, 1H), 4.70-4.63 (m, 2H), 4.54-4.50 (m, 1H), 4.44 (d, J=1.2 Hz, 1H), 4.36 (s, 1H), 4.28-4.22 (m, 1H), 3.30-2.96 (m, 8H), 2.74-2.70 (m, 1H), 2.40-2.20 (m, 12H), 0.82 (t, J=7.2 Hz, 3H), LCMS: m/z 926.2 [M+H]$^+$.

Examples 87: (2S,3aR,4S,5S,5aR,5bS,9S,13S,14R,16aR,16bS)-4-[4-(3-chlorophenyl)-1H-1,2,3-triazol-1-yl]-13-{[(2R,5S,6R)-5-(dimethylamino)-6-methyloxan-2-yl]oxy}-9-ethyl-5-fluoro-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione To a solution of Example 84 (900 mg, 1.0 mmol) in dichloromethane (5 mL) was added DAST (812 mg, 5.0 mmol) at −78° C. under nitrogen. After stirred at −78° C. for 30 min, the mixture was warmed to room temperature and quenched with aqueous sodium bicarbonate (10 mL). After stirred for 15 min, the mixture was extracted with dichloromethane (10 mL×2). The combined organic layer was washed with brine, dried over sodium sulfate, filtered and concentrated. The residue was purified by prep-HPLC to afford the title compound (100 mg, yield 11%) as a white solid. Partial $^1$H NMR (CDCl$_3$, 400 MHz): δ7.90 (s, 1H), 7.87-7.85 (m, 2H), 7.45 (t, J=7.6 Hz, 2H), 7.37-7.33 (m, 1H), 6.79 (s, 1H), 6.18 (t, J=3.2 Hz, 1H), 4.81 (d, J=1.2 Hz 1H), 4.73-4.67 (m, 1H), 4.43 (d, J=7.6 Hz 1H), 4.37-4.33 (m, 1H), 3.90-3.88 (m, 1H), 3.34-2.91 (m, 6H), 0.84 (t, J=7.6 Hz, 3H). LCMS: m/z 895.2 [M+H]$^+$.

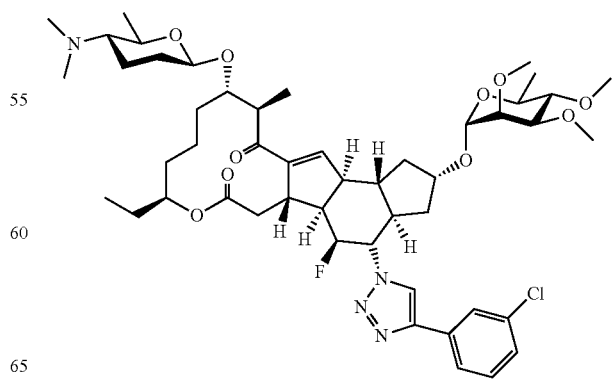

To a solution of Example 86 (150 mg, 0.16 mmol) in dichloromethane (10 mL) was added DAST (3 mL) at −78° C. under nitrogen. After stirred at −78° C. for 30 min, the mixture was warmed to room temperature and quenched with aqueous sodium bicarbonate (30 mL). After stirred for 15 min, the mixture was extracted with dichloromethane (20 mL×3). The combined organic layer was washed with brine, dried over sodium sulfate, filtered and concentrated. The residue was purified by prep-HPLC to afford the title compound (30 mg, yield 20%) as a white solid. Partial $^1$H NMR (CDCl$_3$, 400 MHz): δ 7.85-7.84 (m, 2H), 7.75 (d, J=7.2 Hz, 1H), 7.40-7.31 (m, 2H), 6.81 (s, 1H), 6.29-6.14 (m, 1H), 4.72 (s, 1H), 4.43-4.31 (m, 3H), 4.37-4.32 (m, 1H), 3.84-3.758 (m, 1H), 3.66-3.62 (m, 1H), 3.29-2.99 (m, 4H), 2.63-2.24 (m, 10H), 0.82 (t, J=7.2 Hz, 3H), LCMS: m/z 931.1 [M+H]$^+$.

Example 88: (2S,3aR,4S,5S,5aR,5bS,9S,13S,14R,16aR,16bS)-9-ethyl-5-fluoro-4-[4-(4-methoxyphenyl)-1H-1,2,3-triazol-1-yl]-14-methyl-13-{[(2R,5S,6R)-6-methyl-5-(methylamino)oxan-2-yl]oxy}-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

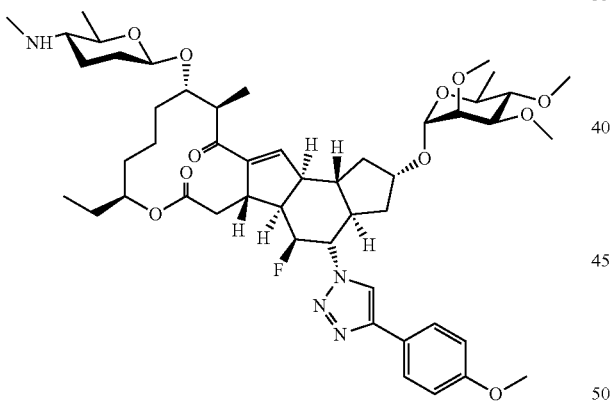

The N,N-dimethyl fluorotriazole intermediate was prepared from the corresponding hydroxy triazole with the representative procedure using DAST. A mixture of the above intermediate (80 mg, 0.08 mmol) and sodium acetate (35 mg, 0.43 mmol) in methanol-H$_2$O (10 mL-2 mL) was heat to 47° C. At this point I$_2$ (33 mg, 0.13 mmol) was added in one portion, and the pH was adjusted between 8-9 using 1N NaOH. After 2.5 h, the reaction was complete asmonitored by LCMS. The reaction was cooled to r.t., quenched with saturated ammonium chloride solution (10 mL) and extracted with ethyl acetate (3×10 mL). The combined organic phase was washed with brine (10 mL), dried over anhydrous sodium sulfate, filtered and concentrated. The residue was purified by prep-HPLC to afford the title compound (30 mg, 38% yield) as a white solid. Partial $^1$H NMR (400 MHz, CDCl$_3$): 7.85 (d, J=8.8 Hz, 2H), 7.73 (s, 1H), 6.97 (d, J=11.6 Hz, 2H), 6.81 (s, 1H), 5.28-5.13 (m, 1H), 4.71 (s, 1H), 4.47-4.31 (m, 3H), 3.84-3.65 (m, 6H), 3.31-3.25 (m, 2H), 3.12-2.99 (m, 3H), 2.62-2.37 (m, 6H), 0.81 (t, J=8.0 Hz, 3H); LCMS: m/z 911.1 [M+H]$^+$.

Example 89: (2S,3aR,4S,5S,5aR,5bS,9S,13S,14R,16aR,16bS)-4-(4-{[1,1'-biphenyl]-4-yl}-1H-1,2,3-triazol-1-yl)-13-{[(2R,5S,6R)-5-(dimethylamino)-6-methyloxan-2-yl]oxy}-9-ethyl-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

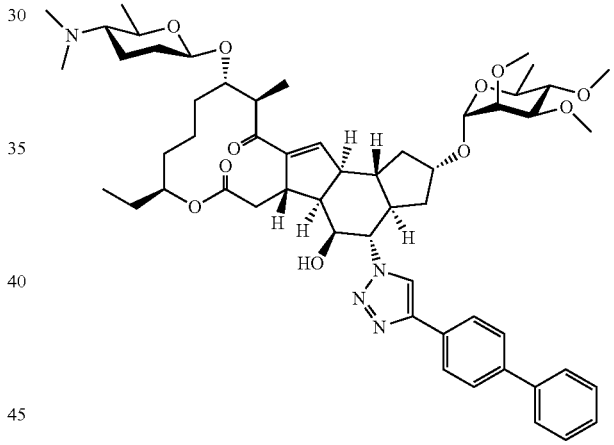

A mixture of Example 69 (50 mg, 0.05 mmol), 4-ethynyl-biphenyl (46 mg, 0.26 mmol), copper sulfate (1.6 mg, 0.01 mmol) and sodium ascorbate (2 mg, 0.01 mmol) in t-butanol/H$_2$O (3 mL/1 mL) was stirred at 80° C. overnight in a sealed tube. The reaction mixture was filtered through kieselguhr and the filtrate was concentrated. The residue was purified by prep-HPLC to afford the title compound (20 mg, 32.8% yield) as a white solid. Partial $^1$H NMR (CDCl$_3$, 400 MHz): δ 8.09 (s, 1H), 7.92 (d, J=8.4 Hz, 2H), 7.68-7.62 (m, 4H), 7.45 (t, J=7.2 Hz, 2H), 7.36 (t, J=7.2 Hz, 1H), 6.88 (s, 1H), 4.70-4.63 (m, 2H), 4.54-4.51 (m, 1H), 4.43 (d, J=8.4 Hz, 1H), 4.38 (s, 1H), 4.27-4.25 (m, 1H), 3.66-3.60 (m, 1H), 3.30-2.96 (m, 6H), 2.77-2.68 (m, 1H), 2.40-2.19 (m, 10H), 0.81 (t, J=7.6 Hz, 3H), LCMS: m/z 969.2 [M+H]$^+$.

Example 90: (2S,3aR,4S,5S,5aR,5bS,9S,13S,14R, 16aR,16bS)-4-(4-{[1,1'-biphenyl]-4-yl}-1H-1,2,3-triazol-1-yl)-13-{[(2R,5S,6R)-5-(dimethylamino)-6-methyloxan-2-yl]oxy}-9-ethyl-5-fluoro-14-methyl-2-{[(2R,3R,4R,5S,6S)-3,4,5-trimethoxy-6-methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-7,15-dione

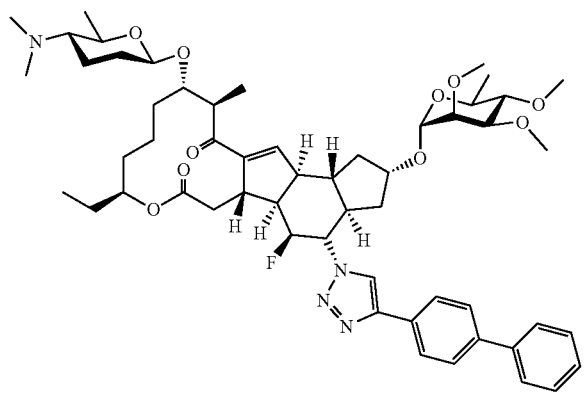

The hydroxytrizole intermediate was prepared from Example 69 using the representative procedure using 4-ethynylbiphenyl. To a solution of the intermediate (290 mg, 0.3 mmol) in dichloromethane (20 mL) was was added DAST (3 mL) at −78° C. under nitrogen. After stirring at −78° C. for 30 min, the mixture was warmed to room temperature and quenched with aqueous sodium bicarbonate (50 mL). After stirring for 15 min, the mixture was extracted with dichloromethane (20 mL×3). The combined organic layer was washed with brine, dried over sodium sulfate, filtered and concentrated. The residue was purified by prep-HPLC to afford the title compound (80 mg, yield 28%) as a white solid. Partial $^1$H NMR (CDCl$_3$, 400 MHz): δ 7.94-7.92 (m, 3H), 7.69-7.62 (m, 4H), 7.45 (t, J=7.2 Hz, 2H), 7.36 (t, J=7.2 Hz, 1H), 6.80 (s, 1H), 6.19 (s, 1H), 4.82 (s, 1H), 4.74-4.68 (m, 1H), 4.43 (d, J=7.6 Hz, 1H), 4.37-4.32 (m, 1H), 3.92-3.88 (m, 1H), 3.66-3.62 (m, 1H), 3.34-2.92 (m, 6H), 2.47-2.33 (m, 2H), 2.27-2.16 (m, 8H), 0.84 (t, J=7.6 Hz, 3H), LCMS: m/z 952.2 [M+H]$^+$.

Intermediate 27: (2S,3aR,4S,9S,13S,14R,16aR, 16bS)-4-azido-13-{[(2R,5S,6R)-5-(dimethylamino)-6-methyloxan-2-yl]oxy}-9-ethyl-14-methyl-2-{[(2R, 3R,4R,5S,6S)-3,4,5-trimethoxy-6-methyloxan-2-yl]oxy}-1H,2H,3H,3aH,4H,5H,5aH,5bH,6H,7H,9H, 10H,11H,12H,13H,14H,15H,16aH,16bH-as-indaceno[3,2-d]oxacyclododecane-5,7,15-trione

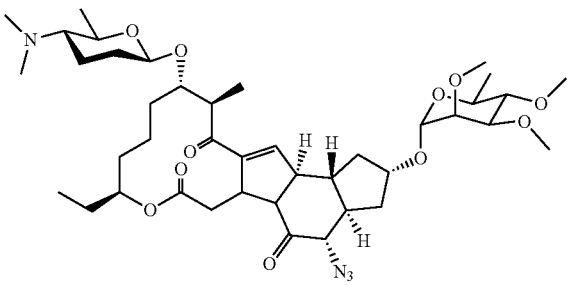

To a solution of Intermediate 25 (11.0 g, 13.3 mmol) in DMF (20 mL) was added Sodium azide (5.2 g, 79.9 mmol) at room temperature. The resulting mixture was stirred at 60° C. for 2 h. The mixture was treated with sat. sodium bicarbonate and extracted with ethyl acetate (3×100 mL). The combined organic phase was washed with brine (30 mL), dried over anhydrous sodium sulfate, filtered and concentrated. The residue was purified by silica gel column chromatography (ethyl acetate to ethyl acetate:methanol=10:1) to afford the title compound (5.4 g, 51% yield) as a yellow solid. LC-MS: m/z 789 [M+H]$^+$.

Intermediate 28: (2S,3aR,4S,9S,13S,14R,16aR, 16bS)-13-{[(2R,5S,6R)-5-(dimethylamino)-6-methyloxan-2-yl]oxy}-9-ethyl-14-methyl-4-(4-phenyl-1H-1,2,3-triazol-1-yl)-2-{[(2R,3R,4R,5S,6S)-3,4,5-trimethoxy-6-methyloxan-2-yl]oxy}-1H,2H,3H,3aH, 4H,5H,5aH,5bH,6H,7H,9H,10H,11H,12H,13H,14H, 15H,16aH,16bH-as-indaceno[3,2-d]oxacyclododecane-5,7,15-trione

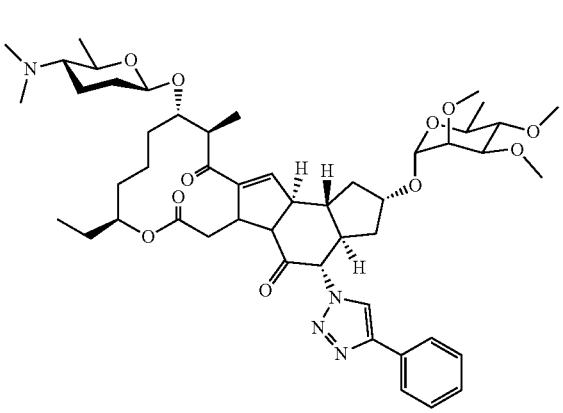

To a solution of Intermediate 27 (1.50 g, 1.90 mmol) and ethynyl-benzene (1.05 mL, 9.50 mmol) in tBuOH (6 mL) and H$_2$O (3 mL) was added copper sulfate (60 mg, 0.38 mmol) and sodium ascorbate (75 mg, 0.38 mmol) in a sealed tube at room temperature. The resulting mixture was stirred vigorously at 100° C. overnight. The mixture was cooled to room temperature, then treated with H$_2$O and extracted with ethyl acetate (3×50 mL). The combined organic phase was washed with brine (30 mL), dried over anhydrous sodium sulfate, filtered and concentrated. The residue was purified by column chromatography over silica gel (dichloromethane:methanol=20:1), followed by Prep-HPLC to afford the title compound (620 mg, 37% yield) as a white solid. LC-MS: m/z 891 [M+H]$^+$.

Example 91: (2S,5bS,9S,13S,4R,16aS,16bS)-5-(4-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,5H,5aH,5bH,6H,7H,9H,10H,11H,12H,13H,14H,15H,16aH,16bH-as-indaceno[3,2-d]oxacyclododecane-7,15-dione

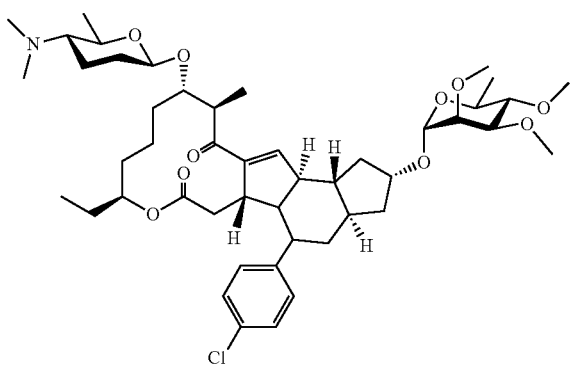

To a solution of Bis(aryl)acenaphthequinonediimine (BIAN, 149 mg, 0.38 mol) in DMF (10 mL) were added Palladium acetate (62 mg, 0.27 mmol) and the system was charged by nitrogen for 3 times. The mixture was stirred for 30 min at r.t. and then Spinosyn A (1.0 g, 1.37 mmol) and 4-chloro-phenylboronic acid (321 mg, 2.06 mmol) were added. The flask was charged with O$_2$ and the reaction mixture was allowed to stir at r.t. for 3 days under O$_2$ (balloon). The reaction mixture was diluted with water (30 mL) and extracted with ethyl acetate (50 mL×3). The combined organic phase was washed with brine (30 mL), dried over anhydrous sodium sulfate, filtered and concentrated. The residue was purified by prep-HPLC to afford the title compound (110 mg, 9.5% yield) as a yellow solid. Partial $^1$H NMR (CDCl$_3$, 400 MHz): δ 7.35-7.23 (m, 4H), 6.78 (s, 1H), 5.67 (s, 1H), 4.93 (s, 1H), 4.61-4.58 (m, 1H), 4.45 (d, J=7.6 Hz, 1H), 4.30-4.24 (m, 1H), 3.18 (t, J=9.2 Hz, 1H), 3.09-3.04 (m, 2H), 2.97-2.91 (m, 1H), 2.82-2.79 (m, 1H), 2.71-2.59 (m, 1H), 2.64-2.40 (m, 2H), 2.02-2.00 (m, 2H), 1.90-1.88 (m, 1H), 0.78 (t, J=7.2 Hz, 3H); LCMS: m/z 841.9 [M+H]$^+$.

Example 92: (2S,5bS,9S,13S,14R,16aS,16bS)-5-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,5H,5aH,5bH,6H,7H,9H,10H,11H,12H,13H,14H,15H,16aH,16bH-as-indaceno[3,2-d]oxacyclododecane-7,15-dione

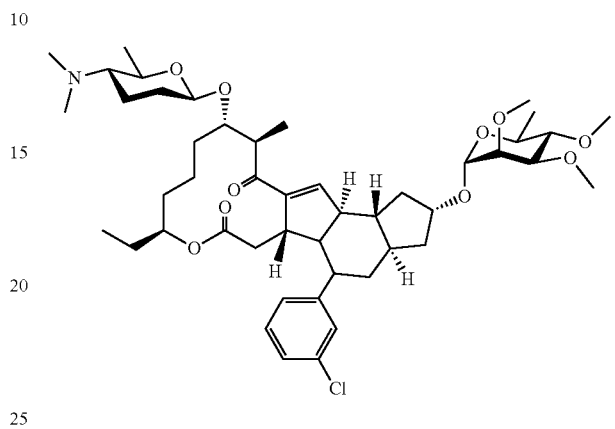

Using a similar procedure as described for Example 91, Spinosyn A (1.0 g, 1.37 mmol) and 3-Chloro-phenylboronic acid (321 mg, 2.06 mmol) yielded Example 92 (90 mg, 7.8% yield) as a yellow solid. Partial $^1$H NMR (CDCl$_3$, 300 MHz): δ 7.27-7.16 (m, 4H), 6.75 (s, 1H), 5.53 (s, 1H), 4.96 (s, 1H), 4.64-4.59 (m, 1H), 4.42 (d, J=7.5 Hz, 1H), 2.96 (br, 1H), 0.79 (t, J=7.5 Hz, 3H); LCMS: m/z 841.9 [M+H]$^+$.

Examples 93 and 94: (2R,3aR,5bS,9S,13S,14R,16aS,16bR)-5-(3-chlorophenyl)-9-ethyl-14-methyl-13-{[(2R,5S,6R)-6-methyl-5-(methylamino)oxan-2-yl]oxy}-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione (93), and (2R,3aR,5bS,9S,13S,14R,16aS,16bR)-5-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione (94)

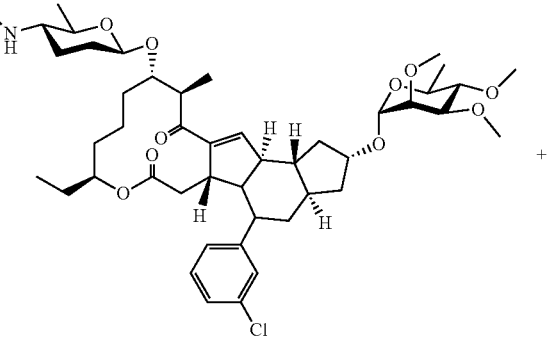

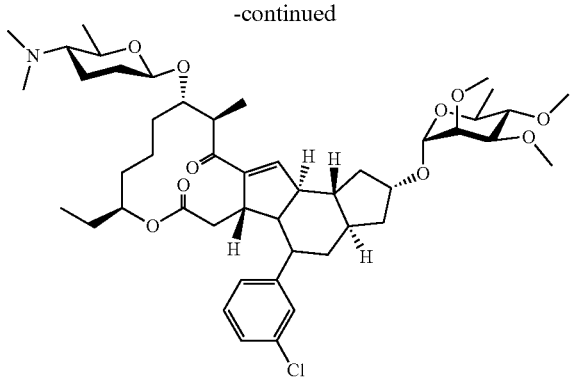

Example 92 (230 mg, 0.27 mmol) and Pt/C (40 mg) in methanol (20 mL) were stirred under 50 psi of hydrogen at r.t. for 30 min. The mixture was filtered through Celite and washed with methanol (80 ml). The filtrate was concentrated under reduced pressure to give a residue, which was purified by prep-HPLC to afford Example 93 (30 mg) and Example 94 (14 mg) yield as a white solid.

Example 93: Partial $^1$H NMR (CDCl$_3$, 400 MHz): δ 7.31-7.19 (m, 4H), 6.77 (s, 1H), 4.90 (s, 1H), 4.61-4.58 (m, 1H), 4.45 (d, J=8.0 Hz, 1H), 4.22-4.19 (m, 1H), 3.38-3.25 (m, 2H), 3.19-3.10 (m, 2H), 3.04 (s, 1H), 2.72 (dd, J=13.2, 4.8 Hz, 1H), 2.27 (s, 6H), 0.80 (t, J=7.5 Hz, 3H); LCMS: m/z 843.9 [M+H]$^+$.

Example 94: Partial $^1$H NMR (CDCl$_3$, 400 MHz): δ 7.30-7.18 (m, 4H), 6.76 (s, 1H), 4.89 (s, 1H), 4.63-4.56 (m, 1H), 4.48 (d, J=8.8 Hz, 1H), 4.23-4.18 (m, 1H), 3.37-3.03 (m, 6H), 2.71 (dd, J=13.4, 5.0 Hz, 1H), 2.45 (s, 3H), 0.79 (t, J=7.6 Hz, 3H); LCMS: m/z 829.9 [M+H]$^+$.

Example 95: (2R,3aR,5bS,9S,13S,14R,16aS,16bR)-13-{[(2R,5S,6R)-5-(dimethylamino)-6-methyloxan-2-yl]oxy}-9-ethyl-14-methyl-5-phenyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

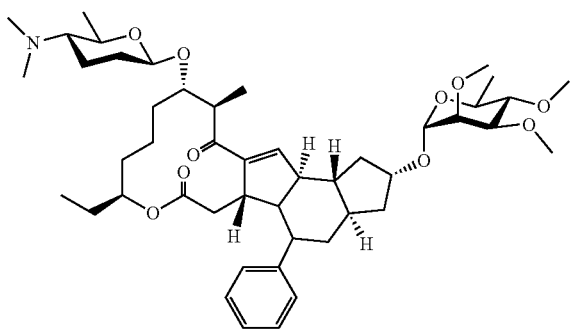

A mixture of the above intermediate (100 mg, 0.12 mmol) and Pt/C (20 mg) in methanol (20 mL) was stirred under 50 psi of H$_2$ at r.t. for 30 min. The mixture was filtered through Celite and washed with methanol (50 ml). The filtrate was concentrated under reduced pressure to give a residue which was purified by prep-HPLC to afford the title compound (24 mg, 24.0% yield) as a white solid. Partial $^1$H NMR (CDCl$_3$, 400 MHz): δ 7.36-7.22 (m, 5H), 6.78 (s, 1H), 4.91 (s, 1H), 4.62-4.57 (m, 1H), 4.45 (d, J=7.6 Hz, 1H), 4.22-4.17 (m, 1H), 3.38-3.15 (m, 4H), 3.07 (s, 1H), 2.68 (dd, J=13.2, 4.8 Hz, 1H), 0.80 (t, J=7.2 Hz, 3H); LCMS: m/z 810.0 [M+H]$^+$.

Example 96: (2R,3aR,5bS,9S,13S,14R,16aS,16bR)-13-{[(2R,5S,6R)-5-(dimethylamino)-6-methyloxan-2-yl]oxy}-9-ethyl-5-(3-fluorophenyl)-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

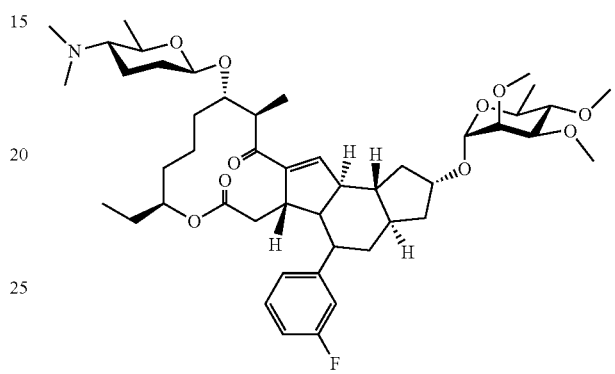

To a solution of bis(aryl)acenaphthequinonediimine (BIAN, 149 mg, 0.38 mol) in DMF (10 mL) were added palladium acetate (62 mg, 0.27 mmol), and the system was charged with nitrogen 3 times. After stirring for 30 min, Spinosyn A (1.0 g, 1.37 mmol) and 3-fluorophenylboronic acid (288 mg, 2.06 mmol) were added. The flask was charged with O$_2$ and the reaction mixture was allowed to stir at r.t. for 2 days under O$_2$ (balloon). The reaction mixture was diluted with water (30 mL) and extracted with ethyl acetate (3×50 mL). The combined organic phase was washed with brine (30 mL), dried over anhydrous sodium sulfate, filtered and concentrated. The residue was purified by prep-HPLC to afford the olefin intermediate (96 mg, 8.5% yield) as a yellow solid. $^1$H NMR (400 MHz, DMSO-d$_6$): δ 7.43-7.38 (m, 2H), 7.71 (s, 1H), 7.13-7.06 (m, 3H), 5.60 (s, 1H), 4.88 (s, 1H), 4.47-4.41 (m, 2H), 4.23-4.16 (m, 1H), 3.55-3.31 (m, 19H), 3.01-2.88 (m, 4H), 2.81-2.75 (m, 1H), 2.60-2.56 (m, 1H), 2.45-2.31 (m, 3H), 2.14 (s, 6H), 2.07-1.84 (m, 18H), 1.19 (d, J=6.4 Hz, 3H), 1.12 (d, J=6.0 Hz, 3H), 1.08 (d, J=6.4 Hz, 3H), 0.88-0.81 (m, 2H), 0.67 (t, J=7.2 Hz, 3H); LCMS: m/z 826.0 [M+H]$^+$.

A mixture of the above intermediate (100 mg, 0.12 mmol) and Pt/C (20 mg) in methanol (20 mL) was stirred under 50 psi of H$_2$ at r.t. for 30 min. The mixture was filtered through Celite and washed with methanol (50 ml). The filtrate was concentrated under reduced pressure to give a residue, which was purified by prep-HPLC to afford the title compound (17 mg, 17.0% yield) as a white solid. Partial $^1$H NMR (CDCl$_3$, 400 MHz): δ 7.34-7.28 (m, 1H), 7.10-6.92 (m, 3H), 6.77 (s, 1H), 4.91 (s, 1H), 4.62-4.59 (m, 1H), 4.46 (d, J=8.0 Hz, 1H), 4.22-4.19 (m, 1H), 3.38-3.06 (m, 5H), 2.72 (dd, J=13.6, 5.2 Hz, 1H), 0.80 (t, J=7.6 Hz, 3H); LCMS: m/z 827.9 [M+H]$^+$.

Example 97: (2R,3aR,5bS,9S,13S,14R,16aS,16bR)-13-{[(2R,5S,6R)-5-(dimethylamino)-6-methyloxan-2-yl]oxy}-9-ethyl-5-(3-methoxyphenyl)-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

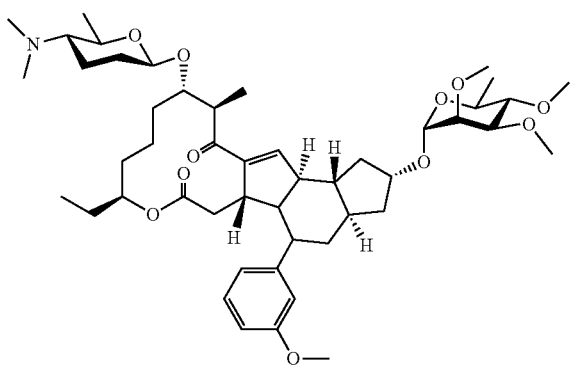

To a solution of bis(aryl)acenaphthequinonediimine (BIAN, 149 mg, 0.38 mol) in DMF (10 mL) was added Palladium acetate (62 mg, 0.27 mmol) and the system was charged with nitrogen 3 times. After stirring for 30 min, Spinosyn A (1.0 g, 1.37 mmol) and 3-methoxyphenylboronic acid (313 mg, 2.06 mmol) were added. The flask was charged with $O_2$ and the reaction mixture was allowed to stir at r.t. for 2 days under $O_2$ (balloon). The reaction mixture was diluted with water (30 mL) and extracted with ethyl acetate (3×50 mL). The combined organic phase was washed with brine (30 mL), dried over anhydrous sodium sulfate, filtered and concentrated. The residue was purified by prep-HPLC to afford the olefin intermediate (90 mg, 7.8% yield) as a white solid. $^1$H NMR (400 MHz, CDCl$_3$): δ 7.27 (t, J=8.0 Hz, 1H), 7.09 (s, 1H), 6.98-6.96 (m, 2H), 6.83 (d, J=8.4 Hz, 1H), 5.60 (s, 1H), 4.98 (s, 1H), 4.80 (brs, 1H), 4.63-4.59 (m, 1H), 4.48 (d, J=8.4 Hz, 1H), 4.25-4.21 (m, 1H), 3.83 (s, 3H), 3.63-3.38 (m, 17H), 3.26-3.22 (m, 1H), 3.09-2.99 (m, 3H), 2.89-2.82 (m, 3H), 2.67-2.54 (m, 5H), 2.23 (s, 6H), 1.96-1.31 (m, 15H), 1.23-1.12 (m, 12H), 0.78 (t, J=7.2 Hz, 3H); LCMS: m/z 838.1 [M+H]$^+$.

A mixture of the above intermediate (100 mg, 0.12 mmol) and Pt/C (20 mg) in methanol (20 mL) was stirred under 50 psi of H$_2$ at r.t. for 30 min. The mixture was filtered through Celite and washed with methanol (50 ml). The filtrate was concentrated under reduced pressure to give a residue which was purified by prep-HPLC to afford the title compound (32 mg, 32.0% yield) as a white solid. Partial $^1$H NMR (CDCl$_3$, 400 MHz): δ 7.23 (t, J=7.6 Hz, 1H), 6.87 (d, J=7.6 Hz, 1H), 6.82 (s, 1H), 6.77-6.75 (m, 2H), 4.87 (s, 1H), 4.59-4.56 (m, 1H), 4.42 (d, J=7.6 Hz, 1H), 4.19-4.13 (m, 1H), 3.81 (s, 3H), 3.05 (s, 1H), 2.68 (dd, J=13.2, 4.8 Hz, 1H), 0.76 (t, J=7.6 Hz, 3H); LCMS: m/z 840.3 [M+H]$^+$.

Example 98: (2R,5aR,5bS,9S,13S,14R,16aR,16bR)-13-{[(2R,5S,6R)-5-(dimethylamino)-6-methyloxan-2-yl]oxy}-9-ethyl-5-methoxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

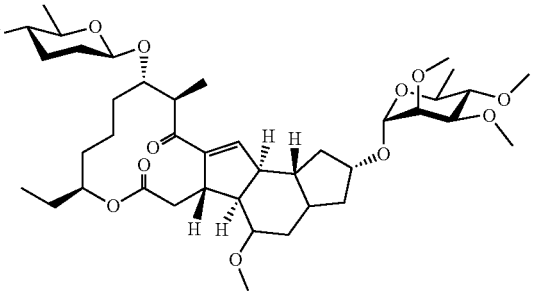

To a solution of Example 48 (200 mg, 1.2 mmol) in tetrahydrofuran (3 mL) was added NaH (60% in mineral oil, 29 mg, 0.71 mmol). The mixture was then heated to reflux for 5 h and cooled to r.t. The mixture was quenched with 0.5 mL of methanol and then diluted with ethyl acetate (20 mL) and saturated ammonium chloride aqueous (15 mL). The organic layer was separated and concentrated under reduced pressure to give an oil which was purified by prep-HPLC to afford the intermediate methoxy olefin (39 mg, yield 21.6%) as white solid. Partial $^1$H NMR (CD$_3$OD, 400 MHz): δ6.91 (s, 1H), 5.76 (s, 1H), 4.77 (s, 1H), 4.49-4.45 (m, 1H), 4.39 (d, J=9.2 Hz, 1H), 4.19-4.17 (m, 1H), 3.11 (br, 1H), 2.97-2.91 (m, 2H), 2.71 (dd, J=12.8, 4.8 Hz, 1H), 2.60-2.55 (m, 1H), 2.41 (br, 2H), 2.31 (dd, J=12.8, 2.8 Hz, 1H), 0.69 (t, J=7.6 Hz, 1H). LCMS: m/z 761.9 [M+H]$^+$.

A mixture of the above intermediate (220 mg, 0.28 mmol) and 5% Pt/C (50 mg) in ethanol (30 mL) was stirred under H$_2$ (50 Psi) at room temperature for 20 h. The mixture was filtered through Celite and washed with methanol (50 ml). The filtrate was concentrated under reduced pressure to give an oil which was purified by prep-chiral-HPLC to afford the title compound (95 mg, 43.0% yield) as a white solid. Partial $^1$H NMR (DMSO-d$_6$, 400 MHz): δ7.01 (s, 1H), 4.81 (d, J=0.8 Hz, 1H), 4.52-4.48 (m, 1H), 4.41 (d, J=9.6 Hz, 1H), 4.08-4.04 (m, 1H), 2.97-2.88 (m, 3H), 2.80-2.76 (m, 1H), 2.59-2.54 (m, 1H), 2.40 (d, J=10.4 Hz, 1H), 0.73 (t, J=7.6 Hz, 1H). LCMS: m/z 763.9 [M+H]$^+$.

Example 99: (1S,2R,6R,8S,10R,11S,15R,16S,20S)-4,4-dichloro-16-{[(2S,5S,6R)-5-(dimethylamino)-6-methyloxan-2-yl]oxy}-20-ethyl-15-methyl-8-{[(2R,3R,4R,5S,6S)-3,4,5-trimethoxy-6-methyloxan-2-yl]oxy}-21-oxapentacyclo[11.10.0.0$^{2,11}$.0$^{3,5}$.0$^{6,10}$]tricos-12-ene-14,22-dione

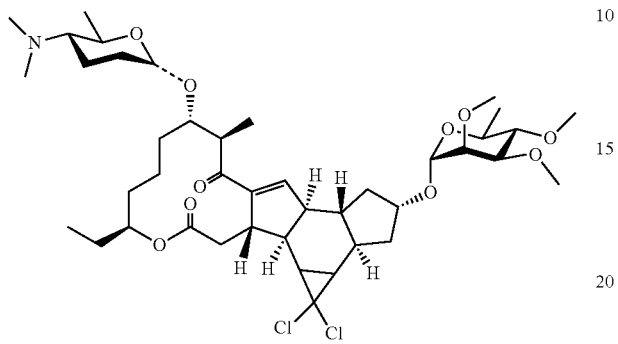

A mixture of Intermediate 27 (266 mg, 0.39 mmol), silver triflate (406 mg, 1.58 mmol) and 4A molecular sieves (800 mg) in anhydrous dichloromethane (5 mL) under nitrogen and protected from light was treated with thioforosamine (200, 0.79 mmol, in 2 mL of dichloromethane) added dropwise over 30 min. The mixture was stirred for 3 h and quenched with saturated sodium bicarbonate solution (10 mL). The mixture was extracted with dichloromethane (50 mL×2). The combined organic layer was dried over sodium sulfate, filtered, and concentrated. The residue was purified by chromatography on silica gel (dichloromethane/methanol=25/1) to give a 1:3 mixture of isomers of the title compound (17.5 mg, 5.4%) as a white solid. Partial $^1$H NMR (DMSO-d$_6$, 300 MHz): δ7.01 (s, 1H), 4.85 (s, 1H), 4.68-4.65 (m, 1H), 4.52-4.48 (m, 1H), 4.38-4.33 (m, 1H); LCMS: m/z 813.8 [M+H]$^+$.

Example 100: (1S,2R,6R,8S,10R,11S,15R,16S,20S)-4-chloro-20-ethyl-16-hydroxy-15-methyl-8-{[(2R,3R,4R,5S,6S)-3,4,5-trimethoxy-6-methyloxan-2-yl]oxy}-21-oxapentacyclo[11.10.0.0$^{2,11}$.0$^{3,5}$.0$^{6,10}$]tricos-12-ene-14,22-dione

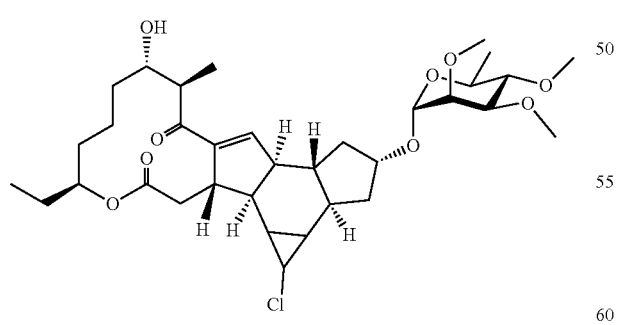

To a solution of compound Intermediate 27 (700 mg, 1.0 mmol) in acetic acid/ethanol (10 mL/6 mL) was added zinc-copper couple (676 mg) followed by zinc power (670 mg, 10.4 mmol). The mixture was heated to reflux over night. Cooled to r.t, 1.1 g of ammonium chloride was added and the mixture was heated to reflux for another 20 h. The mixture was filtered through Celite and washed with ethyl acetate (150 mL). The filtrate was washed with saturated sodium bicarbonate (100 mL×2) and brine, dried over sodium sulfate, filtered and concentrated. The residue was purified by prep-HPLC to afford the title compound (219 mg, 33.0% yield) as a white solid. Partial $^1$H NMR (DMSO-d$_6$, 400 MHz): δ6.94 (s, 1H), 4.79 (s, 1H), 4.72 (d, J=6.4 Hz, 1H), 4.59-4.54 (m, 1H), 4.27-4.22 (m, 1H), 3.58 (t, J=7.6 Hz, 1H), 3.51-3.50 (m, 1H), 3.11-2.89 (m, 5H), 2.21-2.10 (m, 2H), 2.03-1.98 (m, 1H), 0.75 (t, J=7.6 Hz, 3H). LCMS: m/z 655.9 [M+NH$_4$]$^+$.

Examples 101 and 102: (2S,3aR,5aR,5bS,9S,13S,14R,16aR,16bS)-9-ethyl-5,13-dihydroxy-4-[4-(4-methoxyphenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione (101), and (2S,3aR,5aR,5bS,9S,13S,14R,16aR,16bS)-13-{[(2R,5S,6R)-5-(dimethylamino)-6-methyloxan-2-yl]oxy}-9-ethyl-5-hydroxy-4-[4-(4-methoxyphenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione (102)

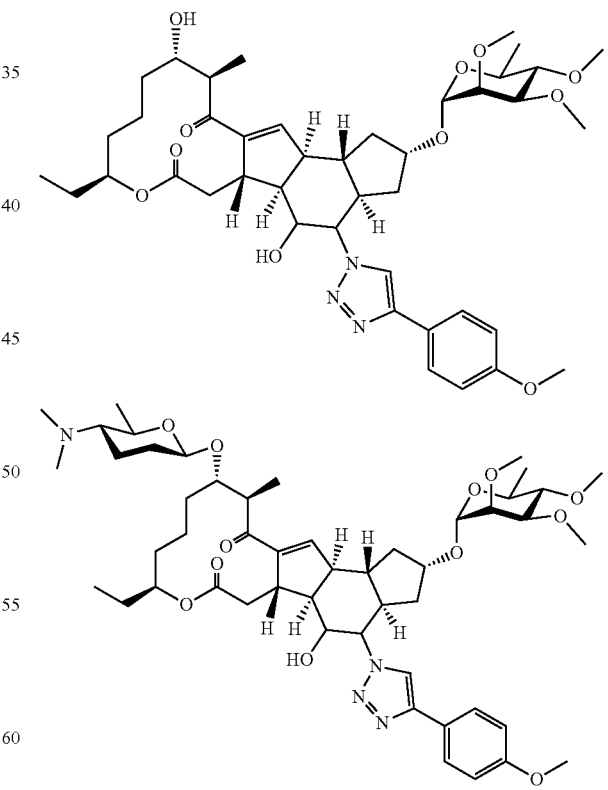

Examples 101 and 102 were prepared using Example 69 and the representative procedure to afford Example 101 (20 mg, 6.7% yield) and Example 102 (80 mg, 22% yield) as a white solid.

Example 101: Partial ¹H NMR (CDCl₃, 400 MHz): δ 7.92 (s, 1H), 7.78 (d, J=8.8 Hz, 2H), 6.97 (d, J=8.8 Hz, 2H), 6.90 (s, 1H), 4.73-4.68 (m, 2H), 4.46 (dd, J=11.2, 2.8 Hz), 4.37 (s, 1H), 4.29-4.23 (m, 1H), 3.85 (s, 3H), 3.28-2.96 (m, 9H), 2.76-2.70 (m, 1H), 2.41-2.23 (m, 3H), 0.82 (t, J=7.2 Hz, 3H), LCMS: m/z 782.1 [M+H]⁺.

Example 102: Partial ¹H NMR (CDCl₃, 400 MHz): δ 7.93 (s, 1H), 7.76 (d, J=8.8 Hz, 2H), 6.96 (d, J=8.8 Hz, 2H), 6.87 (s, 1H), 4.70-4.63 (m, 2H), 4.49-4.42 (m, 2H), 4.36 (s, 1H), 4.28-4.22 (m, 1H), 3.85 (s, 3H), 3.28-2.96 (m, 9H), 2.76-2.70 (m, 1H), 2.39-2.24 (m, 12H), 0.82 (t, J=7.2 Hz, 3H), LCMS: m/z 923.2 [M+H]⁺.

Example 103: (2S,3aR,5aR,5bS,9S,13S,14R,16aR,16bS)-13-{[(2R,5S,6R)-5-(dimethylamino)-6-methyloxan-2-yl]oxy}-9-ethyl-5-hydroxy-14-methyl-4-(1H-1,2,3-triazol-1-yl)-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

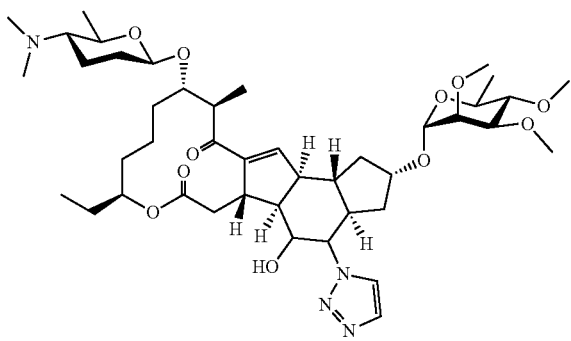

Example 103 was prepared using Example 69 and the representative procedure. Example 69 (300 mg, 0.38 mmol), ethynyl-trimethyl-silane (190 mg, 1.9 mmol), copper sulfate (12 mg, 0.08 mmol), and sodium ascorbate (15 mg, 0.08 mmol) afforded the title compound (90 mg, 29% yield) as a white solid. Partial ¹H NMR (CDCl₃, 400 MHz): δ 7.80 (s, 1H), 7.73 (s, 1H), 6.87 (s, 1H), 4.70-4.62 (m, 2H), 4.52-4.48 (m, 1H), 4.43 (d, J=7.2 Hz, 1H), 4.32 (s, 1H), 4.27-4.22 (m, 1H), 3.28-3.07 (m, 8H), 2.97 (t, J=9.2 Hz, 1H), 2.75-2.65 (m, 1H), 2.37-2.20 (m, 12H), 1.99-1.03 (m, 39H), 0.81 (t, J=7.6 Hz, 3H), LCMS: m/z 817.2 [M+H]⁺.

Example 104: (2S,3aR,5aR,5bS,9S,13S,14R,16aR,16bS)-13-{[(2R,5S,6R)-5-(dimethylamino)-6-methyloxan-2-yl]oxy}-9-ethyl-4-[4-(4-fluorophenyl)-1H-1,2,3-triazol-1-yl]-5-hydroxy-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

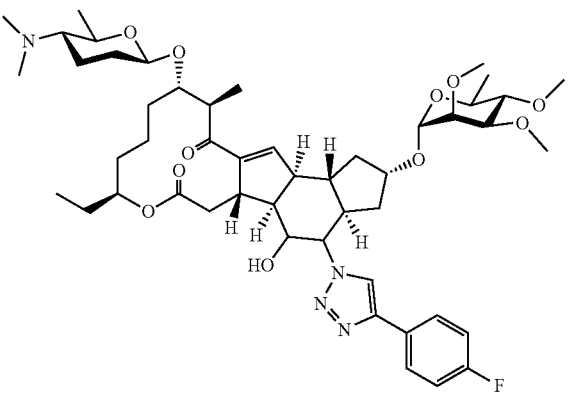

Example 105 was prepared using Example 69 and the representative procedure. Example 69 (300 mg, 0.38 mmol), 1-Ethynyl-4-fluoro-benzene (228 mg, 1.9 mmol), copper sulfate (12 mg, 0.076 mmol) and sodium ascorbate (15 mg, 0.076 mmol) yielded the title compound (80 mg, 14% yield) as a white solid. Partial ¹H NMR (CDCl₃, 400 MHz): δ 7.99 (s, 1H), 7.82-7.78 (m, 2H), 7.14-7.10 (m, 2H), 6.87 (s, 1H), 4.71 (s, 1H), 4.70-4.63 (m, 1H), 4.50 (dd, J=2.4, 11.2 Hz, 1H), 4.43 (d, J=6.8 Hz, 1H), 4.36 (s, 1H), 4.28-4.21 (m, 1H), 3.66-3.60 (m, 1H), 3.52-3.43 (m, 16H), 3.35 (s, 1H), 3.28-3.22 (m, 3H), 3.14-3.07 (m, 2H), 3.00-2.95 (m, 1H), 2.77-2.68 (m, 1H), 2.38-2.32 (m, 2H), 2.24 (s, 1H), 2.01-1.97 (m, 1H), 1.88-1.79 (m, 6H), 1.53-1.06 (m, 28H), 0.81 (t, J=7.6 Hz, 3H), LCMS: m/z 912.4 [M+H]⁺.

Examples 105: (2S,3aR,5aR,5bS,9S,13S,14R,16aR,16bS)-13-{[(2R,5S,6R)-5-(dimethylamino)-6-methyloxan-2-yl]oxy}-9-ethyl-5-fluoro-4-[4-(4-fluorophenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

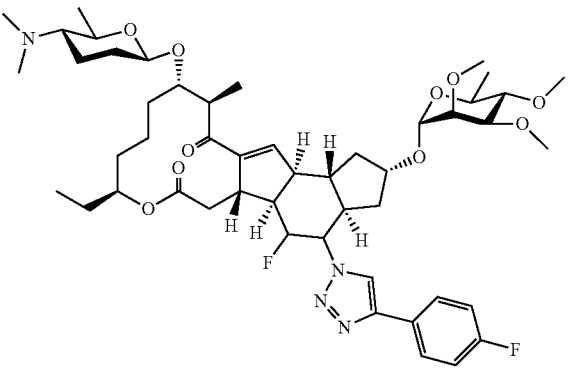

To a solution of compound Example 105 (150 mg, 0.16 mmol) in dichloromethane (10 mL) was was added DAST (53.1 mg, 0.33 mmol) at −78° C. under nitrogen. After stirred at −78° C. for 30 min, the mixture was warmed to room temperature and quenched with aqueous sodium bicarbonate (10 mL). After stirred for 15 min, the mixture was extracted with dichloromethane (10 mL×3). The combined organic layer was washed with brine, dried over sodium sulfate, filtered and concentrated. The residue was purified by prep-HPLC to afford the title compound (20 mg, yield 25%) as a white solid. Partial $^1$H NMR (CDCl$_3$, 400 MHz): δ7.85 (s, 1H), 7.84-7.81 (m, 2H), 7.16-7.11 (m, 2H), 6.79 (s, 1H), 6.17 (t, J=2.8 Hz, 1H), 4.81 (s, 1H), 4.72-4.69 (m, 1H), 4.72-4.69 (m, 1H), 4.43 (d, J=7.8 Hz 1H), 4.37-4.32 (m, 1H), 3.91-3.87 (m, 1H), 3.66-3.44 (m, 15H), 3.32-2.90 (m, 6H), 2.46-2.21 (m, 10H), 0.82 (t, J=7.2 Hz, 3H). LCMS: m/z 894.1 [M+H]$^+$.

Example 106: {1-[(2S,3aR,5aR,5bS,9S,13S,14R, 16aR,16bS)-13-{[(2R,5S,6R)-5-(dimethylamino)-6-methyloxan-2-yl]oxy}-9-ethyl-5-hydroxy-14-methyl-7,15-dioxo-2-{[(2R,3R,4R,5S,6S)-3,4,5-trimethoxy-6-methyloxan-2-yl]oxy}-1H,2H,3H,3aH, 4H,5H,5aH,5bH,6H,7H,9H,10H,11H,12H,13H,14H, 15H,16aH,16bH-as-indaceno[3,2-d] oxacyclododecan-4-yl]-1H-1,2,3-triazol-4-yl}methyl acetate

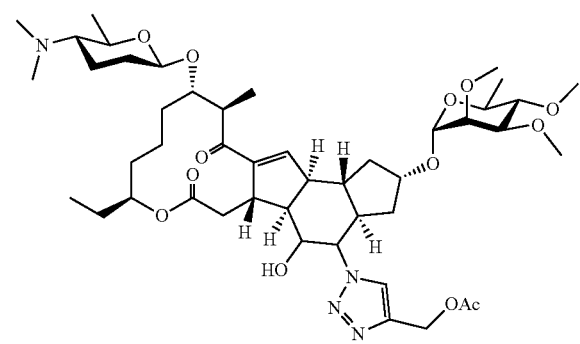

Example 106 was prepared using Example 69 and the representative procedure. Example 69 (300 mg, 0.38 mmol), prop-2-ynyl acetate (186 mg, 1.9 mmol), copper sulfate (12 mg, 0.076 mmol) and sodium ascorbate (15 mg, 0.076 mmol) yielded the title compound (160 mg, 47% yield) as a white solid. Partial $^1$H NMR (CDCl$_3$, 400 MHz): δ7.83 (s, 1H), 6.87 (s, 1H), 5.22 (s, 2H), 4.71-4.65 (m, 2H), 4.46-4.41 (m, 2H), 4.31 (s, 1H), 4.26-4.24 (m, 1H), 3.28-2.67 (m, 8H), 0.81 (t, J=6.4 Hz, 3H), LCMS: 712/z 890.1 [M+H]$^+$.

Examples 107 and 108: {1-[(2S,3aR,5aR,5bR,9S, 13S,14R,16aS,16bS)-13-{[(2R,5S,6R)-5-(dimethylamino)-6-methyloxan-2-yl]oxy}-9-ethyl-14-methyl-7,15-dioxo-2-{[(2R,3R,4R,5S,6S)-3,4,5-trimethoxy-6-methyloxan-2-yl]oxy}-1H,2H,3H,3aH,5aH,5bH, 6H,7H,9H,10H,11H,12H,13H,14H,15H,16aH,16bH-as-indaceno[3,2-d]oxacyclododecan-4-yl]-1H-1,2,3-triazol-4-yl}methyl acetate (109), and {1-[(2S,3aR, 5aR,5bS,9S,13S,4R,16aR,16bS)-13-{[(2R,5S,6R)-5-(dimethylamino)-6-methyloxan-2-yl]oxy}-9-ethyl-5-fluoro-14-methyl-7,15-dioxo-2-{[(2R,3R,4R,5S,6S)-3,4,5-trimethoxy-6-methyloxan-2-yl]oxy}-1H,2H, 3H,3aH,4H,5H,5aH,5bH,6H,7H,9H,10H,11H,12H, 13H,14H,15H,16aH,16bH-as-indaceno[3,2-d] oxacyclododecan-4-yl]-1H-1,2,3-triazol-4-yl}methyl acetate (110)

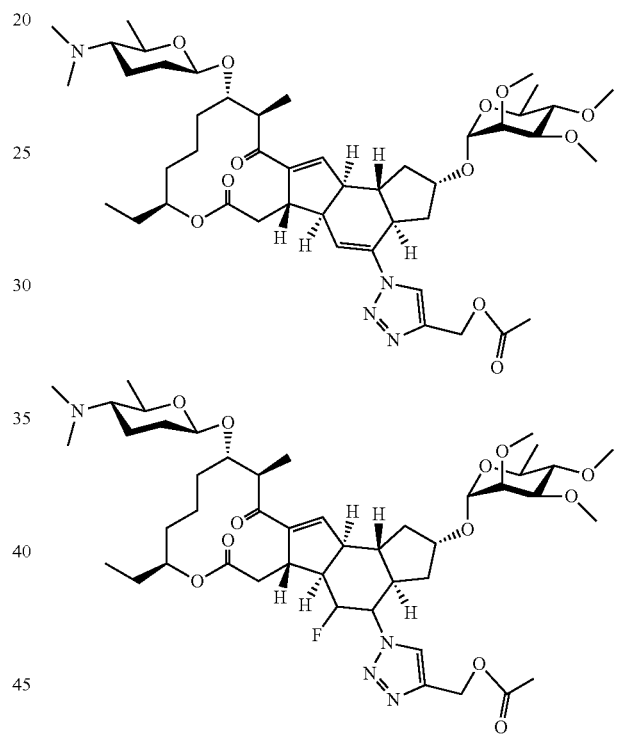

To a solution of Example 106 (80 mg, 0.08 mmol) in dichloromethane (5 mL) was was added DAST (70 mg, 0.43 mmol) at −78° C. under nitrogen. After stirred at −78° C. for 30 min, the mixture was warmed to room temperature and quenched with aqueous sodium bicarbonate (10 mL). After stirred for 15 min, the mixture was extracted with dichloromethane (10 mL×2). The combined organic layer was washed with brine, dried over sodium sulfate, filtered and concentrated. The residue was purified by prep-HPLC to afford Example 107 (40 mg, yield 26.7%) and Example 108 (60 mg, yield 41%) as a white solid.

Example 107: Partial $^1$H NMR (CDCl$_3$, 400 MHz): δ7.66 (s, 1H), 6.80 (s, 1H), 5.23 (s, 2H), 5.16 (td, J=7.0 Hz, 7.6 Hz 1H),4.71-4.68 (m, 2H), 4.42 (d, J=9.6 Hz, 1H), 4.37-4.28 (m, 1H), 3.79-3.71 (m, 1H), 3.66-3.40 (m, 20H), 3.32-2.96 (m, 4H), 2.61-2.09 (m, 17H), 2.00-1.19 (m, 44H), 0.82 (t, J=7.2 Hz, 3H). LCMS: m/z 872.1 [M+H]$^+$.

Example 108: Partial $^1$H NMR (CDCl$_3$, 400 MHz): δ7.73 (s, 1H), 6.77 (s, 1H), 5.23 (s, 2H), 4.80 (s, 1H), 4.72-4.66 (m, 1H), 4.43 (d, J=7.2 Hz, 1H), 4.35-4.30 (m, 1H), 3.89-3.83 (m, 1H), 3.65-3.43 (m, 17H), 3.31-2.86 (m, 6H), 2.42-2.09 (m, 15H),1.99-1.19 (m, 34H), 0.83 (t, J=7.2 Hz, 3H). LCMS: m/z 891.2 [M+H]+

Example 109: (2S,3aR,4R,5aR,5bS,9S,13S,14R, 16aR,16bS)-13-{[(2R,5S,6R)-5-(dimethylamino)-6-methyloxan-2-yl]oxy}-9-ethyl-4-(ethylamino)-14-methyl-2-{[(2R,3R,4R,5S,6S)-3,4,5-trimethoxy-6-methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-7,15-dione

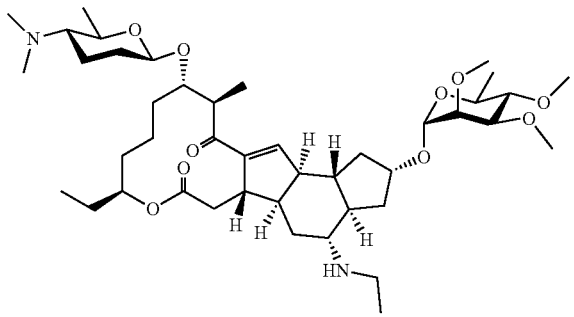

A mixture of Intermediate 28 (150 mg, 0.2 mmol), acetaldehyde (13 mg, 0.3 mmol) and acetic acid (1 drop) in tetrahydrofuran (20 mL) was stirred at room temperature overnight. Sodium tris(acetoxy)borohydride (169 mg, 0.8 mmol) was added. The resulting mixture was stirred at for 2 h. The reaction mixture was quenched with saturated aqueous sodium bicarbonate (100 mL) and extracted with ethyl acetate (100 mL×2). The combined organic layer was washed with brine (200 mL), dried over anhydrous sodium sulfate, filtered and concentrated. The residue was purified by prep-HPLC to afford the title compound (30 mg, 19% yield) as a yellow solid. Partial $^1$H NMR (CDCl$_3$, 400 MHz): δ 6.77 (s, 1H), 4.83 (s, 1H), 4.66-4.63 (m, 1H), 4.42 (d, J=8.0 Hz, 1H), 4.27-4.23 (m, 1H), 3.63-3.59 (m, 1H), 2.66-2.71 (m, 1H), 2.43-2.40 (m, 1H), 2.26 (s, 6H), 1.98-1.96 (m, 1H), 1.17 (d, J=6.8 Hz, 1H), 1.00-0.95 (m, 1H), 0.80 (t, J=7.6 Hz, 3H). LCMS: m/z 776.9 [M+H]+.

Example 110: (2R,3aR,5R,5aR,5bS,9S,13S,14R, 16aR,16bR)-5-(4-tert-butyl-1H-1,2,3-triazol-1-yl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H, 3H,3aH,4H,5H,5aH,5bH,6H,7H,9H,10H,11H,12H, 13H,14H,15H,16aH,16bH-as-indaceno[3,2-d] oxacyclododecane-7,15-dione

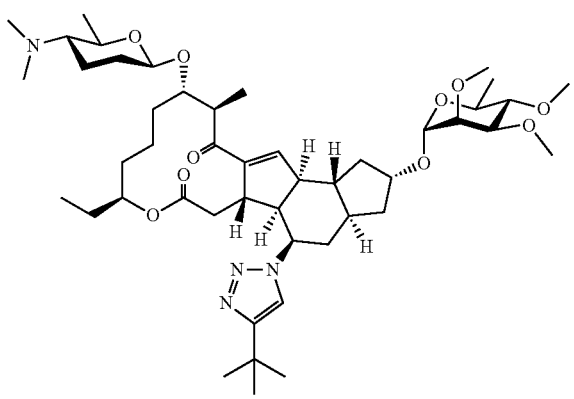

A mixture of Intermediate 12 (200 mg, 0.26 mmol), 3,3-Dimethyl-but-1-yne (106 mg, 1.29 mmol), copper sulfate (8 mg, 0.05 mmol) and sodium ascorbate (10 mg, 0.05 mmol) in t-butanol/H$_2$O (3 mL/1.5 mL) was stirred at 110° C. for 17 h in a sealed tube. The reaction mixture was filtered through kieselguhr and the filtrate was concentrated. The residue was purified by prep-HPLC to afford the title compound (17 mg, 7% yield) as a white solid. Partial $^1$H NMR (CDCl$_3$, 400 MHz): δ7.47 (s, 1H), 6.83 (s, 1H), 4.84 (d, J=1.2 Hz, 1H), 4.81-4.75 (m, 1H), 4.39 (d, J=6.8 Hz, 1H), 4.31-4.26 (m, 1H), 3.67-3.61 (m, 5H), 3.26-3.18 (m, 2H), 3.12 (t, J=9.2 Hz, 1H), 2.74-2.67 (m, 2H), 2.23 (s, 6H), 1.31 (s, 9H), 1.16 (d, J=6.8 Hz, 3H), 0.84-0.77 (m, 1H), 0.71 (t, J=7.6 Hz, 3H). LCMS: m/z 856.9 [M+H]+.

Example 111: (2R,3aR,5R,5aR,5bS,9S,13S,14R, 16aR,16bR)-13-{[(2R,5S,6R)-5-(dimethylamino)-6-methyloxan-2-yl]oxy}-9-ethyl-5-[4-(4-fluorophenyl)-1H-1,2,3-triazol-1-yl]-14-methyl-2-{[(2R,3R, 4R,5S,6S)-3,4,5-trimethoxy-6-methyloxan-2-yl] oxy}-1H,2H,3H,3aH,4H,5H,5aH,5bH,6H,7H,9H, 10H,11H,12H,13H,14H,15H,16aH,16bH-as-indaceno[3,2-d]oxacyclododecane-7,15-dione

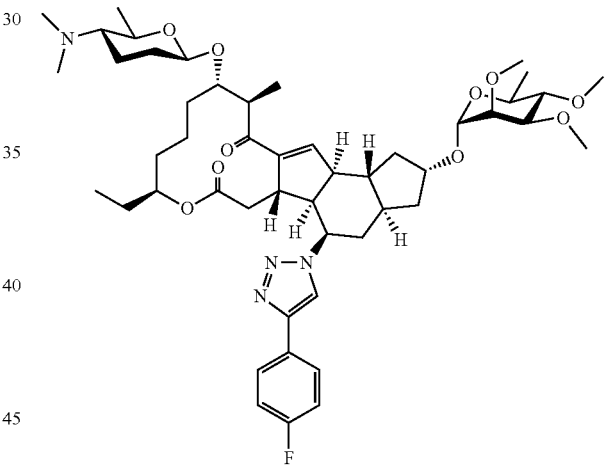

A mixture of compound Intermediate 12 (250 mg, 0.32 mmol), 1-Ethynyl-4-fluoro-benzene (194 mg, 1.6 mmol), copper sulfate (10 mg, 0.06 mmol) and sodium ascorbate (13 mg, 0.06 mmol) in t-butanol/H$_2$O (4 mL/2 mL) was stirred at 110° C. for 17 h in a sealed tube. The reaction mixture was filtered through kieselguhr and the filtrate was concentrated. The residue was purified by prep-HPLC to afford the title compound (25 mg, 8% yield) as a white solid. Partial $^1$H NMR (CDCl$_3$, 400 MHz): δ 7.95 (s, 1H), 7.81-7.77 (m, 2H), 7.12-7.09 (m, 2H), 6.86 (s, 1H), 4.91-4.87 (m, 1H), 4.85 (d, J=1.2 Hz, 1H), 4.56-4.53 (m, 1H), 4.40 (d, J=7.6 Hz, 1H), 4.33-4.29 (m, 1H), 3.74-3.68 (m, 1H), 3.35-3.32 (m, 1H), 3.24-3.20 (m, 1H), 3.13 (t, J=9.2 Hz, 1H), 2.80-2.73 (m, 2H), 2.23 (s, 6H), 1.17 (d, J=6.4 Hz, 3H), 0.86-0.82 (m, 1H), 0.64 (t, J=7.6 Hz, 3H). LCMS: m/z 894.9 [M+H]+.

Example 112: (2R,3aR,5R,5aR,5bS,9S,13S,14R, 16aR,16bR)-13-{[(2R,5S,6R)-5-(dimethylamino)-6-methyloxan-2-yl]oxy}-9-ethyl-14-methyl-2-{[(2R, 3R,4R,5S,6S)-3,4,5-trimethoxy-6-methyloxan-2-yl] oxy}-5-[4-(trimethylsilyl)-1H-1,2,3-triazol-1-yl]-1H, 2H,3H,3aH,4H,5H,5aH,5bH,6H,7H,9H,10H,11H, 12H,13H,14H,15H,16aH,16bH-as-indaceno[3,2-d] oxacyclododecane-7,15-dione

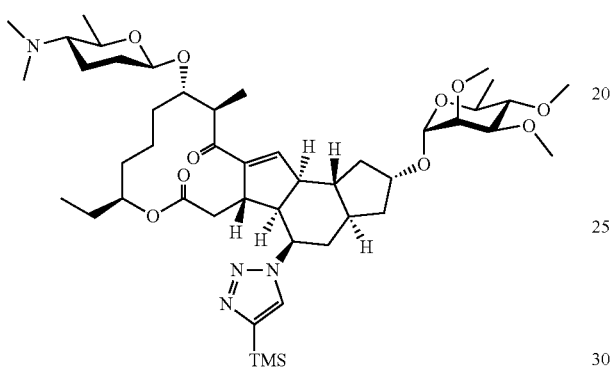

A mixture of compound Intermediate 12 (400 mg, 0.52 mmol), Ethynyl-trimethyl-silane (253 mg, 2.6 mmol), copper sulfate (16 mg, 0.1 mmol) and sodium ascorbate (20 mg, 0.1 mmol) in t-butanol/$H_2O$ (8 mL/3 mL) was stirred at 110° C. for 17 h in a sealed tube. The reaction mixture was filtered through kieselguhr and the filtrate was concentrated. The residue was purified by prep-HPLC to afford the title compound (320 mg, 71% yield) as a white solid. Partial $^1$H NMR (CDCl$_3$, 400 MHz): δ 7.72 (s, 1H), 6.84 (s, 1H), 4.85-4.83 (m, 1H), 4.84 (s, 1H), 4.59-4.55 (m, 1H), 4.39 (d, J=7.2 Hz, 1H), 4.31-4.29 (m, 1H), 3.69-3.63 (m, 1H), 3.27-3.18 (m, 2H), 3.15-3.10 (m, 1H), 2.73-2.66 (m, 2H), 2.18 (s, 6H), 1.28 (d, J=6.0 Hz, 3H), 1.23 (d, J=6.0 Hz, 3H), 1.16 (d, J=6.8 Hz, 3H), 0.86-0.78 (m, 1H), 0.70 (t, J=7.6 Hz, 3H), 0.28 (s, 9H). LCMS: m/z 872.9 [M+H]$^+$.

Examples 113 and 115: (2S,3aR,4R,5aR,5bS,9S, 13S,14R,16aR,16bS)-9-ethyl-4-[4-(4-methoxyphenyl)-1H-1,2,3-triazol-1-yl]-14-methyl-13-{[(2R,5S, 6R)-6-methyl-5-(methylamino)oxan-2-yl]oxy}-2-{ [(2R,3R,4R,5S,6S)-3,4,5-trimethoxy-6-methyloxan-2-yl]oxy}-1H,2H,3H,3aH,4H,5H,5aH,5bH,6H,7H, 9H,10H,11H,12H,13H,14H,15H,16aH,16bH-as-indaceno[3,2-d]oxacyclododecane-7,15-dione (115), and N-[(2R,3S,6R)-6-{[(2S,3aR,4R,5aR,5bS,9S, 13S,14R,16aR,16bS)-9-ethyl-4-[4-(4methoxyphenyl)-1H-1,2,3-triazol-1-yl]-14-methyl-7,15-dioxo-2-{[(2R,3R,4R,5S,6S)-3,4,5trimethoxy-6-methyloxan-2-yl]oxy}-1H,2H,3H,3aH,4H,5H,5aH,5bH,6H,7H, 9H,10H,11H,12H,13H,14H,15H,16aH,16bH-as-indaceno[3,2-d]oxacyclododecan-13-yl]oxy}-2-methyloxan-3-yl]-N-methyldodecanamide (116)

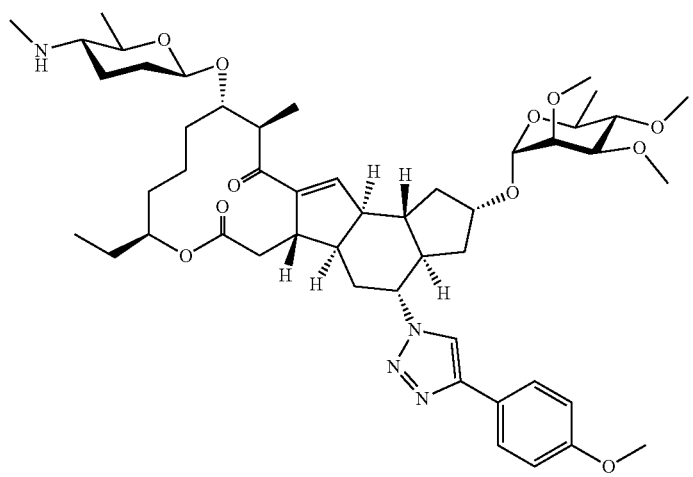

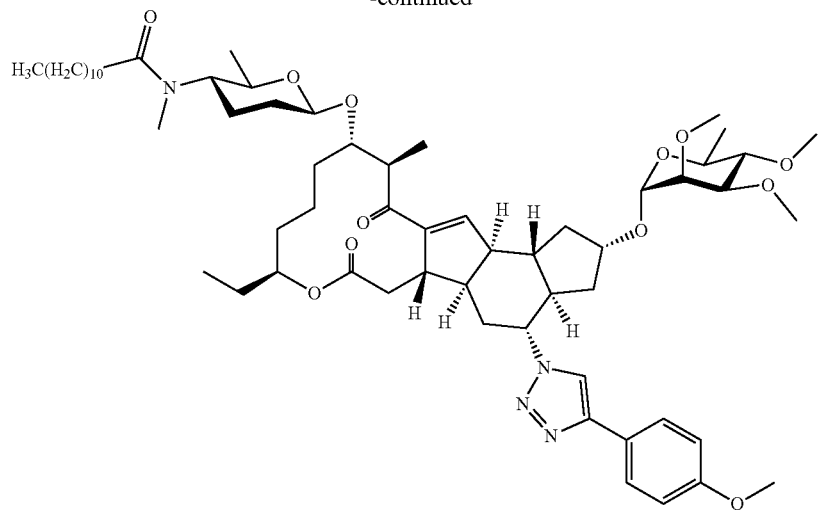

A mixture of Example 73 (110 mg, 0.12 mmol) and sodium acetate (50 mg, 0.61 mmol) in methanol/H$_2$O (10 mL/2 mL) was heated to 47° C., followed by addition of iodine (46 mg, 0.18 mmol). The reaction mixture was adjusted to PH=8-9 by 1M aqueous NaOH. The mixture was quenched with saturated aqueous sodium bicarbonate (10 mL) and extracted with dichloromethane (20 mL×3). The combined organic layer was washed with brine (50 mL) and concentrated to give crude product Example 113 which was used in the next step without further purification. LCMS: m/z 893.6 [M+H]$^+$.

To a solution of dodecanoic acid (26 mg, 0.13 mmol) in DMF (2 mL) was added DIEA (77 mg, 0.6 mmol) and HATU (68 mg, 0.18 mmol). After stirring for 5 min, a solution of Example 113 (107 mg, 0.12 mmol) in DMF (5 mL) was added. The reaction was stirred at room temperature overnight. The reaction mixture was poured into water (10 mL) and extracted with EA (15 mL×3). The combined organic layer was washed with water (20 mL×3), dried over anhydrous sodium sulfate, filtered and concentrated. The residue was purified by prep-HPLC to afford Example 114 (20 mg, 15% yield) as a white solid. Partial $^1$H NMR (CDCl$_3$, 400 MHz): δ 7.79-7.77 (m, 2H), 7.72 (s, 1H), 6.99-6.96 (m, 2H), 6.87 (s, 1H), 4.71 (s, 1H), 4.70-4.66 (m, 1H), 4.29-4.24 (m, 1H), 3.85 (s, 1H), 3.69-3.62 (m, 1H), 3.31-3.26 (m, 2H), 3.18 (dd, J=13.6, 4.8 Hz, 1H), 3.11-3.07 (m, 2H), 2.76 (s, 3H), 1.30-1.07 (m, 29H), 0.88 (t, J=6.8 Hz, 3H), 0.81 (t, J=7.6 Hz, 3H). LCMS: m/z 1075.8 [M+H]$^+$.

Example 115: (2S,3aR,5aR,5bS,9S,13S,14R,16aR, 16bS)-4-bromo-13-{[(2R,5S,6R)-5-(dimethyl-amino)-6-methyloxan-2-yl]oxy}-9-ethyl-5-fluoro-14-methyl-2-{[(2R,3R,4R,5S,6S)-3,4,5-trimethoxy-6-methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-7,15-dione

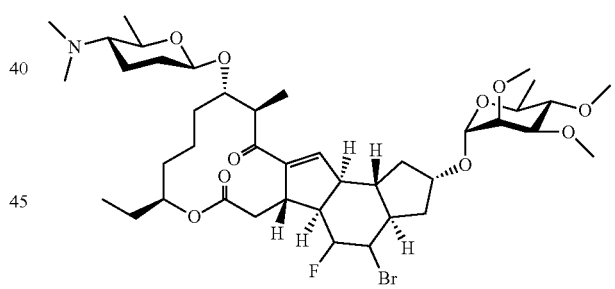

To a solution of compound Intermediate 1 (200 mg, 0.24 mmol) in dichloromethane (20 mL) was added DAST (155 mg, 0.97 mmol) at −78° C. under nitrogen. After stirring at −78° C. for 30 min, the mixture was warmed to room temperature and quenched with aqueous sodium bicarbonate (10 mL). After stirring for 15 min, the mixture was extracted with dichloromethane (10 mL×2). The combined organic layer was washed with brine, dried over anhydrous sodium sulfate, filtered and concentrated. The residue was purified by prep-HPLC to afford the title compound (100 mg, yield 50%). Partial $^1$H NMR (CDCl$_3$, 400 MHz): δ6.73 (s, 1H), 5.03-4.91 (m, 1H), 4.83 (s, 1H), 4.69-4.63 (m, 1H), 4.53 (td, J=3.2 Hz, 14.8 Hz, 1H), 4.42 (d, J=8.0 Hz, 1H), 4.25 (s, 1H), 3.65-3.43 (m, 15H), 3.30-3.09 (m, 5H), 2.97 (t, J=8.8 Hz, 1H), 2.44-2.15 (m, 10H), 0.82 (t, J=7.6 Hz, 3H). LCMS: m/z 830.0 [M+H]$^+$.

Example 116: (2R,3aR,5aR,5bS,9S,13S,14R,16aR, 16bR)-5-(benzylamino)-13-{[(2R,5S,6R)-5-(dimeth- ylamino)-6-methyloxan-2-yl]oxy}-9-ethyl-14- methyl-2-{[(2R,3R,4R,5S,6S)-3,4,5-trimethoxy-6- methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-7,15- dione

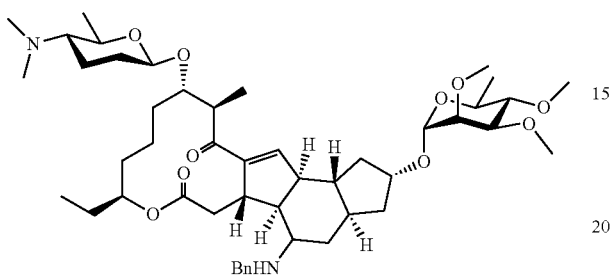

To a solution of Example 10 (1.0 g, 1.3 mmol) in 20 mL of methanol were added benzylamine (280 mg, 2.6107 mmol) and a drop of acetic acid. After stirring overnight at r.t, sodium cyanoborohydride (0.42 g, 6.7 mmol) was added and the mixture was stirred for 5 h. The reaction was quenched with saturated sodium bicarbonate (10 mL) and extracted with dichloromethane (5×10 mL). The combined organic phase was concentrated to give the crude product which was purified by prep-HPLC to give the title compound (15 mg). Partial $^1$H NMR (CDCl$_3$, 400 MHz): 7.28-7.31 (m, 4H), 7.21-7.25 (m, 1H), 6.87 (s, 1H), 4.80 (s, 1H), 4.68-4.60 (m, 1H), 4.43-4.41 (m, 1H), 4.21-4.19 (m, 1H), 3.98-3.88 (m, 2H), 3.65-3.61 (m, 1H), 3.28-3.24 (m, 3H), 3.16-3.00 (m, 4H), 2.47-2.43 (m, 1H), 2.23-2.14 (m, 8H), 1.04-1.10 (m, 1H), 0.81 (t, J=7.8 Hz, 3H), 0.62-0.66 (m, 1H). LC-MS: m/z 839.4[M+H]$^+$.

Example 117: (2R,3aR,5aR,5bS,9S,13S,14R,16aR, 16bR)-5-amino-13-{[(2R,5S,6R)-5-(dimethyl- amino)-6-methyloxan-2-yl]oxy}-9-ethyl-14-methyl- 2-{[(2R,3R,4R,5S,6S)-3,4,5-trimethoxy-6- methyloxan-2-yl]oxy}-1H,2H,3H,3aH,4H,5H,5aH, 5bH,6H,7H,9H,10H,11H,12H,13H,14H,15H,16aH, 16bH-as-indaceno[3,2-d]oxacyclododecane-7,15- dione

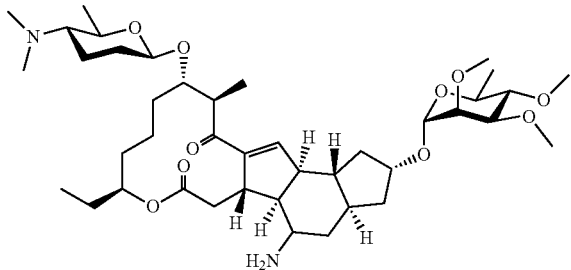

To a solution of Example 10 (1.0 g, 1.3 mmol) in 20 mL of methanol was added ammonium acetate (300 mg, 3.9 mmol) and a drop of acetic acid. After stirring overnight at r.t, sodium cyanoborohydride (0.42 g, 6.7 mmol) was added and the mixture was stirred for 5 h. The reaction was quenched with saturated sodium bicarbonate (10 mL) and extracted with dichloromethane (5×10 mL). The combined organic phase was concentrated to give the crude product, which was purified by prep-HPLC to give the title compound (150 mg). Partial $^1$H NMR (CDCl$_3$, 400 MHz): 6.86 (s, 1H), 4.80 (s, 1H), 4.62-4.59 (m, 1H), 4.42-4.41 (m, 1H), 4.23-4.19 (m, 1H), 3.65-3.60 (m, 1H), 3.29-3.20 (m, 3H), 3.12-3.07 (m, 1H), 2.99-2.90 (m, 2H), 2.51-2.45 (m, 1H), 0.84-0.79 (t, J=10 Hz, 4H), 0.67-0.61 (m, 1H). LC-MS: m/z 748.9[M+H]$^+$.

Representative Procedure for Conjugate 1,4-Addition of Cuprates

Example 118: (2R,3aS,5aS,5bS,9S,13S,14R,16aS, 16bR)-13-{[(2R,5S,6R)-5-(dimethylamino)-6-meth- yloxan-2-yl]oxy}-9-ethyl-14-methyl-16-phenyl-2-{ [(2R,3R,4R,5S,6S)-3,4,5-trimethoxy-6-methyloxan- 2-yl]oxy}-1H,2H,3H,3aH,5aH,5bH,6H,7H,9H,10H, 11H,12H,13H,14H,15H,15aH,16H,16aH,16bH-as- indaceno[3,2-d]oxacyclododecane-7,15-dione

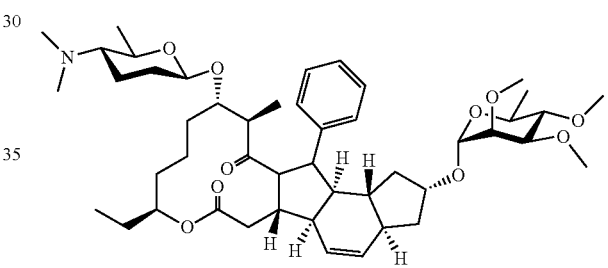

tert-Butyllithium (1.6 M in hexane, 6.3 mL, 10 mmol) was added to anhydrous diethyl ether (20 mL) under nitrogen and cooled to −78° C. Maintaining the temperature between −78° C. and −60° C., a solution of iodobenzene (2.04 g, 10 mmol) in anhydrous diethylether (10 mL) was added dropwise. After stirring for 30 min at −78° C., the resulting mixture was added dropwise to a suspension of CuI (0.76 g, 4 mmol) in anhydrous diethyl ether (10 mL) at 0° C. using a syringe under nitrogen. The mixture was stirred for another 30 minutes, and a solution of Spinosyn A (1.46 g, 2 mmol) in anhydrous diethylether (10 mL) was added. The resulting mixture was allowed to warm to room temperature and stirred for 1 h. The reaction mixture was diluted with water (100 mL) and extracted with diethyl ether (3×100 mL). The combined organic phase was washed with brine (100 mL), dried over anhydrous sodium sulfate, filtered and concentrated. The residue was purified by prep-HPLC to afford the title compound (180 mg, 11.1% yield) as a white solid. $^1$H NMR (400 MHz, Acetone-d$_6$): δ 7.28-7.26 (m, 4H), 7.18-7.15 (m, 1H), 5.78 (s, 1H), 4.75-4.68 (m, 2H), 4.20-4.17 (m, 2H), 3.34-3.12 (m, 17H), 2.83-2.52 (m, 10H), 2.36-2.22 (m, 3H), 2.04 (s, 6H), 1.62-1.16 (m, 21H), 1.08 (d, J=5.6 Hz, 3H), 0.98 (d, J=6.0 Hz, 3H), 0.72 (t, J=7.2 Hz, 3H), 0.63 (d, J=6.4 Hz, 3H); LC-MS: m/z 810.1 [M+H]$^+$.

Example 119: (2R,5bS,9S,13S,14R,16aS,16bR)-13-{[(2R,5S,6R)-5-(dimethylamino)-6-methyloxan-2-yl]oxy}-9-ethyl-14-methyl-16-phenyl-2-{[(2R,3R,4R,5S,6S)-3,4,5-trimethoxy-6-methyloxan-2-yl]oxy}-icosahydro-1H-as-indaceno[3,2-d]oxacyclododecane-7,15-dione

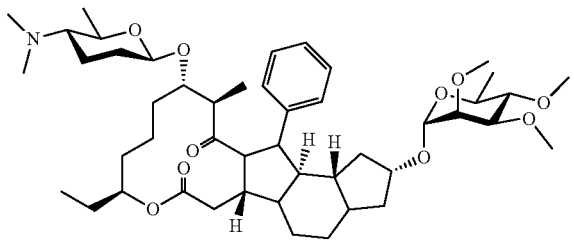

A mixture of Example 118 (100 mg, 0.12 mmol) and palladium on carbon (20 mg) in methanol (20 mL) was stirred under 50 psi of hydrogen at 40° C. for 4 h. The mixture was filtered through Celite and washed with methanol (50 ml). The filtrate was concentrated under reduced pressure to give a residue, which was purified by prep-HPLC to afford the title compound (50 mg, 50% yield) as a white solid. $^1$H NMR (400 MHz, Acetone-$d_6$): δ 7.27-7.22 (m, 4H), 7.14-7.11 (m, 1H), 4.68-4.62 (m, 2H), 4.23 (d, J=8.4 Hz, 1H), 4.14-4.10 (m, 1H), 3.38-3.21 (m, 14H), 3.18 (dd, $J_1$=9.2 Hz, $J_2$=3.2 Hz, 1H), 3.02 (t, J=8.4 Hz, 1H), 2.85 (t, J=9.2 Hz, 1H), 2.69-2.60 (m, 6H), 2.43 (dd, $J_1$=14.4 Hz, $J_2$=2.4 Hz, 1H), 2.35-2.19 (m, 3H), 2.04 (s, 6H), 1.96 (s, 10H), 1.70-1.10 (m, 22H), 1.03-1.00 (m, 6H), 0.97-0.91 (m, 2H), 0.87 (d, J=6.4 Hz, 3H), 0.73 (t, J=7.2 Hz, 1H); LC-MS: m/z 811.9 [M+H]$^+$.

Example 120: (2R,3aS,5aS,5bS,9S,13S,4R,16aS,16bR)-13-{[(2R,5S,6R)-5-(dimethylamino)-6-methyloxan-2-yl]oxy}-9-ethyl-16-(3-methoxyphenyl)-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,15aH,16H,16aH,16bH-as-indaceno[3,2-d]oxacyclododecane-7,15-dione

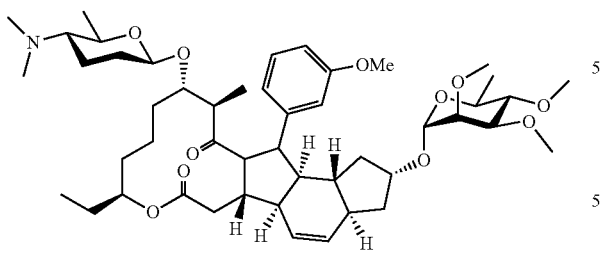

Example 120 was prepared according to the similar procedure as described for the preparation of Example 118. From 3-methoxy-iodobenzene (2.34 g, 10 mmol) and Spinosyn A (1.46 g, 2 mmol), 200 mg of the title compound was obtained as a white solid (11.9% yield). $^1$H NMR (400 MHz, Acetone-$d_6$): δ 7.21 (t, J=8.0 Hz, 1H), 6.90-6.88 (m, 2H), 6.74 (d, J=8.8 Hz, 1H), 5.82 (s, 2H), 4.75-4.71 (m, 2H), 4.25-4.21 (m, 2H), 3.72 (s, 3H), 3.42-3.13 (m, 17H), 2.87 (t, J=9.2 Hz, 1H), 2.69-2.57 (m, 2H), 2.38-2.32 (m, 3H), 2.13-1.92 (s, 7H), 1.84-1.11 (m, 15H), 1.07 (d, J=6.4 Hz, 3H), 1.01 (d, J=6.0 Hz, 3H), 0.95-0.87 (m, 2H), 0.77 (t, J=7.6 Hz, 3H), 0.73 (d, J=6.8 Hz, 3H); LC-MS: m/z 839.9 [M+H]$^+$.

Example 121: (2R,5bS,9S,13S,14R,16aS,16bR)-13-{[(2R,5S,6R)-5-(dimethylamino)-6-methyloxan-2-yl]oxy}-9-ethyl-16-(3-methoxyphenyl)-14-methyl-2-{[(2R,3R,4R,5S,6S)-3,4,5-trimethoxy-6-methyloxan-2-yl]oxy}-icosahydro-1H-as-indaceno[3,2-d]oxacyclododecane-7,15-dione

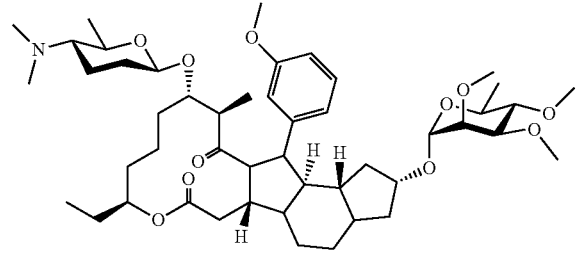

A mixture of Example 120 (100 mg, 0.12 mmol) and palladium on carbon (20 mg) in methanol (20 mL) was stirred under 50 psi of $H_2$ at 40° C. for 4 h. The mixture was filtered through Celite and washed with methanol (50 ml). The filtrate was concentrated under reduced pressure to give a residue, which was purified by prep-HPLC to afford the title compound (50 mg, 50% yield) as a white solid. $^1$H NMR (400 MHz, Acetone-$d_6$): δ 7.16 (t, J=8.0 Hz, 1H), 6.82-6.80 (m, 2H), 6.72-6.69 (m, 1H), 4.67-4.65 (m, 2H), 4.26 (d, J=8.8 Hz, 1H), 4.14-4.11 (m, 1H), 3.37 (s, 3H), 3.40-3.18 (m, 15H), 3.03 (t, J=8.4 Hz, 1H), 2.86 (t, J=9.2 Hz, 1H), 2.69-2.65 (m, 6H), 2.45 (dd, $J_1$=14.4 Hz, $J_2$=2.4 Hz, 1H), 2.37-2.25 (m, 3H), 2.06 (s, 6H), 1.87-1.82 (m, 1H), 1.71-1.11 (m, 19H), 1.05-1.01 (m, 6H), 0.96-0.92 (m, 2H), 0.91 (d, J=6.4 Hz, 3H), 074 (t, J=7.2 Hz, 1H); LC-MS: m/z 841.9 [M+H]$^+$.

Example 122: (2R,3aS,5aS,5bS,9S,13S,14R,16aS,16bR)-13-{[(2R,5S,6R)-5-(dimethylamino)-6-methyloxan-2-yl]oxy}-9-ethyl-16-(4-fluorophenyl)-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,15aH,16H,16aH,16bH-as-indaceno[3,2-d]oxacyclododecane-7,15-dione

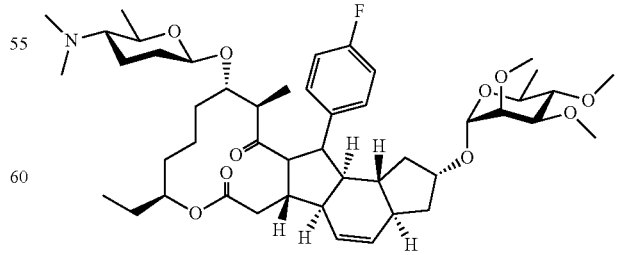

Example 122 was prepared according the representative procedure as described for the preparation of Example 118. From 4-fluoro-iodobenzene (2.22 g, 10 mmol) and Spinosyn A (1.46 g, 2 mmol), 220 mg of the title compound was obtained as a white solid (13.3% yield). $^1$H NMR (400 MHz, Acetone-d$_6$): δ 7.34-7.30 (m, 2H), 7.02 (t, J=8.8 Hz, 2H), 5.76 (s, 2H), 4.71-4.64 (m, 2H), 4.19-4.14 (m, 2H), 3.35-3.10 (m, 15H), 3.12 (dd, J=9.4, 3.0 Hz, 1H), 3.06 (t, J=10.4 Hz, 1H), 2.82 (t, J=5.6 Hz, 1H), 2.69-2.63 (m, 2H), 2.56-2.51 (m, 1H), 2.32-2.21 (m, 3H), 2.02 (s, 6H), 2.02-1.95 (s, 4H), 1.79-1.04 (m, 16H), 1.01 (d, J=6.4 Hz, 3H), 0.95 (d, J=6.0 Hz, 3H), 0.86-0.76 (m, 2H), 0.71 (t, J=7.6 Hz, 3H), 0.61 (d, J=6.8 Hz, 3H); LC-MS: m/z 827.9 [M+H]$^+$.

Example 123: (2R,5bS,9S,13S,14R,16aS,16bR)-13-{[(2R,5S,6R)-5-(dimethylamino)-6-methyloxan-2-yl]oxy}-9-ethyl-16-(4-fluorophenyl)-14-methyl-2-{[(2R,3R,4R,5S,6S)-3,4,5-trimethoxy-6-methyloxan-2-yl]oxy}-icosahydro-1H-as-indaceno[3,2-d]oxacyclododecane-7,15-dione

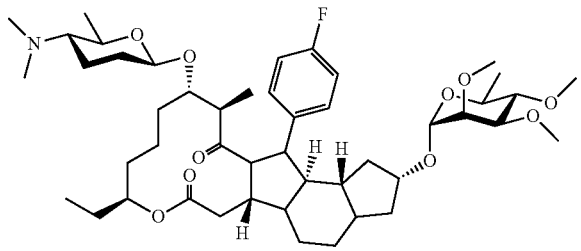

A mixture of Example 122 (150 mg, 0.18 mmol) and Palladium on carbon (30 mg) in methanol (20 mL) was stirred under 50 psi of H$_2$ at 40° C. for 4 h. The mixture was filtered through Celite and washed with methanol (50 ml). The filtrate was concentrated under reduced pressure to give a residue, which was purified by prep-HPLC to afford the title compound (70 mg, 46.7% yield) as a white solid. $^1$H NMR (400 MHz, Acetone-d$_6$): δ 7.35-7.31 (m, 2H), 7.10-7.05 (m, 2H), 4.73-4.69 (m, 2H), 4.29 (d, J=8.8 Hz, 1H), 4.18-4.15 (m, 1H), 3.46-3.22 (m, 15H), 3.02 (t, J=8.4 Hz, 1H), 2.91 (t, J=9.2 Hz, 1H), 2.77-2.67 (m, 6H), 2.49 (dd, J$_1$=14.4 Hz, J$_2$=2.4 Hz, 1H), 2.39-2.25 (m, 3H), 2.10 (s, 6H), 1.91-1.86 (m, 1H), 1.75-1.17 (m, 20H), 1.09-1.05 (m, 6H), 1.03-0.96 (m, 2H), 0.92 (d, J=6.4 Hz, 3H), 078 (t, J=7.6 Hz, 1H); LC-MS: m/z 829.9 [M+H]$^+$ Example 124: (2R,3aS,5aS,5bS,9S,13S,4R,16aS,16bR)-16-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,15aH,16H,16aH,16bH-as-indaceno[3,2-d]oxacyclododecane-7,15-dione

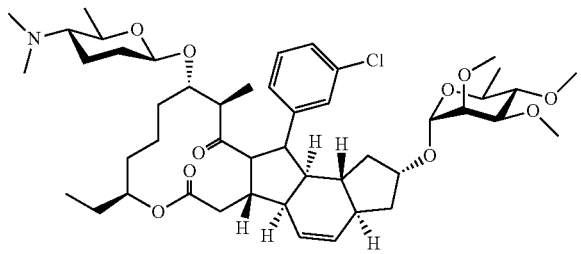

Example 124 was prepared according the similar procedure as described for the preparation of Example 118. From 3-chloro-iodobenzene (2.38 g, 10 mmol) and Spinosyn A (1.46 g, 2 mmol), 215 mg of the title compound was obtained as a white solid (12.7% yield). $^1$H NMR (400 MHz, Acetone-d$_6$): δ 7.34-7.27 (m, 3H), 7.19-7.17 (m, 1H), 5.78 (s, 2H), 4.71-4.66 (m, 2H), 4.22-4.15 (m, 2H), 3.42-3.07 (m, 17H), 2.83 (t, J=8.8 Hz, 1H), 2.71-2.67 (m, 2H), 2.57 (dd, J=14.4, 2.8 Hz, 1H), 2.35-2.24 (m, 3H), 2.02-1.96 (s, 6H), 1.81-1.76 (m, 1H), 1.67-1.07 (m, 15H), 1.03 (d, J=4.2 Hz, 3H), 0.97 (d, J=6.0 Hz, 3H), 0.92-0.80 (m, 2H), 0.73 (t, J=7.6 Hz, 3H), 0.65 (d, J=6.8 Hz, 3H); LC-MS: m/z 844.1 [M+H]$^+$.

Example 125: (2R,5bS,9S,13S,14R,16aS,16bR)-16-(3-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-icosahydro-1H-as-indaceno[3,2-d]oxacyclododecane-7,15-dione

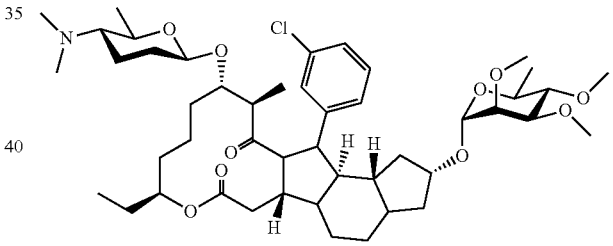

A mixture of Example 124 (75 mg, 0.1 mmol) and Palladium on carbon (15 mg) in methanol (15 mL) was stirred under 50 psi of H$_2$ at 40° C. for 4h. The mixture was filtered through Celite and washed with methanol (50 ml). The filtrate was concentrated under reduced pressure to give a residue, which was purified by prep-HPLC to afford the title compound (25 mg, 33.3% yield) as a white solid. $^1$H NMR (400 MHz, Acetone-d$_6$): δ 7.31-7.27 (m, 2H), 7.22-7.16 (m, 2H), 4.69-4.65 (m, 2H), 4.25 (d, J=8.8 Hz, 1H), 4.13-4.10 (m, 1H), 3.41-3.17 (m, 15H), 2.99 (t, J=8.4 Hz, 1H), 2.86 (t, J=9.2 Hz, 1H), 2.73-2.63 (m, 10H), 2.45 (dd, J$_1$=14.4 Hz, J$_2$=2.4 Hz, 1H), 2.37-2.39 (m, 2H), 2.24-2.20 (m, 1H), 2.05 (s, 6H), 1.85-1.82 (m, 1H), 1.71-1.10 (m, 21H), 1.04-1.00 (m, 6H), 0.97-0.92 (m, 2H), 0.89 (d, J=6.4 Hz, 3H), 074 (t, J=7.2 Hz, 1H); LC-MS: m/z 845.8 [M+H]$^+$.

Example 126: (2R,3aS,5aS,5bS,9S,13S,14R,16aS,
16bR)-13-{[(2R,5S,6R)-5-(dimethylamino)-6-methyloxan-2-yl]oxy}-16-ethenyl-9-ethyl-14-methyl-2-{
[(2R,3R,4R,5S,6S)-3,4,5-trimethoxy-6-methyloxan-2-yl]oxy}-1H,2H,3H,3aH,5aH,5bH,6H,7H,9H,10H,
11H,12H,13H,14H,15H,15aH,16H,16aH,16bH-as-indaceno[3,2-d]oxacyclododecane-7,15-dione

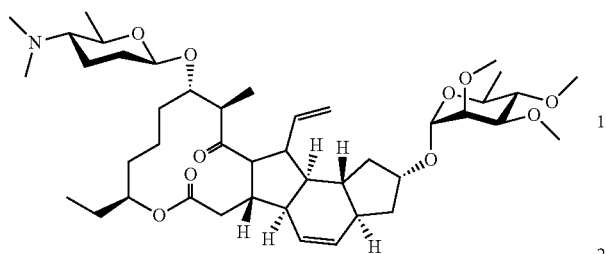

To a suspension of copper (I) iodide (26 mg, 0.13 mmol) in diethyl ether (10 mL) were added a solution of vinylmagnesium bromide (2.05 mL, 2.05 mmol), and spinosyn A (500 mg, 0.68 mmol) at −40° C. The mixture was allowed to warm to r.t. The mixture was diluted with ethyl acetate (60 mL), washed with saturated ammonium chloride aqueous (30 mL) and concentrated ammonia. The organic layer was dried over sodium sulfate, filtered and concentrated in vacuo to give an oil which was further purified by prep-HPLC to afford the title compound (120 mg, 23.0%) as a white solid. Partial $^1$H NMR (DMSO-$d_6$, 400 MHz): δ6.06-5.97 (m, 1H), 5.88-5.79 (m, 2H), 5.09 (d, J=16.0 Hz, 1H), 5.01 (d, J=10.4 Hz, 1H), 4.78 (s, 1H), 4.68-4.66 (m, 1H), 4.39 (d, J=9.2 Hz, 1H), 4.24-4.20 (m, 1H), 3.26 (dd, J=9.2, 3.2 Hz, 1H), 2.95-2.85 (m, 2H), 2.72-2.62 (m, 2H), 2.52 (dd, J=15.6, 3.2 Hz, 1H), 2.31-2.27 (m, 2H), 0.95 (d, J=6.4 Hz, 3H), 0.78 (t, J=7.2 Hz, 3H). LC-MS: m/z 760.0 [M+H]$^+$.

Example 127: (2R,3aR,5aS,5bS,9S,13S,14R,16aS,
16bR)-13-{[(2R,5S,6R)-5-(dimethylamino)-6-methyloxan-2-yl]oxy}-9,16-diethyl-14-methyl-2-{[(2R,
3R,4R,5S,6S)-3,4,5-trimethoxy-6-methyloxan-2-yl]
oxy}-icosahydro-1H-as-indaceno[3,2-d]
oxacyclododecane-7,15-dione

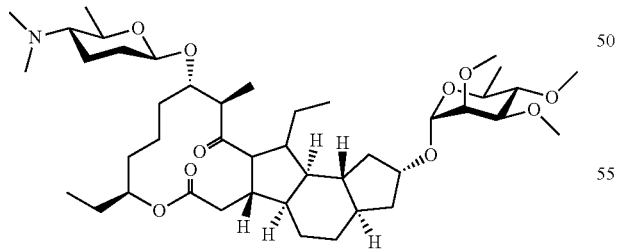

A mixture of Example 126 (100 mg, 0.13 mmol) and 10% palladium on carbon (20 mg) in ethyl acetate (10 mL) was stirred under H$_2$ (1 atm) at room temperature for 0.5 h. The mixture was filtered through Celite and washed with ethyl acetate (20 mL). The filtrate was concentrated under reduced pressure to give an oil, which was purified by pre-HPLC to afford the title compound (85 mg, yield 84.5%) as a white solid. Partial $^1$H NMR (DMSO-$d_6$, 400 MHz): δ4.76 (s, 1H), 4.64-4.61 (m, 1H), 4.40 (d, J=13.2 Hz, 1H), 4.12-4.08 (m, 1H), 2.96-2.92 (m, 1H), 2.77-2.72 (m, 1H). LCMS: m/z 764.0 [M+H]$^+$.

Example 128: (2S,3aR,5aS,5bS,9S,13S,14R,16aS,
16bS)-13-{[(2R,5S,6R)-5-(dimethylamino)-6-methyloxan-2-yl]oxy}-16-ethenyl-9-ethyl-4,14-dimethyl-
2-{[(2R,3R,4R,5S,6S)-3,4,5-trimethoxy-6-
methyloxan-2-yl]oxy}-1H,2H,3H,3aH,5aH,5bH,6H,
7H,9H,10H,11H,12H,13H,14H,15H,15aH,16H,
16aH,16bH-as-indaceno[3,2-d]oxacyclododecane-7,
15-dione

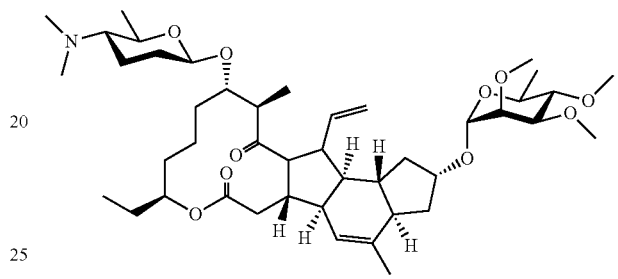

To a suspension of CuI (10 mg, 0.053 mmol) in ether (3 mL) was added a solution of vinylmagnesium bromide (0.8 mL, 0.8 mmol) at −40° C. To the cold solution was added Spinosyn D (200 mg, 0.26 mmol) and the mixture was allowed to warm to r.t. The mixture was diluted with ethyl acetate (30 mL), washed with saturated ammonium chloride aqueous (20 mL) and concentrated ammonia, then dried over sodium sulfate, filtered and concentrated in vacuo to give an oil, which was further purified by prep-HPLC to afford the title compound (42 mg, 20.2%) as a white solid. Partial Partial $^1$H NMR (DMSO-$d_6$, 400 MHz): δ6.05-5.96 (m, 1H), 5.45 (s, 1H), 5.07 (d, J=17.6 Hz, 1H), 5.00 (d, J=10.0 Hz, 1H), 4.79 (s, 1H), 4.66-4.63 (m, 1H), 4.39 (d, J=9.6 Hz, 1H), 4.24-4.19 (m, 1H), 3.26 (dd, J=9.2, 3.2 Hz, 1H), 2.93 (t, J=9.2 Hz, 1H), 2.85-2.78 (m, 1H), 2.70-2.62 (m, 2H), 2.31-2.27 (m, 2H), 0.95 (d, J=6.4 Hz, 3H). LC-MS: m/z 774.0 [M+H]$^+$.

Example 129: (2R,3aS,5aS,5bS,9S,13S,4R,16aS,
16bR)-13-{[(2R,5S,6R)-5-(dimethylamino)-6-methyloxan-2-yl]oxy}-9-ethyl-16-(3-fluorophenyl)-14-
methyl-2-{[(2R,3R,4R,5S,6S)-3,4,5-trimethoxy-6-
methyloxan-2-yl]oxy}-1H,2H,3H,3aH,5aH,5bH,6H,
7H,9H,10H,11H,12H,13H,14H,15H,15aH,16H,
16aH,16bH-as-indaceno[3,2-d]oxacyclododecane-7,
15-dione

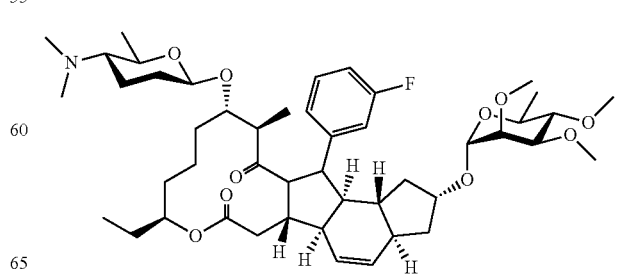

Example 129 was prepared according the representative procedure as described for the preparation of Example 118. From 3-fluoro-iodobenzene (2.22 g, 10 mmol) and Spinosyn A (1.46 g, 2 mmol), 200 mg of the title compound was obtained as a white solid (12.1% yield). $^1$H NMR (400 MHz, Acetone-d$_6$): δ 7.37-7.31 (m, 1H), 7.17 (d, J=7.6 Hz, 1H), 7.11 (d, J=10.0 Hz, 1H), 6.94 (t, J=7.6 Hz, 1H), 5.81 (s, 2H), 4.74-4.69 (m, 2H), 4.24-4.18 (m, 2H), 3.45-3.10 (m, 17H), 2.86 (t, J=5.6 Hz, 1H), 2.75-2.71 (m, 2H), 2.61-2.57 (m, 1H), 2.38-2.26 (m, 3H), 2.07 (s, 6H), 1.84-1.08 (m, 16H), 1.05 (d, J=6.4 Hz, 3H), 0.98 (d, J=6.0 Hz, 3H), 0.93-0.83 (m, 2H), 0.71 (t, J=7.6 Hz, 3H), 0.68 (d, J=6.8 Hz, 3H); LC-MS: m/z 827.9 [M+H]$^+$.

Example 130: (2S,5bS,9S,13S,4R,16aS,16bS)-5-(4-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,5H,5aH,5bH,6H,7H,9H,10H,11H,12H,13H,14H,15H,16aH,16bH-as-indaceno[3,2-d]oxacyclododecane-7,15-dione

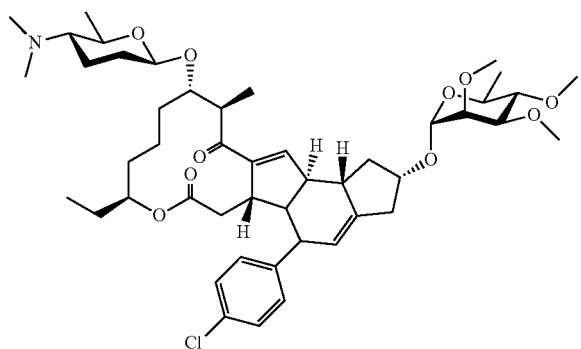

To a solution of Bis(aryl)acenaphthequinonediimine (BIAN, 149 mg, 0.38 mol) in DMF (10 mL) were added Palladium acetate (62 mg, 0.27 mmol) and the system was charged with nitrogen 3 times. The mixture was stirred for 30 min at r.t., then Spinosyn A (1.0 g, 1.37 mmol) and 4-Chloro-phenylboronic acid (321 mg, 2.06 mmol) were added. The flask was charged with oxygen, and the reaction mixture was allowed to stir at r.t. for 3 days under O$_2$ (balloon). The reaction mixture was diluted with water (30 mL) and extracted with ethyl acetate (50 mL×3). The combined organic phase was washed with brine (30 mL), dried over anhydrous sodium sulfate, filtered and concentrated. The residue was purified by prep-HPLC to afford the title compound (110 mg, 9.5% yield) as a yellow solid. Partial $^1$H NMR (CDCl$_3$, 400 MHz): δ 7.35-7.23 (m, 4H), 6.78 (s, 1H), 5.67 (s, 1H), 4.93 (s, 1H), 4.61-4.58 (m, 1H), 4.45 (d, J=7.6 Hz, 1H), 4.30-4.24 (m, 1H), 3.18 (t, J=9.2 Hz, 1H), 3.09-3.04 (m, 2H), 2.97-2.91 (m, 1H), 2.82-2.79 (m, 1H), 2.71-2.59 (m, 1H), 2.64-2.40 (m, 2H), 2.02-2.00 (m, 2H), 1.90-1.88 (m, 1H), 0.78 (t, J=7.2 Hz, 3H); LCMS: m/z 841.9 [M+H]$^+$.

Example 131: (2S,5aR,5bS,9S,13S,14R,16aS,16bS)-13-{[(2R,5S,6R)-5-(dimethylamino)-6-methyloxan-2-yl]oxy}-9-ethyl-5-(4-methoxyphenyl)-14-methyl-2-{[(2R,3R,4R,5S,6S)-3,4,5-trimethoxy-6-methyloxan-2-yl]oxy}-1H,2H,3H,5H,5aH,5bH,6H,7H,9H,10H,11H,12H,13H,14H,15H,16aH,16bH-as-indaceno[3,2-d]oxacyclododecane-7,15-dione To a solution of bis(aryl)acenaphthequinonediimine (BIAN, 149 mg, 0.38 mol) in DMF (10 mL) was added Palladium acetate (62 mg, 0.27 mmol), and the system was charged with nitrogen 3 times. After stirring for 30 min, Spinosyn A (1.0 g, 1.37 mmol) and 4-methoxyphenylboronic acid (313 mg, 2.06 mmol) were added. The flask was charged with O$_2$ and the reaction mixture was allowed to stir at r.t. for 2 days under an O$_2$ (balloon). The reaction mixture was diluted with water (30 mL) and extracted with ethyl acetate (3×50 mL). The combined organic phase was washed with brine (30 mL), dried over anhydrous sodium sulfate, filtered and concentrated. The residue was purified by prep-HPLC to afford the title compound (95 mg, 8.3% yield) as a white solid. $^1$H NMR (400 MHz, CDCl$_3$): δ 7.18 (d, J=8.4 Hz, 2H), 6.87 (d, J=8.8 Hz, 2H), 6.75 (s, 1H), 5.68 (s, 1H), 4.89 (s, 1H), 4.57-4.54 (m, 1H), 4.42 (d, J=8.4 Hz, 1H), 4.25-4.21 (m, 1H), 3.81 (s, 3H), 3.65-3.50 (m, 14H), 3.39-3.35 (m, 1H), 3.14 (t, J=9.6 Hz, 1H), 3.04-2.67 (m, 3H), 2.75-2.54 (m, 3H), 2.42-2.35 (m, 2H), 2.23 (s, 6H), 2.00-1.95 (m, 2H), 1.86 (d, J=8.8 Hz, 1H), 1.73-1.37 (m, 12H), 1.31 (d, J=6.0 Hz, 3H), 1.25 (d, J=6.0 Hz, 3H), 1.21 (d, J=6.4 Hz, 3H), 1.08-1.02 (m, 1H), 0.74 (t, J=7.6 Hz, 3H); LCMS: m/z 838.1 [M+H]$^+$.

Example 132: (2S,5aR,5bS,9S,13S,14R,16aS,16bS)-13-{[(2R,5S,6R)-5-(dimethylamino)-6-methyloxan-2-yl]oxy}-9-ethyl-5-(4-fluorophenyl)-14-methyl-2-{[(2R,3R,4R,5S,6S)-3,4,5-trimethoxy-6-methyloxan-2-yl]oxy}-1H,2H,3H,5H,5aH,5bH,6H,7H,9H,10H,11H,12H,13H,14H,15H,16aH,16bH-as-indaceno[3,2-d]oxacyclododecane-7,15-dione Example 133: (2S,5aR,5bS,9S,13S,14R,16aS,16bS)-13-{[(2R,5S,6R)-5-(dimethylamino)-6-methyloxan-2-yl]oxy}-9-ethyl-5-(3-fluorophenyl)-14-methyl-2-{[(2R,3R,4R,5S,6S)-3,4,5-trimethoxy-6-methyloxan-2-yl]oxy}-1H,2H,3H,5H,5aH,5bH,6H,7H,9H,10H,11H,12H,13H,14H,15H,16aH,16bH-as-indaceno[3,2-d]oxacyclododecane-7,15-dione

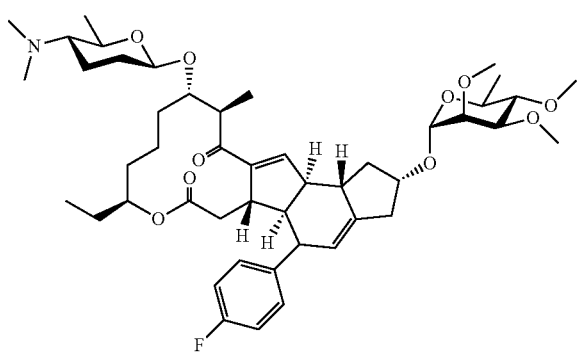
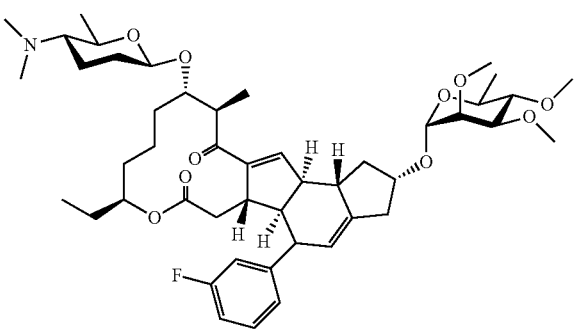

To a solution of bis(aryl)acenaphthequinonediimine (BIAN, 149 mg, 0.38 mol) in DMF (10 mL) were added Palladium acetate (62 mg, 0.27 mmol) and the system was charged with nitrogen 3 times. After stirring for 30 min, Spinosyn A (1.0 g, 1.37 mmol) and 4-fluorophenylboronic acid (288 mg, 2.06 mmol) were added. The flask was charged with $O_2$ and the reaction mixture was allowed to stir at r.t. for 2 days under an $O_2$ (balloon). The reaction mixture was diluted with water (30 mL) and extracted with ethyl acetate (3×50 mL). The combined organic phase was washed with brine (30 mL), dried over anhydrous sodium sulfate, filtered and concentrated. The residue was purified by prep-HPLC to afford the title compound (90 mg, 8.0% yield) as a white solid. $^1$H NMR (400 MHz, Acetone-$d_6$): δ 7.24-7.21 (m, 2H), 7.03-6.99 (m, 3H), 5.55 (s, 1H), 5.68 (s, 1H), 4.77 (d, J=1.2 Hz, 1H), 4.43-4.40 (m, 1H), 4.33 (d, J=8.8 Hz, 1H), 4.20-4.14 (m, 1H), 3.47-3.40 (m, 4H), 3.34-3.26 (m, 11H), 2.94-2.86 (m, 3H), 2.80-2.79 (m, 2H), 2.52-2.48 (m, 1H), 2.42-2.33 (m, 3H), 2.07 (s, 6H), 2.00-1.95 (m, 3H), 1.79 (d, J=10.8 Hz, 1H), 1.69-1.21 (m, 11H), 1.07-1.04 (m, 6H), 1.00 (d, J=6.4 Hz, 3H), 0.96-0.91 (m, 1H), 0.60 (t, J=7.6 Hz, 3H); LCMS: m/z 826.0 [M+H]$^+$.

To a solution of bis(aryl)acenaphthequinonediimine (BIAN, 149 mg, 0.38 mol) in DMF (10 mL) were added Palladium acetate (62 mg, 0.27 mmol) and the system was charged with nitrogen 3 times. After stirring for 30 min, Spinosyn A (1.0 g, 1.37 mmol) and 3-fluorophenylboronic acid (288 mg, 2.06 mmol) were added. The flask was charged with $O_2$ and the reaction mixture was allowed to stir at r.t. for 2 days under an $O_2$ (balloon). The reaction mixture was diluted with water (30 mL) and extracted with ethyl acetate (3×50 mL). The combined organic phase was washed with brine (30 mL), dried over anhydrous sodium sulfate, filtered and concentrated. The residue was purified by prep-HPLC to afford the title compound (96 mg, 8.5% yield) as a yellow solid. $^1$H NMR (400 MHz, DMSO-$d_6$): δ 7.43-7.38 (m, 2H), 7.71 (s, 1H), 7.13-7.06 (m, 3H), 5.60 (s, 1H), 4.88 (s, 1H), 4.47-4.41 (m, 2H), 4.23-4.16 (m, 1H), 3.55-3.31 (m, 19H), 3.01-2.88 (m, 4H), 2.81-2.75 (m, 1H), 2.60-2.56 (m, 1H), 2.45-2.31 (m, 3H), 2.14 (s, 6H), 2.07-1.84 (m, 18H), 1.19 (d, J=6.4 Hz, 3H), 1.12 (d, J=6.0 Hz, 3H), 1.08 (d, J=6.4 Hz, 3H), 0.88-0.81 (m, 2H), 0.67 (t, J=7.2 Hz, 3H); LCMS: m/z 826.0 [M+H]$^+$.

Example 134: (2R,3aR,5bS,9S,13S,14R,16aR,16bR)-13-{[(2R,5S,6R)-5-(dimethylamino)-6-methyloxan-2-yl]oxy}-9-ethyl-4-(4-fluorophenyl)-14-methyl-2-{[(2R,3R,4R,5S,6S)-3,4,5-trimethoxy-6-methyloxan-2-yl]oxy}-1H,2H,3H,3aH,4H,5bH,6H,7H,9H,10H,11H,12H,13H,14H,15H,16aH,16bH-as-indaceno[3,2-d]oxacyclododecane-7,15-dione

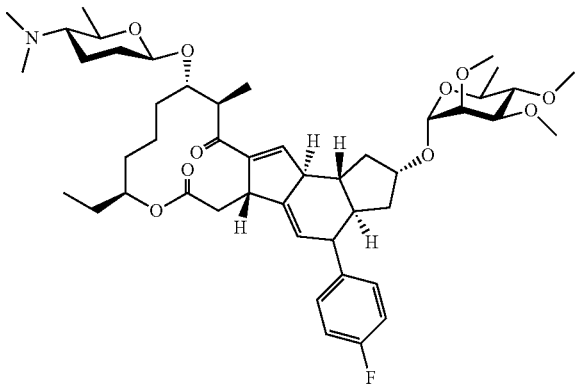

To a mixture of Spinosyn A (1.0 g, 1.37 mmol) and 1-fluoro-4-iodo-benzene (912 mg, 4.11 mmol) in Triethylamine (15 mL) was added Palladium acetate (76 mg, 0.34 mmol) under nitrogen. The mixture was stirred at 100° C. overnight. The mixture was evaporated under reduced pressure and the residue was diluted with ethyl acetate (100 mL) and washed with brine. The organic layer was dried over anhydrous sodium sulfate, filtered and concentrated. The residue was purified by prep-HPLC to give the title compound (80 mg, yield 7.1%) as a white solid. Partial $^1$H NMR (CDCl$_3$, 300 MHz): δ7.23-7.19 (dd, J=8.4, 5.4 Hz, 1H), 7.01 (t, J=8.4 Hz, 2H), 6.89 (s, 1H), 5.85 (s, 1H), 4.74 (s, 1H), 4.70-4.59 (m, 1H), 4.44 (d, J=4.2 Hz, 2H), 4.36-4.29 (m, 1H), 3.16-3.06 (m, 2H), 2.94 (dd, 1H), 2.60 (dd, 1H), 2.48-2.39 (m, 1H), 2.29 (s, 6H), 0.84 (t, J=7.5 Hz, 3H). LCMS: m/z 825.9 [M+H]$^+$.

Example 135: (2R,3aR,5bS,9S,13S,14R,16aS,16bR)-5-(4-chlorophenyl)-13-{[(2R,5S,6R)-5-(dimethylamino)-6-methyloxan-2-yl]oxy}-9-ethyl-14-methyl-2-{[(2R,3R,4R,5S,6S)-3,4,5-trimethoxy-6-methyloxan-2-yl]oxy}-1H,2H,3H,3aH,4H,5H,5aH,5bH,6H,7H,9H,10H,11H,12H,13H,14H,15H,16aH,16bH-as-indaceno[3,2-d]oxacyclododecane-7,15-dione

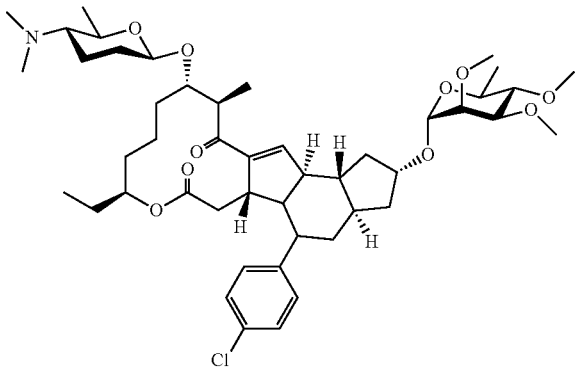

A mixture of Example 91 (100 mg, 0.12 mmol) and Pt/C (20 mg) in methanol (20 mL) was stirred under 50 psi of H$_2$ at room temperature for 30 min. The mixture was filtered through Celite and washed with methanol (50 ml). The filtrate was concentrated under reduced pressure to give a residue, which was purified by prep-HPLC to afford the title compound (26 mg, 26.0% yield) as a white solid. Partial $^1$H NMR (CDCl$_3$, 400 MHz): δ 7.32 (d, J=8.4 Hz, 2H), 7.24 (d, J=8.0 Hz, 2H), 6.78 (s, 1H), 4.90 (s, 1H), 4.65-4.58 (m, 1H), 4.45 (d, J=7.6 Hz, 1H), 4.21-4.18 (m, 1H), 3.39-3.33 (m, 1H), 2.73-2.69 (m, 1H), 0.80 (t, J=7.2 Hz, 3H); LCMS: m/z 844.0 [M+H]$^+$.

Example 136: (2S,3aR,5aR,5bS,9S,13S,14R,16aS,16bS)-13-{[(2R,5S,6R)-5-(dimethylamino)-6-methyloxan-2-yl]oxy}-9-ethyl-4-[4-(4-methoxyphenyl)-1H-1,2,3-triazol-1-yl]-14-methyl-2-{[(2R,3R,4R,5S,6S)-3,4,5-trimethoxy-6-methyloxan-2-yl]oxy}-1H,2H,3H,3aH,5aH,5bH,6H,7H,9H,10H,11H,12H,13H,14H,15H,16aH,16bH-as-indaceno[3,2-d]oxacyclododecane-7,15-dione

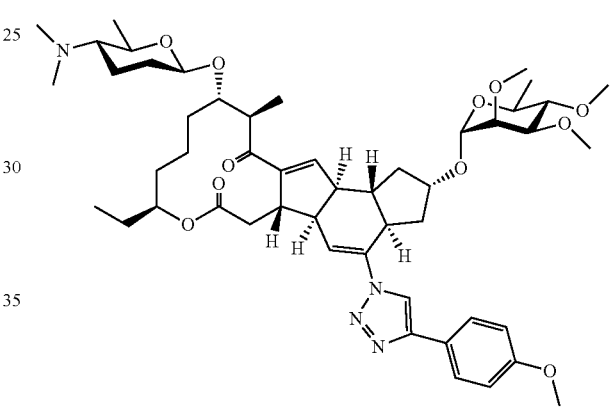

The hydroxytriazole intermediate was prepared using the representative procedure using 1-ethynyl-4-methoxybenzene. To a solution of the hydroxytriazole intermediate (80 mg, 0.08 mmol) in dichloromethane (5 mL) was was added DAST (70 mg, 0.43 mmol) at −78° C. under N$_2$. After stirring at −78° C. for 30 min, the mixture was warmed to room temperature and quenched with aqueous sodium bicarbonate (10 mL). After stirring for 15 min, the mixture was extracted with dichloromethane (10 mL×2). The combined organic layer was washed with brine, dried over sodium sulfate, filtered and concentrated. The residue was purified by prep-HPLC to afford the title compound (30 mg, yield 11%). Partial $^1$H NMR (CDCl$_3$, 400 MHz): δ 7.81 (s, 1H), 7.78 (d, J=8.8 Hz, 2H), 7.34 (t, J=8.8 Hz, 2H), 6.79 (s, 1H), 6.16-6.15 (m, 1H) 4.81 (s, 1H), 4.73-4.67 (m, 1H), 4.44 (d, J=7.6 Hz, 1H) 4.364.32 (m, 1H), 3.89-3.85 (m, 4H), 3.32-2.91 (m, 6H), 0.81 (t, J=7.6 Hz, 3H). LCMS: m/z 905.1 [M+H]$^+$.

Example 136: Testing Compounds For Insecticide, Miticide, and Nematicide Utility The compounds produced by the methods described above are tested for activity against a number of insects, mites, and nematodes. Successful compounds are useful for reducing populations of insects, mites, and/or nematodes, and are used in a method of inhibiting an insect, mite, and/or nematode population after application to a locus of the pest an effective insect-, mite-, or nematode-inactivating amount of a compound.

Activity Against *Spodoptera* Species:

Cotton leaf discs are placed on agar in 24-well microtiter plates and sprayed with serial dilutions of aqueous test solutions prepared from DMSO stock solutions, with a highest dose of 200 ppm. After drying, the leaf discs are infested with L1 larvae and samples are assessed for mortality after 4 to 8 days.

Activity Against *Plutella* Species:

Artificial diet optimized for *Lepidopteran* species is aliquoted into 24-well microtiter plates and treated with aqueous test solutions prepared from DMSO stock solutions by pipetting, with a highest dose of 200 ppm. After drying, the plates are infested with L2 larvae and mortality is assessed after 4 to 8 days.

Activity Against *Diabrotica* Species:

Artificial diet optimized for *Coleopteran* species is aliquoted into 24-well microtiter plates and treated with aqueous test solutions prepared from DMSO stock solutions by pipetting, with a highest dose of 200 ppm. After drying, the plates are infested with L2 larvae and mortality is assessed after 4 to 8 days.

Activity Against *Myzus* Species:

Sunflower Leaf Discs are Placed on Agar in a 24-Well Microtiter Plate and Sprayed with serial dilutions of aqueous test solutions prepared from DMSO stock solutions, with a highest dose of 200 ppm. After drying, the leaf discs are infested with a mixed age aphid population and samples are assessed for mortality after 4 to 8 days.

Activity Against *Thrips* Species:

Sunflower leaf discs are placed on agar in a 24-well microtiter plate and sprayed with serial dilutions of aqueous test solutions prepared from DMSO stock solutions, with a highest dose of 200 ppm. After drying, the leaf discs are infested with a mixed age *thrips* population and samples are assessed for mortality after 4 to 8 days.

Activity Against *Euschistus* Species:

Sunflower leaf discs are placed on agar in a 24-well microtiter plate and sprayed with serial dilutions of aqueous test solutions prepared from DMSO stock solutions, with a highest dose of 200 ppm. After drying, the leaf discs are infested N2 nymphs and samples are assessed for mortality after 4 to 8 days.

Activity Against *Tetranychus* Species:

Bean leaf discs are placed on agar in a 24-well microtiter plate and sprayed with serial dilutions of aqueous test solutions prepared from DMSO stock solutions, with a highest dose of 200 ppm. After drying, the leaf discs are infested with mixed mobile populations and samples are assessed for mortality after 4 to 8 days.

Activity Against *Meloidogyne* Species:

Untreated cucumber seeds are placed into the bottom of a clear cup to which clean white sand is added. The cups are sprayed with aqueous test solution while rotating on a pedestal allowing the test solution to be deposited on the sand. To each cup is dispensed water containing nematodes. After 10 to 14 days the nematode populations are assessed for mortality.

Activity Against *Blattella* Species:

Green insect diet material is dispensed into a diet cup onto which aqueous test solution is sprayed. Treated cups are air dried and infested with late third or early fourth instar cockroaches. After 10 to 14 days the cockroach populations are assessed for mortality.

Activity Against *Aedes* Species:

L2 *Aedes* larvae in a nutrition mixture are placed in 96-well microtiter plates. Aqueous test solutions are pipetted into the wells. After 1 to 3 days the mosquito populations are assessed for mortality.

All examples described above were active at test solution concentrations of 200 ppm or below against at least one of the above test organisms.

It is understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

What is claimed is:

1. A spinosyn compound of the following formula:

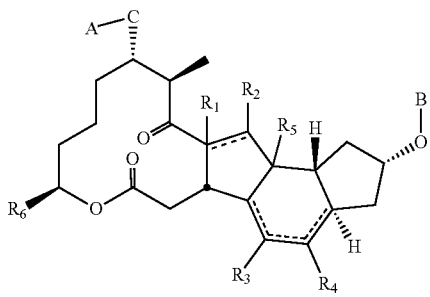

or a salt thereof, wherein:
 --- is a single bond or a double bond;
A is hydrogen or is selected from the group consisting of substituted or unsubstituted carbonyl, substituted or unsubstituted cycloalkyl, substituted or unsubstituted heterocycloalkyl, substituted or unsubstituted aryl, and substituted or unsubstituted heteroaryl;
B is selected from the group consisting of substituted or unsubstituted cycloalkyl, substituted or unsubstituted heterocycloalkyl, substituted or unsubstituted aryl, and substituted or unsubstituted heteroaryl;
C is O or NH;
$R^1$ is absent or is selected from hydrogen, hydroxyl, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;
$R^2$, $R^3$, and $R^4$ are each independently selected from hydrogen carbonyl, substituted or unsubstituted amino, substituted or unsubstituted thio, substituted or unsubstituted alkoxy, substituted or unsubstituted aryloxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl, wherein when $R^3$ is hydrogen $R^4$ is selected from substituted or unsubstituted amino, substituted or unsubstituted thio, substituted or unsubstituted alkoxy, substituted or unsubstituted aryloxy, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;
$R^5$ is hydrogen, halogen, hydroxyl, substituted or unsubstituted amino, substituted or unsubstituted thio, or substituted or unsubstituted alkoxy; and
$R^6$ is substituted or unsubstituted alkyl or substituted or unsubstituted aryl,
wherein $R^1$ and $R^2$ can combine to form a substituted cycloalkyl, substituted or unsubstituted cycloalkenyl, substituted or unsubstituted heterocycloalkenyl, substituted or unsubstituted aryl, substituted or unsubstituted heteroaryl, or substituted or unsubstituted cyclic ester, wherein the cyclic ester may be saturated or unsaturated; and
wherein $R^3$ and $R^4$ can combine to form a substituted or unsubstituted cycloalkyl, substituted or unsubstituted cycloalkenyl, substituted or unsubstituted heterocycloalkenyl, substituted or unsubstituted aryl, substituted or unsubstituted heteroaryl, or substituted or unsubstituted cyclic ester, wherein the cyclic ester may be saturated or unsaturated.

2. The spinosyn compound of claim 1, wherein $R^1$ is absent or is selected from substituted or unsubstituted $C_{1-6}$ alkyl and aryl, and wherein $R^2$, $R^3$, and $R^4$ are each independently selected from substituted or unsubstituted $C_{1-6}$ alkyl and aryl.

3. The spinosyn compound of claim 1, having the formula represented by Structure I-A:

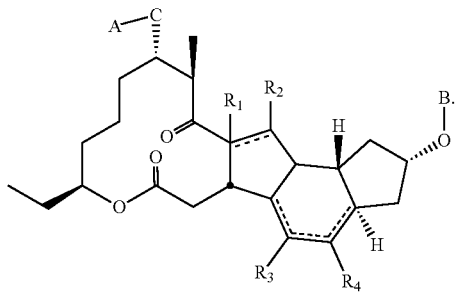

4. The spinosyn compound of claim 1, having the formula represented by Structure I-B:

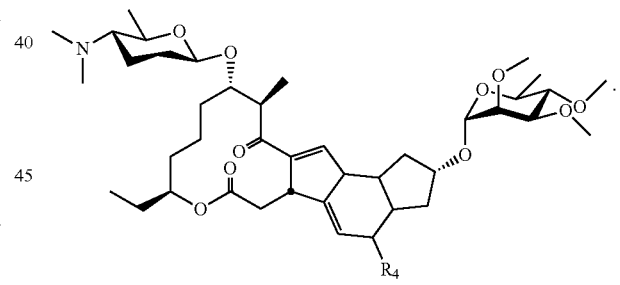

5. The spinosyn compound of claim 1, having the formula represented by Structure I-C:

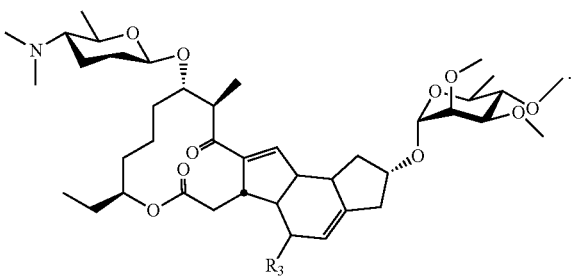

6. The spinosyn compound of claim 1, having the formula represented by Structure I-D:

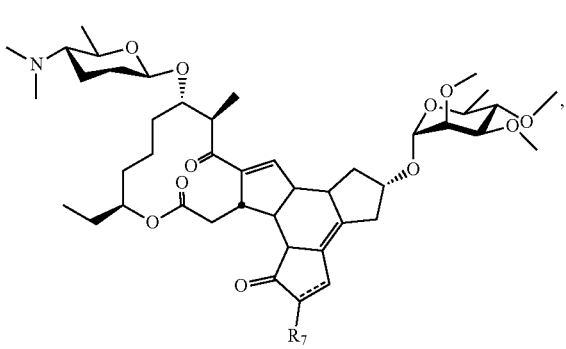

wherein $R^7$ is hydrogen, alkyl, pyrimidinyl, or substituted or unsubstituted phenyl.

7. The spinosyn compound of claim 1, having the formula represented by Structure I-F:

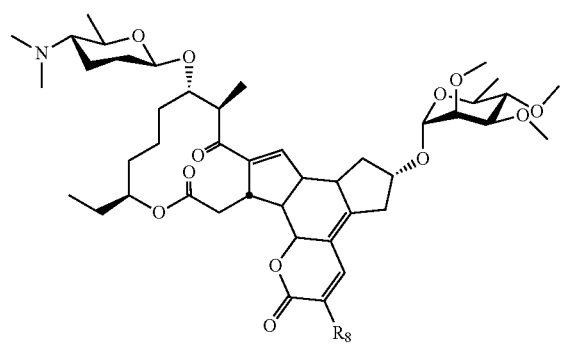

wherein $R^8$ is alkyl, substituted or unsubstituted phenyl, pyrimidinyl, or a thiophene group.

8. The spinosyn compound of claim 1, having the formula represented by Structure I-G:

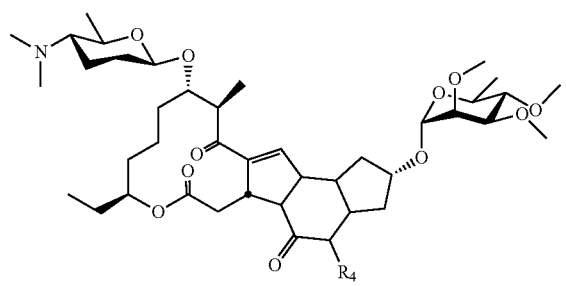

or Structure I-G':

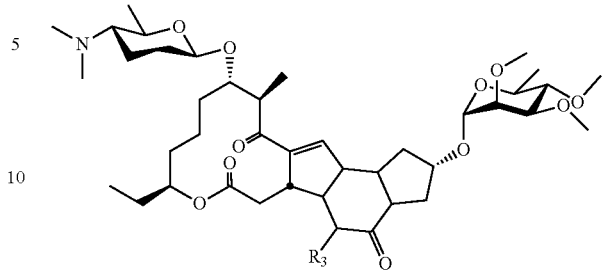

wherein the one of $R^3$ and $R^4$ that is not carbonyl is alkoxy.

9. The spinosyn compound of claim 1, having the formula represented by Structure I-H:

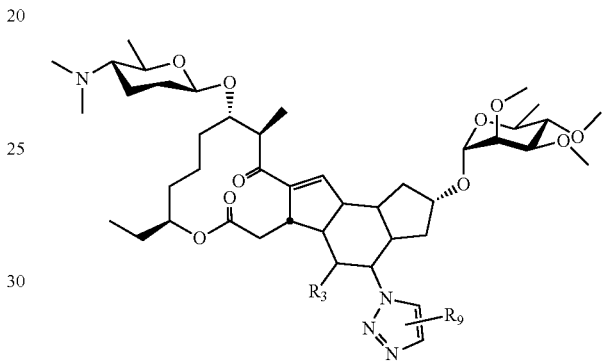

or Structure I-H':

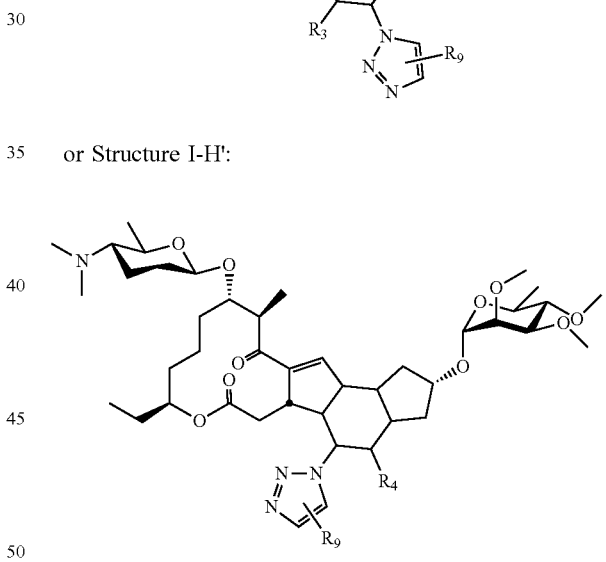

wherein the one of $R^3$ and $R^4$ that is not a substituted triazole is hydrogen, and $R^9$ is selected from alkyl, thiophene, trimethylsiloxy, $C_1$-$C_4$ methyl ester, substituted or unsubstituted phenyl, and wherein the substituted phenyl triazole has one or more substitutions comprising halogen, alkyl, alkoxy, phenyl, or amino.

10. A formulation, comprising at least one spinosyn compound of claim 1 and an acceptable carrier.

11. The formulation of claim 10, further comprising at least one additional active ingredient.

12. The formulation of claim 10, further comprising at least one plant or plant product treatment compound.

13. The formulation of claim 11, wherein the additional active ingredient is a contact-acting insecticide.

14. The formulation of claim 11, wherein the additional active ingredient is a contact-acting miticide.

15. A method for controlling pests, comprising contacting a pest with an effective amount of the spinosyn compound of claim 1.

16. The method of claim 15, wherein the pest is an insect.

17. The method of claim 15, wherein the pest is an arachnid.

18. The method of claim 15, wherein the pest is a nematode.

19. A method for making a spinosyn compound of claim 1, comprising using a substitution modification on a natural spinosyn to form a spinosyn compound according to claim 1.

20. The method of claim 19, wherein the substitution modification is selected from the group consisting of a Meerwein arylation, a Schwartz hydrozirconation, a Woehl-Ziegler bromination, a Prius reaction, and a Wacker oxidation.

21. A spinosyn compound having the formula represented by Structure I-E:

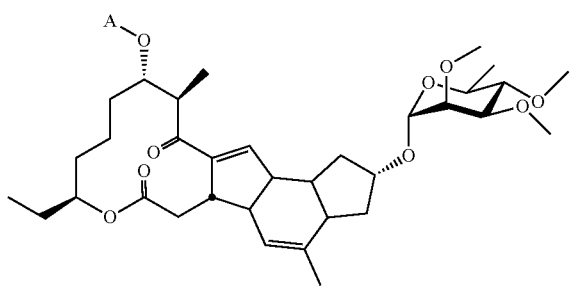

or Structure I-E':

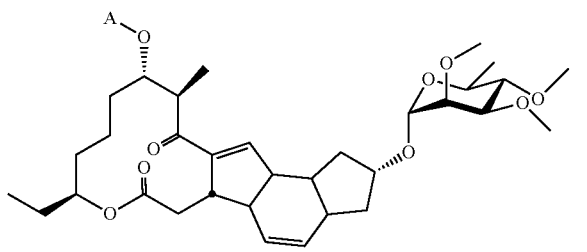

wherein A is a forosamine derivative comprising one or both of the methyl groups on the forosamine nitrogen group substituted with substituted or unsubstituted alkyl, substituted or unsubstituted cycloalkyl, substituted or unsubstituted heterocycloalkyl, substituted or unsubstituted alkenyl, substituted or unsubstituted aryl, substituted or unsubstituted heteroaryl, substituted or unsubstituted aldehyde, substituted or unsubstituted benzyl, or substituted or unsubstituted benzoyl.

22. A spinosyn compound having the formula represented by Structure I-I

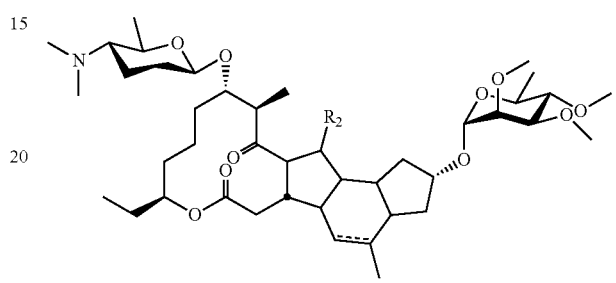

or Structure I-I':

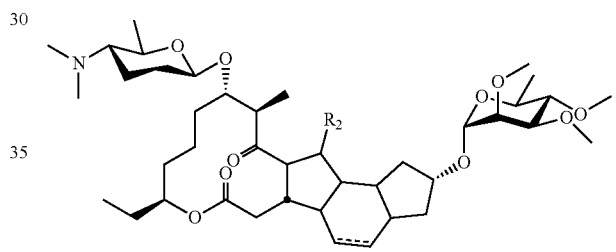

wherein $R^2$ is alkenyl, or substituted or unsubstituted phenyl, wherein the substituted phenyl has one or more substitutions comprising halogen, alkyl, halo alkyl, alkoxy, haloalkoxy, or ester.

* * * * *